(12) United States Patent
Zhou et al.

(10) Patent No.: US 11,723,908 B2
(45) Date of Patent: Aug. 15, 2023

(54) QUINAZOLINE DERIVATIVES AS ANTITUMOR AGENTS

(71) Applicant: SUZHOU ZANRONG PHARMA LIMITED, Suzhou (CN)

(72) Inventors: Ding Zhou, Shanghai (CN); Ziqiang Cheng, Shanghai (CN)

(73) Assignee: SUZHOU ZANRONG PHARMA LIMITED, Suzhou (CN)

( * ) Notice: Subject to any disclaimer, the term of this patent is extended or adjusted under 35 U.S.C. 154(b) by 316 days.

(21) Appl. No.: 17/051,176

(22) PCT Filed: Sep. 17, 2019

(86) PCT No.: PCT/CN2019/106233
§ 371 (c)(1),
(2) Date: Oct. 28, 2020

(87) PCT Pub. No.: WO2020/057511
PCT Pub. Date: Mar. 26, 2020

(65) Prior Publication Data
US 2021/0386742 A1    Dec. 16, 2021

(30) Foreign Application Priority Data

Sep. 18, 2018 (WO) ............... PCT/CN2018/106098
Jun. 13, 2019 (WO) ............... PCT/CN2019/091078

(51) Int. Cl.
| | | |
|---|---|---|
| *A61K 31/519* | (2006.01) | |
| *A61P 35/00* | (2006.01) | |
| *A61K 31/5377* | (2006.01) | |
| *A61K 31/7068* | (2006.01) | |
| *C07D 487/04* | (2006.01) | |
| *C07D 519/00* | (2006.01) | |
| *A61K 39/395* | (2006.01) | |

(52) U.S. Cl.
CPC ........ *A61K 31/519* (2013.01); *A61K 31/5377* (2013.01); *A61K 31/7068* (2013.01); *A61K 39/3955* (2013.01); *A61P 35/00* (2018.01); *C07D 487/04* (2013.01); *C07D 519/00* (2013.01)

(58) Field of Classification Search
CPC .............. A61K 31/519; A61K 31/5377; A61K 31/7068; A61K 31/3955; A61P 35/00; C07D 487/04; C07D 519/00
See application file for complete search history.

(56) References Cited

U.S. PATENT DOCUMENTS 7,452,895 B2    11/2008   Wallace et al.

FOREIGN PATENT DOCUMENTS

| CN | 101356171 A | 1/2009 |
|---|---|---|
| CN | 107141293 A | 9/2017 |
| WO | 01/98277 A2 | 12/2001 |
| WO | 2007/059257 A2 | 5/2007 |
| WO | WO 2007/059257 * | 5/2007 |
| WO | 2017/148391 A1 | 9/2017 |
| WO | 2018/055023 A1 | 3/2018 |
| WO | 2019/042409 A1 | 3/2019 |
| WO | 2019/214634 A1 | 11/2019 |

OTHER PUBLICATIONS

Ismail, R. S. M. et al., "Recent advances in 4-aminoquinazoline based scaffold derivatives targeting EGFR kinases as anticancer agents", Future Journal of Pharmaceutical Sciences (2016), vol. 2, pp. 9-19.
Reweastle, G. W. et al., "Tyrosine Kinase Inhibitors. 5. Synthesis and Structure-Activity Relationships for 4-[(Phenylmethyl)amino]- and 4-(Phenylamino)quinazolines as Potent Adenosine 5'-Triphosphate Binding Site Inhibitors of the Tyrosine Kinase Domain of the Epidermal Growth Factor Receptor", Journal of Medicinal Chemistry (1995), vol. 38, pp. 3482-3487.
The First Office Action and Search Report for the corresponding Chinese application 201980044137.8, dated Mar. 28, 2022.

* cited by examiner

*Primary Examiner* — Erich A Leeser
(74) *Attorney, Agent, or Firm* — Jun He Law Offices P.C.; James J. Zhu

(57) ABSTRACT

The present application relates to novel quinazoline compounds as inhibitors of type I receptor tyrosine kinases, the pharmaceutical compositions comprising one or more of the compounds and salts thereof as an active ingredient, and the use of the compounds and salts thereof in the treatment of hyperproliferative diseases, such as cancer and inflammation, in mammals and especially in humans.

36 Claims, 1 Drawing Sheet

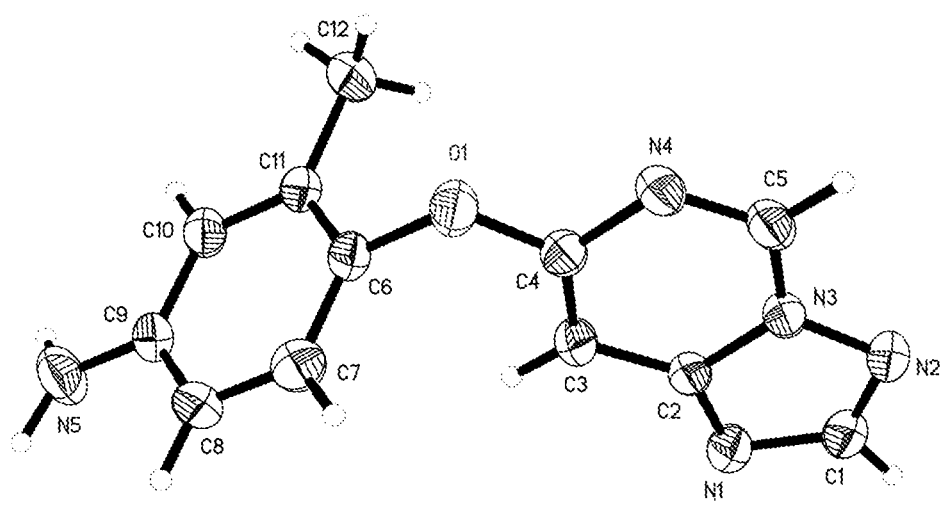

QUINAZOLINE DERIVATIVES AS ANTITUMOR AGENTS

FIELD OF THE DISCLOSURE

The present application relates to novel quinazoline compounds as inhibitors of type I receptor tyrosine kinases, the pharmaceutical compositions comprising one or more of the compounds and salts thereof as an active ingredient, and the use of the compounds and salts thereof in the treatment of hyperproliferative diseases, such as cancer and inflammation, in mammals and especially in humans.

BACKGROUND OF THE DISCLOSURE

The type I tyrosine kinase receptor family consists of four structurally related receptors: EGFR (ErbB1 or HER1), ErbB2 (HER2), ErbB3 (HER3), and ErbB4 (HER4) (Reviewed in Riese and Stern, Bioessays (1998) 20:41-48; Olayioye et ah, EMBO Journal (2000) 19:3159-3167; and Schlessinger, Cell (2002) 110:669-672). The structures of all the four family members are nearly the same, made up of an extracellular region or ectodomain or ligand binding region, a single transmembrane-spanning region, and an intracellular cytoplasmic tyrosine kinase domain.

It has been demonstrated that HER2 plays a role in development of cancer. HER2 overexpression occurs in 20-25% of breast cancer (BC) patients (Leyland-Jones B, *J Clin Oncol.* 2009, 5278-86). About 1.7 million new BC incidences are diagnosed every year (Cardoso F, et al. *Breast* 2018, 131-138) and 80% of BC are invasive, which require chemotherapy, radiation or target therapy besides surgery (Dai X., et al. *Am J Cancer Res*, 2015, 2929-2943). Brain metastases are a frequent occurrence in metastatic breast cancer patients. Overall survival for breast cancer brain metastases (BCBM) patients ranges from 2-25.3 months (Leone J. P. *Exp. Hematol. Oncol.* 2015, 4, 33). Surgery, whole brain radiation therapy (WBRT) and stereotactic radiosurgery (SRS) are the three main treatment options for BCBM. Surgery is used for solitary or up to three brain metastases. SRS can be used in patients with four or fewer intracranial lesions. WBRT is used to manage multiple brain metastases, but can lead to significant neuro-cognitive decline (Venur V. A. et al. *Int. J. Mol. Sci.* 2016, 1543).

Compared to other types of breast cancer, HER2 positive tumors have a higher incidence of brain metastases, up to 50% of HER2 positive breast cancer patients develop intracranial metastases (Leyland-Jones B, *J Clin Oncol.* 2009, 5278-86). The high prevalence of BCBM in HER2 positive patients is ascribed to inherent tropism of HER2 positive breast cancer cells to the brain, prolonged survival of patients treated with anti-HER2 therapy and limited intracranial activity of anti-HER2 therapy (Venur V. A. et al. *Int. J. Mol. Sci.* 2016, 17, 1543).

Several anti-HER2 agents have been developed for clinical use, but none of them is central nervous system (CNS) penetrable. The blood-brain barrier (BBB) is essential to protect the CNS from potentially harmful agents in the peripheral circulation; however it also prevents potential therapeutics from reaching the site of action. It is estimated that 98% of all small molecules and 100% large molecules, such as antibodies and antibody drug conjugate do not cross the BBB (Pardridge W. M. NeuroRx, 2005, 2, 3-14), which presents great challenges to CNS drug discovery. Efflux transport is a major determinant of drug disposition to the CNS. Several ATP-dependent efflux pumps from the ABC superfamily (P-gp and BCRP) have been localized at the luminal side of human brain capillary endothelial cells (Giacomini K. M. et al. Nature Reviews Drug Discovery, 2010, 9, 215-236) and Pgp and BCRP have been shown to play an important role in limiting entry of various drugs into the CNS (Enokizono, J. et al. Drug Metabolism and Disposition, 2008, 36, 995-1002. Zhou, L. et al. Drug Metabolism and Disposition, 2009, 37, 946-955).

Trastuzumab, like other monoclonal antibodies, does not cross blood-brain barrier (BBB) with brain to blood ratio $(K_p)<0.01$ (Kabraji S. et al. *Clinical Cancer Research.* 2018, 3351). T-DM1, an antibody drug conjugate (ADC), does not cross BBB either with $K_p<0.01$ (Askoxylakis V, et al. *JNCI J Natl Cancer Inst*, 2015, 763-763). Approved tyrosine kinase inhibitors (TKIs) lapatinib, neratinib and afatinib are strong Pgp substrates, and have poor brain brain penetration with $K_p$ of 0.04, 0.079 and <0.08, respectively (Tanaka, Y. et al, *Scientific Reports,* 2018, 343; Zhang, Shirong, et al, *Acta Pharmacologica Sinica,* 2017, 233-240). Tucatinib, a HER2 reversible inhibitor in phase 1/2 clinical trial, is also a strong Pgp substrate and does not cross BBB with $K_p$ at 0.02-0.05 (Dinkel V, et al. *Cancer Research,* 2012, 72). In addition, the evaluation of resected brain metastases have revealed that the BBB was preserved in patients with HER2-positive breast cancer, despite having brain metastases (Yonemori K, et al. *Cancer,* 2010, 302-308). Limited clinical efficacy observed when treating BCBM patients with non-brain penetrable aforementioned antibody, ADC and TKIs. Accordingly, there remains a need to develop new compounds that act as BBB penentratable HER2 inhibitor to treat HER2 positive BCBM patients.

SUMMARY OF THE DISCLOSURE

Disclosed herein are novel quinazoline compounds that inhibit type I receptor tyrosine kinases, demonstrate good brain penetration in animals, and possess favourable toxicity profiles (for example a decreased activity against hERG). As a result, the compounds of the present application are particularly useful in the treatment of type I receptor tyrosine kinases mediated diseases or conditions, in particular HER2-associated disease or conditions, including cancer (e.g., metastatic cancer, such as brain metastases).

In one aspect, the present disclosure provides compounds of Formula (I):

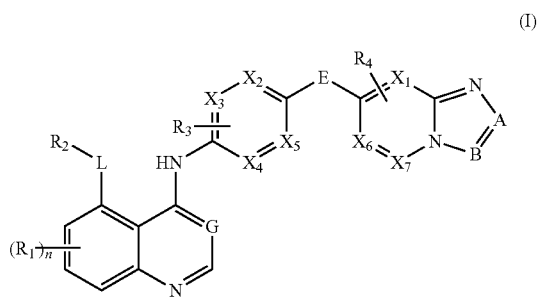

(I)

or a pharmaceutically acceptable salt thereof, wherein:
G is $C(R_5)$ or N;
A is CH or N;
B is CH or N;
$X_1, X_2, X_3, X_4, X_5, X_6$, and $X_7$ are each independently CH or N, with the provision that $X_6$ and $X_7$ are not each CH or N;

E is O, NH, or S;

L is selected from the group consisting of O, S and N($R_6$);

$R_1$ is each independently selected from the group consisting of hydrogen, halogen, cyano, nitro, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, N($R_7$)($R_8$), and O($R_9$), wherein said cycloalkyl and heterocyclyl are optionally substituted with one or more groups independently selected from the group consisting of halogen, cyano, nitro, hydroxyl, carboxy, carbamoyl, acyl, alkyl, alkenyl, alkynyl, and haloalkyl;

$R_2$ is selected from the group consisting of alkyl, saturated or partially unsaturated cycloalkyl, saturated or partially unsaturated heterocyclyl, wherein said alkyl, cycloalkyl, and heterocyclyl are optionally substituted with one or more groups independently selected from the group consisting of halogen, cyano, nitro, hydroxyl, carboxy, carbamoyl, alkyl, alkenyl, alkynyl, haloalkyl, saturated or partially unsaturated cycloalkyl, and N($R_{10}$)($R_{11}$);

$R_6$ is hydrogen or alkyl; or when L is N($R_6$), $R_2$ and $R_6$ together with the nitrogen atom to which they are attached form a 3 to 10 membered saturated or partially unsaturated heterocyclyl ring optionally containing one or more additional heteroatoms selected from N, O and S, wherein said 3 to 10 membered heterocyclyl ring is optionally substituted with one or more groups independently selected from the group consisting of halogen, cyano, nitro, carboxy, carbamoyl, alkyl, alkenyl, alkynyl, haloalkyl, saturated and partially unsaturated cycloalkyl, and N($R_{10}$)($R_{11}$);

$R_3$ and $R_4$ are each independently selected from the group consisting of hydrogen, halogen, cyano, nitro, alkyl, alkenyl, alkynyl and alkoxyl;

$R_5$ is selected from the group consisting of hydrogen, halogen and cyano;

$R_7$ and $R_8$ are each independently selected from the group consisting of hydrogen, alkyl, alkenyl, alkynyl, heteroalkyl, heteroalkenyl, heteroalkynyl, acyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, acyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, alkylamino, saturated and partially unsaturated cycloalkyl, saturated and partially unsaturated heterocyclyl optionally substituted by alkyl, aryl, and heteroaryl; or $R_7$ and $R_8$ together with the atom to which they are attached form a 3 to 10 membered saturated or partially unsaturated heterocyclyl ring optionally containing one or more additional heteroatoms selected from N, O, S, SO, $SO_2$ and $NR_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

$R_9$ is selected from the group consisting of alkyl, alkenyl, alkynyl, acyl, saturated or partially unsaturated cycloalkyl, saturated or partially unsaturated heterocyclyl, wherein said alkyl, alkenyl, alkynyl, acyl, cycloalkyl, heterocyclyl are optionally substituted by one or more groups independently selected from the group consisting of halogen, alkyl, alkenyl, alkynyl, alkoxyl, acyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

$R_{10}$ and $R_{11}$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl; or $R_{10}$ and $R_{11}$ together with the atom to which they are attached form a 3 to 10 membered saturated or partially unsaturated heterocyclyl ring optionally containing one or more additional heteroatoms selected from N, O, S, SO, $SO_2$ and $NR_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

$R_{12}$ is selected from the group consisting of hydrogen, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from halogen, alkyl, alkenyl, alkynyl, saturated and partially unsaturated cycloalkyl, saturated and partially unsaturated heterocyclyl, cycloalkylalkyl, cyano, nitro, aryl, heteroaryl, arylalkyl, heteroarylalkyl, and heterocyclylalkyl;

n is 0, 1 or 2.

In another aspect, there is provided a pharmaceutical composition comprising the compound of Formula (I) or a pharmaceutically acceptable salt thereof, and at least one pharmaceutically acceptable excipient.

In a further aspect, there is provided a method of treating type I receptor kinases-associated diseases or conditions in a subject in need thereof, comprising administering to the subject a therapeutically effective amount of the compound of Formula (I) or a pharmaceutically acceptable salt thereof.

In a further aspect, there is provided a method of treating HER2-associated diseases or conditions in a subject in need thereof, comprising administering to the subject a therapeutically effective amount of the compound of Formula (I) or a pharmaceutically acceptable salt thereof.

In a further aspect, there is provided a compound of Formula (I) or a pharmaceutically acceptable salt thereof, for use in the treatment of type I receptor kinases-associated diseases or conditions, in particular HER2-associated diseases or conditions.

In a further aspect, there is provided use of a compound of Formula (I) or a pharmaceutically acceptable salt thereof, in the manufacture of a medicament for the treatment of type I receptor kinases-associated diseases or conditions, in particular HER2-associated diseases or conditions.

In a further aspect, there is provided a compound of Formula (I) or a pharmaceutically acceptable salt thereof for use in the treatment of type I receptor kinases-associated diseases or conditions, in particular HER2-associated diseases or conditions, wherein the compound of Formula (I) is administered simultaneously, separately or sequentially with radiotherapy.

In a further aspect, there is provided a compound of Formula (I) or a pharmaceutically acceptable salt thereof, administered simultaneously, separately or sequentially with one or more additional chemotherapeutic agents.

In a further aspect, there is provided a kit for the treatment or prevention of type I receptor kinases-associated diseases or conditions, in particular HER2-associated diseases or conditions, said kit comprising a compound of Formula (I) or a pharmaceutically acceptable salt thereof, a container, and optionally a package insert or label indicating a treatment. The kit may further comprise a second compound or formulation comprising a second pharmaceutical agent useful for treating said disease or disorder.

DESCRIPTION OF DRAWINGS

FIG. 1 shows an ORTEP drawing of 4-([1,2,4]triazolo[1,5-c]pyrimidin-7-yloxy)-3-methylaniline obtained in Step 4 of Example 1, as measured by the single crystal X-ray diffraction.

DETAILED DESCRIPTION OF THE DISCLOSURE

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub-combination.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. The term "substituent", as used herein, has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i\text{-}j}$" indicates a range of the carbon atoms numbers, wherein i and j are integers and the range of the carbon atoms numbers includes the endpoints (i.e. i and j) and each integer point in between, and wherein j is greater than i. For examples, $C_{1\text{-}6}$ indicates a range of one to six carbon atoms, including one carbon atom, two carbon atoms, three carbon atoms, four carbon atoms, five carbon atoms and six carbon atoms. In some embodiments, the term "$C_{1\text{-}12}$" indicates 1 to 12, particularly 1 to 10, particularly 1 to 8, particularly 1 to 6, particularly 1 to 5, particularly 1 to 4, particularly 1 to 3 or particularly 1 to 2 carbon atoms.

As used herein, the term "alkyl", whether as part of another term or used independently, refers to a saturated linear or branched-chain hydrocarbon radical, which may be optionally substituted independently with one or more substituents described below. The term "$C_{i\text{-}j}$ alkyl" refers to an alkyl having i to j carbon atoms. In some embodiments, alkyl groups contain 1 to 12 carbon atoms. In some embodiments, alkyl groups contain 1 to 11 carbon atoms. In some embodiments, alkyl groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of alkyl group include, but are not limited to, methyl, ethyl, 1-propyl (n-propyl), 2-propyl (isopropyl), 1-butyl (n-butyl), 2-methyl-1-propyl (i-butyl), 2-butyl (s-butyl), 2-methyl-2-propyl (t-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Examples of "$C_{1\text{-}12}$ alkyl" include, but are not limited to, methyl, ethyl, propyl, butyl, pentyl, hexyl, heptyl, octyl, nonyl, decyl, undecyl, dodecyl. Examples of "$C_{1-6}$ alkyl" are methyl, ethyl, propyl, isopropyl, n-butyl, i-butyl, s-butyl, t-butyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, and the like.

The alkyl groups can be further substituted by substituents which independently replace one or more hydrogen atoms on one or more carbons of the alkyl groups. Examples of such substituents can include, but are not limited to, acyl, alkyl, alkenyl, alkynyl, halogen, hydroxyl, alkoxyl, haloalkyl, haloalkoxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonate, sulfamoyl, sulfonamido, nitro, trifluoromethyl, cyano, nitro, azido, heterocyclyl, alkylaryl, or an aromatic or heteroaromatic moiety. Alkenyl, alkynyl, saturated or practically unsaturated cycloalkyl, heteroalkyl, heterocyclyl, arylalkyl, heteroarylalkyl, heterocyclylalkyl, cycloalkylalkyl, aryl and heteroaryl groups as described below may also be similarly substituted.

As used herein, the term "alkenyl", whether as part of another term or used independently, refers to linear or branched-chain hydrocarbon radical having at least one carbon-carbon double bond, which may be optionally substituted independently with one or more substituents described herein, and includes radicals having "cis" and "trans" orientations, or alternatively, "E" and "Z" orientations. In some embodiments, alkenyl groups contain 2 to 12 carbon atoms. In some embodiments, alkenyl groups contain 2 to 11 carbon atoms. In some embodiments, alkenyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkenyl groups contain 2 carbon atoms. Examples of alkenyl group include, but are not limited to, ethylenyl (or vinyl), propenyl, butenyl, pentenyl, 1-methyl-2 buten-1-yl, 5-hexenyl, and the like.

As used herein, the term "alkynyl", whether as part of another term or used independently, refers to a linear or branched hydrocarbon radical having at least one carbon-carbon triple bond, which may be optionally substituted independently with one or more substituents described herein. In some embodiments, alkenyl groups contain 2 to 12 carbon atoms. In some embodiments, alkynyl groups contain 2 to 11 carbon atoms. In some embodiments, alkynyl groups contain 2 to 11 carbon atoms, 2 to 10 carbon atoms, 2 to 9 carbon atoms, 2 to 8 carbon atoms, 2 to 7 carbon atoms, 2 to 6 carbon atoms, 2 to 5 carbon atoms, 2 to 4 carbon atoms, 2 to 3 carbon atoms, and in some embodiments, alkynyl groups contain 2 carbon atoms. Examples of alkynyl group include, but are not limited to, ethynyl, 1-propynyl, 2-propynyl, and the like.

As used herein, the term "alkoxy" or "alkoxyl", whether as part of another term or used independently, refers to an alkyl group, as previously defined, attached to the parent molecule through an oxygen atom. The term "$C_{i-j}$ alkoxy" means that the alkyl moiety of the alkoxy group has i to j carbon atoms. In some embodiments, alkoxy groups contain 1 to 12 carbon atoms. In some embodiments, alkoxy groups contain 1 to 11 carbon atoms. In some embodiments, alkoxy groups contain 1 to 11 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atoms, or 1 to 2 carbon atoms. Examples of "$C_{1-12}$ alkoxyl" include, but are not limited to, methoxy, ethoxy, propoxy (e.g. n-propoxy and isopropoxy), t-butoxy, neopentoxy, n-hexoxy, and the like.

As used herein, the term "acyl" refers to a carbonyl-containing functionality, e.g., —C(=O)R, wherein R is hydrogen or an optionally substituted aliphatic, heteroaliphatic, heterocyclic, aryl, heteroaryl group, or is a substituted (e.g., with hydrogen or aliphatic, heteroaliphatic, aryl, or heteroaryl moieties) oxygen or nitrogen containing functionality (e.g., forming a carboxylic acid, ester, or amide functionality). Examples of the "acyl" group include but not limited to a formyl group, a carboxy group, a $C_{1-6}$ alkyl-carbonyl group, a $C_{2-6}$ alkenyl-carbonyl group (e.g., acryloyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered heteroaryl-carbonyl group, a 3- to 14-membered heterocyclyl-carbonyl group (e.g., piperzyl-carbonyl), a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, and the like. As used herein, the term "acyloxy" refers to an acyl group attached to the parent molecule through an oxygen atom.

As used herein, the term "amino" or "amine" refers to moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

As used herein, the term "amide" or "aminocarboxy" refers to compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

As used herein, the term "aryl", whether as part of another term or used independently, refers to monocyclic and polycyclic ring systems having a total of 5 to 20 ring members, wherein at least one ring in the system is aromatic and wherein each ring in the system contains 3 to 12 ring members. Examples of "aryl" include, but are not limited to, phenyl, biphenyl, naphthyl, anthracyl and the like, which may bear one or more substituents. Also included within the scope of the term "aryl", as it is used herein, is a group in which an aromatic ring is fused to one or more additional rings. In the case of polycyclic ring system, only one of the rings needs to be aromatic (e.g., 2,3-dihydroindole), although all of the rings may be aromatic (e.g., quinoline). The second ring can also be fused or bridged. Examples of polycyclic aryl include, but are not limited to, benzofuranyl, indanyl, phthalimidyl, naphthimidyl, phenanthridinyl, or tetrahydronaphthyl, and the like. Aryl groups can be substituted at one or more ring positions with substituents as described above.

As used herein, the term "arylalkyl", whether as part of another term or used independently, means an alkyl moiety substituted with one or more aryl moiety. Examples of arylalkyl radicals include, but are not limited to, benzyl, phenylethyl, and the like.

As used herein, the term "azido", whether as part of another term or used independently, refers to —$N_3$ group.

As used herein, the term "carboxy", whether as part of another term or used independently, refers to a group represented by formula —COOH.

As used herein, the term "carbamoyl", whether as part of another term or used independently, refers to aminocarbonyl group as defined above. Examples of "N—($C_{1-12}$ alkyl) carbamoyl" include, but are not limited to, methylaminocarbonyl and ethylaminocarbonyl. Examples of "N,N—($C_{1-12}$ alkyl)$_2$carbamoyl" include, but are not limited to, dimethylaminocarbonyl and methylethylaminocarbonyl.

As used herein, the terms "cycloalkyl", "carbocyclyl" and "carbocycle" are interchangeable and whether as part of another term or used independently, refer to a monovalent non-aromatic, saturated or partially unsaturated monocyclic and polycyclic ring system, in which all the ring atoms are carbon and which contains at least three ring forming carbon atoms. In some embodiments, the cycloalkyl may contain 3 to 12 ring forming carbon atoms, 3 to 10 ring forming carbon atoms, 3 to 9 ring forming carbon atoms, 3 to 8 ring forming carbon atoms, 3 to 7 ring forming carbon atoms, 3 to 6 ring forming carbon atoms, 3 to 5 ring forming carbon atoms, 4 to 12 ring forming carbon atoms, 4 to 10 ring forming carbon atoms, 4 to 9 ring forming carbon atoms, 4 to 8 ring forming carbon atoms, 4 to 7 ring forming carbon atoms, 4 to 6 ring forming carbon atoms, 4 to 5 ring forming carbon atoms. Cycloalkyl groups may be saturated or partially unsaturated. Cycloalkyl groups may be substituted. In some embodiments, the cycloalkyl group may be a saturated cyclic alkyl group. In some embodiments, the cycloalkyl group may be a partially unsaturated cyclic alkyl group that contains at least one double bond or triple bond in its ring system.

In some embodiments, the cycloalkyl group may be saturated or partially unsaturated monocyclic carbocyclic ring system, examples of which include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl.

In some embodiments, the cycloalkyl group may be saturated or partially unsaturated polycyclic (e.g., bicyclic and tricyclic) carbocyclic ring system, which can be arranged as a fused, spiro or bridged ring system. As used herein, the term "fused ring" refers to a ring system having two rings sharing two adjacent atoms, the term "spiro ring" refers to a ring systems having two rings connected through one single common atom, and the term "bridged ring" refers to a ring system with two rings sharing three or more atoms. Examples of fused carbocyclyl include, but are not limited to, naphthyl, benzopyrenyl, anthracenyl, acenaphthenyl, fluorenyl and the like. Examples of spiro carbocyclyl include, but are not limited to, spiro[5.5]undecanyl, spiropentadienyl, spiro[3.6]-decanyl, and the like. Examples of bridged carbocyclyl include, but are not limited to bicyclo[1,1,1]pentenyl, bicyclo[2,2,1]heptenyl, bicyclo[2.2.1]heptanyl, bicyclo[2.2.2]octanyl, bicyclo[3.3.1]nonanyl, bicyclo[3.3.3]undecanyl, and the like.

As used herein, the term "cycloalkylalkyl" means an alkyl moiety substituted with a cycloalkyl moiety. Examples of cycloalkylalkyl include, for example, 5- or 6-membered cycloalkyl-$C_{1-3}$ alkyl, such as, but not limited to, cyclopropylmethyl.

As used herein, the term "cyano" refers to —CN.

As used herein, the term "halo" or "halogen" refers to an atom selected from fluorine (or fluoro), chlorine (or chloro), bromine (or bromo) and iodine (or iodo).

As used herein, the term "haloalkyl" refers to an alkyl group substituted with one or more halogen atoms.

As used herein, the term "haloalkoxy" or "haloalkoxyl" refers to an alkoxyl group substituted with one or more halogen atoms.

As used herein, the term "heteroalkyl" refers to an alkyl, at least one of the carbon atoms of which is replaced with a heteroatom selected from N, O, or S. The heteroalkyl may be a carbon radical or heteroatom radical (i.e., the heteroatom may appear in the middle or at the end of the radical), and may be optionally substituted independently with one or more substituents described herein. The term "heteroalkyl" encompasses alkoxy and heteroalkoxy radicals.

As used herein, the term "heteroalkenyl" refers to an alkenyl, at least one of the carbon atoms of which is replaced with a heteroatom selected from N, O, or S. The heteroalkenyl may be a carbon radical or heteroatom radical (i.e., the heteroatom may appear in the middle or at the end of the radical), and may be optionally substituted independently with one or more substituents described herein.

As used herein, the term "heteroalkynyl" refers to an alkynyl, at least one of the carbon atoms of which is replaced with a heteroatom selected from N, O, or S. The heteroalkynyl may be a carbon radical or heteroatom radical (i.e., the heteroatom may appear in the middle or at the end of the radical), and may be optionally substituted independently with one or more substituents described herein.

As used herein, the term "heteroatom" refers to nitrogen, oxygen, or sulfur, and includes any oxidized form of nitrogen or sulfur, and any quaternized form of a basic nitrogen.

As used herein, the term "heteroaryl", whether as part of another term or used independently, refers to an aryl group having, in addition to carbon atoms, one or more heteroatoms. Examples of heteroaryl include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The heteroaryl also includes groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. In some embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the term "heterocycle" or "heterocyclyl" refers to a saturated or unsaturated carbocyclyl group in which one or more ring atoms are heteroatoms independently selected from oxygen, sulfur, nitrogen, phosphorus, and the like, the remaining ring atoms being carbon, wherein one or more ring atoms may be optionally substituted independently with one or more substitutents. In some embodiments, the heterocyclyl is a saturated heterocyclyl. In some embodiments, the heterocyclyl is a practically unsaturated heterocyclyl having one or more double bonds in its ring system. In some embodiments, the heterocyclyl may contains any oxidized form of carbon, nitrogen or sulfur, and any quaternized form of a basic nitrogen. "Heterocyclyl" also includes radicals wherein the heterocyclyl radicals are fused with a saturated, partially unsaturated, or fully unsaturated (i.e., aromatic) carbocyclic or heterocyclic ring. The heterocyclyl radical may be carbon linked or nitrogen linked where such is possible. In some embodiments, the heterocycle is carbon linked. In some embodiments, the heterocycle is nitrogen linked. For example, a group derived from pyrrole may be pyrrol-1-yl (nitrogen linked) or pyrrol-3-yl (carbon linked). Further, a group derived from imidazole may be imidazol-1-yl (nitrogen linked) or imidazol-3-yl (carbon linked).

In some embodiments, the term "3- to 12-membered heterocyclyl" refers to a 3- to 12-membered saturated or partially unsaturated monocyclic or polycyclic heterocyclic ring system having 1 to 3 heteroatoms independently selected from nitrogen, oxygen, or sulfur. The fused, spiro and bridged ring systems are also included within the scope of this definition. Examples of monocyclic heterocyclyl include, but are not limited to oxetanyl, 1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, pyrrolidinyl, triazinonyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of spiro heterocyclyl include, but are not limited to, spiropyranyl, spirooxazinyl, and the like. Examples of bridged heterocyclyl include, but are not limited to, morphanyl, hexamethylenetetraminyl, 3-aza-bicyclo[3.1.0]hexane, 8-aza-bicyclo[3.2.1]octane, 1-aza-bicyclo[2.2.2]octane, 1,4-diazabicyclo[2.2.2]octane (DABCO), and the like.

As used herein, the term "heteroarylalkyl" means an alkyl moiety substituted with a heteroaryl moiety. Examples of heteroarylalkyl include 5- or 6-membered heteroaryl-$C_{1-3}$alkyl such as, but not limited to, oxazolylmethyl, pyridylethyl and the like.

As used herein, the term "heterocyclylalkyl" means an alkyl moiety substituted with a heterocyclyl moiety. Examples of heterocyclylalkyl radicals include 5- or 6-membered heterocyclyl-$C_{1-3}$ alkyls such as, but not limited to, tetrahydropyranylmethyl.

As used herein, the term "hydroxy" refers to —OH group.

As used herein, the term "nitro" refers to —$NO_2$ group.

As used herein, the term "partially unsaturated" refers to a radical that includes at least one double or triple bond. The term "partially unsaturated" is intended to encompass rings having multiple sites of unsaturation, but is not intended to include aromatic (i.e., fully unsaturated) moieties.

As used herein, the term "substituted", whether preceded by the term "optionally" or not, means that one or more hydrogens of the designated moiety are replaced with a suitable substituent. It will be understood that "substitution" or "substituted with" includes the implicit proviso that such substitution is in accordance with permitted valence of the substituted atom and that the substitution results in a stable or chemically feasible compound, e.g., which does not spontaneously undergo transformation such as by rearrangement, cyclization, elimination, etc. Unless otherwise indicated, an "optionally substituted" group may have a suitable substituent at each substitutable position of the group, and when more than one position in any given structure may be substituted with more than one substituent selected from a specified group, the substituent may be either the same or different at every position. It will be understood by those skilled in the art that substituents can themselves be substituted, if appropriate. Unless specifically stated as "unsubstituted", references to chemical moieties herein are understood to include substituted variants. For example, reference to an "aryl" group or moiety implicitly includes both substituted and unsubstituted variants.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R^i$) occurs more than one time in any constituent or formula for a compound, its definition at each occurrence is independent of its definition at every other occurrence. Thus, for example, if a group is shown to be substituted with 0-2 $R^i$ moieties, then the group may optionally be substituted with up to two $R^i$ moieties and $R^i$ at each occurrence is selected independently from the definition of $R^i$. Also, combinations of substituents and/or variables are permissible, but only if such combinations result in stable compounds.

Compound

The present disclosure provides novel compounds of Formula (I) and pharmaceutically acceptable salts thereof, synthetic methods for making the compounds, pharmaceutical compositions containing them and various uses of the disclosed compounds.

In one aspect, the present disclosure provides a compound of Formula (I):

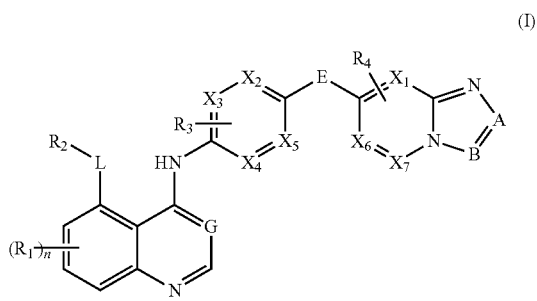

or a pharmaceutically acceptable salt thereof, wherein:

G is $C(R_5)$ or N;

A is CH or N;

B is CH or N;

$X_1, X_2, X_3, X_4, X_5, X_6$, and $X_7$ are each independently CH or N, with the provision that $X_6$ and $X_7$ are not each CH or N;

E is O, NH, or S;

L is selected from the group consisting of O, S and $N(R_6)$;

$R_1$ is each independently selected from the group consisting of hydrogen, halogen, cyano, nitro, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, $N(R_7)(R_8)$, and $O(R_9)$, wherein said cycloalkyl and heterocyclyl are optionally substituted with one or more groups independently selected from the group consisting of halogen, cyano, nitro, hydroxyl, carboxy, carbamoyl, acyl, alkyl, alkenyl, alkynyl, and haloalkyl;

$R_2$ is selected from the group consisting of alkyl, saturated or partially unsaturated cycloalkyl, saturated or partially unsaturated heterocyclyl, wherein said alkyl, cycloalkyl, and heterocyclyl are optionally substituted with one or more groups independently selected from the group consisting of halogen, cyano, nitro, hydroxyl, carboxy, carbamoyl, alkyl, alkenyl, alkynyl, haloalkyl, saturated or partially unsaturated cycloalkyl, and $N(R_{10})(R_{11})$;

$R_6$ is hydrogen or alkyl; or when L is $N(R_6)$, $R_2$ and $R_6$ together with the nitrogen atom to which they are attached form a 3 to 10 membered saturated or partially unsaturated heterocyclyl ring optionally containing one or more additional heteroatoms selected from N, O and S, wherein said 3 to 10 membered heterocyclyl ring is optionally substituted with one or more groups independently selected from the group consisting of halogen, cyano, nitro, carboxy, carbamoyl, alkyl, alkenyl, alkynyl, haloalkyl, saturated and partially unsaturated cycloalkyl, and $N(R_{10})(R_{11})$;

$R_3$ and $R_4$ are each independently selected from the group consisting of hydrogen, halogen, cyano, nitro, alkyl, alkenyl, alkynyl and alkoxyl;

$R_5$ is selected from the group consisting of hydrogen, halogen and cyano;

$R_7$ and $R_8$ are each independently selected from the group consisting of hydrogen, alkyl, alkenyl, alkynyl, heteroalkyl, heteroalkenyl, heteroalkynyl, acyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, acyl, cycloalkyl, heterocyclyl, cycloalkylalkyl, aryl, arylalkyl, heteroaryl, heteroarylalkyl, and heterocyclylalkyl are optionally substituted with one or more groups independently selected from the group consisting of alkyl, alkenyl, alkynyl, heteroalkyl, heteroalkenyl, heteroalkynyl, alkylamino, saturated and partially unsaturated cycloalkyl, saturated and partially unsaturated heterocyclyl optionally substituted by alkyl, aryl, and heteroaryl; or $R_7$ and $R_8$ together with the atom to which they are attached form a 3 to 10 membered saturated or partially unsaturated heterocyclyl ring optionally containing one or more additional heteroatoms selected from N, O, S, SO, $SO_2$ and $NR_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

$R_9$ is selected from the group consisting of alkyl, alkenyl, alkynyl, acyl, saturated or partially unsaturated cycloalkyl, saturated or partially unsaturated heterocyclyl, wherein said alkyl, alkenyl, alkynyl, acyl, cycloalkyl, heterocyclyl are optionally substituted by one or more groups independently selected from the group consisting of halogen, alkyl, alkenyl, alkynyl, alkoxyl, acyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroaryl alkyl, and heterocyclylalkyl;

$R_{10}$ and $R_{11}$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl; or $R_{10}$ and $R_{11}$ together with the atom to which they are attached form a 3 to 10 membered saturated or partially unsaturated heterocyclyl ring optionally containing one or more additional heteroatoms selected from N, O, S, SO, $SO_2$ and $NR_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclyl alkyl;

$R_{12}$ is selected from the group consisting of hydrogen, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from halogen, alkyl, alkenyl, alkynyl, saturated and partially unsaturated cycloalkyl, saturated and partially unsaturated heterocyclyl, cycloalkylalkyl, cyano, nitro, aryl, heteroaryl, arylalkyl, heteroarylalkyl, and heterocyclyl alkyl;

n is 0, 1 or 2.

In some embodiments, the compounds of the present disclosure have a formula of:

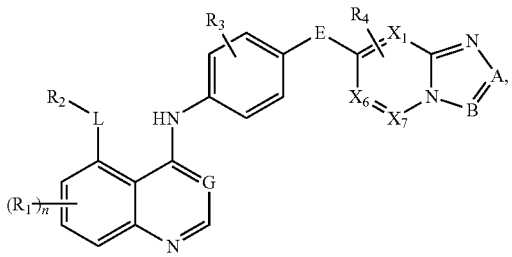

(I')

wherein G, A, B, $X_1$, $X_6$, $X_7$, E, L, $R_1$, $R_2$, $R_3$ and $R_4$ are defined as supra.

In some embodiments, $X_1$ is CH.
In some embodiments, $X_1$ is N.
In some embodiments, one of $X_2$, $X_3$, $X_4$, and $X_5$ is N.
In some embodiments, two of $X_2$, $X_3$, $X_4$, and $X_5$ are N.
In some embodiments, three of $X_2$, $X_3$, $X_4$, and $X_5$ are N.
In some embodiments, $X_2$, $X_3$, $X_4$, and $X_5$ are N.
In some embodiments, $X_6$ is N and $X_7$ is CH.
In some embodiments, $X_6$ is CH and $X_7$ is N.
In some embodiments, G is N.
In some embodiments, A is CH.
In some embodiments, A is N.
In some embodiments, B is CH.
In some embodiments, B is N.
In some embodiments, E is O.
In some embodiments, L is $N(R_6)$.
In some embodiments, L is O.
In some embodiments, $R_1$ is selected from hydrogen, $N(R_7)(R_8)$, $O(R_9)$, or saturated or partially unsaturated heterocyclyl optionally substituted by acyl.

In some embodiments, $R_1$ is $N(R_7)(R_8)$, and $R_7$ and $R_8$ are each independently selected from hydrogen, alkyl, acyl, saturated or partially unsaturated cycloalkyl, saturated or partially unsaturated heterocyclyl, wherein said alkyl, acyl cycloalkyl, and heterocyclyl are optionally substituted with one or more groups independently selected from alkyl, alkenyl, alkynyl, heteroalkyl, heteroalkenyl, heteroalkynyl, alkylamino, saturated and partially unsaturated cycloalkyl, saturated and partially unsaturated heterocyclyl optionally substituted by alkyl, aryl, and heteroaryl.

In some embodiments, $R_1$ is $N(R_7)(R_8)$, $R_7$ is hydrogen, and $R_8$ is saturated or partially unsaturated cycloalkyl substituted by alkyl.

In some embodiments, $R_1$ is $N(R_7)(R_8)$, $R_7$ is hydrogen, and $R_8$ is 4,4-dimethyl-4,5-dihydrooxazol-2-yl.

In some embodiments, $R_1$ is $N(R_7)(R_8)$, $R_7$ is hydrogen, and $R_8$ is acyl substituted by alkylamino or saturated and partially unsaturated heterocyclyl substituted by alkyl.

In some embodiments, $R_1$ is $N(R_7)(R_8)$, $R_7$ is hydrogen, and $R_8$ is (dimethyamino)but-2-ene-carbonyl or (1-methyl-pyrrolidin-2-yl)-acryloyl.

In some embodiments, $R_1$ is $O(R_9)$, and $R_9$ is selected from the group consisting of alkyl, acyl, saturated or partially unsaturated cycloalkyl, saturated or partially unsaturated heterocyclyl, wherein said alkyl, cycloalkyl, and heterocyclyl are optionally substituted by one or more groups independently selected from the group consisting of halogen, alkyl, alkenyl, alkynyl, acyl, and alkoxyl.

In some embodiments, $R_1$ is $O(R_9)$, and $R_9$ is selected from the group consisting of $C_{1-6}$alkyl, $C_{1-6}$ acyl, 3 to 6 membered saturated or partially unsaturated cycloalkyl, 3 to 6 membered saturated or partially unsaturated heterocyclyl, wherein said alkyl, acyl, cycloalkyl, and heterocyclyl are optionally substituted by one or more groups independently selected from halogen, alkyl, or alkoxyl.

In some embodiments, $R_1$ is $O(R_9)$, and $R_9$ is selected from methyl, ethyl, isopropyl, piperazinylcarbonyl, cyclopropyl, or tetrahydrofuranyl, each of which is optionally substituted by one or more fluoro or methyl.

In some embodiments, $R_1$ is partially unsaturated heterocyclyl optionally substituted by acyl. In some embodiments, $R_1$ is partially unsaturated hetercyclyl substituted by acryloyl. In some embodiments, $R_1$ is tetrahydropyridyl substituted by acryloyl.

In some embodiments, L is $N(R_6)$, and $R_2$ and $R_6$ together with the nitrogen atom to which they are attached form a 3 to 10 membered saturated or partially unsaturated heterocyclyl ring optionally containing one or more additional heteroatoms selected from N, O and S, wherein said 3 to 10 membered heterocyclyl ring is optionally substituted with one or more groups independently selected from the group consisting of halogen, cyano, nitro, carboxy, carbamoyl, alkyl, alkenyl, alkynyl, haloalkyl, saturated and partially unsaturated cycloalkyl, and $N(R_{10})(R_{11})$.

In some embodiments, L is $N(R_6)$, and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$.

In some embodiments, the phrase "$R_2$ and $R_6$ together with the nitrogen atom to which they are attached form a 4 to 9 membered saturated heterocyclyl ring" refers to a 4 to 9 membered monocyclic hetercyclic ring formed from $R_2$ and $R_6$ together with the nitrogen atom to which they are attached. In certain embodiments, such phrase refers to a 4 to 9 membered spirocyclic ring formed from $R_2$ and $R_6$ together with the nitrogen atom to which they are attached. In certain embodiments, such phrase refers to a 4 to 9 membered fused ring formed from $R_2$ and $R_6$ together with the nitrogen atom to which they are attached.

In some embodiments, L is N(R$_6$), and R$_2$ and R$_6$ together with the nitrogen atom to which they are attached form:

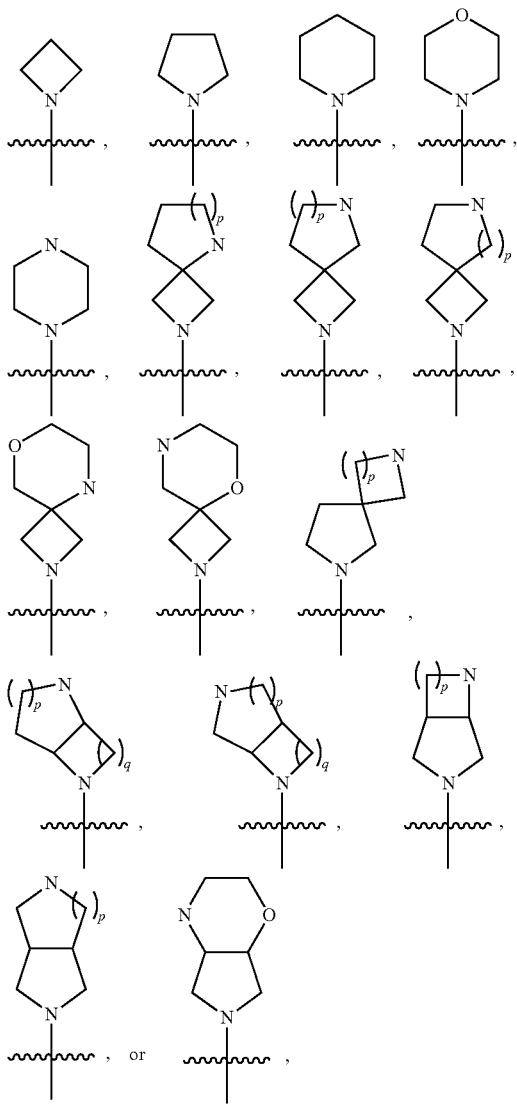

each of which is optionally substituted with one or more groups independently selected from the group consisting of halogen, alkyl, and N(R$_{10}$)(R$_{11}$), wherein p is 1, 2 or 3, and q is 1, 2 or 3.

In certain embodiments, p is 1 or 2.
In certain embodiments, p is 1.
In certain embodiments, p is 2.
In certain embodiments, q is 1 or 2.
In certain embodiments, q is 1.
In certain embodiments, q is 2.

In some embodiments, the heterocyclyl ring formed by R$_2$ and R$_6$ together with the nitrogen atom to which they are attached is substituted with one or more groups selected from fluoro, methyl, 2-fluoroethyl, 2,2-difluoroethyl, cyclopropyl, or dimethylamino. In certain embodiments, said heterocyclyl ring is substituted with one or more fluoro groups. In certain embodiment, said heterocyclyl ring is substituted with one or more methyl groups. In certain embodiments, said heterocyclyl ring is substituted with one or more 2-fluoroethyl. In certain embodiments, said hetero- cyclyl ring is substituted with one or more 2,2-difluoroethyl. In certain embodiments, said heterocyclyl ring is substituted with one or more cyclopropyl. In certain embodiments, said heterocyclyl ring is substituted with one or more dimethylamino. In certain embodiment, said heterocyclyl ring is substituted with fluoro and methyl.

In some embodiments, L is O, and R$_2$ is selected from saturated or partially unsaturated cycloalkyl and saturated or partially unsaturated heterocyclyl, wherein said cycloalkyl and heterocyclyl are optionally substituted with one or more groups independently selected from the group consisting of halogen, alkyl, saturated or partially unsaturated cycloalkyl, and N(R$_{10}$)(R$_{11}$).

In some embodiments, L is O, and R$_2$ is selected from C$_{4-6}$ saturated cycloalkyl or 5 to 6 membered saturated heterocyclyl, wherein said C$_{4-6}$ saturated cycloalkyl and 5 to 6 membered saturated heterocyclyl are optionally substituted with one or more groups independently selected from the group consisting of halogen, alkyl, saturated or partially unsaturated cycloalkyl, and N(R$_{10}$)(R$_{11}$).

In some embodiments, L is O, and R$_2$ is selected from cyclobutyl, cyclopentyl, cyclohexyl, pyrrolidinyl, or piperidinyl, each of which is optionally substituted with one or more groups independently selected from the group consisting of halogen, alkyl, saturated or partially unsaturated cycloalkyl, and N(R$_{10}$)(R$_{11}$).

In some embodiments, R$_2$ is optionally substituted with one or more of groups selected from methyl, fluoro, cyclopropyl and dimethylamino. In certain embodiments, R$_2$ is substituted with one or more methyl groups. In certain embodiments, R$_2$ is substituted with one or more fluoro groups. In certain embodiments, R$_2$ is substituted with one or more cyclopropyl groups. In certain embodiments, R$_2$ is substituted with one or more dimethylamino groups. In certain embodiments, R$_2$ is substituted with one or more methyl groups and one or more fluoro groups.

In some embodiments, R$_3$ is halogen.
In certain embodiments, R$_3$ is chloro.
In some embodiments, R$_3$ is C$_{1-6}$ alkyl.
In certain embodiments, R$_3$ is methyl.
In some embodiments, R$_4$ is hydrogen.

In a further aspect, the present disclosure provides a compound of Formula (IVa), (IVb), (IVc), (IVd), (IVe) or (IVf):

(IVa)

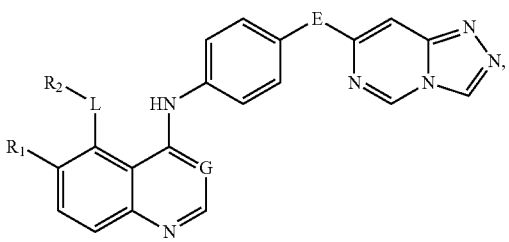

(IVb)

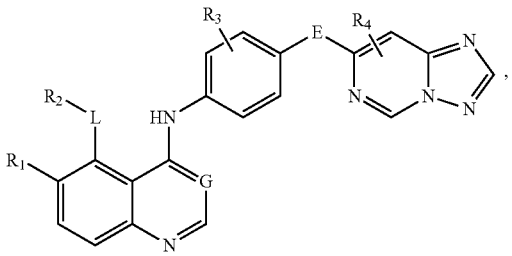

-continued

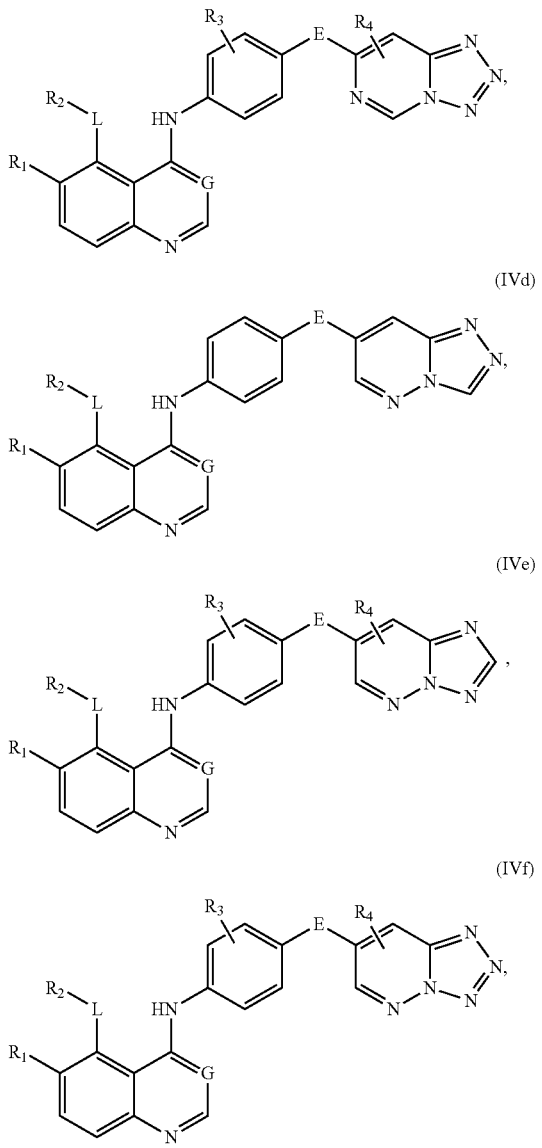

or a pharmaceutically acceptable salt thereof, and G, E, $R_1$, $R_2$, $R_3$ and $R_4$ are defined as supra.

In some embodiments, L is $N(R_6)$, $R_1$ is selected from the group consisting of halogen, cyano, nitro, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, $N(R_7)(R_8)$, and $O(R_9)$, and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$.

In certain embodiments, L is $N(R_6)$, $R_1$ is $N(R_7)(R_8)$, and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$. In certain embodiments, $R_7$ is hydrogen, and $R_8$ is saturated or partially unsaturated cycloalkyl substituted by alkyl. In certain embodiments, $R_7$ is hydrogen, and $R_8$ is 4,4-dimethyl-4,5-dihydrooxazol-2-yl.

In certain embodiments, L is $N(R_6)$, $R_1$ is $O(R_9)$, $R_9$ is selected from the group consisting of $C_{1-6}$ alkyl, 3 to 6 membered saturated or partially unsaturated cycloalkyl, 3 to 6 membered saturated or partially unsaturated heterocyclyl, wherein said alkyl, cycloalkyl, and heterocyclyl are optionally substituted by one or more groups independently selected from halogen, alkyl, or alkoxyl, and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$.

In certain embodiments, L is $N(R_6)$, $R_1$ is $O(R_9)$, $R_9$ is selected from methyl, ethyl, isopropyl, cyclopropyl, or tetrahydrofuranyl, each of which is optionally substituted by one or more fluoro, and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$.

In some embodiments, L is O, and $R_2$ is selected from saturated or partially unsaturated cycloalkyl and saturated or partially unsaturated heterocyclyl, wherein said cycloalkyl and heterocyclyl are optionally substituted with one or more groups independently selected from the group consisting of halogen, alkyl, saturated or partially unsaturated cycloalkyl, and $N(R_{10})(R_{11})$.

In some embodiments, L is O, and $R_2$ is selected from $C_{4-6}$ saturated cycloalkyl or 5 to 6 membered saturated heterocyclyl, wherein said $C_{4-6}$ saturated cycloalkyl and 5 to 6 membered saturated heterocyclyl are optionally substituted with one or more groups independently selected from the group consisting of halogen, alkyl, saturated or partially unsaturated cycloalkyl, and $N(R_{10})(R_{11})$.

In some embodiments, L is O, and $R_2$ is selected from cyclobutyl, cyclopentyl, cyclohexyl, pyrrolidinyl, or piperidinyl, each of which is optionally substituted with one or more groups independently selected from the group consisting of halogen, alkyl, saturated or partially unsaturated cycloalkyl, and $N(R_{10})(R_{11})$.

In a further aspect, the present disclosure provides a compound of Formula (Va), (Vb), (Vc), (Vd), (Ve) or (Vf):

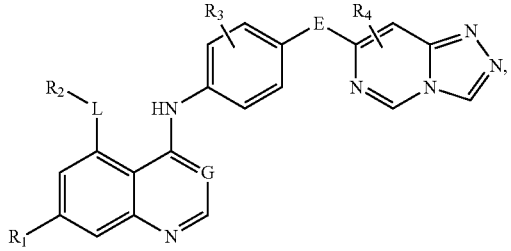
(Va)

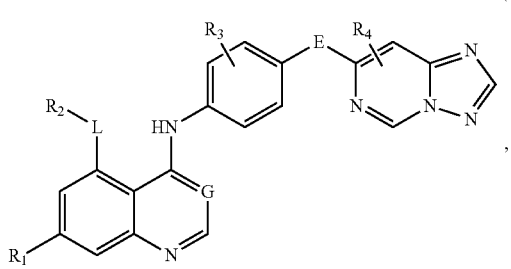
(Vb)

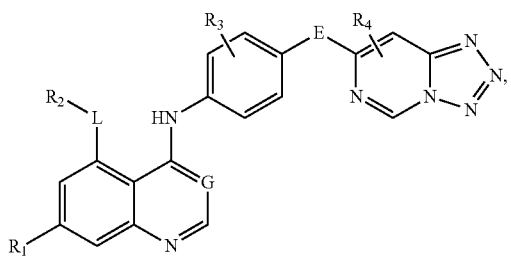
(Vc)

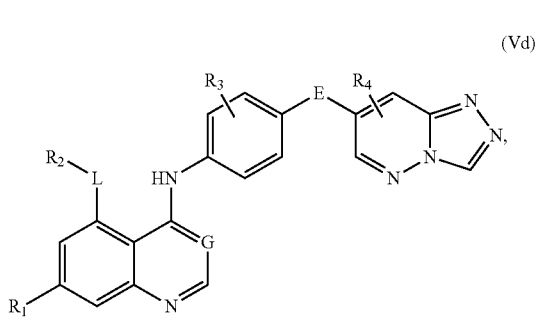
(Vd)

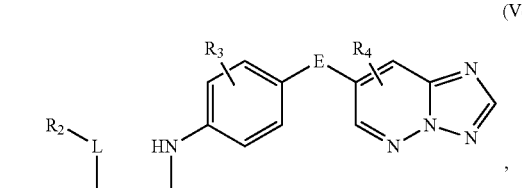
(Ve)

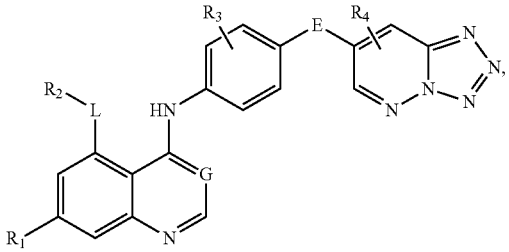
(Vf)

or a pharmaceutically acceptable salt thereof, and G, E, $R_1$, $R_2$, $R_3$ and $R_4$ are defined as supra.

In some embodiments, $R_1$ is $O(R_9)$, $R_9$ is selected from the group consisting of $C_{1-6}$ alkyl, 3 to 6 membered saturated or partially unsaturated cycloalkyl, 3 to 6 membered saturated or partially unsaturated heterocyclyl, wherein said alkyl, cycloalkyl, and heterocyclyl are optionally substituted by one or more groups independently selected from halogen, alkyl, or alkoxyl, L is O, and $R_2$ is selected from saturated or partially unsaturated cycloalkyl and saturated or partially unsaturated heterocyclyl, wherein said cycloalkyl and heterocyclyl are optionally substituted with one or more groups independently selected from the group consisting of halogen, alkyl, saturated or partially unsaturated cycloalkyl, and $N(R_{10})(R_{11})$.

In certain embodiments, $R_1$ is $O(R_9)$, $R_9$ is $C_{1-6}$ alkyl, L is O, and $R_2$ is selected from $C_4$-6 saturated cycloalkyl or 5 to 6 membered saturated heterocyclyl, wherein said $C_{4-6}$ saturated cycloalkyl and 5 to 6 membered saturated heterocyclyl are optionally substituted with one or more groups independently selected from the group consisting of halogen, alkyl, saturated or partially unsaturated cycloalkyl, and $N(R_{10})(R_{11})$.

In a further aspect, the present disclosure provides a compound of Formula (I) or a pharmaceutically acceptable salt thereof selected from the group consisting of:

N-(4-([1,2,4]triazolo[1,5-c]pyrimidin-7-yloxy)-3-methylphenyl)-5-(3-(dimethylamino)azetidin-1-yl)-6-methoxyquinazolin-4-amine;

(R)—N-(4-([1,2,4]triazolo[1,5-c]pyrimidin-7-yloxy)-3-methylphenyl)-5-(3-(dimethylamino)pyrrolidin-1-yl)-6-methoxyquinazolin-4-amine;

(S)—N-(4-([1,2,4]triazolo[1,5-c]pyrimidin-7-yloxy)-3-methylphenyl)-5-(3-(dimethylamino)pyrrolidin-1-yl)-6-methoxyquinazolin-4-amine;

N-(4-([1,2,4]triazolo[1,5-c]pyrimidin-7-yloxy)-3-methylphenyl)-6-methoxy-5-morpholinoquinazolin-4-amine;

N-(4-([1,2,4]triazolo[1,5-c]pyrimidin-7-yloxy)-3-methylphenyl)-6-methoxy-5-((1-methylpiperidin-4-yl)oxy)quinazolin-4-amine;

N-(4-([1,2,4]triazolo[1,5-c]pyrimidin-7-yloxy)-3-methylphenyl)-6-methoxy-5-((1-methylpyrrolidin-3-yl)oxy)quinazolin-4-amine;

N-(4-([1,2,4]triazolo[1,5-c]pyrimidin-7-yloxy)-3-methylphenyl)-5-(3-(dimethylamino)cyclobutoxy)-6-methoxyquinazolin-4-amine;

N-(4-([1,2,4]triazolo[1,5-c]pyrimidin-7-yloxy)-3-methylphenyl)-5-((3-(dimethylamino)cyclopentyl)oxy)-6-methoxyquinazolin-4-amine;

N-(4-([1,2,4]triazolo[1,5-c]pyrimidin-7-yloxy)-3-methylphenyl)-5-((4-(dimethylamino)cyclohexyl)oxy)-6-methoxyquinazolin-4-amine;

N-(4-([1,2,4]triazolo[1,5-c]pyrimidin-7-yloxy)-3-methylphenyl)-6-methoxy-5-(4-methylpiperazin-1-yl)quinazolin-4-amine;

N-(4-([1,2,4]triazolo[1,5-c]pyrimidin-7-yloxy)-3-methylphenyl)-5-(3-(dimethylamino)azetidin-1-yl)-6-ethoxyquinazolin-4-amine;

N-(4-([1,2,4]triazolo[1,5-c]pyrimidin-7-yloxy)-3-methylphenyl)-5-(3-(dimethylamino)azetidin-1-yl)-6-(2-fluoroethoxy)quinazolin-4-amine;

N-(4-([1,2,4]triazolo[1,5-c]pyrimidin-7-yloxy)-3-methylphenyl)-6-(difluoromethoxy)-5-((1S,5S)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine;

cis-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine;

trans-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-5-amine;

N-(4-([1,2,4]triazolo[1,5-c]pyrimidin-7-yloxy)-3-methylphenyl)-5-((1S,5S)-2-methyl-2,6-diazabicyclo[3.2.0]heptan-6-yl)-6-(((S)-tetrahydrofuran-3-yl)oxy)quinazolin-4-amine;

N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine;

N-(4-([1,2,4]triazolo[1,5-c]pyrimidin-7-yloxy)-3-methylphenyl)-5-(((R)-3,3-difluoro-1-methylpiperidin-4-yl)oxy)-6-(((S)-tetrahydrofuran-3-yl)oxy)quinazolin-4-amine;

N-(4-([1,2,4]triazolo[1,5-c]pyrimidin-7-yloxy)-3-methylphenyl)-5-(((S)-3,3-difluoro-1-methylpiperidin-4-yl)oxy)-6-(((S)-tetrahydrofuran-3-yl)oxy)quinazolin-4-amine;

N-(4-([1,2,4]triazolo[1,5-c]pyrimidin-7-yloxy)-3-methylphenyl)-6-cyclopropoxy-5-((1S,5S)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-6-cyclopropoxy-5-((1R,5R)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-6-isopropoxy-5-((1S,5S)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-6-isopropoxy-5-((1R,5R)-2-methyl-2,6-diazabicyclo[3.2.0]heptan-6-yl)quinazolin-4-amine;

(R)—N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine;

(S)—N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine;

(R)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine;

(S)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine;

N-(4-([1,2,4]triazolo[1,5-c]pyrimidin-7-yloxy)-3-methylphenyl)-5-((3,3-difluoro-1-(methyl-d3)piperidin-4-yl)oxy)-6-methoxyquinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine;

N-(4-([1,2,4]triazolo[1,5-c]pyrimidin-7-yloxy)-3-methylphenyl)-6-methoxy-5-(8-methyl-5-oxa-2,8-diazaspiro[3.5]nonan-2-yl)quinazolin-4-amine;

N-(4-([1,2,4]triazolo[1,5-c]pyrimidin-7-yloxy)-3-methylphenyl)-5-((3R,4S)-3-(dimethylamino)-4-fluoropyrrolidin-1-yl)-6-methoxyquinazolin-4-amine;

N-(4-([1,2,4]triazolo[1,5-c]pyrimidin-7-yloxy)-3-methylphenyl)-5-((3R,4R)-3-(dimethylamino)-4-fluoropyrrolidin-1-yl)-6-methoxyquinazolin-4-amine;

N-(4-([1,2,4]triazolo[1,5-c]pyrimidin-7-yloxy)-3-methylphenyl)-6-methoxy-5-(5-methyl-8-oxa-2,5-diazaspiro[3.5]nonan-2-yl)quinazolin-4-amine;

N-(4-([1,2,4]triazolo[1,5-c]pyrimidin-7-yloxy)-3-methylphenyl)-6-methoxy-5-(4-methylhexahydropyrrolo[3,4-b][1,4]oxazin-6(2H)-yl)quinazolin-4-amine;

(S)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine;

(R)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine;

N-(4-([1,2,4]triazolo[1,5-c]pyrimidin-7-yloxy)-3-methylphenyl)-6-methoxy-5-((1S,5S)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-6-methoxy-5-((1R,5R)-2-methyl-2,6-diazabicyclo[3.2.0]heptan-6-yl)quinazolin-4-amine;

(R)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine;

(S)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine;

N-(4-([1,2,4]triazolo[1,5-c]pyrimidin-7-yloxy)-3-methylphenyl)-6-methoxy-5-(6-methyl-2,6-diazaspiro[3.4]octan-2-yl)quinazolin-4-amine;

N-(4-([1,2,4]triazolo[1,5-c]pyrimidin-7-yloxy)-3-methylphenyl)-6-methoxy-5-(7-methyl-2,7-diazaspiro[3.5]nonan-2-yl)quinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine;

N-(4-([1,2,4]triazolo[1,5-c]pyrimidin-7-yloxy)-3-methylphenyl)-7-methoxy-5-((1-methylpiperidin-4-yl)oxy)quinazolin-4-amine;

N4-(4-([1,2,4]triazolo[1,5-c]pyrimidin-7-yloxy)-3-methylphenyl)-N6-(4,4-dimethyl-4,5-dihydrooxazol-2-yl)-5-(3-(dimethylamino)azetidin-1-yl)quinazoline-4,6-diamine;

N-(4-([1,2,4]triazolo[1,5-c]pyrimidin-7-yloxy)-3-methylphenyl)-5-(8-methyl-5-oxa-2,8-diazaspiro[3.5]nonan-2-yl)quinazolin-4-amine;

N-(4-([1,2,4]triazolo[1,5-c]pyrimidin-7-yloxy)-3-methylphenyl)-6-(methoxy-d3)-5-((1S,5S)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-6-(methoxy-d3)-5-((1R,5R)-2-methyl-2,6-diazabicyclo[3.2.0]heptan-6-yl)quinazolin-4-amine;

N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-methoxyquinazolin-4-amine;

N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(difluoromethoxy)quinazolin-4-amine;

N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(methoxy-d3)quinazolin-4-amine;

(S)—N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-((tetrahydrofuran-3-yl)oxy)quinazolin-4-amine;

N-(4-([1,2,4]triazolo[1,5-c]pyrimidin-7-yloxy)-3-methylphenyl)-6-methoxy-5-(6-methyl-2,6-diazabicyclo[3.2.0]heptan-2-yl)quinazolin-4-amine;

N-(4-([1,2,4]triazolo[1,5-c]pyrimidin-7-yloxy)-3-methylphenyl)-6-methoxy-5-(5-methylhexahydropyrrolo[3,4-c]pyrrol-2(1H)-yl)quinazolin-4-amine;

N-(4-([1,2,4]triazolo[1,5-c]pyrimidin-7-yloxy)-3-methylphenyl)-6-methoxy-5-(4-methyloctahydro-1H-pyrrolo[3,2-b]pyridin-1-yl)quinazolin-4-amine;

N-(4-([1,2,4]triazolo[1,5-c]pyrimidin-7-yloxy)-3-methylphenyl)-6-methoxy-5-(3-methyl-3,7-diazabicyclo[4.2.0]octan-7-yl)quinazolin-4-amine;

N-(4-([1,2,4]triazolo[1,5-c]pyrimidin-7-yloxy)-3-methylphenyl)-6-methoxy-5-(3-methyl-3,6-diazabicyclo[3.2.0]heptan-6-yl)quinazolin-4-amine;

N-(4-([1,2,4]triazolo[1,5-c]pyrimidin-7-yloxy)-3-methylphenyl)-5-(2-cyclopropyl-2,6-diazabicyclo[3.2.0]heptan-6-yl)-6-methoxyquinazolin-4-amine;

N-(4-([1,2,4]triazolo[1,5-c]pyrimidin-7-yloxy)-3-methylphenyl)-5-(2-(2,2-difluoroethyl)-2,6-diazabicyclo[3.2.0]heptan-6-yl)-6-methoxyquinazolin-4-amine;

N-(4-([1,2,4]triazolo[1,5-c]pyrimidin-7-yloxy)-3-methylphenyl)-6-methoxy-5-((1S,5S)-2-(methyl-d3)-2,6-diazabicyclo[3.2.0]heptan-6-yl)quinazolin-4-amine;

N-(4-([1,2,4]triazolo[1,5-c]pyrimidin-7-yloxy)-3-methylphenyl)-5-((1S,5S)-2-(2-fluoroethyl)-2,6-diazabicyclo[3.2.0]heptan-6-yl)-6-methoxyquinazolin-4-amine;

N-(4-([1,2,4]triazolo[1,5-c]pyrimidin-7-yloxy)-3-methylphenyl)-6-methoxy-5-((1S,5S)-2-(2,2,2-trifluoroethyl)-2,6-diazabicyclo[3.2.0]heptan-6-yl)quinazolin-4-amine;

(R)—N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine;

(S)—N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine;

(R)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine;

(S)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine;

(R)—N-(4-([1,2,4]triazolo[1,5-c]pyrimidin-7-yloxy)-3-methylphenyl)-5-((3,3-difluoropiperidin-4-yl)oxy)-6-methoxyquinazolin-4-amine;

(R)—N-(4-([1,2,4]triazolo[1,5-c]pyrimidin-7-yloxy)-3-methylphenyl)-5-((3,3-difluoro-1-(methyl-d3)piperidin-4-yl)oxy)-6-(methoxy-d3)quinazolin-4-amine;

(R)—N-(4-([1,2,4]triazolo[1,5-c]pyrimidin-7-yloxy)-3-methylphenyl)-5-((3,3-difluoro-1-isopropylpiperidin-4-yl)oxy)-6-methoxyquinazolin-4-amine;

(R)—N-(4-([1,2,4]triazolo[1,5-c]pyrimidin-7-yloxy)-3-methylphenyl)-5-((1-cyclopropyl-3,3-difluoropiperidin-4-yl)oxy)-6-methoxyquinazolin-4-amine;

1-(4-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one;

(R)-1-(4-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-3,6-dihydropyridin-1(2H)-yl)prop-2-en-1-one;

1-(5-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one;

1-(4-(4-((4-([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one;

1-(5-(4-((4-([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one;

1-(4-((4-((4-([1,2,4]triazolo[1,5-c]pyrimidin-7-yloxy)-3-methylphenyl)amino)-5-(3-(dimethylamino)pyrrolidin-1-yl)quinazolin-6-yl)oxy)piperidin-1-yl)prop-2-en-1-one;

(R)-4-((4-([1,2,4]triazolo[1,5-c]pyrimidin-7-yloxy)-3-methylphenyl)amino)-5-((3,3-difluoro-1-methylpiperidin-4-yl)oxy)-6-methoxyquinoline-3-carbonitrile;

(R)-4-((4-([1,2,4]triazolo[1,5-c]pyrimidin-7-yloxy)-3-methylphenyl)amino)-5-((3,3-difluoro-1-methylpiperidin-4-yl)oxy)-7-methoxyquinoline-3-carbonitrile;

4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl 2,4-dimethylpiperazine-1-carboxylate;

(R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)quinolin-6-yl)-4-(dimethylamino)but-2-enamide;

(R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)-7-ethoxyquinolin-6-yl)-4-(dimethylamino)but-2-enamide;

(R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)-7-ethoxyquinolin-6-yl)-4-(dimethylamino)but-2-enamide;

(R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-4-(dimethylamino)but-2-enamide;

(E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)quinolin-6-yl)-3-((R)-1-methylpyrrolidin-2-yl)acrylamide;

(E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)-7-ethoxyquinolin-6-yl)-3-((R)-1-methylpyrrolidin-2-yl)acrylamide (E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl)-3-((R)-1-methylpyrrolidin-2-yl)acrylamide;

(E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)-7-ethoxyquinazolin-6-yl)-3-((R)-1-methylpyrrolidin-2-yl)acrylamide;

(E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-4-(dimethylamino)but-2-enamide;

(R,E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-3-(1-methylpyrrolidin-2-yl)acrylamide; and (R)—N-(4-([1,2,4]triazolo[1,5-c]pyrimidin-7-yloxy)-3-methylphenyl)-5-((3,3-difluoro-1-methylpiperidin-4-yl)oxy)-6,7-dimethoxyquinazolin-4-amine.

Exemplary compounds of the present disclosure are set forth in Table 1 below.

TABLE 1

| Cmpd No. | Compound Structure and Name |
|---|---|
| 1 | 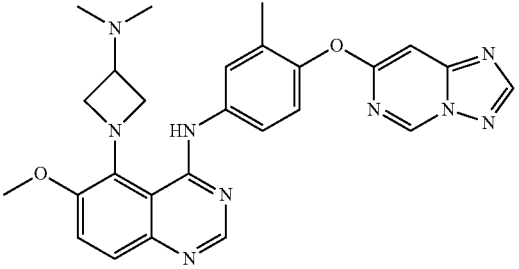 [SMILES: COc1ccc2ncnc(Nc3ccc(Oc4cc5ncnn5cn4)c(C)c3)c2c1N1CC(N(C)C)C1]<br>N-(4-([1,2,4]triazolo[1,5-c]pyrimidin-7-yloxy)-3-methylphenyl)-5-(3-(dimethylamino)azetidin-1-yl)-6-methoxyquinazolin-4-amine |
| 2 | 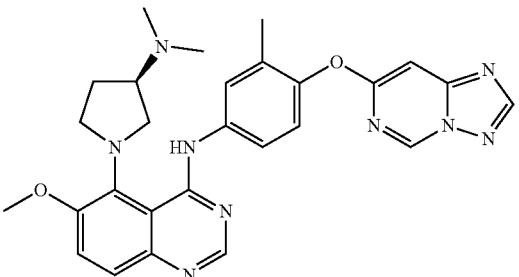<br>(R)-N-(4-([1,2,4]triazolo[1,5-c]pyrimidin-7-yloxy)-3-methylphenyl)-5-(3-(dimethylamino)pyrrolidin-1-yl)-6-methoxyquinazolin-4-amine |
| 3 | 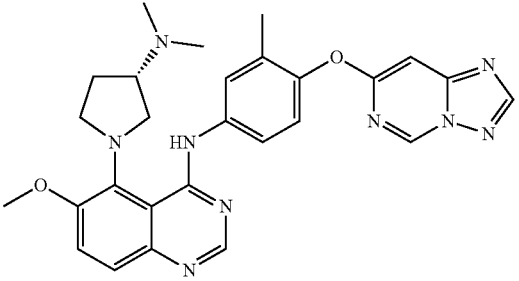 [SMILES: COc1ccc2ncnc(Nc3ccc(Oc4cc5ncnn5cn4)c(C)c3)c2c1N1CC[C@H](N(C)C)C1]<br>(S)-N-(4-([1,2,4]triazolo[1,5-c]pyrimidin-7-yloxy)-3-methylphenyl)-5-(3-(dimethylamino)pyrrolidin-1-yl)-6-methoxyquinazolin-4-amine |

TABLE 1-continued

| Cmpd No. | Compound Structure and Name |
|---|---|
| 4 | 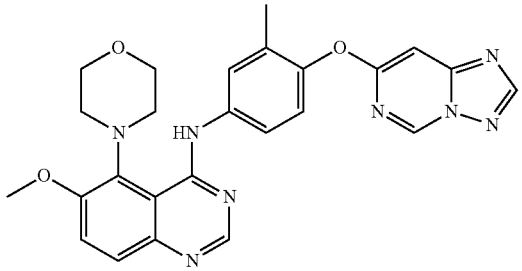 [SMILES: COc1ccc2ncnc(Nc3ccc(Oc4cc5ncnn5cn4)c(C)c3)c2c1N1CCOCC1]<br>N-(4-([1,2,4]triazolo[1,5-c]pyrimidin-7-yloxy)-3-methylphenyl)-6-methoxy-5-morpholinoquinazolin-4-amine |
| 5 | 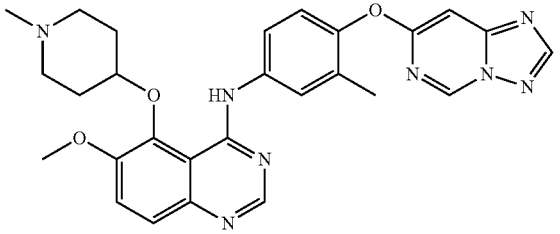 [SMILES: COc1ccc2ncnc(Nc3ccc(Oc4cc5ncnn5cn4)c(C)c3)c2c1OC1CCN(C)CC1]<br>N-(4-([1,2,4]triazolo[1,5-c]pyrimidin-7-yloxy)-3-methylphenyl)-6-methoxy-5-((1-methylpiperidin-4-yl)oxy)quinazolin-4-amine |
| 6 | 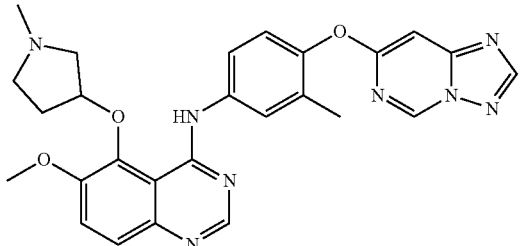<br>N-(4-([1,2,4]triazolo[1,5-c]pyrimidin-7-yloxy)-3-methylphenyl)-6-methoxy-5-((1-methylpyrrolidin-3-yl)oxy)quinazolin-4-amine |
| 7 | 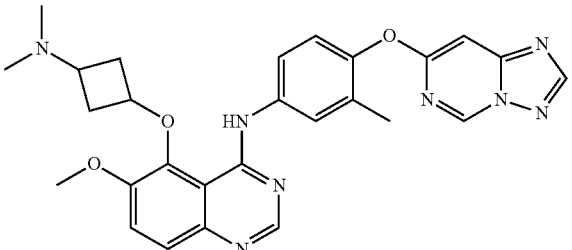<br>N-(4-([1,2,4]triazolo[1,5-c]pyrimidin-7-yloxy)-3-methylphenyl)-5-(3-(dimethylamino)cyclobutoxy)-6-methoxyquinazolin-4-amine |
| 8 | 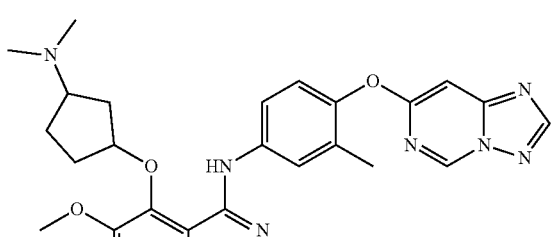<br>N-(4-([1,2,4]triazolo[1,5-c]pyrimidin-7-yloxy)-3-methylphenyl)-5-((3-(dimethylamino)cyclopentyl)oxy)-6-methoxyquinazolin-4-amine |

TABLE 1-continued

| Cmpd No. | Compound Structure and Name |
|---|---|
| 9 | 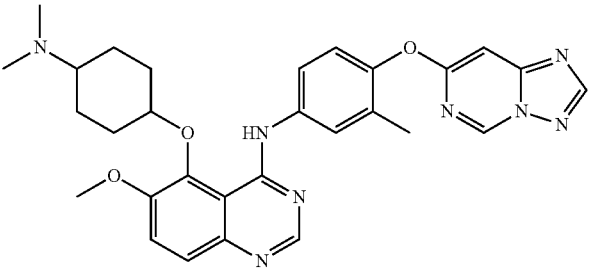 [SMILES: COc1ccc2ncnc(Nc3ccc(Oc4cc5ncnn5cn4)c(C)c3)c2c1OC1CCC(N(C)C)CC1]<br>N-(4-([1,2,4]triazolo[1,5-c]pyrimidin-7-yloxy)-3-methylphenyl)-5-((4-(dimethylamino)cyclohexyl)oxy)-6-methoxyquinazolin-4-amine |
| 10 | 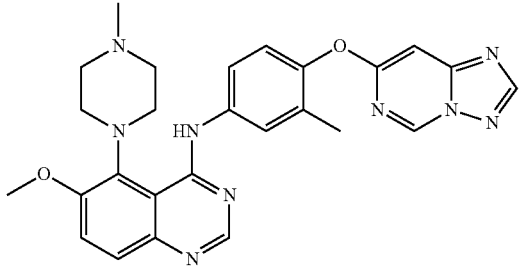 [SMILES: COc1ccc2ncnc(Nc3ccc(Oc4cc5ncnn5cn4)c(C)c3)c2c1N1CCN(C)CC1]<br>N-(4-([1,2,4]triazolo[1,5-c]pyrimidin-7-yloxy)-3-methylphenyl)-6-methoxy-5-(4-methylpiperazin-1-yl)quinazolin-4-amine |
| 11 | 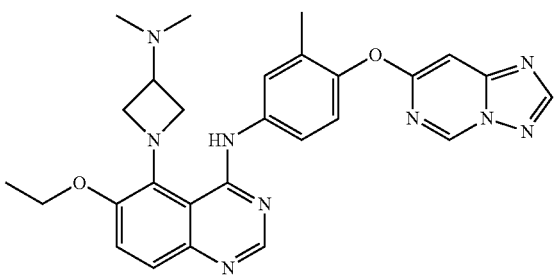 [SMILES: CCOc1ccc2ncnc(Nc3ccc(Oc4cc5ncnn5cn4)c(C)c3)c2c1N1CC(N(C)C)C1]<br>N-(4-([1,2,4]triazolo[1,5-c]pyrimidin-7-yloxy)-3-methylphenyl)-5-(3-(dimethylamino)azetidin-1-yl)-6-ethoxyquinazolin-4-amine |
| 12 | 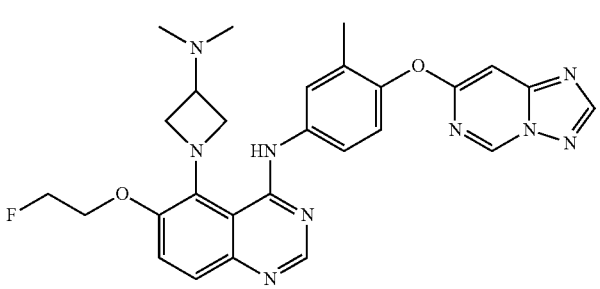 [SMILES: Cc1cc(Nc2ncnc3ccc(OCCF)c(N4CC(N(C)C)C4)c23)ccc1Oc1cc2ncnn2cn1]<br>N-(4-([1,2,4]triazolo[1,5-c]pyrimidin-7-yloxy)-3-methylphenyl)-5-(3-(dimethylamino)azetidin-1-yl)-6-(2-fluoroethoxy)quinazolin-4-amine |

TABLE 1-continued

| Cmpd No. | Compound Structure and Name |
|---|---|
| 13 | 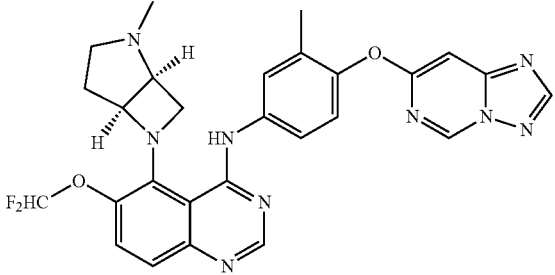<br>N-(4-([1,2,4]triazolo[1,5-c]pyrimidin-7-yloxy)-3-methylphenyl)-6-(difluoromethoxy)-5-((1S,5S)-2-methyl-2,6-diazabicyclo[3.2.0]heptan-6-yl)quinazolin-4-amine |
| 14 | 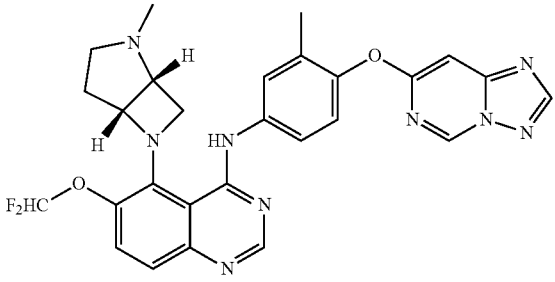 [SMILES: Cc1cc(Nc2ncnc3ccc(OC(F)F)c(N4C[C@@H]5[C@H]4CCN5C)c23)ccc1Oc1cc2ncnn2cn1]<br>N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine |
| 15 | 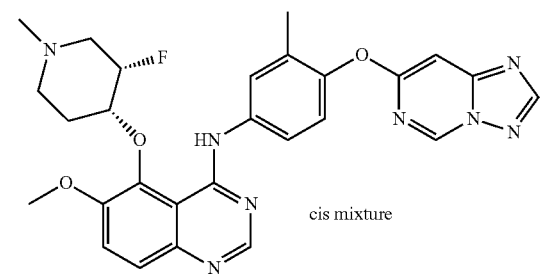 [SMILES: COc1ccc2ncnc(Nc3ccc(Oc4cc5ncnn5cn4)c(C)c3)c2c1O[C@@H]1CCN(C)C[C@@H]1F]<br>cis-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine |
| 16 | 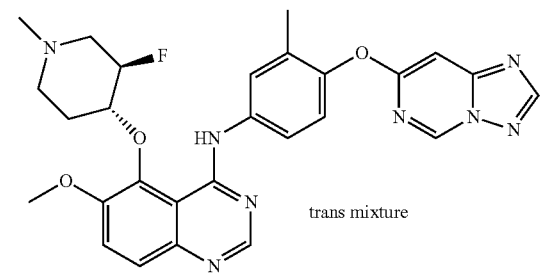 [SMILES: COc1ccc2ncnc(Nc3ccc(Oc4cc5ncnn5cn4)c(C)c3)c2c1O[C@@H]1CCN(C)C[C@H]1F]<br>trans-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine |

TABLE 1-continued

| Cmpd No. | Compound Structure and Name |
|---|---|
| 17 | 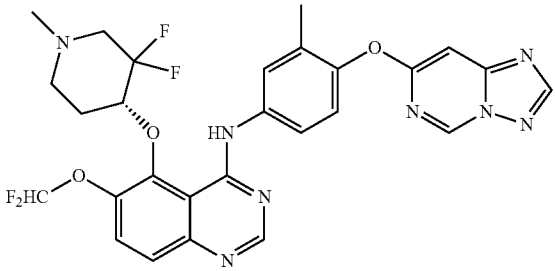 [SMILES: Cc1cc(Nc2ncnc3ccc(OC(F)F)c(O[C@@H]4CCN(C)CC4(F)F)c23)ccc1Oc1cc2ncnn2cn1]

(R)-N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine |
| 18 | 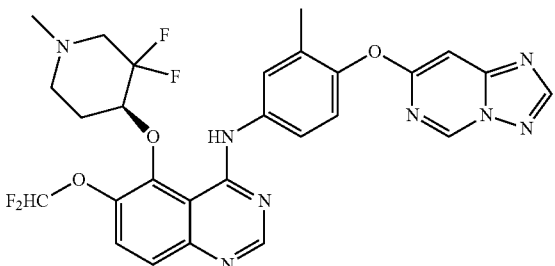

(S)-N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-5-amine |
| 19 | 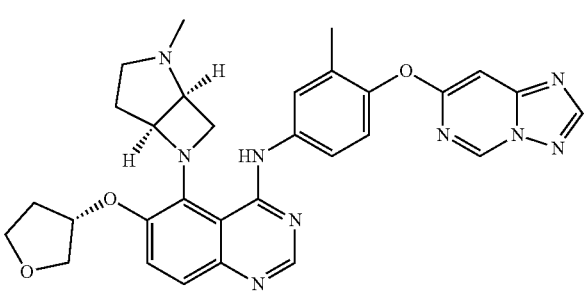 [SMILES: Cc1cc(Nc2ncnc3ccc(O[C@H]4CCOC4)c(N4C[C@H]5[C@@H]4CCN5C)c23)ccc1Oc1cc2ncnn2cn1]

N-(4-([1,2,4]triazolo[1,5-c]pyrimidin-7-yloxy)-3-methylphenyl)-5-((1S,5S)-2-methyl-2,6-diazabicyclo[3.2.0]heptan-6-yl)-6-(((S)-tetrahydrofuran-3-yl)oxy)quinazolin-4-amine |
| 20 | 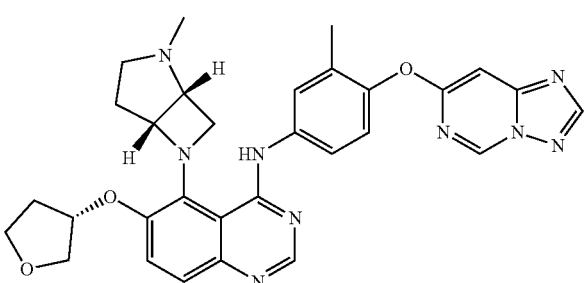

N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine |

TABLE 1-continued

| Cmpd No. | Compound Structure and Name |
|---|---|
| 21 | 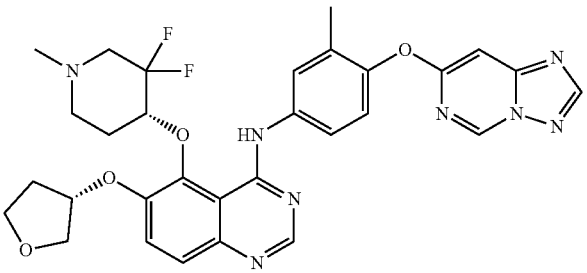 [SMILES: Cc1cc(Nc2ncnc3ccc(O[C@H]4CCOC4)c(O[C@@H]4CCN(C)CC4(F)F)c23)ccc1Oc1cc2ncnn2cn1]N-(4-([1,2,4]triazolo[1,5-c]pyrimidin-7-yloxy)-3-methylphenyl)-5-(((R)-3,3-difluoro-1-methylpiperidin-4-yl)oxy)-6-(((S)-tetrahydrofuran-3-yl)oxy)quinazolin-4-amine |
| 22 | 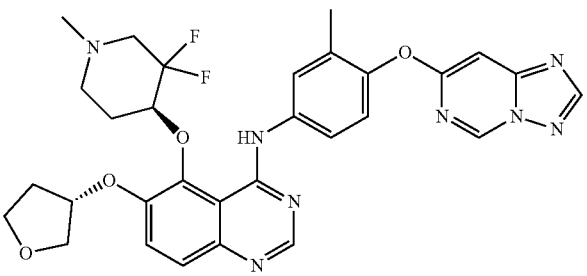 [SMILES: Cc1cc(Nc2ncnc3ccc(O[C@H]4CCOC4)c(O[C@H]4CCN(C)CC4(F)F)c23)ccc1Oc1cc2ncnn2cn1]N-(4-([1,2,4]triazolo[1,5-c]pyrimidin-7-yloxy)-3-methylphenyl)-5-(((S)-3,3-difluoro-1-methylpiperidin-4-yl)oxy)-6-(((S)-tetrahydrofuran-3-yl)oxy)quinazolin-4-amine |
| 23 | 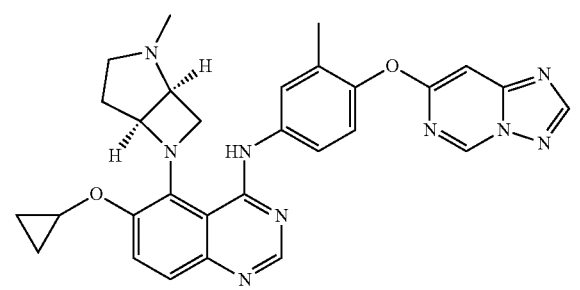 [SMILES: Cc1cc(Nc2ncnc3ccc(OC4CC4)c(N4C[C@H]5[C@@H]4CCN5C)c23)ccc1Oc1cc2ncnn2cn1]N-(4-([1,2,4]triazolo[1,5-c]pyrimidin-7-yloxy)-3-methylphenyl)-6-cyclopropoxy-5-((1S,5S)-2-methyl-2,6-diazabicyclo[3.2.0]heptan-6-yl)quinazolin-4-amine |
| 24 | 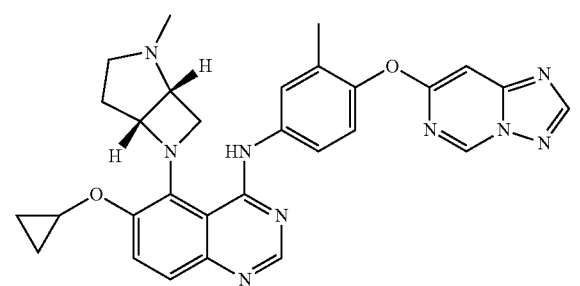 [SMILES: Cc1cc(Nc2ncnc3ccc(OC4CC4)c(N4C[C@@H]5[C@H]4CCN5C)c23)ccc1Oc1cc2ncnn2cn1]N-(4-([1,2,4]triazolo[1,5-c]pyrimidin-7-yloxy)-3-methylphenyl)-6-cyclopropoxy-5-((1R,5R)-2-methyl-2,6-diazabicyclo[3.2.0]heptan-6-yl)quinazolin-4-amine |

TABLE 1-continued

| Cmpd No. | Compound Structure and Name |
|---|---|
| 25 | N-(4-([1,2,4]triazolo[1,5-c]pyrimidin-7-yloxy)-3-methylphenyl)-6-isopropoxy-5-((1S,5S)-2-methyl-2,6-diazabicyclo[3.2.0]heptan-6-yl)quinazolin-4-amine |
| 26 | N-(4-([1,2,4]triazolo[1,5-c]pyrimidin-7-yloxy)-3-methylphenyl)-6-isopropoxy-5-((1R,5R)-2-methyl-2,6-diazabicyclo[3.2.0]heptan-6-yl)quinazolin-4-amine |
| 27 | (R)-N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine |
| 28 | (S)-N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine |

TABLE 1-continued

| Cmpd No. | Compound Structure and Name |
|---|---|
| 29 | 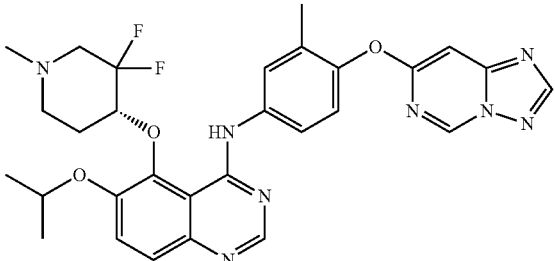<br>(R)-N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine |
| 30 | 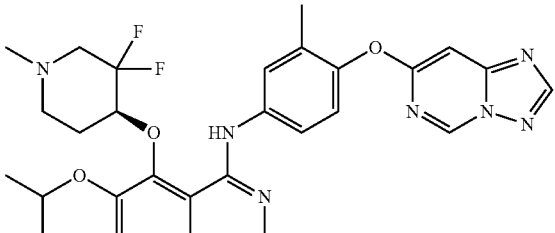<br>(S)-N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine |
| 31 | 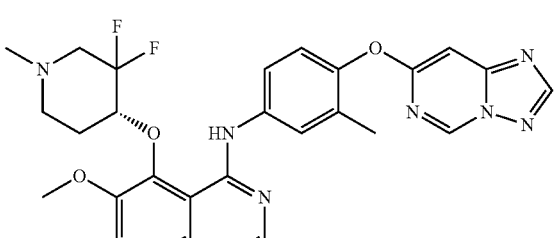<br>(R)-N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine |
| 32 | 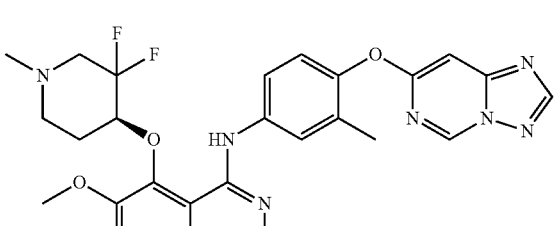<br>(S)-N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine |
| 33 | 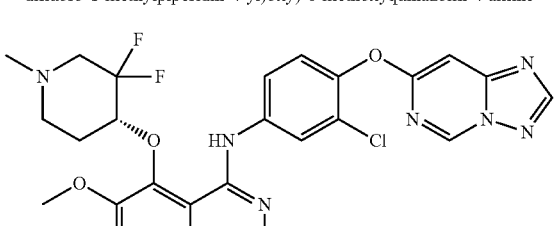<br>(R)-N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine |

TABLE 1-continued

| Cmpd No. | Compound Structure and Name |
|---|---|
| 34 | 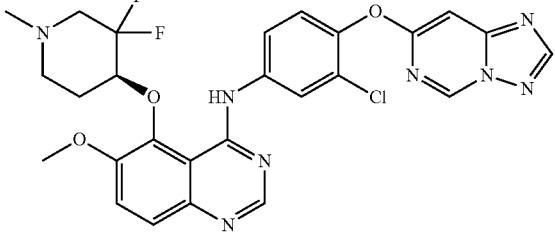<br>(S)-N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine |
| 35 | 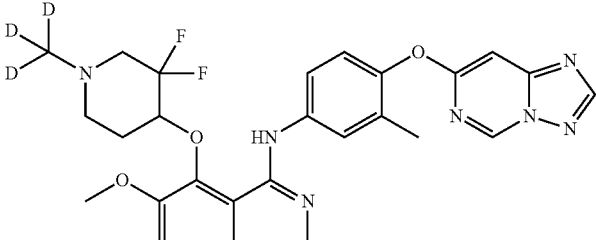<br>N-(4-([1,2,4]triazolo[1,5-c]pyrimidin-7-yloxy)-3-methylphenyl)-5-((3,3-difluoro-1-(methyl-d3)piperidin-4-yl)oxy)-6-methoxyquinazolin-4-amine |
| 36 | 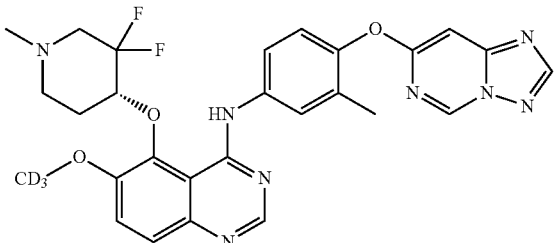<br>(R)-N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine |
| 37 | 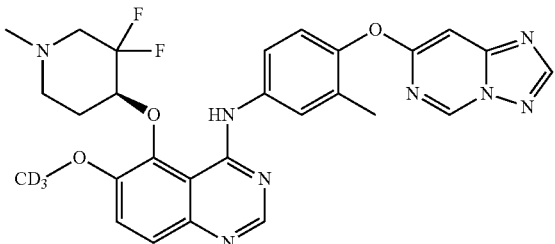<br>(S)-N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine |
| 38 | 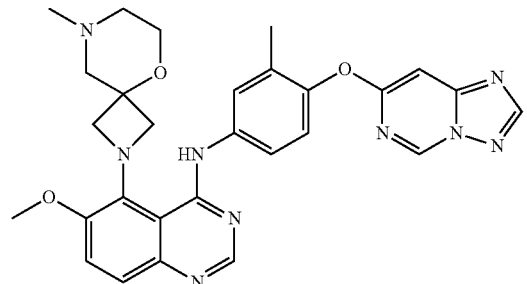<br>N-(4-([1,2,4]triazolo[1,5-c]pyrimidin-7-yloxy)-3-methylphenyl)-6-methoxy-5-(8-methyl-5-oxa-2,8-diazaspiro[3.5]nonan-2-yl)quinazolin-4-amine |

TABLE 1-continued

| Cmpd No. | Compound Structure and Name |
|---|---|
| 39 | 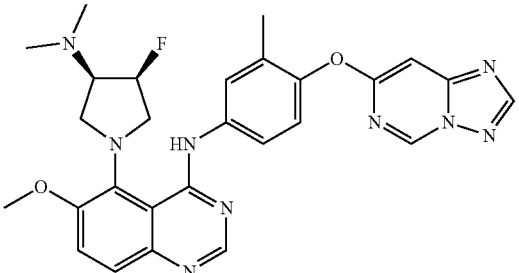<br>N-(4-([1,2,4]triazolo[1,5-c]pyrimidin-7-yloxy)-3-methylphenyl)-5-((3R,4S)-3-(dimethylamino)-4-fluoropyrrolidin-1-yl)-6-methoxyquinazolin-4-amine |
| 40 | 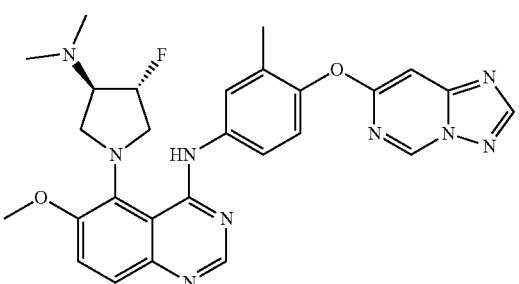<br>N-(4-([1,2,4]triazolo[1,5-c]pyrimidin-7-yloxy)-3-methylphenyl)-5-((3R,4R)-3-(dimethylamino)-4-fluoropyrrolidin-1-yl)-6-methoxyquinazolin-4-amine |
| 41 | 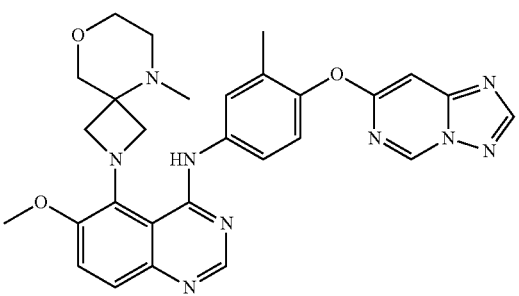 [SMILES: COc1ccc2ncnc(Nc3ccc(Oc4cc5ncnn5cn4)c(C)c3)c2c1N1CC2(COCCN2C)C1]<br>N-(4-([1,2,4]triazolo[1,5-c]pyrimidin-7-yloxy)-3-methylphenyl)-6-methoxy-5-(5-methyl-8-oxa-2,5-diazaspiro[3.5]nonan-2-yl)quinazolin-4-amine |
| 42 | 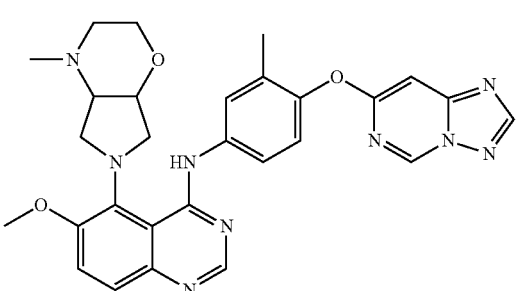<br>N-(4-([1,2,4]triazolo[1,5-c]pyrimidin-7-yloxy)-3-methylphenyl)-6-methoxy-5-(4-methylhexahydropyrrolo[3,4-b][1,4]oxazin-6(2H)-yl)quinazolin-4-amine |

TABLE 1-continued

| Cmpd No. | Compound Structure and Name |
|---|---|
| 43 | 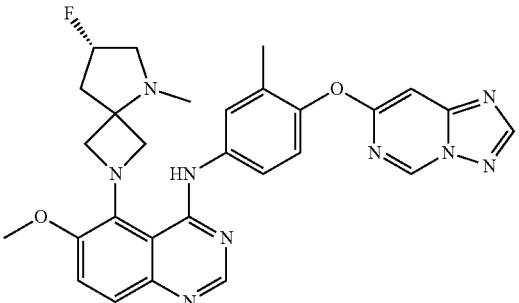<br>(S)-N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine |
| 44 | 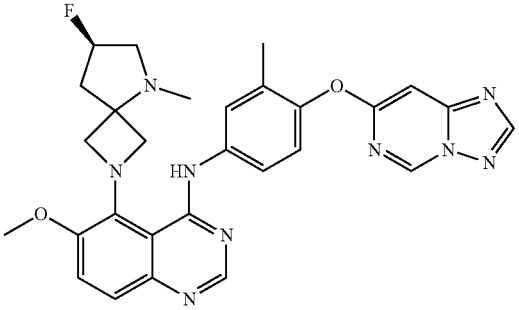 [SMILES: COc1ccc2ncnc(Nc3ccc(Oc4cc5ncnn5cn4)c(C)c3)c2c1N1CC2(C[C@@H](F)CN2C)C1]<br>(R)-N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine |
| 45 | 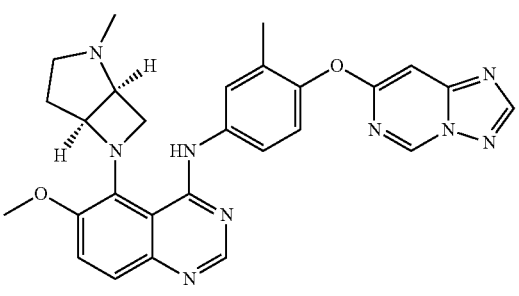 [SMILES: COc1ccc2ncnc(Nc3ccc(Oc4cc5ncnn5cn4)c(C)c3)c2c1N1C[C@H]2[C@@H]1CCN2C]<br>N-(4-([1,2,4]triazolo[1,5-c]pyrimidin-7-yloxy)-3-methylphenyl)-6-methoxy-5-((1S,5S)-2-methyl-2,6-diazabicyclo[3.2.0]heptan-6-yl)quinazolin-4-amine |
| 46 | 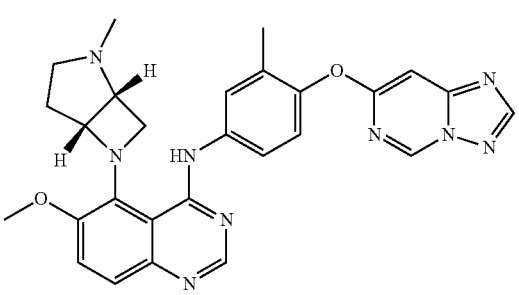 [SMILES: COc1ccc2ncnc(Nc3ccc(Oc4cc5ncnn5cn4)c(C)c3)c2c1N1C[C@@H]2[C@H]1CCN2C]<br>N-(4-([1,2,4]triazolo[1,5-c]pyrimidin-7-yloxy)-3-methylphenyl)-6-methoxy-5-((1R,5R)-2-methyl-2,6-diazabicyclo[3.2.0]heptan-6-yl)quinazolin-4-amine |

TABLE 1-continued

| Cmpd No. | Compound Structure and Name |
|---|---|
| 47 | 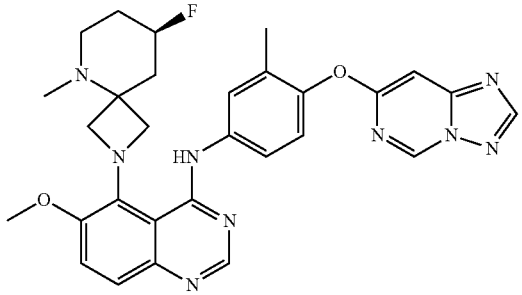 [SMILES: COc1ccc2ncnc(Nc3ccc(Oc4cc5ncnn5cn4)c(C)c3)c2c1N1CC2(C[C@H](F)CCN2C)C1](R)-N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine |
| 48 | 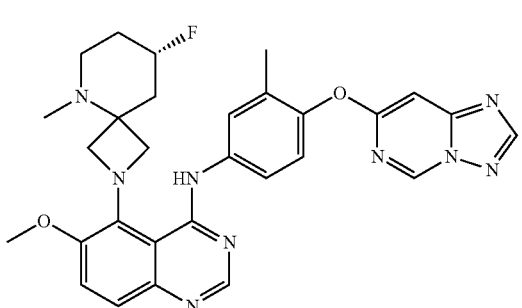(S)-N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine |
| 49 | 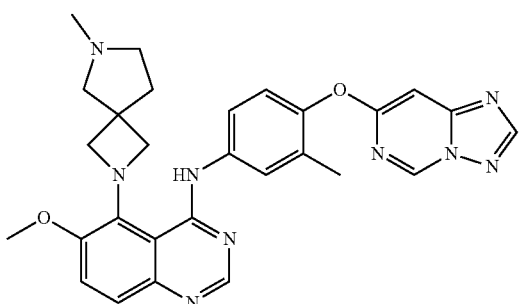N-(4-([1,2,4]triazolo[1,5-c]pyrimidin-7-yloxy)-3-methylphenyl)-6-methoxy-5-(6-methyl-2,6-diazaspiro[3.4]octan-2-yl)quinazolin-4-amine |
| 50 | 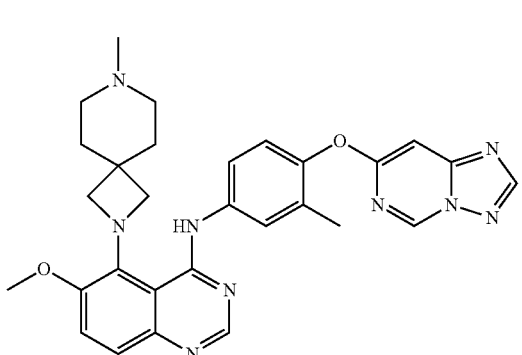N-(4-([1,2,4]triazolo[1,5-c]pyrimidin-7-yloxy)-3-methylphenyl)-6-methoxy-5-(7-methyl-2,7-diazaspiro[3.5]nonan-2-yl)quinazolin-4-amine |

TABLE 1-continued

| Cmpd No. | Compound Structure and Name |
|---|---|
| 51 | 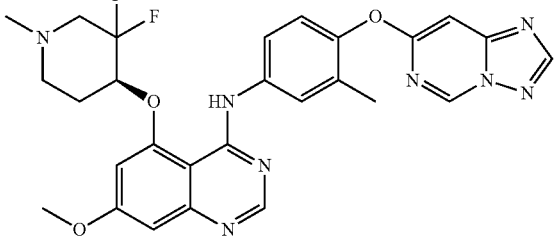<br>(S)-N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine |
| 52 | 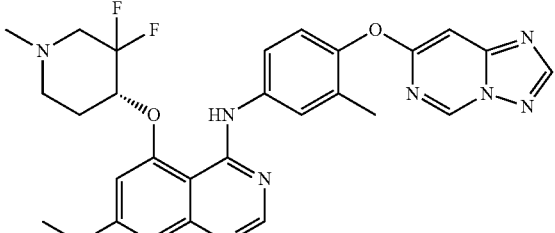<br>(R)-N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine |
| 53 | 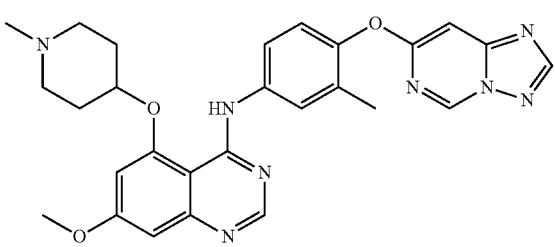 [SMILES: COc1cc(OC2CCN(C)CC2)c2c(Nc3ccc(Oc4cc5ncnn5cn4)c(C)c3)ncnc2c1]<br>N-(4-([1,2,4]triazolo[1,5-c]pyrimidin-7-yloxy)-3-methylphenyl)-7-methoxy-5-((1-methylpiperidin-4-yl)oxy)quinazolin-4-amine |
| 54 | 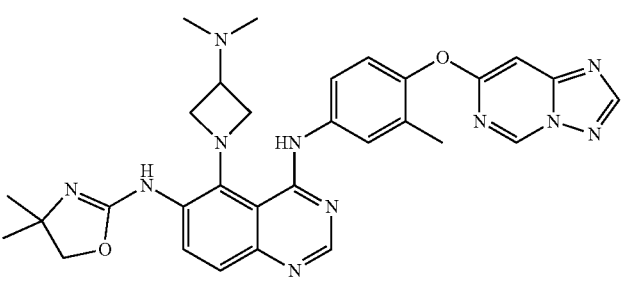 [SMILES: Cc1cc(Nc2ncnc3ccc(NC4=NC(C)(C)CO4)c(N4CC(N(C)C)C4)c23)ccc1Oc1cc2ncnn2cn1]<br>N4-(4-([1,2,4]triazolo[1,5-c]pyrimidin-7-yloxy)-3-methylphenyl)-N6-(4,4-dimethyl-4,5-dihydrooxazol-2-yl)-5-(3-(dimethylamino)azetidin-1-yl)quinazoline-4,6-diamine |
| 55 | 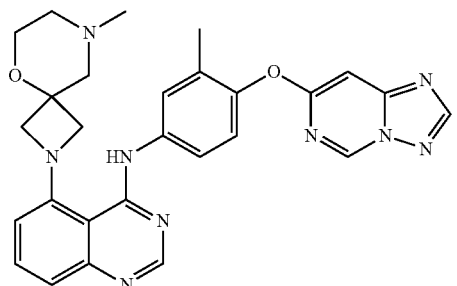<br>N-(4-([1,2,4]triazolo[1,5-c]pyrimidin-7-yloxy)-3-methylphenyl)-5-(8-methyl-5-oxa-2,8-diazaspiro[3.5]nonan-2-yl)quinazolin-4-amine |

TABLE 1-continued

| Cmpd No. | Compound Structure and Name |
|---|---|
| 56 | 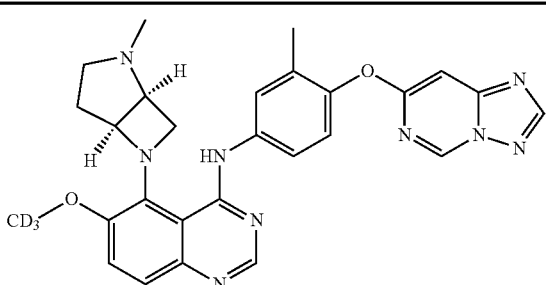<br>N-(4-([1,2,4]triazolo[1,5-c]pyrimidin-7-yloxy)-3-methylphenyl)-6-(methoxy-d3)-5-((1S,5S)-2-methyl-2,6-diazabicyclo[3.2.0]heptan-6-yl)quinazolin-4-amine |
| 57 | 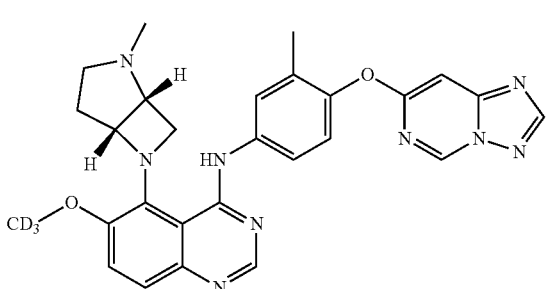<br>N-(4-([1,2,4]triazolo[1,5-c]pyrimidin-7-yloxy)-3-methylphenyl)-6-(methoxy-d3)-5-((1R,5R)-2-methyl-2,6-diazabicyclo[3.2.0]heptan-6-yl)quinazolin-4-amine |
| 58 | 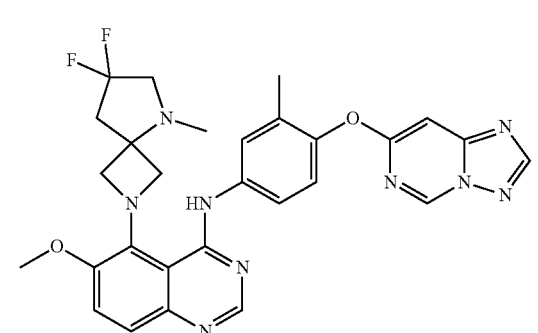<br>N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-methoxyquinazolin-4-amine |
| 59 | 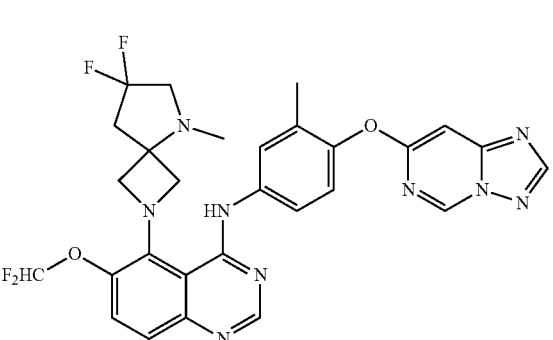<br>N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(difluoromethoxy)quinazolin-4-amine |

TABLE 1-continued

| Cmpd No. | Compound Structure and Name |
|---|---|
| 60 | N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(methoxy-d3)quinazolin-4-amine |
| 61 | (S)-N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-((tetrahydrofuran-3-yl)oxy)quinazolin-4-amine |
| 62 | N-(4-([1,2,4]triazolo[1,5-c]pyrimidin-7-yloxy)-3-methylphenyl)-6-methoxy-5-(6-methyl-2,6-diazabicyclo[3.2.0]heptan-2-yl)quinazolin-4-amine |
| 63 | N-(4-([1,2,4]triazolo[1,5-c]pyrimidin-7-yloxy)-3-methylphenyl)-6-methoxy-5-(5-methylhexahydropyrrolo[3,4-c]pyrrol-2(1H)-yl)quinazolin-4-amine |

TABLE 1-continued

| Cmpd No. | Compound Structure and Name |
|---|---|
| 64 | 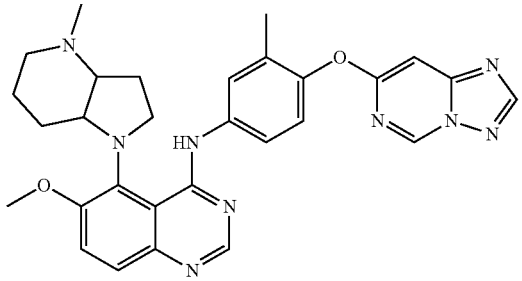 [SMILES: COc1ccc2ncnc(Nc3ccc(Oc4cc5ncnn5cn4)c(C)c3)c2c1N1CCC2C1CCCN2C]<br>N-(4-([1,2,4]triazolo[1,5-c]pyrimidin-7-yloxy)-3-methylphenyl)-6-methoxy-5-(4-methyloctahydro-1H-pyrrolo[3,2-b]pyridin-1-yl)quinazolin-4-amine |
| 65 | 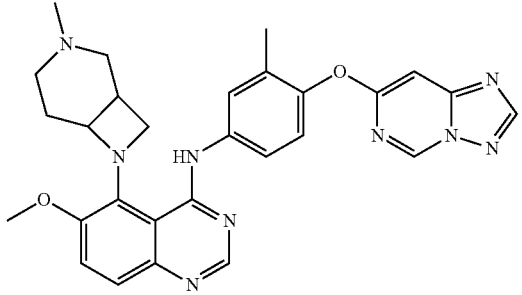 [SMILES: COc1ccc2ncnc(Nc3ccc(Oc4cc5ncnn5cn4)c(C)c3)c2c1N1CC2CN(C)CCC21]<br>N-(4-([1,2,4]triazolo[1,5-c]pyrimidin-7-yloxy)-3-methylphenyl)-6-methoxy-5-(3-methyl-3,7-diazabicyclo[4.2.0]octan-7-yl)quinazolin-4-amine |
| 66 | 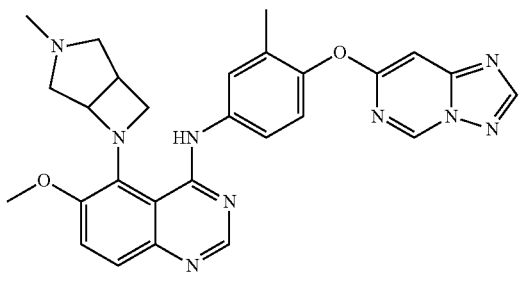 [SMILES: COc1ccc2ncnc(Nc3ccc(Oc4cc5ncnn5cn4)c(C)c3)c2c1N1CC2CN(C)CC21]<br>N-(4-([1,2,4]triazolo[1,5-c]pyrimidin-7-yloxy)-3-methylphenyl)-6-methoxy-5-(3-methyl-3,6-diazabicyclo[3.2.0]heptan-6-yl)quinazolin-4-amine |
| 67 | 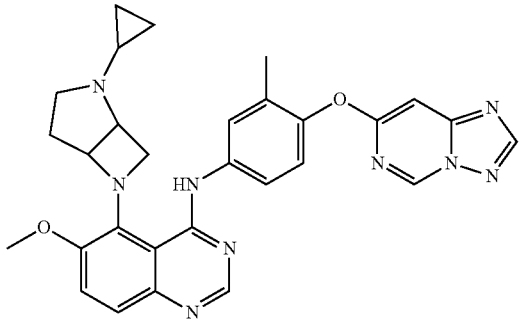 [SMILES: COc1ccc2ncnc(Nc3ccc(Oc4cc5ncnn5cn4)c(C)c3)c2c1N1CC2C1CCN2C1CC1]<br>N-(4-([1,2,4]triazolo[1,5-c]pyrimidin-7-yloxy)-3-methylphenyl)-5-(2-cyclopropyl-2,6-diazabicyclo[3.2.0]heptan-6-yl)-6-methoxyquinazolin-4-amine |

TABLE 1-continued

| Cmpd No. | Compound Structure and Name |
|---|---|
| 68 | 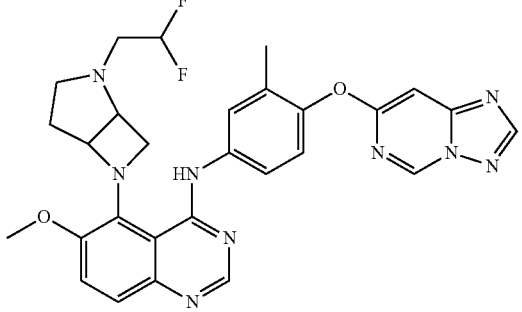<br>N-(4-([1,2,4]triazolo[1,5-c]pyrimidin-7-yloxy)-3-methylphenyl)-5-(2-(2,2-difluoroethyl)-2,6-diazabicyclo[3.2.0]heptan-6-yl)-6-methoxyquinazolin-4-amine |
| 69 | 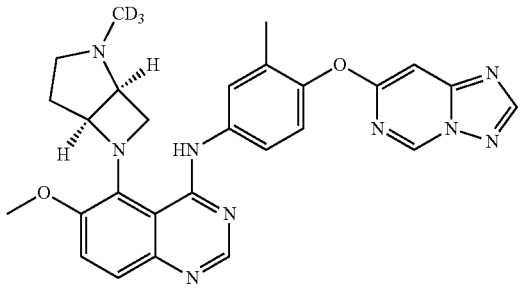 [SMILES: [2H]C([2H])([2H])N1CC[C@H]2[C@@H]1CN2c1c(OC)ccc2ncnc(Nc3ccc(Oc4cc5ncnn5cn4)c(C)c3)c12]<br>N-(4-([1,2,4]triazolo[1,5-c]pyrimidin-7-yloxy)-3-methylphenyl)-6-methoxy-5-((1S,5S)-2-(methyl-d3)-2,6-diazabicyclo[3.2.0]heptan-6-yl)quinazolin-4-amine |
| 70 | 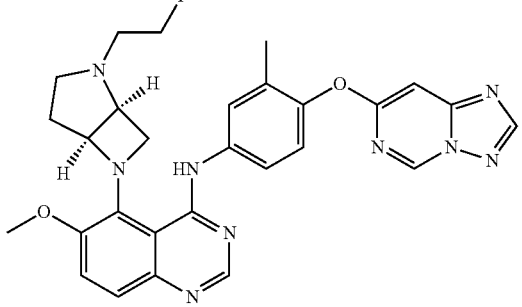<br>N-(4-([1,2,4]triazolo[1,5-c]pyrimidin-7-yloxy)-3-methylphenyl)-5-((1S,5S)-2-(2-fluoroethyl)-2,6-diazabicyclo[3.2.0]heptan-6-yl)-6-methoxyquinazolin-4-amine |
| 71 | 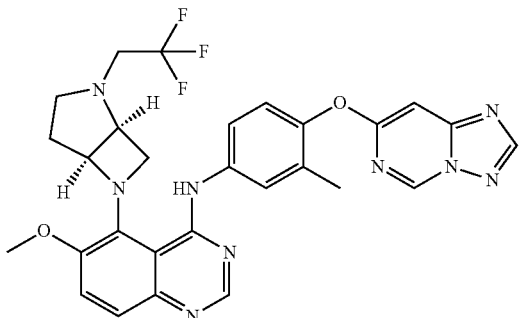<br>N-(4-([1,2,4]triazolo[1,5-c]pyrimidin-7-yloxy)-3-methylphenyl)-6-methoxy-5-((1S,5S)-2-(2,2,2-trifluoroethyl)-2,6-diazabicyclo[3.2.0]heptan-6-yl)quinazolin-4-amine |

TABLE 1-continued

| Cmpd No. | Compound Structure and Name |
|---|---|
| 72 | 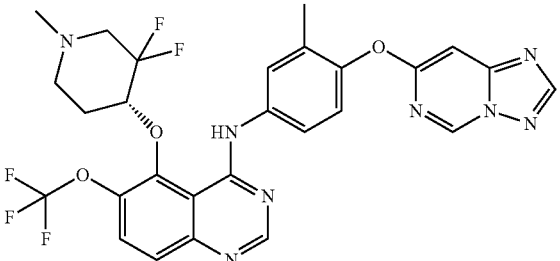<br>(R)-N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine |
| 73 | 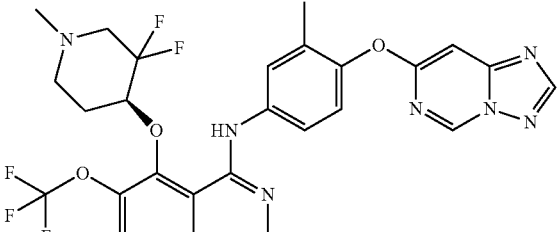<br>(S)-N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine |
| 74 | 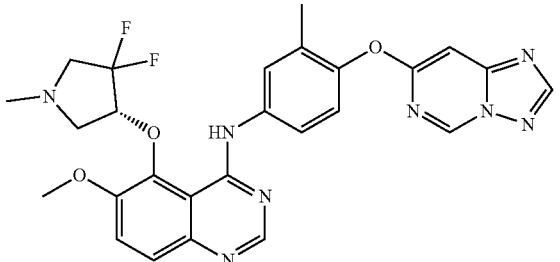<br>(R)-N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine |
| 75 | 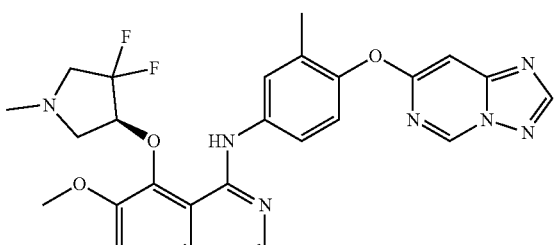<br>(S)-N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine |
| 76 | 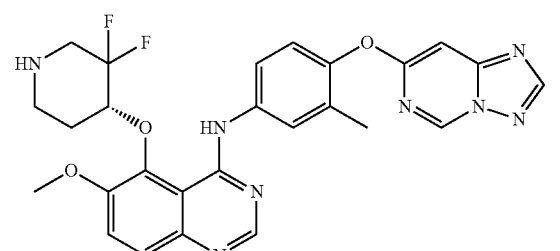<br>(R)-N-(4-([1,2,4]triazolo[1,5-c]pyrimidin-7-yloxy)-3-methylphenyl)-5-((3,3-difluoropiperidin-4-yl)oxy)-6-methoxyquinazolin-4-amine |

TABLE 1-continued

| Cmpd No. | Compound Structure and Name |
|---|---|
| 77 | 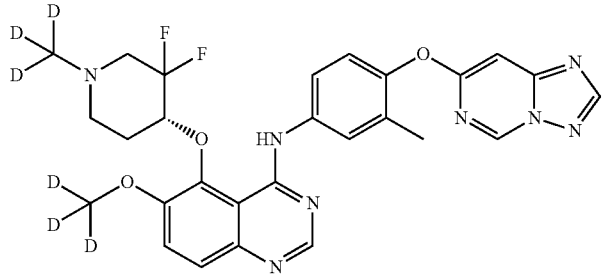 [SMILES: [2H]C([2H])([2H])Oc1ccc2ncnc(Nc3ccc(Oc4cc5ncnn5cn4)c(C)c3)c2c1O[C@@H]1CCN(C([2H])([2H])[2H])CC1(F)F]<br>(R)-N-(4-([1,2,4]triazolo[1,5-c]pyrimidin-7-yloxy)-3-methylphenyl)-5-((3,3-difluoro-1-(methyl-d3)piperidin-4-yl)oxy)-6-(methoxy-d3)quinazolin-4-amine |
| 78 | 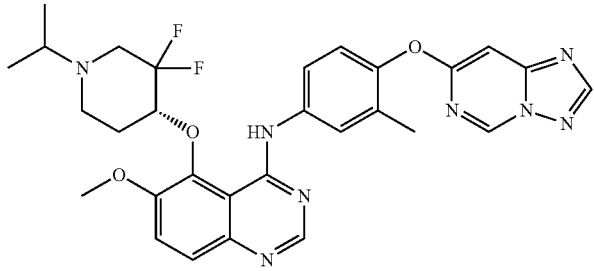 [SMILES: COc1ccc2ncnc(Nc3ccc(Oc4cc5ncnn5cn4)c(C)c3)c2c1O[C@@H]1CCN(C(C)C)CC1(F)F]<br>(R)-N-(4-([1,2,4]triazolo[1,5-c]pyrimidin-7-yloxy)-3-methylphenyl)-5-((3,3-difluoro-1-isopropylpiperidin-4-yl)oxy)-6-methoxyquinazolin-4-amine |
| 79 | 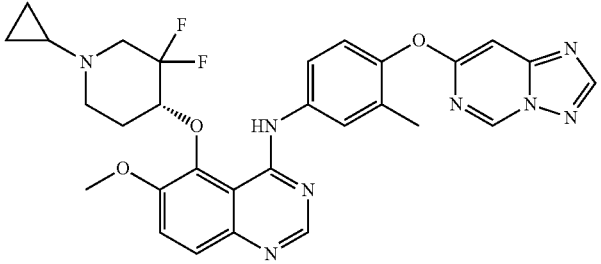 [SMILES: COc1ccc2ncnc(Nc3ccc(Oc4cc5ncnn5cn4)c(C)c3)c2c1O[C@@H]1CCN(C2CC2)CC1(F)F]<br>(R)-N-(4-([1,2,4]triazolo[1,5-c]pyrimidin-7-yloxy)-3-methylphenyl)-5-((1-cyclopropyl-3,3-difluoropiperidin-4-yl)oxy)-6-methoxyquinazolin-4-amine |
| 80 | 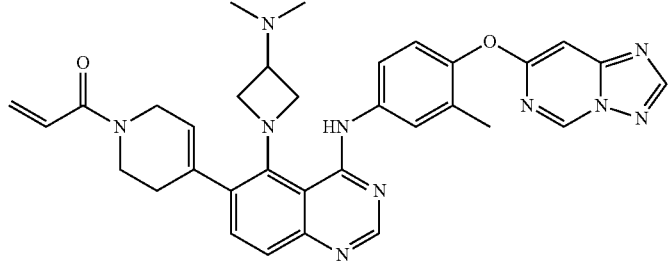 [SMILES: C=CC(=O)N1CC=C(c2ccc3ncnc(Nc4ccc(Oc5cc6ncnn6cn5)c(C)c4)c3c2N2CC(N(C)C)C2)CC1]<br>1-(4-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one |

TABLE 1-continued

| Cmpd No. | Compound Structure and Name |
|---|---|
| 81 | (R)-1-(4-(4-((4-(([1,2,4]triazolo[1,5-c]pyrimidin-7-yloxy)-3-methylphenyl)amino)-5-((3,3-difluoro-1-methylpiperidin-4-yl)oxy)quinazolin-6-yl)-3,6-dihydropyridin-1(2H)-yl)prop-2-en-1-one |
| 82 | 1-(5-(4-(((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one |
| 83 | 1-(4-(4-((4-(([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one |
| 84 | 1-(5-(4-(((4-([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one |

TABLE 1-continued

| Cmpd No. | Compound Structure and Name |
|---|---|
| 85 | 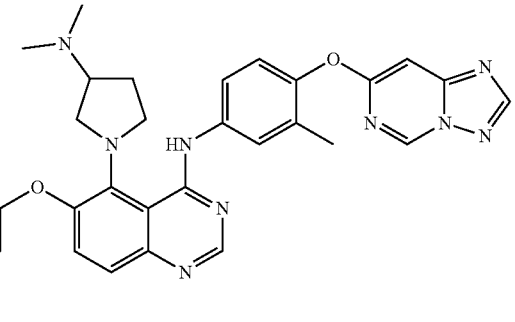<br>1-(4-((4-((4-([1,2,4]triazolo[1,5-c]pyrimidin-7-yloxy)-3-methylphenyl)amino)-5-(3-(dimethylamino)pyrrolidin-1-yl)quinazolin-6-yl)oxy)piperidin-1-yl)prop-2-en-1-one |
| 86 | 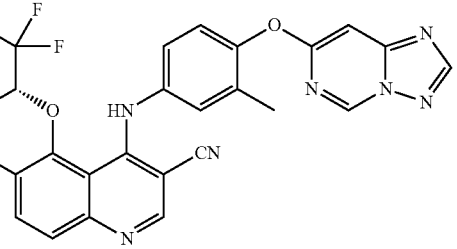<br>(R)-4-((4-([1,2,4]triazolo[1,5-c]pyrimidin-7-yloxy)-3-methylphenyl)amino)-5-((3,3-difluoro-1-methylpiperidin-4-yl)oxy)-6-methoxyquinoline-3-carbonitrile |
| 87 | 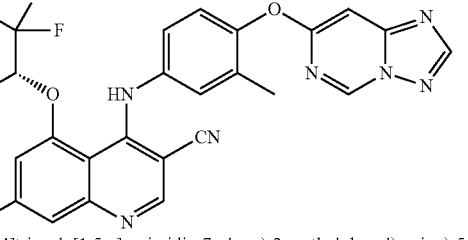<br>(R)-4-((4-([1,2,4]triazolo[1,5-c]pyrimidin-7-yloxy)-3-methylphenyl)amino)-5-((3,3-difluoro-1-methylpiperidin-4-yl)oxy)-7-methoxyquinoline-3-carbonitrile |
| 88 | 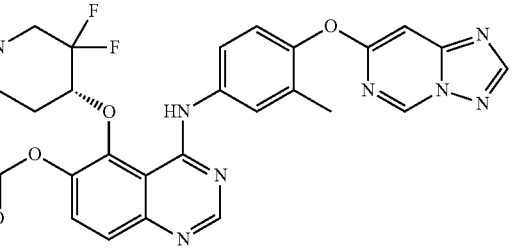<br>4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl 2,4-dimethylpiperazine-1-carboxylate |
| 89 | 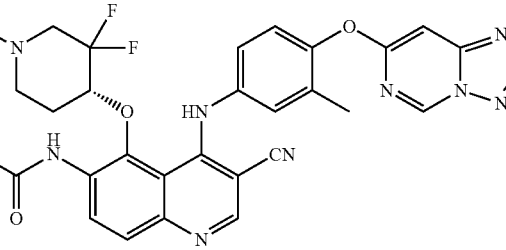 |

TABLE 1-continued

| Cmpd No. | Compound Structure and Name |
|---|---|
| | (R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)quinolin-6-yl)-4-(dimethylamino)but-2-enamide |
| 90 | (R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)-7-ethoxyquinolin-6-yl)-4-(dimethylamino)but-2-enamide |
| 91 | (R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)-7-ethoxyquinazolin-6-yl)-4-(dimethylamino)but-2-enamide |
| 92 | (R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-4-(dimethylamino)but-2-enamide |
| 93 | (E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)quinolin-6-yl)-3-((R)-1-methylpyrrolidin-2-yl)acrylamide |

TABLE 1-continued

| Cmpd No. | Compound Structure and Name |
|---|---|
| 94 | 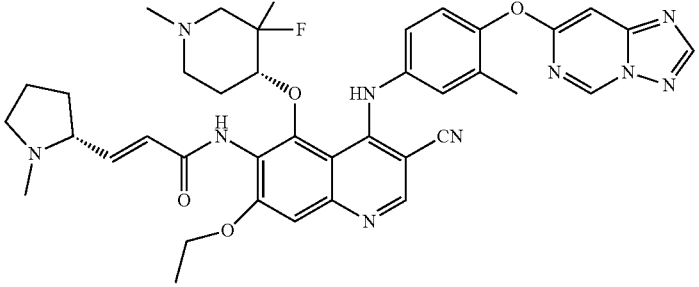<br>(E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)-7-ethoxyquinolin-6-yl)-3-((R)-1-methylpyrrolidin-2-yl)acrylamide |
| 95 | 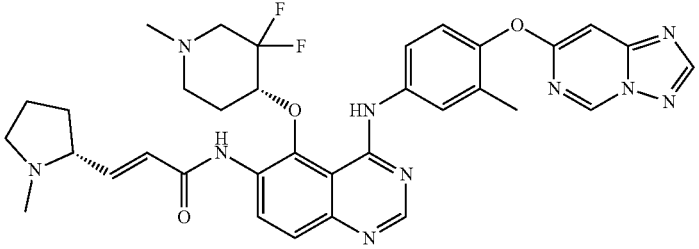 [SMILES: Cc1cc(Nc2ncnc3ccc(NC(=O)/C=C/[C@H]4CCCN4C)c(O[C@@H]4CCN(C)CC4(F)F)c23)ccc1Oc1cc2ncnn2cn1]<br>(E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl)-3-((R)-1-methylpyrrolidin-2-yl)acrylamide |
| 96 | 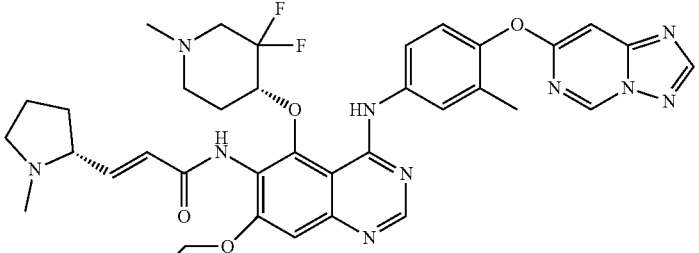<br>(E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)-7-ethoxyquinazolin-6-yl)-3-((R)-1-methylpyrrolidin-2-yl)acrylamide |
| 97 | 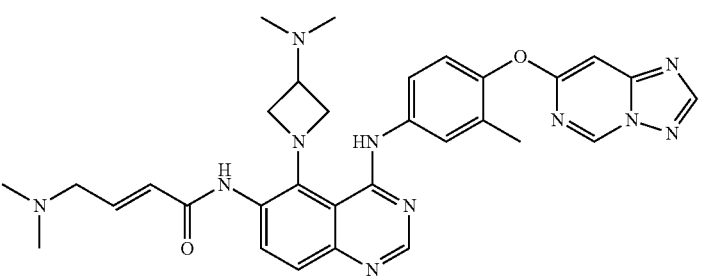 [SMILES: Cc1cc(Nc2ncnc3ccc(NC(=O)/C=C/CN(C)C)c(N4CC(N(C)C)C4)c23)ccc1Oc1cc2ncnn2cn1]<br>(E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-4-(dimethylamino)but-2-enamide |

TABLE 1-continued

| Cmpd No. | Compound Structure and Name |
|---|---|
| 98 | 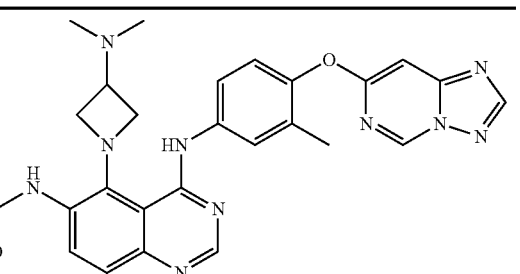(R,E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-3-(1-methylpyrrolidin-2-yl)acrylamide |
| 99 | 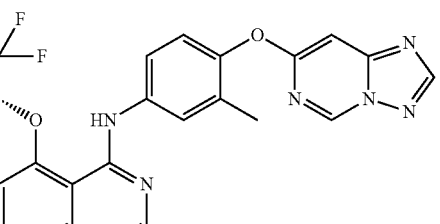(R)-N-(4-([1,2,4]triazolo[1,5-c]pyrimidin-7-yloxy)-3-methylphenyl)-5-((3,3-difluoro-1-methylpiperidin-4-yl)oxy)-6,7-dimethoxyquinazolin-4-amine |

Compounds provided herein are described with reference to both generic formulae and specific compounds. In addition, compounds of the present disclosure may exist in a number of different forms or derivatives, all within the scope of the present disclosure. These include, for example, tautomers, stereoisomers, racemic mixtures, regioisomers, salts, prodrugs, solvated forms, different crystal forms or polymorphs, and active metabolites.

The compounds of present disclosure can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the present disclosure are enantiopure compounds. In certain embodiments, mixtures of enantiomers or diastereomers are provided.

The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

Furthermore, certain compounds, as described herein may have one or more double bonds that can exist as either the Z or E isomer, unless otherwise indicated. The present disclosure additionally encompasses the compounds as individual isomers substantially free of other isomers and alternatively, as mixtures of various isomers, e.g., racemic mixtures of enantiomers. In addition to the above-mentioned compounds per se, this disclosure also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched".

Where a particular enantiomer is preferred, it may, in some embodiments be provided substantially free of the opposite enantiomer, and may also be referred to as "optically enriched". "Optically enriched", as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972).

The compounds of the present disclosure may also exist in different tautomeric forms, and all such forms are embraced within the scope of the present disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol, amide-imidic acid, lactam-lactim, imine-enamine isomerizations and annular forms where a proton can occupy two or more positions of a heterocyclic system (for example, 1H- and 3H-imidazole, 1H-, 2H- and 4H-1,2,4-triazole, 1H- and 2H-isoindole, and 1H- and 2H-pyrazole). Valence tautomers include interconversions by reorganization of some of the bonding electrons. Tautomers can be in equilibrium or sterically locked into one form by appropriate substitution. Compounds of the present disclosure identified by name or structure as one particular tautomeric form are intended to include other tautomeric forms unless otherwise specified.

The compounds of the present disclosure also include prodrugs, active metabolic derivatives (active metabolites), active intermediates, and their pharmaceutically acceptable salts.

As used herein, the term "prodrugs" refers to compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolism, the ester group is cleaved to yield the active drug. Also, some prodrugs are activated enzymatically to yield the active compound, or a compound which, upon further chemical reaction, yields the active compound. Prodrugs may proceed from prodrug form to active form in a single step or may have one or more intermediate forms which may themselves have activity or may be inactive. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

As used herein, the term "metabolite", e.g., active metabolite overlaps with prodrug as described above. Thus, such metabolites are pharmacologically active compounds or compounds that further metabolize to pharmacologically active compounds that are derivatives resulting from metabolic process in the body of a subject. For example, such metabolites may result from oxidation, reduction, hydrolysis, amidation, deamidation, esterification, deesterification, enzymatic cleavage, and the like, of the administered compound or salt or prodrug. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, J Med Chem 40:2011-2016; Shan et al., J Pharm Sci 86:756-757; Bagshawe, 1995, DrugDev Res 34:220-230; Wermuth, supra.

As used herein, the term "active intermediate" refers to intermediate compound in the synthetic process, which exhibits the same or essentially the same biological activity as the final synthesized compound.

Compounds of the present disclosure can be formulated as or be in the form of pharmaceutically acceptable salts.

Unless specified to the contrary, a compound provided herein includes pharmaceutically acceptable salts of such compound.

As used herein, the term "pharmaceutically acceptable" indicates that the substance or composition is compatible chemically and/or toxicologically, with the other ingredients comprising a formulation, and/or the subjects being treated therewith.

As used herein, the term "pharmaceutically acceptable salt", unless otherwise indicated, includes salts that retain the biological effectiveness of the free acids and bases of the specified compound and that are not biologically or otherwise undesirable. Contemplated pharmaceutically acceptable salt forms include, but are not limited to, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19$^{th}$ ed., Mack Publishing Co., Easton, Pa., Vol. 2, p. 1457, 1995; "Handbook of Pharmaceutical Salts: Properties, Selection, and Use" by Stahl and Wermuth, Wiley-VCH, Weinheim, Germany, 2002. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. Thus, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

It is also to be understood that the compounds of present disclosure can exist in unsolvated forms, solvated forms (e.g., hydrated forms), and solid forms (e.g., crystal or polymorphic forms), and the present disclosure is intended to encompass all such forms.

As used herein, the term "solvate" or "solvated form" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. Examples of solvents that form solvates include, but are not limited to, water, isopfopanol, ethanol, methanol, DMSO, ethyl acetate, acetic acid, and ethanolamine.

As used herein, the terms "crystal form", "crystalline form", "polymorphic forms" and "polymorphs" can be used interchangeably, and mean crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The present disclosure is also intended to include all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the compounds of present disclosure are meant to also include their isotopes, such as but not limited to $^1H$, $^2H$, $^3H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$ $^{127}I$ and $^{131}I$. In some embodiments, hydrogen includes protium, deuterium and tritium. In some embodiments, carbon includes $^{12}C$ and $^{13}C$.

Synthesis of the Compounds

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^1H$ or $^{13}C$), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^1H$-NMR spectra is recorded in $CDCl_3$, $CD_3OD$ or DMSO-$d_6$ solutions (reported in ppm) on a Varian instrument (400 MHz), using tetramethylsilane (TMS) as the reference standard (0.0 ppm).

MS measurement is carried out using Shimadzu 2010 Mass Spectrometer or Agilent 6110A MSD or 1969A TOF mass spectrometer using electrospray, chemical and electron impact ionization methods from a range of instruments.

TLC measurement is carried out using Yantai Huanghai HSGF254 silica gel or Anhui Liang Chen Gui Yuan plates. The silica gel plates used for TLC are 0.15 mm~0.2 mm. The silica gel plates used for separating and purifying products by TLC are 0.4 mm~0.5 mm.

Column chromatography was done on a Biotage system (Manufacturer: Dyax Corporation) having a silica gel column or on a silica SepPak cartridge (Waters).

The known starting materials of the present disclosure can be synthesized by using or according to the known methods in the art, or can be purchased from commercial suppliers such as Aldrich Chemical Company, Adamas-beta, TCI or Accela ChemBio Co., Ltd, and were used without further purification unless otherwise indicated. Tetrahydrofuran (THF), N,N-dimethylformamide (DMF), dichloromethane (DCM), dichloroethane (DCE), dioxane and 1,1,2,2-tetrachloroethane were purchased from Aldrich in Sure seal bottles and used as received.

Unless otherwise specified, the reactions of the present disclosure were all done under a positive pressure of nitrogen or argon or with a drying tube in anhydrous solvents, and the reaction flasks were typically fitted with rubber septa for the introduction of substrates and reagents via syringe. Glassware was oven dried and/or heat dried.

For illustrative purposes, the following shows general synthetic route for preparing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

General Synthetic Route

In some embodiments, compounds of Formula (I) provided herein may be prepared by the reaction of a compound of Formula (II):

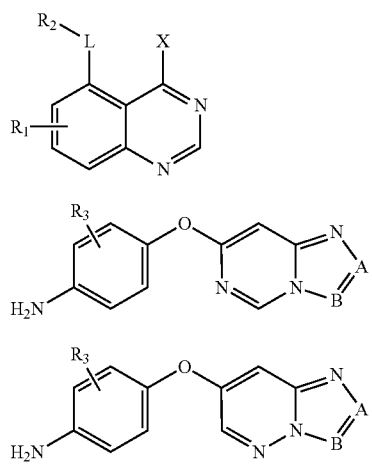

wherein X is a leaving group (for example a halogen atom) with a compound of Formula (IIIa) or (IIIb) (free base, when it is desired to obtain the free base from the salt, the salt may be treated with a suitable base, for example, an alkali or alkaline earth metal carbonate or hydroxide, for example sodium carbonate, potassium carbonate, calcium carbonate, sodium hydroxide or potassium hydroxide) in the presence of a suitable acid. $R_1$, $R_2$, $R_3$ and L have any of the meanings defined herein except that any functional group is protected if necessary. A suitable acid is, for example, organic acid such as pTSOH. The reaction is conveniently carried out in the presence of a suitable solvent, for example an alcohol such as isopropanol at a suitable temperature (for example a temperature in the range of about 20-100° C.).

In certain embodiments, the compound of the Formula (II), wherein X is a halogen atom, may be reacted with the compound of the Formula (IIIa) or (IIIb) in the absence of any solvent and acid or base. In such reaction, displacement of the halogen leaving group X results in the formation of the acid HX in situ and the auto-catalysis of the reaction. Conveniently, the reaction may be carried out in a suitable inert organic solvent, for example isopropanol, dioxane or N,N-dimethylacetamide. Suitable conditions for this reaction are as described above.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such as methods being chosen so as to effect removal of the protecting group with minimum disturbance of groups elsewhere in the molecule.

Scheme 1 illustrates the synthesis of some ether linked quinazolines of Formula (Ia) (when $R_1$ in the compounds of Formula (I) of the present disclosure is $O(R_9)$), wherein PG is a suitable protecting group (such as MOM). According to Scheme 1, 4-chloro-6-oxy-quinazoline of Formula (IIa) (wherein X is chloro) can be reacted with suitable aniline Formula (IIIa) or (IIIb) under standard coupling conditions as described above to provide compound of Formula (B7). After reaction with the aniline, the optional protection group can be removed under suitable conditions, such as in the presence of TFA, to provide compound of Formula (B8). The hydroxyl group of compound of Formula (B8) can be coupled with a suitable alkyl halide $R_9$—X in the presence of an appropriate base, such as $K_2CO_3$, $CS_2CO_3$ or $Cs(OH)_2$ in an organic solvent (such as DMF or acetone) to provide compound of Formula (Ia). Alternatively, $R_9$—OH can be used in place of $R_9$—X if the alcohol has been converted to an activated leaving group, such as a tosylate. In yet another approach, the hydroxyl group of compound of Formula (B8) can be coupled with an alcohol $R_9$—OH under standard Mitsunobu conditions, such as DIAD/PPh$_3$ in THF, to provide compound of Formula (Ia).

Scheme 1

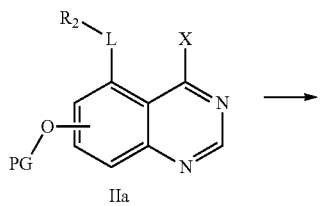

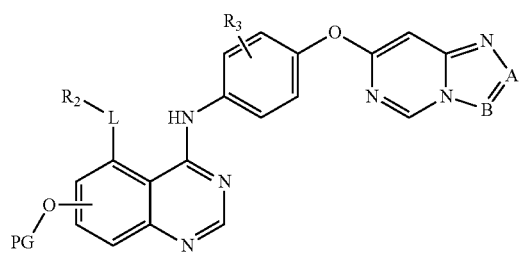

B7a

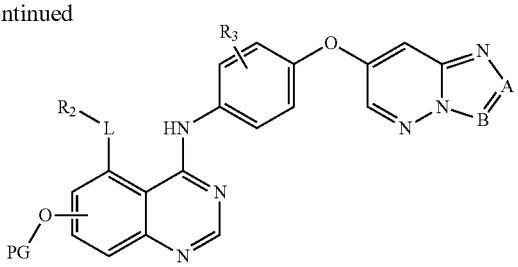

B7b

TFA →

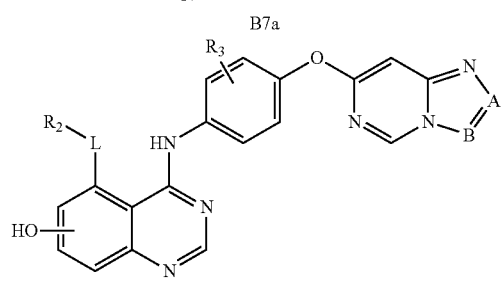

B8a

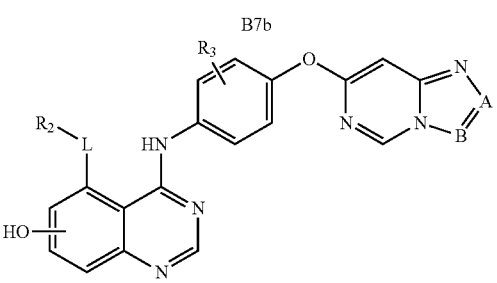

B8b

CCl₄, PPh₃ →

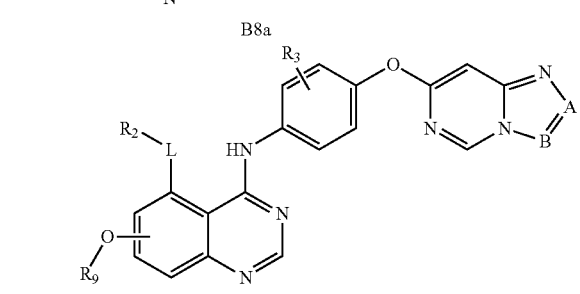

Ia

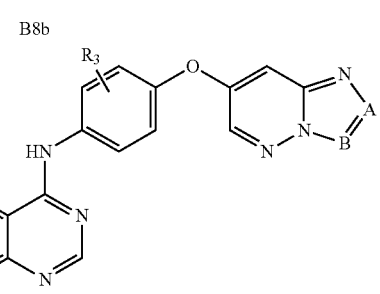

Ib

In some embodiments, the compound of the Formula (II) may be obtained by conventional procedures. Scheme 2 illustrates the synthesis of compounds of the Formula (II). As shown in Scheme 2, a compound of Formula (A9) wherein $R_1$, $R_2$ and L have any of the meanings defined herein except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means. The reaction is conveniently carried out in a suitable inert solvent, for example 1,2-dichloroethane or N,N-dimethylformamide in the presence of an base such as an organic base, for example di-isopropylethylamine. The reaction is conveniently carried out at a temperature in the range, for example, 0 to 150° C., preferably at or near the reflux temperature of the reaction solvent.

Scheme 2

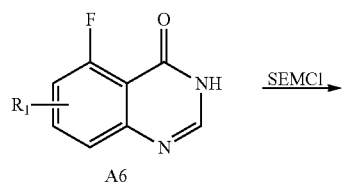

A6

SEMCl →

-continued

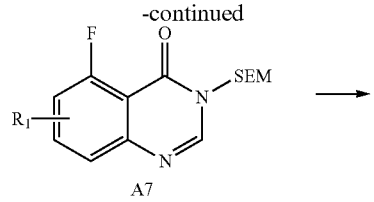

A7

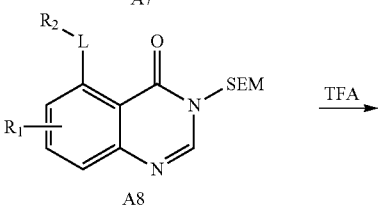

A8

TFA →

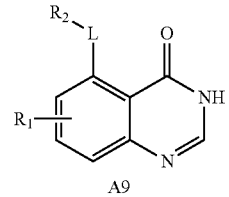

A9

→ II

Step 1:
The starting material of Formula (A6) is commercially available or can be prepared using conventional methods, for example as described in J. Org. Chem. 1952, 17, 164-176 and J. Med. Chem. 1996, 39, 1823-1835.
The starting material of Formula (A6) was protected with suitable amino protecting group, for example SEM in the presence of suitable base.

Step 2:

The reaction is conveniently performed in the presence of a suitable base. Suitable bases are as herein described, for example sodium hydride. The reaction is conveniently performed in a suitable inert solvent, for example N,N-dimethylacetamide. Scheme 1 is particularly suitable for the preparation of compounds of the formula II in which L is O.

Step 3:

The optional protection group in the compound of Formula (A9) can be removed under suitable conditions, such as TFA for SEM deprotection.

In some embodiments, the compound of Formula (Ma) suitable for use in Scheme 1 can be prepared according to the method shown in Scheme 3. A suitably di-chloro-substituted pyrimidine can reacted with $NH_2NH_2$—$H_2O$ in EtOH to provide a hydrazinylpyrimidine intermediate. Conversion of this intermediate to a 7-chloro-[1,2,4]triazolo[1,5-c]pyrimidine can be accomplished by treatment with a $HC(OMe)_3$ at elevated temperatures, for example at 90° C. Phenol is reacted with an optionally substituted 7-chloro-[1,2,4]triazolo[1,5-c]pyrimidine in the presence of $CS_2CO_3$ in MeCN at 60° C. The nitro group of 4-nitrophenoxy)-[1,2,4]triazolo[1,5-c]pyrimidine can be reduced to the desired aniline compound of Formula (Ma) using standard reduction methods such as Fe/$NH_4Cl$.

Previously, it was believed that the cyclization reaction of the hydrazinylpyrimidine intermediate with $HC(OMe)_3$ produces 7-chloro-[1,2,4]triazolo[4,3-c]pyrimidine, as shown in Scheme 3 of the PCT application PCT/CN2018/106098, which is assigned to the same applicant and discloses the present invention. However, the inventors have surprisingly found that, in fact, it was 7-chloro-[1,2,4]triazolo[1,5-c]pyrimidine that was produced from the above mentioned cyclization reaction, instead of 7-chloro-[1,2,4]triazolo[4,3-c]pyrimidine, as a result of a rearrangement spontaneously occurred during the cyclization reaction (see Scheme 3 below).

Scheme 3

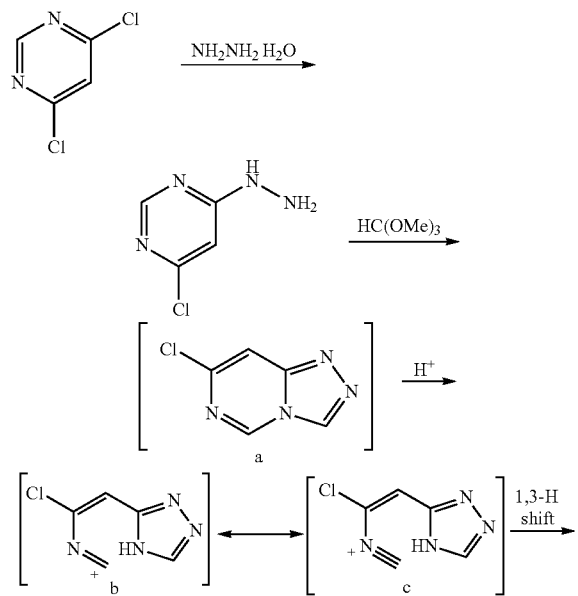

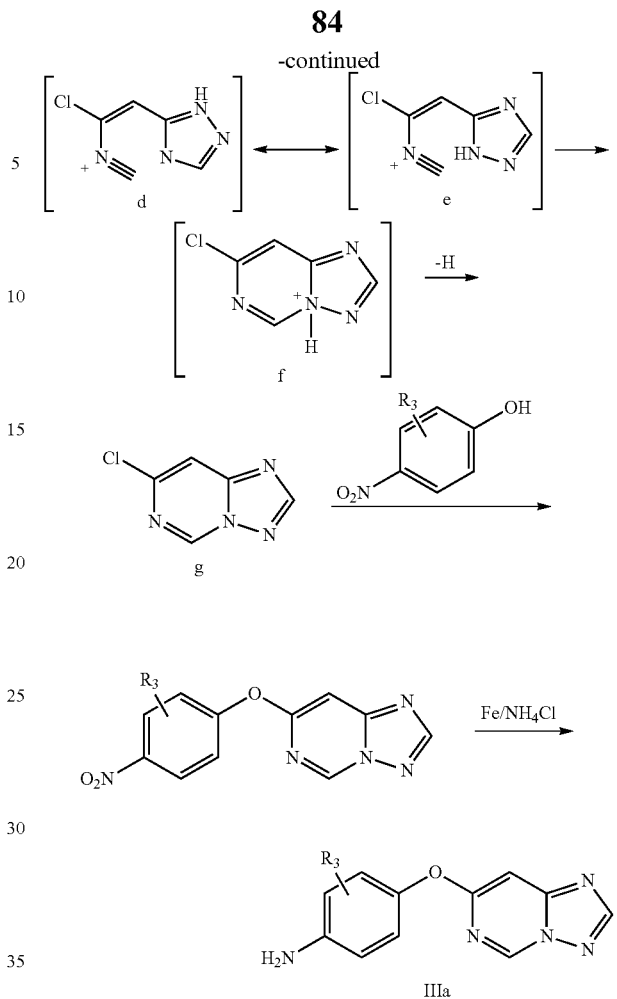

Specifically, as shown in Scheme 3, in this case, compound a is assumed to be protonated to generate an ammonium salt, facilitating the ring opening to give the iminium salt b that is in resonance with the nitrilium salt c. Subsequently, hydrogen shift results in the formation of the triazole-tethered vinyliminium salt d. Recyclization by intramolecular nucleophilic attack at another nitrogen atom of the triazole ring affords, after deprotonation of f, the isolated [1,2,4]triazolo[1,5-c]pyrimidine g. The driving force for the observed rearrangement relies on the fact that [1,2,4]triazolo[1,5-c]pyrimidine ring system is thermodynamically more stable than its isomer, namely, [1,2,4]triazolo[4,3-c]pyrimidine.

This unexpected spontaneous rearrangement was confirmed by the growth and characterization of single crystals of the intermediate of Formula (Ma), which pinpointed the correct chemical structure (see FIG. 1). It has also been confirmed that, the reaction of the hydrazinylpyrimidine intermediate with $HC(OMe)_3$ as illustrated in Scheme 3 of PCT/CN2018/106098 necessarily yielded 7-chloro-[1,2,4]triazolo[1,5-c]pyrimidine, and thus all the compounds obtained in subsequent steps were based on the intermediates comprising [1,2,4]triazolo[1,5-c]pyrimidin-7-yl instead of [1,2,4]triazolo[4,3-c]pyrimidin-7-yl, as corrected in the present disclosure.

In some embodiments, the compounds of Formula (I) can be prepared according to the method shown in Scheme 4.

Scheme 4

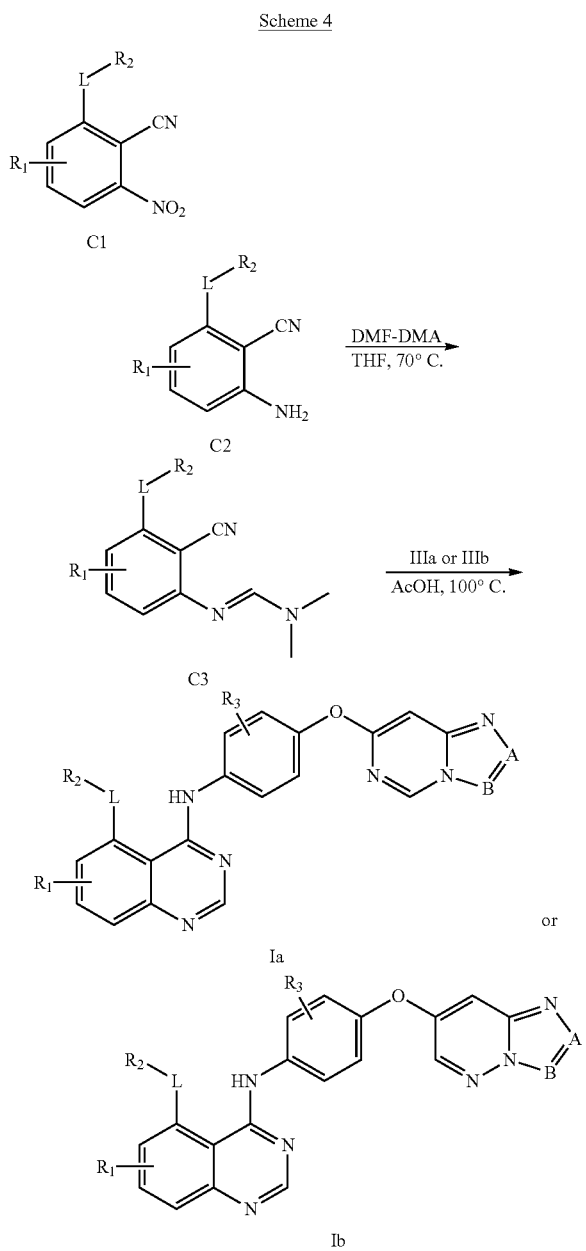

Step 1:

The starting material of Formula (C1) is commercially available or can be prepared using conventional methods, for example as described in J. Org. Chem. 1952, 17, 164-176. Selectively reduction of compounds of Formula (C1) was carried out using suitable reductant, for example, $H_2$ with Pd/C in solvents such as THF or methanol.

Step 2:

The reaction of compounds of Formula (C2) with DMF-DMA can be carried out in a suitable solvent (such as THF) at a temperature in the range, for example from 50-100° C. to obtain compounds of Formula (C3).

Step 3:

The quinazoline ring closure reaction was performed with compounds of Formula (IIIa) or (IIIb) in the present of acid (such as AcOH, pTSOH) at a temperature from 50-120° C.

Use of Compounds

In an aspect, the present disclosure provides compounds of formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)) or pharmaceutically acceptable salts thereof, which show high inhibitory activity against type I receptor tyrosine kinase, in particular HER2.

As used herein, the term "inhibitory activity against type I receptor tyrosine kinase" refers to a decrease in the activity of type I receptor tyrosine kinase as a direct or indirect response to the presence of a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salt thereof, relative to the activity of type I receptor tyrosine kinase in the absence of compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salt thereof. Such a decrease in activity may be due to the direct interaction of the compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salt thereof with type I receptor tyrosine kinase, or due to the interaction of the compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salt thereof with one or more other factors that in turn affect activity of type I receptor tyrosine kinase. For example, the compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salt thereof may decrease activity of type I receptor tyrosine kinase by directly binding to the type I receptor tyrosine kinase, by causing (directly or indirectly) another factor to decrease type I receptor tyrosine kinase activity, or by (directly or indirectly) decreasing the amount of type I receptor tyrosine kinase present in the cell or organism.

In some embodiments, the compounds of the present disclosure are selective inhibitors for HER2 over other type I receptor tyrosine kinases, such as wild type EGFR (wt-EGFR).

As used herein, the term "selective inhibitor of HER2" or "selectively inhibits HER2" means that a provided compound inhibits HER2 in at least one assay described herein (e.g., biochemical or cellular) over other type I receptor tyrosine kinases, such as wt-EGFR. In some embodiments, the term "selective inhibitor of HER2 over EGFR" or "selectively inhibits HER2 over EGFR" means that a provided compound has the $IC_{50}$ for wt-EGFR at least 10 fold higher, at least 20 fold higher, at least 30 fold higher, at least 40 fold higher, at least 50 fold higher, at least 60 fold higher, at least 70 fold higher, at least 80 fold higher, at least 90 fold higher, at least 100 fold higher, at least 200 fold higher, at least 300 fold higher, at least 400 fold higher, at least 500 fold higher, at least 600 fold higher, at least 700 fold higher, at least 800 fold higher, at least 900 fold higher, at least 1000 fold higher, at least 2000 fold higher than the $IC_{50}$ for HER2, as determined by assays described herein.

Accordingly, there is provided compounds of Formula I (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf), or pharmaceutically acceptable salts thereof which are highly potent HER2 inhibitors and are highly selective for HER2 relative to EGFR. Such compounds would allow treatment of cancers which can be treated by inhibiting HER2, for example cancers which express or overexpress HER2, in a relatively selective manner, thereby minimizing potential side effects associated with the inhibition of other kinases such as EGFR.

In some embodiments, the compounds of the present disclosure are not P-glycoprotein (Pgp) substrates, nor ATP-binding cassette sub-family G member 2 (ABCG2, or BCRP) substrates. As used herein, the term "Pgp substrate" means that a given compound is susceptible to transporation back into the intestinal lumen (in the case of Pgp distributed in intestinal epithelium), bile ducts (in the case of Pgp distributed in liver cells), urinar filtrate (in the case of Pgp distributed in the cells of the proximal tubule of the kidney), capillaries (in the case of Pgp distributed in the capillary endothelial cells composing the blood-brain barrier and blood-testis barrier) and the like, by Pgp. As used herein, the term "BCRP substrate" means that a given compound is blocked from being absorption at the apical membrane of the intestine, the blood-testis barrier, the blood-brain barrier, and the membranes of hematopoietic progenitor and other stem cells, in particular the blood-brain barrier, by BCRP. Therefore, there is provided compounds or pharmaceutically acceptable salts thereof, which demonstrate good brain penetration in subjects, allowing for applications in treating both extracranial cancers and metastatic cancer, such as brain metastases.

In some embodiments, the Pgp and BCRP susceptibility of a compound can be evaluated by MDCK-MDR1 Pgp permeability assay and Caco-2 BCRP permeability assay, respectively, as described in detail in Example section below. In some embodiments, the compounds of the present disclosure show low Pgp susceptibility with a MDCK-Pgp efflux ratio (MDCK-Pgp ER) of less than about 5, less than about 4, less than about 3, less than about 2, less than about 1.

In some embodiments, the compounds of the present disclosure are capable of in vivo brain penetration, as determined by mouse SOA study described in detail in Example section below. In some embodiments, the compounds of the present disclosure show a brain to blood concentration ratio $K_p$ of greater than about 0.1, greater than about 0.15, greater than about 0.2, greater than about 0.25, greater than about 0.3, greater than about 0.35, greater than about 0.4, greater than about 0.45, greater than about 0.5.

Accordingly, there is provided compounds of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or pharmaceutically acceptable salts thereof that are capable of crossing blood-brain barrier, without the need of any agent for facilitating the blood-brain barrier entry. Such compounds would allow treatment of metastatic cancer, such as brain metastases, in particular brain metastases of breast cancer.

In some embodiments, the compounds of the present disclosure show low hERG inhibition, as determined by hEGR inhibition assay described in detail in Example section below. In some embodiments, the compounds of the present disclosure show a hERG inhibition $IC_{50}$ of greater than about 2 μM, greater than about 3 μM, greater than about 4 μM, greater than about 5 μM, greater than about 6 μM, greater than about 7 μM, greater than about 8 μM, greater than about 9 greater than about 10 μM. This indicates the compounds provided herein have low risk of cardiac toxicity in vivo.

As a result of their inhibitory activity against type I receptor tyrosine kinase (optionally selective HER2 inhibitory activity), the compounds of Formula (I), and pharmaceutically acceptable salts thereof are useful in therapy, for example in the treatment of diseases or medical conditions mediated at least in part by one or more type I receptor tyrosine kinases, including cancer.

As used herein, the term "cancer" is intented to encompass both non-metastatic cancer and metastatic cancer. In this context, treating cancer involves treatment of both primary tumors and tumor metastases.

As used herein, the term "therapy" is intended to have its normal meaning of dealing with a disease in order to entirely or partially relieve one, some or all of its symptoms, or to correct or compensate for the underlying pathology, thereby achieving beneficial or desired clinical results. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Therapy" can also mean prolonging survival as compared to expected survival if not receiving it. Those in need of therapy include those already with the condition or disorder as well as those prone to have the condition or disorder or those in which the condition or disorder is to be prevented. The term "therapy" also encompasses prophylaxis unless there are specific indications to the contrary. The terms "therapeutic" and "therapeutically" should be interpreted in a corresponding manner.

As used herein, the term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In some embodiments, the compounds of the present disclosure possess anti-cell-proliferation properties, which are believed to arise from their type I receptor tyrosine kinase inhibitory activity. Accordingly, the compounds of the present disclosure are expected to be useful in the treatment of diseases or conditions mediated alone or in part by type I receptor tyrosine kinases, i.e. the compounds may be used to produce an anti-proliferative effect mediated alone or in part by inhibiting type I receptor tyrosine kinases. In some embodiments, such disease or condition treated by providing an anti-proliferative effect is type I receptor tyrosine kinase sensitive cancers, including but not limited to breast cancer, lung cancer, colon cancer, rectum cancer, stomach cancer, prostate cancer, bladder cancer, pancreas cancer and ovary cancer, or other cell-proliferation diseases such as psoriasis.

Therefore, in one aspect, there is provided a compound of Formula (I), or a pharmaceutically acceptable salt thereof, for use in therapy.

In some embodiments, there is provided a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or a pharmaceutically acceptable salt thereof, for use as a medicament.

In some embodiments, there is provided a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or a pharmaceutically acceptable salt thereof, for use in the treatment of diseases or conditions mediated alone or in part by type I receptor tyrosine kinases.

In some embodiments, there is provided a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or a pharmaceutically acceptable salt thereof, for use in the manufacture of a medicament for the treatment of type I receptor tyrosine kinase-associated diseases or conditions.

In some embodiments, there is provided a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or a pharmaceutically acceptable salt thereof, for use in the manufacture of a medicament for the treatment of HER2-associated diseases or conditions.

In some embodiments, there is provided a compound of Formula (I) (or Formula (I'), Formula (IVa), Formula (IVb), Formula (IVc), Formula (IVd), Formula (IVe), Formula (IVf), Formula (Va), Formula (Vb), Formula (Vc), Formula (Vd), Formula (Ve), Formula (Vf)), or a pharmaceutically acceptable salt thereof, for use in the manufacture of a medicament for the treatment of cancer.

Pharmaceutical Composition

The present disclosure provides pharmaceutical compositions comprising one or more compound of the present disclosure, or a pharmaceutically acceptable salt thereof. In some embodiments, the pharmaceutical composition comprises one or more compounds of the present disclosure, or a pharmaceutically acceptable salt thereof, and at lease one pharmaceutical acceptable excipient.

A "pharmaceutical composition", as used herein, is a formulation containing the compounds of the present disclosure in a form suitable for administration to a subject. In some embodiments, the pharmaceutical composition is in bulk or in unit dosage form. The unit dosage form is any of a variety of forms, including, for example, tablets, capsules, pills, powders, granules, sachets, cachets, lozenges, suspensions, emulsions, solutions, syrups, aerosols (as a solid or in a liquid medium), spray, ointment, paste, cream, lotion, gel, patch, inhalant, or suppository. The quantity of active ingredient (e.g., a formulation of the disclosed compound or salt, hydrate, solvate or isomer thereof) in a unit dose of composition is a therapeutically effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In some embodiments, the compound of the present disclosure is mixed under sterile conditions with a pharmaceutically acceptable excipient, and with any preservatives, buffers or propellants that are required.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. The term "pharmaceutically acceptable excipient" also encompasses "pharmaceutically acceptable carrier" and "pharmaceutically acceptable diluent".

The particular excipient, carrier, or diluent or used will depend upon the means and purpose for which the compounds of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable excipients, diluents, and carriers, and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The composition may also comprise one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the compounds disclosed herein and, optionally, a chemotherapeutic agent) to a mammal. The components of the liposome are commonly arranged in a bilayer formation, similar to the lipid arrangement of biological membranes.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Compositions suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The pharmaceutical compositions of the present disclosure may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

Formulations for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as *arachis* oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the present disclosure may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Formulations for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or—by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical composition in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The compositions may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

In another aspect, there is also provided veterinary compositions comprising a compound of Formula (I) or pharmaceutically acceptable salts thereof together with a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

As used herein, the term "therapeutically effective amount" refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; the rate of administration; the therapeutic or combination of therapeutics selected for administration; and the discretion of the prescribing physician. Therapeutically effective amounts for a given situation can be determined by routine experimentation that is within the skill and judgment of the clinician.

In some embodiments, the pharmaceutical compositions can be formulated so that a dosage of between 0.001-500 mg/kg body weight/day, for example, 0.01-400 mg/kg body weight/day, 0.01-300 mg/kg body weight/day, 0.1-200 mg/kg body weight/day, 0.1-150 mg/kg body weight/day, 0.1-100 mg/kg body weight/day, 0.5-100 mg/kg body weight/day, 0.5-80 mg/kg body weight/day, 0.5-60 mg/kg body weight/day, 0.5-50 mg/kg body weight/day, 1-50 mg/kg body weight/day, 1-40 mg/kg body weight/day of the compounds of the present disclosure, or a pharmaceutically acceptable salt thereof, can be administered. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

In some embodiments, the pharmaceutical compositions comprise one or more compounds of the present disclosure, or a pharmaceutically acceptable salt thereof, as a first active ingredient, and further comprise a second active ingredient.

In some embodiments, the second active ingredient of the pharmaceutical combination formulation or dosing regimen has complementary activities to the compound of Formula I such that they do not adversely affect each other. Such ingredients are suitably present in combination in amounts that are effective for the purpose intended.

In certain embodiments, the second active ingredient can be any anti-tumor agent known in the art. The anti-tumor agent can be selected from the following categories:

(i) antiproliferative/anti-neoplastic drugs and combinations thereof, such as TKIs (such as lapatinib, neratinib and afatinib); DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example capecitabine, gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE 1 kinase (such as AZD1775/MK-1775);

(ii) cytostatic agents such as antiestrogens (for example, tamoxifen, toremifene, raloxifene, droloxifene and iodoxyfene); estrogen receptor down regulators (for example, fulvestratrant); antiandrogens (for example, bicalutamide, flutamide, nilutamide, cyproxerone acetate and CASODEX™ (4'-cyano-3-(4-fluorophenylsulphonyl)-2-hydroxy-2-methyl-3'-(trifluoromethyl)propionanilide)); LHRH antagonists or LHRH agonists (for example, goserelin, leuporelin and buserelin); progestogens (for example, megestrol acetate); aromatase inhibitors (for example, asanastrozole, letrozole, vorazole and exemestane); inhibitors of 5α-reductase such as finasteride; and p38 inhibitors such as those disclosed in U.S. Publication Nos. 2004/0176325, 2004/0180896, and 2004/0192635;

(iii) agents which inhibit cancer cell invasion (for example, metalloproteinase inhibitors like marimastat and inhibitors of urokinase plasminogne activator receptor function);

(iv) inhibitors of growth factor function such as growth factor antibodies, growth factor receptor antibodies (for example, the anti-ErbB2 antibody such as trastumuzab [HERCEPTIN™] and the anti-ErbB1 antibody cetuximab [C225]), antibody drug conjugates (for example, T-DM1), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-mopholinopropoxy)quinazolin-4-amine (CI 1033)); inhibitors of the platelet-derived growth factor family; inhibitors of the hepatocyte growth factor family; and MEK inhibitors such as PD325901 and compounds such as those disclosed in U.S. Patent Publication 2004/0116710;

(v) antiangiogenic agents such as those which inhibit the effects of vascular endothelial growth factor, such as but not limited to, the anti-vascular endothelial cell growth factor antibody bevacizumab, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171); compounds such as those disclosed in International Patent Applications WO97/22596, WO 97/30035, WO 97/32856 and WO 98/13354; and compounds that work by other mechanisms (for example linomide, inhibitors of integrin αvβ3 function and angiostatin), or inhibitors of angiopoietins and their receptors (Tie-1 and Tie-2), inhibitors of PLGF, inhibitors of delta-like ligand (DLL-4);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCAI or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon;

(x) immunotherapy approaches, including, but not limited to, ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-1 (for example BMS-936558 or AMP-514), PD-L1 (for example MEDI4736) and agonist antibodies to CD137; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9;

(xi) efficacy enhancers, such as leucovorin.

Accordingly, there is provided pharmaceutical composition comprising a compound of Formula (I), or a pharmaceutically acceptable salt thereof, and at least one additional anti-tumour agent.

In some embodiment, the additional anti-tumour agent is selected from the group consisting of TKIs (such as lapatinib, neratinib and afatinib), anti-HER2 agents (for example, monoclonal antibodies such as Trastuzumab, ADCs such as T-DM1) and combination thereof. In some embodiments, the additional anti-tumour agent includes capecitabine, anti-HER2 antibodies, and T-DM1. In some embodiments, there is one additional anti-tumour agent. In some embodiments, there are two additional anti-tumour agents. In some embodiments, there are three or more additional anti-tumour agents.

In some embodiments, the amount of additional anti-tumour agent present in the composition of the present disclosure can be no more than the amount that would normally be administered in a composition comprising that anti-tumour agent as the only active agent. In certain embodiments, the amount of the additional anti-tumor agent in the composition of the present disclosure will range from about 50% to 100% of the amount normally present in a composition comprising that anti-tumor agent as the only therapeutically active agent.

The compound(s) of Formula (I), or a pharmaceutically acceptable salt thereof and the second active ingredient(s) may be administered together in a unitary pharmaceutical composition or separately and, when administered separately this may occur simultaneously or sequentially in any order. Such sequential administration may be close in time or remote in time. The amounts of the compound(s) of Formula (I) and the second agent(s) and the relative timings of administration will be selected in order to achieve the desired combined therapeutic effect Suitable dosages for any of the above coadministered agents are those presently used and may be lowered due to the combined action (synergy) of the newly identified agent and other chemotherapeutic agents or treatments.

As used herein, the term "combination" refers to simultaneous, separate or sequential administration. In some embodiments, "combination" refers to simultaneous administration. In some embodiments, "combination" refers to separate administration. In some embodiments, "combination" refers to sequential administration. Where the administration is sequential or separate, the delay in administering the second component should not be such as to lose the beneficial effect of the combination.

Therefore, in another aspect, there is provided a compound of formula (I) or a pharmaceutically acceptable salt thereof in combination with one or more active ingredients such as anti-tumor agents listed above.

In a further aspect, there is provided a pharmaceutical composition comprising a compound of formula (I) or a pharmaceutically acceptable salt thereof in combination with one or more active ingredients such as anti-tumor agents listed above, in association with a pharmaceutically acceptable excipient.

In a further aspect, there is provided a kit comprising a compound of formula (I) or a pharmaceutically acceptable salt thereof in combination with one or more anti-tumour agents listed above.

In a further aspect, there is provided a kit comprising:
(a) a compound of formula (I) or a pharmaceutically acceptable salt thereof in a first unit dosage form;
(b) an anti-tumour agent selected from those listed above in a second unit dosage form; and
(c) container for containing the first and second unit dosage forms.

Method for Treatment

In a further aspect, there is provided a method of treating type I receptor tyrosine kinase-associated diseases or conditions in a subject in need thereof, which comprises administering to the subject a therapeutically effective amount of a compound of Formula (I) or a pharmaceutically acceptable salt thereof, or a pharmaceutical composition of the present disclosure, owning to the type I receptor tyrosine kinase inhibitory activity, non-Pgp and non-BCRP susceptibility and brain penetration capability of the compounds of the present disclosure.

As used herein, the term "subject in need thereof" is a subject having a type I receptor tyrosine kinase-associated disease or condition (e.g., cancer), or a subject having an increased risk of developing a type I receptor tyrosine kinase-associated disease or condition (e.g., cancer) relative to the population at large. In the case of cancer, a subject in need thereof can have a precancerous condition. A "subject" includes a warm-blooded animal. In some embodiments, the warm-blooded animal is a human.

In this context, the term "therapeutically effective amount" refers to an amount of a compound of Formula (I) or pharmaceutically acceptable salts thereof which is effective to provide "therapy" in a subject, or to "treat" a type I receptor tyrosine kinase-associated disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of type I receptor tyrosine kinase activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of type I receptor tyrosine kinase activity as described above.

In generally, "therapeutically effective amount" may be determined by one skilled in the art by, for example, starting with the dosage range described in this specification for the compound of formula (I) or pharmaceutically acceptable salt thereof and an approved or otherwise published dosage range(s) of the other pharmaceutically active compound(s).

In some embodiments, the type I receptor tyrosine kinase-associated disease or condition is abnormal cell growth or hyperproliferative disorder. The terms "abnormal cell growth" and "hyperproliferative disorder" are used interchangeably in this application. "Abnormal cell growth", as used herein, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threoine kinase activation occurs.

In certain embodiments, abnormal cell growth in cancer. According, there is provided a methods of treating cancer in a subject in need thereof, which comprises administering to the subject a therapeutically effective amount of a compound of Formula (I) or a pharmaceutically acceptable salt thereof, or a pharmaceutical composition of the present disclosure.

In some embodiment, the cancer is a HER2-expressing cancer, a HER2-overexpressing cancer, or a HER ligand overexpressing cancer.

A "HER2-expressing cancer" is one that involves cancer cells or tumor cells having HER2 protein present at their cell surface. A "HER2-overexpressing cancer" is one which has significantly higher levels of a HER receptor, such as HER2, at the cell surface of a cancer or tumor cell, compared to a noncancerous cell of the same tissue type. Such overexpression may be caused by gene amplification or by increased transcription or translation.

A "HER-ligand overexpressing cancer" is one which produces significantly higher levels of the HER2 ligand compared to a noncancerous cell of the same tissue type. "HER ligand" as used herein refers to a polypeptide which binds to and/or activates a HER receptor. Examples include, without limitation, epidermal growth factor (EGF), transforming growth factor alpha (TGF-alpha); amphiregulin; betacellulin; heparin-binding epidermal growth factor (HB-EGF); a heregulin; epiregulin; neuregulin-2 (NRG-2); NRG-3; NRG-4 or cripto (CR-1). HER ligands which bind EGFR include EGF, TGF-.alpha., amphiregulin, betacellulin, HB-EGF and epiregulin.

HER receptor or HER ligand expression or overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). One may also study HER receptor overexpression by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

HER receptor or HER ligand expression or overexpression may be determined in a diagnostic or prognostic assay by evaluating increased levels of the HER or levels of the HER ligand in a biological sample (such as cancer cell) from the subject to be treated. Various methods can be used. For example, the test biological sample can be exposed to an anti-HER2 antibody which binds to and detects the expressed HER2 protein. Alternatively, HER2 can also be detected at nucleic acid expression level, using methods such as qPCR, reverse transcriptase PCR, microarray, SAGE, FISH, and the like. One may also study HER receptor overexpression by measuring shed antigen (e.g., HER extracellular domain) in a biological fluid such as serum (see, e.g., U.S. Pat. No. 4,933,294; WO91/05264; U.S. Pat. No. 5,401,638; and Sias et al. J. Immunol. Methods 132: 73-80 (1990)). In some embodiments, the test sample is derived from a cancer cell or tissue, or tumor infiltrating immune cells.

In certain embodiments, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma, of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancer.

In some embodiments, the cancer is metastatic cancer. In some embodiments, the metastatic cancer comprises metastases of the central nervous system. In some embodiments, the metastases of the central nervous system comprise brain metastases. In some embodiments, the metastases of the central nervous system comprise leptomeningeal metastases. "Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges. In certain embodiments, the metastatic cancer is breast cancer brain metastases.

Accordingly, in a further aspect, there is provided a method of treating breast cancer brain metastases in a subject in need thereof, which comprises administering to the subject a therapeutically effective amount of a compound of Formula (I) or a pharmaceutically acceptable salt thereof, or a pharmaceutical composition of the present disclosure.

The method of treating type I receptor tyrosine kinase-associated diseases or conditions described in this specification may be used as a monotherapy. As used herein, the term "monotherapy" refers to the administration of a single active or therapeutic compound to a subject in need thereof. In some embodiments, monotherapy will involve administration of a therapeutically effective amount of one of the compounds of the present disclosure, or a pharmaceutically acceptable salt thereof, to a subject in need of such treatment.

Depending upon the particular diseases or conditions to be treated, the method of treating type I receptor tyrosine kinase-associated diseases or conditions described in this specification may involve, in addition to administration of the compound of Formula (I), one or more additional therapies, for example, conventional surgery, radiotherapy, chemotherapy, or a combination of such additional therapies. As used herein, the term "combination therapy" refers to the administration of a combination of multiple active compounds.

The additional therapies, such as additional anti-tumor agents, may be administered separately from the compounds of the present disclosure, as part of a multiple dosage regimen. Alternatively, these additional therapies may be part of a single dosage form, mixed with the compounds of the present disclosure in a single composition.

In some embodiments, the compounds of the present disclosure may be administered simultaneously, sequentially or separately to treatment with the conventional surgery, radiotherapy or chemotherapy.

Radiotherapy may include one or more of the following categories of therapy: (i) external radiation therapy using electromagnetic radiation, and intraoperative radiation therapy using electromagnetic radiation; (ii) internal radiation therapy or brachytherapy; including interstitial radiation therapy or intraluminal radiation therapy; or (iii) systemic radiation therapy, including but not limited to iodine 131 and strontium 89.

Chemotherapy may include anti-tumor agents known in the art, for example, antineoplastic agents, cytostatic agents, antiangiogenic agents, immunotherapy approaches, efficacy enhancers, and the like described in this specification.

Therefore, in one aspect, there is provided a method of treating type I receptor tyrosine kinase-associated diseases or conditions in a subject in need thereof, wherein the compound of Formula (I) or pharmaceutically acceptable salts thereof is administered simultaneously, separately or sequentially with one or more additional anti-tumour agents.

In some embodiments, the one or more additional anti-tumour agents include capecitabine, anti-HER2 antibodies, and T-DM1.

In some embodiments, the type I receptor tyrosine kinase-associated disease or condition is a HER2-associated disease or condition. In some embodiments, the type I receptor tyrosine kinase-associated disease or condition is cancer. In some embodiments, the HER2-associated disease or condition includes breast cancer, gastric cancer, mCRC, NSCLC or metastasis thereof. In certain embodiments, the amounts of the compound of Formula (I), or a pharmaceutically acceptable salt thereof, and the one or more additional anti-tumour agents are jointly effective in producing an anti-cancer effect.

In a further aspect, there is provided a method of treating breast cancer brain metastases in a subject in need thereof, wherein the compound of Formula (I) or pharmaceutically acceptable salts thereof is administered simultaneously, separately or sequentially with one or more additional anti-tumour agents.

EXAMPLES

For the purpose of illustration, the following examples are included. However, it is to be understood that these examples do not limit the invention and are only meant to suggest a method of practicing the present disclosure. Persons skilled in the art will recognize that the chemical reactions described may be readily adapted to prepare a number of other compounds of the present disclosure, and alternative methods for preparing the compounds of the present disclosure are deemed to be within the scope of the present disclosure. For example, the synthesis of non-exemplified compounds according to the present disclosure may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the present disclosure.

The following abbreviations have been used in the examples:

| | |
|---|---|
| Ac$_2$O | acetic anhydride |
| AcOH | acetic acid |
| AcONa | sodium acetate |
| aq. | aqueous |
| BBr$_3$ | boron tribromide |
| Boc$_2$O | di-tert-butyl dicarbonate |
| CD$_3$I | deuterated iodomethane |
| CH$_2$Cl$_2$ | dichloromethane |
| CH$_3$COOH | acetic acid |
| Cs$_2$CO$_3$ | cesium carbonate |
| Cu(OAc)$_2$ | copper acetate |
| DAST | diethylaminosulfur trifluoride |
| DBU | 1,8-diazabicyclo[5.4.0]undec-7-ene |
| DCE | dichloroethane |
| DCM | dichloromethane |
| DHP | di-n-hexyl phthalate |
| DIEA or DIPEA | diisopropylethylamine |
| DMA | N,N-dimethylacetamide |
| DMF | N,N-dimethylformamide |
| DMSO | dimethyl sulfoxide |
| EtOH | ethanol |
| Et$_3$N | triethylamine |
| EtOAc | ethyl acetate |
| HCHO | formaldehyde |
| HCOOH | formic acid |
| H$_2$SO$_4$ | sulfuric acid |
| hr(s) | hour(s) |
| IPA | isopropyl alcohol |
| K$_2$CO$_3$ | potassium carbonate |
| LDA | lithium diisopropylamide |
| LiAlH$_4$ | lithium aluminium hydride |
| MeCN | acetonitrile |
| MeI | methyl iodide |
| MeOH | methanol |
| NaBH(OAc)$_3$ | sodium triacetoxyborohydride |
| NaH | sodium hydride |
| NaHCO$_3$ | sodium bicarbonate |
| NaIO$_4$ | sodium periodate |
| NaNO$_2$ | sodium nitrite |
| NaOH | sodium hydroxide |
| Na$_2$SO$_4$ | sodium sulfate |
| NH$_4$Cl | ammonium chloride |
| NH$_4$OH | ammonium hydroxide |
| Pd$_2$(dba)$_3$ | tris(dibenzylideneacetone)dipalladium(0) |
| Pd(OAc)$_2$ | palladium(II) acetate |
| Pd(OH)$_2$ | palladium(II) hydroxide |
| PE | petroleium ether |
| POCl$_3$ | phosphoric trichloride |
| i-PrOAc | isopropyl acetate |
| TsCl | 4-toluene sulfonyl chloride |
| TsOH | p-toluenesulfonic acid |
| SEMCl | 2-(trimethylsilyl)ethoxymethyl chloride |
| SOCl$_2$ | thionyl dichloride |
| TEA | triethylamine |
| THF | tetrahydrofuran |
| TFA | trifluoroacetic acid |
| TMS-CHN$_2$ | trimethylsilyldiazomethane |
| Xant-phos | 9,9-dimethyl-4,5-bis(diphenylphosphino)xanthene |

Example 1

N-(4-([1,2,4]triazolo[4,3-c]pyrimidin-7-yloxy)-3-methylphenyl)-5-(3-(dimethylamino)azetidin-1-yl)-6-methoxyquinazolin-4-amine

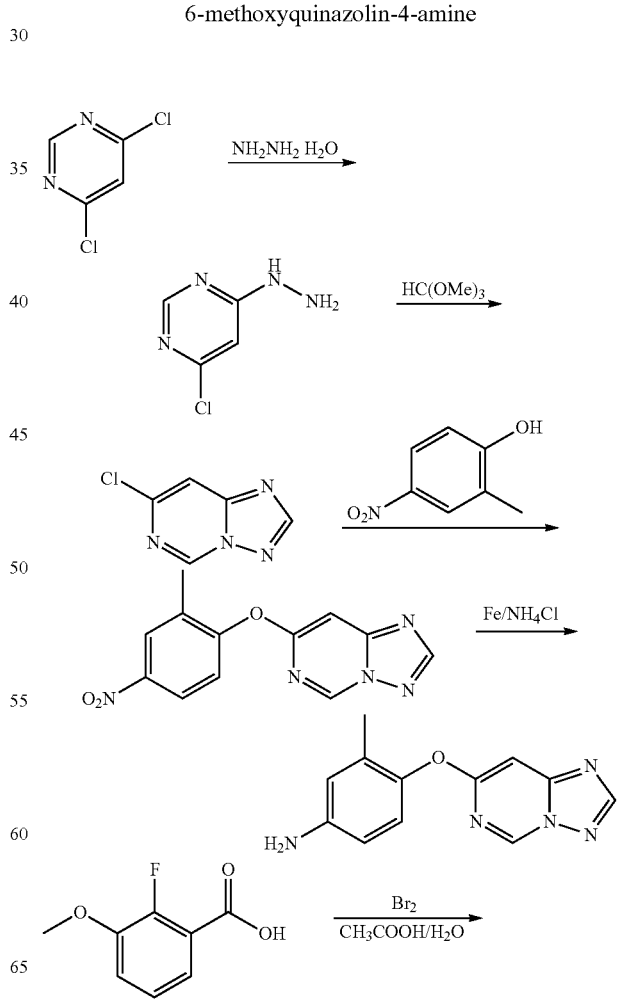

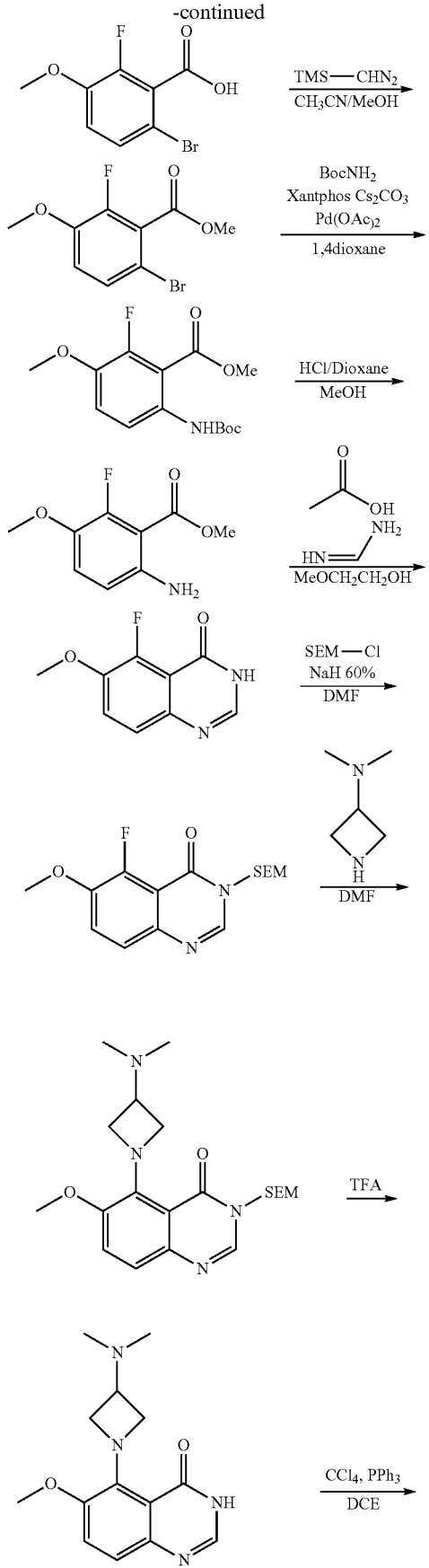

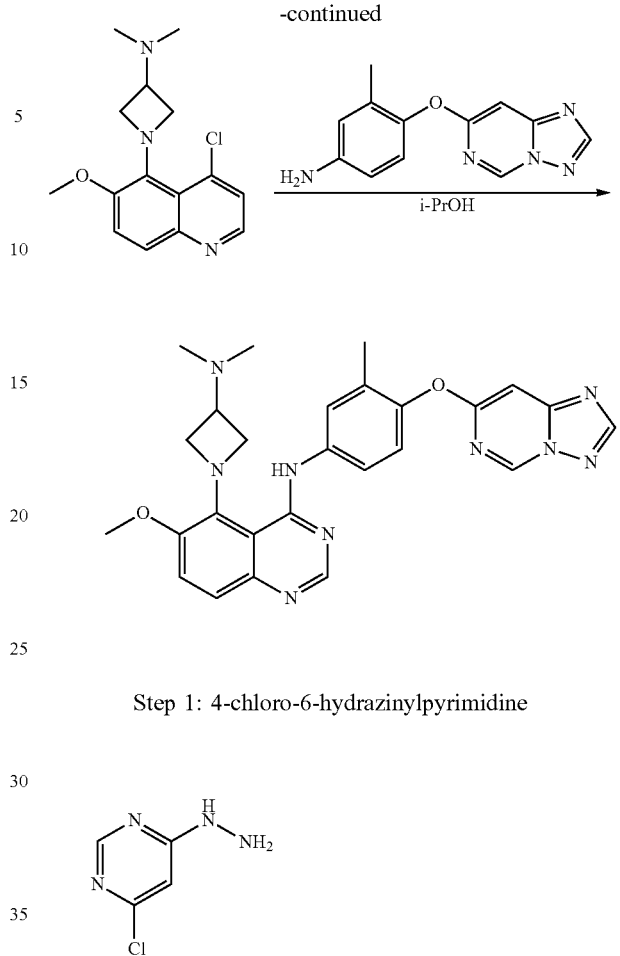

Step 1: 4-chloro-6-hydrazinylpyrimidine

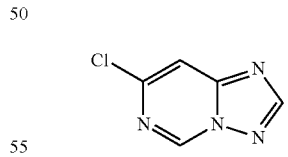

To a solution of 4,6-dichloropyrimidine (100 g, 675.7 mmol) in EtOH (900 mL) was added dropwise 50 wt % aqueous solution of hydrazine (130 mL) at 45° C. for 2 hrs. Then the reaction was stirred at 45-50° C. for 2 hrs. The crude mixture was filtered and the solid was washed with water to give the desired product (91 g, 94%) as a yellow solid. MS (ESI) m/z: 145.1 (M+H)$^+$.

Step 2: 7-chloro-[1,2,4]triazolo[1,5-c]pyrimidine

The solution of 4-chloro-6-hydrazinylpyrimidine (91 g, 632 mmol) in HC(OMe)$_3$ was stirred at 90° C. overnight. The crude mixture was concentrated and diluted with aq. NaHCO$_3$ (500 mL). The resulting mixture was extracted with EtOAc (500 mL×2). The organic phase was washed with water and brine, dried over anhydrous Na$_2$SO$_4$, filtered and concentrated. The residue was purified by column chromatography on silica gel (PE:EtOAc=5:1) to give the desired product (70 g, 72%) as a yellow solid. MS (ESI) m/z: 155.1.

Step 3: 7-(2-methyl-4-nitrophenoxy)-[1,2,4]triazolo[1,5-c]pyrimidine

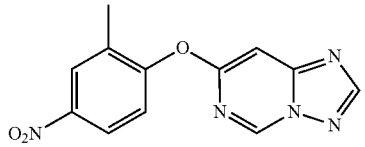

To a solution of 2-methyl-4-nitrophenol (30 g, 196 mmol) in MeCN (500 mL) was added K$_2$CO$_3$ (67.6 g, 490 mmol) at 0° C. and the crude mixture was stirred at room temperature for 15 min. Then 7-chloro-[1,2,4]triazolo[1,5-c]pyrimidine (33 g, 214 mmol) was added to the mixture. The reaction was stirred at 60° C. for 72 hrs. The crude mixture was filtered and the filtrate was concentrated. The residue was triturated with MeOH (50 mL) and filtered to give the desired product (13 g, 24%) as a brown solid. MS (ESI) m/z: 272.1 (M+H)$^+$.

Step 4: 4-([1,2,4]triazolo[1,5-c]pyrimidin-7-yloxy)-3-methylaniline

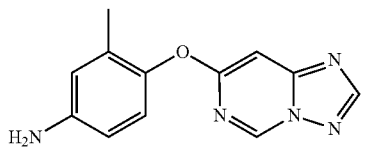 [SMILES: Cc1cc([N+](=O)[O-])ccc1Oc1cc2ncnn2cn1]

To a solution of 7-(2-methyl-4-nitrophenoxy)-[1,2,4]triazolo[1,5-c]pyrimidine (13 g, 48 mmol) in propan-2-ol (200 mL) was added Fe (53.7 g, 960 mmol), NH$_4$Cl (25.7 g, 480 mmol) and water (20 mL). The reaction was stirred at 120° C. for 1 hr. The crude mixture was cooled and filtered. The filtrate was concentrate and diluted with aq. NaHCO$_3$ (200 mL). The resulting mixture was extracted with DCM (200 mL×2). The organic phase was washed with water and brine, dried over anhydrous Na$_2$SO$_4$, filtered and concentrated. The residue was purified by column chromatography on silica gel (DCM:MeOH=20:1) to give the desired product (8.3 g, 72%) as a yellow solid. MS (ESI) m/z: 242.2 (M+H)$^+$.

A solution of 4-([1,2,4]triazolo[1,5-c]pyrimidin-7-yloxy)-3-methylaniline (25 mg) in DCM (2 mL) was added into one clean and dry tube (15 mm×105 mm) and sealed with parafilm. The tube was put in a shady place at r.t. for 3 days to form crystals. A single crystal of sufficient size was obtained for single crystal X-ray diffraction analysis.

Analysis of the single crystal of compound obtained, as presented in FIG. 1, shows the presence of the [1,2,4]triazolo[1,5-c]pyrimidine ring in the compound. The single crystal data and structure refinement parameters for the compound obtained are reported in Table 2.

TABLE 2

| Crystal data and structure refinement for the compound obtained | |
|---|---|
| Empirical formula | C$_{12}$ H$_{11}$ N$_5$ O |
| Formula weight | 241.26 |
| Temperature | 293(2) K |
| Wavelength | 0.71073 Å |
| Crystal system | Monoclinic |
| Space group | P 21 |
| Unit cell dimensions | a = 9.8361(6) Å    α = 90° |
|  | b = 4.4433(3) Å    β = 97.354(2)° |
|  | c = 13.2388(10) Å   γ = 90° |
| Volume | 573.84(7) Å$^3$ |
| Z | 2 |
| Density (calculated) | 1.396 mg/m$^3$ |
| Absorption coefficient | 0.096 mm$^{-1}$ |
| F(000) | 252 |
| Crystal size | 0.170 × 0.130 × 0.100 mm$^3$ |
| Theta range for data collection | 3.103 to 25.996° |
| Index ranges | −11 <= h <= 12, −5 <= k <= 5, −16 <= l <= 15 |
| Reflections collected | 6278 |
| Independent reflections | 2189 [R(int) = 0.0247] |
| Completeness to theta = 25.242° | 98.1% |
| Absorption correction | Semi-empirical from equivalents |
| Max. and min. transmission | 0.7456 and 0.6251 |
| Refinement method | Full-matrix least-squares on F$^2$ |
| Data/restraints/parameters | 2189/1/173 |
| Goodness-of-fit on F$^2$ | 1.064 |
| Final R indices [I > 2sigma(I)] | R1 = 0.0306, wR2 = 0.0697 |
| R indices (all data) | R1 = 0.0350, wR2 = 0.0730 |
| Absolute structure parameter | 1.4(7) |
| Extinction coefficient | 0.15(4) |
| Largest diff. peak and hole | 0.110 and −0.090 e · Å$^{-3}$ |

Step 5: 6-bromo-2-fluoro-3-methoxybenzoic acid

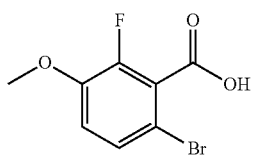

To a solution of 2-fluoro-3-methoxybenzoic acid (90.0 g, 529.4 mmol) was added in CH$_3$COOH/H$_2$O (300 mL/300 mL). The mixture was stirred at 0° C. and then Br$_2$ (41 mL, 794.12 mmol) in CH$_3$COOH (50 mL) was added thereto dropwise. The reaction mixture was stirred from 0° C. to room temperature for 1 h. When LCMS showed the reaction was complete, H$_2$O (2.5 L) was added. The precipitate was filtered and the filter cake was wash with water. The crude product was precipitated in petroleum ether to get the title compound (110 g, 84% yield) as white solid. MS (ESI) m/z: 247.1 (M+H)$^+$.

Step 6: methyl 6-bromo-2-fluoro-3-methoxybenzoate

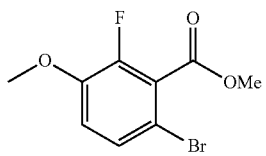

To a stirred solution of 6-bromo-2-fluoro-3-methoxybenzoic acid (90 g, 361.4 mmol) in 1.05 L of MeCN/MeOH (6/1) was added TMS-CHN$_2$ (450 mL, 904.0 mmol) at 0° C. under Ar$_2$ protection. Then the solution was allowed to warm to room temperature and stirred for 1 h. When LCMS showed the reaction was completed, H$_2$O (1.5 L) was added and the mixture was extracted with EtOAc (800 mL×3). The organic layers were washed with brine, concentrated and the residue was purified by column chromatography (PE:EtOAc=20:1) to give the title compound (75 g, 79% yield) as a white solid. MS (ESI) m/z: 263.0 (M+H)$^+$.

Step 7: methyl 6-((tert-butoxycarbonyl)amino)-2-fluoro-3-methoxybenzoate

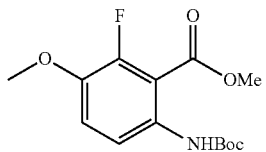 [SMILES: COC(=O)c1c(NC(=O)OC(C)(C)C)ccc(OC)c1F]

To a solution of methyl 6-bromo-2-fluoro-3-methoxybenzoate (75 g, 284.1 mmol) and tert-butyl carbamate in 1,4-Dioxane (2000 mL) were added Pd(OAc)$_2$ (4.45 g 19.8 mmol), Xantphos (32.84 g, 56.8 mmol) and Cs$_2$CO$_3$ (185.23 g, 568.2 mmol). The mixture was stirred at 100° C. for 4 h under Ar$_2$ protection. When LCMS showed the reaction was complete, the mixture was filtered and concentrated. The residue was purified by column chromatography (PE:EtOAc=25:1) to give the title compound (70 g, 82% yield) as a white solid. MS (ESI) m/z: 200.2 (M+H-100)$^+$.

Step 8: methyl 6-amino-2-fluoro-3-methoxybenzoate hydrochloride

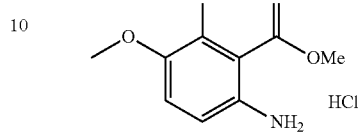

To a solution of methyl 6-((tert-butoxycarbonyl)amino)-2-fluoro-3-methoxybenzoate (70 g, 234.1 mmol) in methanol (1.5 L) was added HCl/Dioxane solution (4 M, 200 mL). The mixture was stirred at room temperature overnight. When LCMS indicated the reaction was completed, the reaction mixture was concentrated to dryness to get crude product (55 g, 100% yield) as a white solid. MS (ESI) m/z: 199.9 (M+H)$^+$.

Step 9: 5-fluoro-6-methoxyquinazolin-4(3H)-one

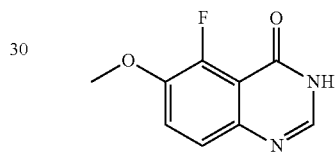

To a solution of methyl 6-amino-2-fluoro-3-methoxybenzoate hydrochloride (55 g, 234 mmol) in 2-Methoxyethanol (300 mL) was added formamidine acetate (36.5 g, 351 mmol). The mixture was stirred at 100° C. overnight. When LCMS showed reaction was complete, the reaction mixture was concentrated in vacuum and diluted with H$_2$O (1.5 L). The precipitate was filtered and the filter cake was washed with H$_2$O (100 mL) and PE (200 mL). The solid was collected and dried in vacuum to afford the title compound (42 g, 92% yield) as a brown solid. MS (ESI) m/z: 195.1 (M+H)$^+$. $^1$H NMR (400 MHz, DMSO-d$_6$): δ 12.12 (s, 1H), 7.93 (s, 1H), 7.72-7.68 (t, J=8.48 Hz, 1H), 7.49-7.46 (m, 1H), 3.92 (s, 3H).

Step 10: 5-fluoro-6-methoxy-3-((2-(trimethylsilyl)ethoxy)methyl)quinazolin-4(3H)-one

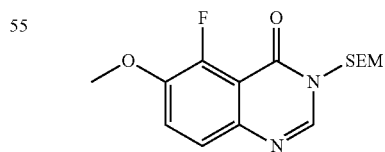

To a solution of 5-fluoro-6-methoxyquinazolin-4(3H)-one (42 g, 216.5 mmol) in dry DMF (300 mL) was added 60% NaH (12.98 g, 324.7 mmol) in batches at 0° C. The mixture was stirred at this temperature for 0.5 h then SEMCl (54.2 g, 324.7 mmol) was added dropwise. After stirred at room temperature for 0.5 h, the mixture was diluted with water (200 mL) and extracted with EtOAc (200 mL×3). The organic layers were washed with water (150 mL), brine (100 mL), dried over anhydrous $Na_2SO_4$ and filtered. The filtrate was concentrated and the residue was purified by column chromatography (EtOAc:PE=1:50) to afford the title compound (40 g, 60% yield) as white solid. MS (ESI) m/z: 325.1 (M+H)+. $^1$H NMR (400 MHz, CDCl$_3$) δ 8.01 (s, 1H), 7.51-7.42 (m, 2H), 5.40 (s, 1H), 3.98 (s, 3H), 3.71-3.67 (t, J=8.4 Hz, 2H), 0.98-0.94 (t, J=8.4 Hz, 2H), 0.00 (s, 9H).

Step 11: 5-(3-(dimethylamino)azetidin-1-yl)-6-methoxy-3-((2-(trimethylsilyl)ethoxy)methyl)quinazolin-4(3H)-one

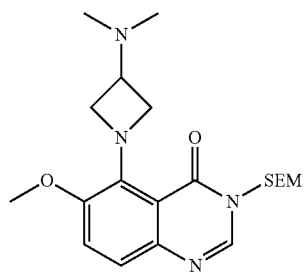 [SMILES: COc1ccc2ncn(COCC[Si](C)(C)C)c(=O)c2c1N1CC(N(C)C)C1]

To a solution of 5-fluoro-6-methoxy-3-((2-(trimethylsilyl)ethoxy)methyl)quinazolin-4(3H)-one (3.2 g, 10 mmol) and $Cs_2CO_3$ (9.8 g, 30 mmol) in DMF (200 mL) stirred at room temperature, was added N,N-dimethylazetidin-3-aminedihydrochloride (2 g, 12 mmol). The resulting mixture was stirred at 90° C. for 16 hrs. The crude mixture was filtered and washed with EtOAc (100 mL). The filtrate was poured into ice water and extracted with EtOAc (300 mL). The organic phase was separated, washed with water and brine, dried over anhydrous $Na_2SO_4$, filtered and concentrated. The residue was purified by column chromatography on silica gel to give the desired product (1.8 g, 45% yield) as oil. MS (ESI) m/z: 405 (M+H)+.

Step 12: 5-(3-(dimethylamino)azetidin-1-yl)-6-methoxyquinazolin-4(3H)-one

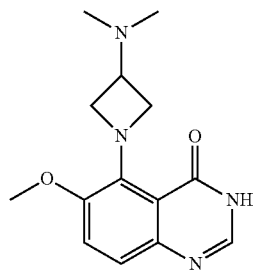 [SMILES: COc1ccc2nc[nH]c(=O)c2c1N1CC(N(C)C)C1]

To a solution of 5-(3-(dimethylamino)azetidin-1-yl)-6-methoxy-3-((2-(trimethylsilyl)ethoxy)methyl)quinazolin-4(3H)-one (1.1 g, 2.7 mmol) in DCM (50 mL) stirred at room temperature, was added TFA (10 mL). The resulting mixture was stirred at room temperature for 4 hrs and concentrated to dryness. The residue was basified with aq.NaHCO$_3$ to adjusted pH=9, extracted with DCM (100 mL), dried over anhydrous $Na_2SO_4$, filtered and concentrated to give the desired product (0.7 g, 94% yield) as oil. MS (ESI) m/z: 275 (M+H)+.

Step 13: 1-(4-chloro-6-methoxyquinazolin-5-yl)-N,N-dimethylazetidin-3-amine

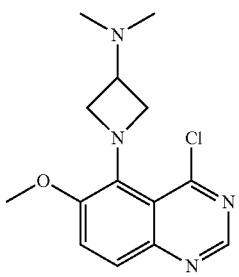 [SMILES: COc1ccc2ncnc(Cl)c2c1N1CC(N(C)C)C1]

To a solution of 5-(3-(dimethylamino)azetidin-1-yl)-6-methoxyquinazolin-4(3H)-one (100 mg, 0.36 mmol) and triphenylphosphine (191 mg, 0.73 mmol) in 1,2-dichloroethane (5 mL) stirred at room temperature, was added carbon tetrachloride (167 mg, 1.10 mmol). The resulting mixture was heated to 70° C. overnight. After cooled down, the solvent was evaporated to dryness, and the crude was purified by prep-TLC to afford the desired product (82 mg, 75% yield) as a yellow solid. MS (ESI) m/z: 293 (M+H)+.

Step 14: N-(4-([1,2,4]triazolo[1,5-c]pyrimidin-7-yloxy)-3-methylphenyl)-5-(3-(dimethylamino)azetidin-1-yl)-6-methoxyquinazolin-4-amine

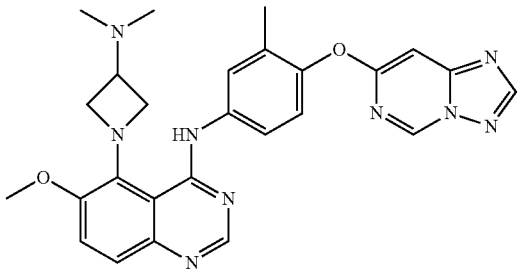 [SMILES: COc1ccc2ncnc(Nc3ccc(Oc4cc5ncnn5cn4)c(C)c3)c2c1N1CC(N(C)C)C1]

A mixture of 1-(4-chloro-6-methoxyquinazolin-5-yl)-N,N-dimethylazetidin-3-amine (82 mg, 0.27 mmol) and 4-([1,2,4]triazolo[1,5-c]pyrimidin-7-yloxy)-3-methylaniline (66 mg, 0.27 mmol) in propan-2-ol (20 mL) was heated to 70° C. overnight. The crude mixture was cooled down and quenched with aq. NaHCO$_3$ solution (10 mL). The resulting mixture was extracted with DCM (20 mL). The organic phase was washed with water and brine, dried over anhydrous $Na_2SO_4$, filtered and concentrated. The residue was purified by prep-TLC to afford the desired product as a white solid (32 mg, 23% yield). MS (ESI) m/z: 498 (M+H)+. $^1$H NMR (400 MHz, CDCl$_3$) δ 14.40 (br, 0.5H), 14.00 (br, 0.5H), 9.20 (d, J=1.3 Hz, 1H), 8.56 (s, 1H), 8.26 (d, J=44.7 Hz, 2H), 7.97-7.63 (m, 1H), 7.47 (d, J=9.2 Hz, 1H), 7.12 (d, J=8.9 Hz, 1H), 6.88 (s, 1H), 4.70-4.41 (m, 2H), 4.06 (s, 3H), 3.90-3.64 (m, 2H), 3.36-3.14 (m, 1H), 2.44-2.20 (m, 9H).

Example 2

(R)—N-(4-([1,2,4]-triazolo[1,5-c]pyrimidin-7-yloxy)-3-methylphenyl)-5-(3-(dimethylamino)pyrrolidin-1-yl)-6-methoxyquinazolin-4-amine

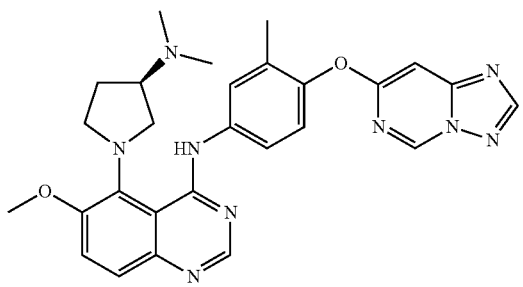 [SMILES: COc1ccc2ncnc(Nc3ccc(Oc4cc5ncnn5cn4)c(C)c3)c2c1N1CC[C@@H](N(C)C)C1]

The title compound was prepared using similar procedure as in Example 1 to afford the desired product as a white solid. MS: m/z 512 (M+H)$^+$. $^1$H NMR (400 MHz, CDCl$_3$) δ 13.66 (d, J=24.1 Hz, 1H), 9.20 (dd, J=3.6, 1.2 Hz, 1H), 8.57 (s, 1H), 8.32 (d, J=4.1 Hz, 1H), 8.06-7.63 (m, 4H), 7.49 (dd, J=9.2, 4.3 Hz, 1H), 7.12 (dd, J=13.5, 8.7 Hz, 1H), 6.88 (dd, J=16.3, 1.3 Hz, 1H), 4.01 (d, J=3.7 Hz, 3H), 3.69-3.24 (m, 4H), 3.02 (d, J=33.0 Hz, 1H), 2.44-2.20 (m, 11H).

Example 3

(S)—N-(4-([1,2,4]triazolo[1,5-c]pyrimidin-7-yloxy)-3-methylphenyl)-5-(3-(dimethylamino)pyrrolidin-1-yl)-6-methoxyquinazolin-4-amine

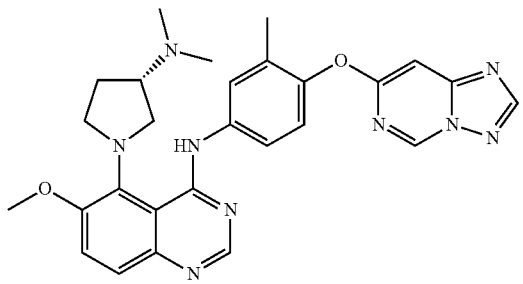 [SMILES: COc1ccc2ncnc(Nc3ccc(Oc4cc5ncnn5cn4)c(C)c3)c2c1N1CC[C@H](N(C)C)C1]

The title compound was prepared using similar procedure as in Example 1 to give the desired product as a yellow solid. MS: 512 (M+H)$^+$. $^1$H NMR (400 MHz, CDCl$_3$) δ 13.68 (d, J=23.0 Hz, 1H), 9.20 (d, J=3.6 Hz, 1H), 8.57 (s, 1H), 8.32 (d, J=4.0 Hz, 1H), 8.07-7.63 (m, 4H), 7.48 (dd, J=9.2, 4.0 Hz, 1H), 7.11 (dd, J=13.9, 8.7 Hz, 1H), 6.88 (d, J=16.3 Hz, 1H), 4.01 (d, J=2.7 Hz, 3H), 3.70-3.22 (m, 4H), 3.12-2.89 (m, 1H), 2.59-2.03 (m, 11H).

Example 4

N-(4-([1,2,4]triazolo[1,5-c]pyrimidin-7-yloxy)-3-methylphenyl)-6-methoxy-5-morpholinoquinazolin-4-amine

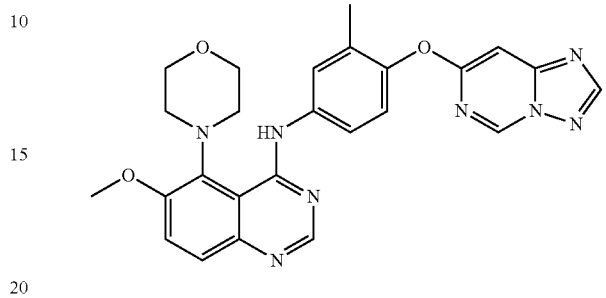

The title compound was prepared using similar procedure as in Example 1 to give the desired product as a white solid. MS: m/z 485 (M+H)$^+$. $^1$H NMR (400 MHz, CDCl$_3$) δ 13.60 (s, 1H), 9.20 (d, J=1.3 Hz, 1H), 8.56 (s, 1H), 8.32 (s, 1H), 7.90 (d, J=2.6 Hz, 1H), 7.86-7.68 (m, 2H), 7.49 (d, J=9.3 Hz, 1H), 7.14 (d, J=8.6 Hz, 1H), 6.90 (d, J=1.3 Hz, 1H), 4.17-3.84 (m, 9H), 2.93 (d, J=10.6 Hz, 2H), 2.27 (s, 3H).

Example 5

N-(4-([1,2,4]triazolo[1,5-c]pyrimidin-7-yloxy)-3-methylphenyl)-6-methoxy-5-((1-methylpiperidin-4-yl)oxy)quinazolin-4-amine

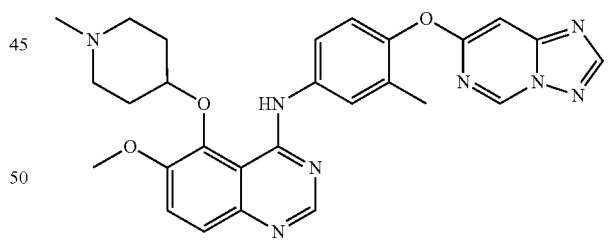

The title compound was prepared using similar procedure as in Example 1 to give the desired product as a white solid. MS: m/z 513 (M+H)$^+$. $^1$H NMR (400 MHz, CDCl$_3$) δ 10.26 (s, 1H), 9.20 (s, 1H), 8.59 (s, 1H), 8.32 (s, 1H), 7.85 (d, J=2.4 Hz, 1H), 7.72-7.69 (m, 1H) 7.66 (d, J=9.2 Hz, 1H), 7.51 (d, J=9.2 Hz, 1H), 7.12 (d, J=8.8 Hz, 1H), 6.90 (s, 1H), 4.57-4.51 (m, 1H), 4.00 (s, 3H), 2.91-2.88 (m, 2H), 2.27 (s, 6H), 2.13-2.04 (m, 2H), 2.01-1.94 (m, 2H), 1.94-1.81 (m, 2H).

The following compounds were prepared using similar procedure as in Example 1 but with different starting materials.

| Ex # | Structure | Name | MS m/z |
|---|---|---|---|
| 6 | 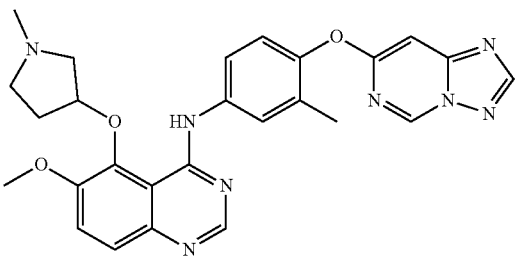 [SMILES: COc1ccc2ncnc(Nc3ccc(Oc4cc5ncnn5cn4)c(C)c3)c2c1OC1CCN(C)C1] | N-(4-([1,2,4]triazolo[1,5-c]pyrimidin-7-yloxy)-3-methylphenyl)-6-methoxy-5-((1-methylpyrrolidin-3-yl)oxy)quinazolin-4-amine | 499 (M + H)+ |
| 7 | 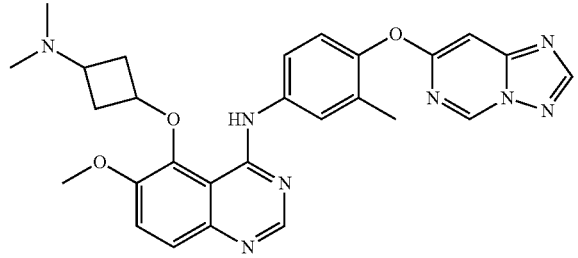 [SMILES: COc1ccc2ncnc(Nc3ccc(Oc4cc5ncnn5cn4)c(C)c3)c2c1OC1CC(N(C)C)C1] | N-(4-([1,2,4]triazolo[1,5-c]pyrimidin-7-yloxy)-3-methylphenyl)-5-(3-(dimethylamino)cyclobutoxy)-6-methoxyquinazolin-4-amine | 513 (M + H)+ |
| 8 | 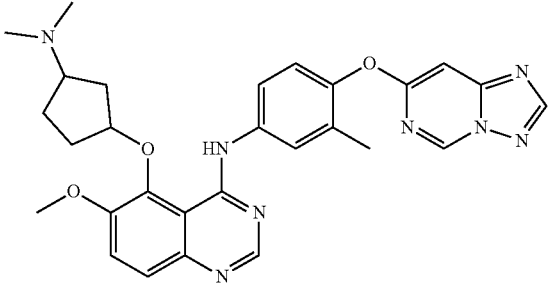 [SMILES: COc1ccc2ncnc(Nc3ccc(Oc4cc5ncnn5cn4)c(C)c3)c2c1OC1CCC(N(C)C)C1] | N-(4-([1,2,4]triazolo[1,5-c]pyrimidin-7-yloxy)-3-methylphenyl)-5-((3-(dimethylamino)cyclopentyl)oxy)-6-methoxyquinazolin-4-amine | 527 (M + H)+ |
| 9 | 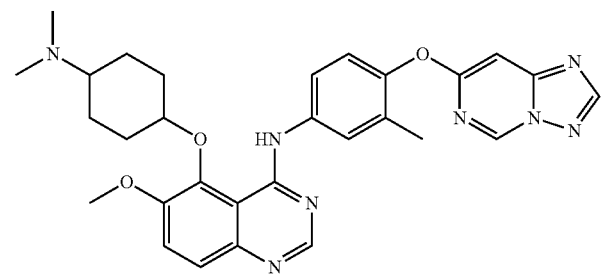 [SMILES: COc1ccc2ncnc(Nc3ccc(Oc4cc5ncnn5cn4)c(C)c3)c2c1OC1CCC(N(C)C)CC1] | N-(4-([1,2,4]triazolo[1,5-c]pyrimidin-7-yloxy)-3-methylphenyl)-5-((4-(dimethylamino)cyclohexyl)oxy)-6-methoxyquinazolin-4-amine | 541 (M + H)+ |
| 10 | 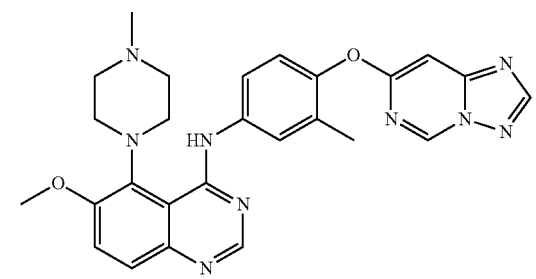 [SMILES: COc1ccc2ncnc(Nc3ccc(Oc4cc5ncnn5cn4)c(C)c3)c2c1N1CCN(C)CC1] | N-(4-([1,2,4]triazolo[1,5-c]pyrimidin-7-yloxy)-3-methylphenyl)-6-methoxy-5-(4-methylpiperazin-1-yl)quinazolin-4-amine | 498 (M + H)+ |

Example 11

N-(4-([1,2,4]triazolo[1,5-c]pyrimidin-7-yloxy)-3-methylphenyl)-5-(3-(dimethylamino)azetidin-1-yl)-6-ethoxyquinazolin-4-amine

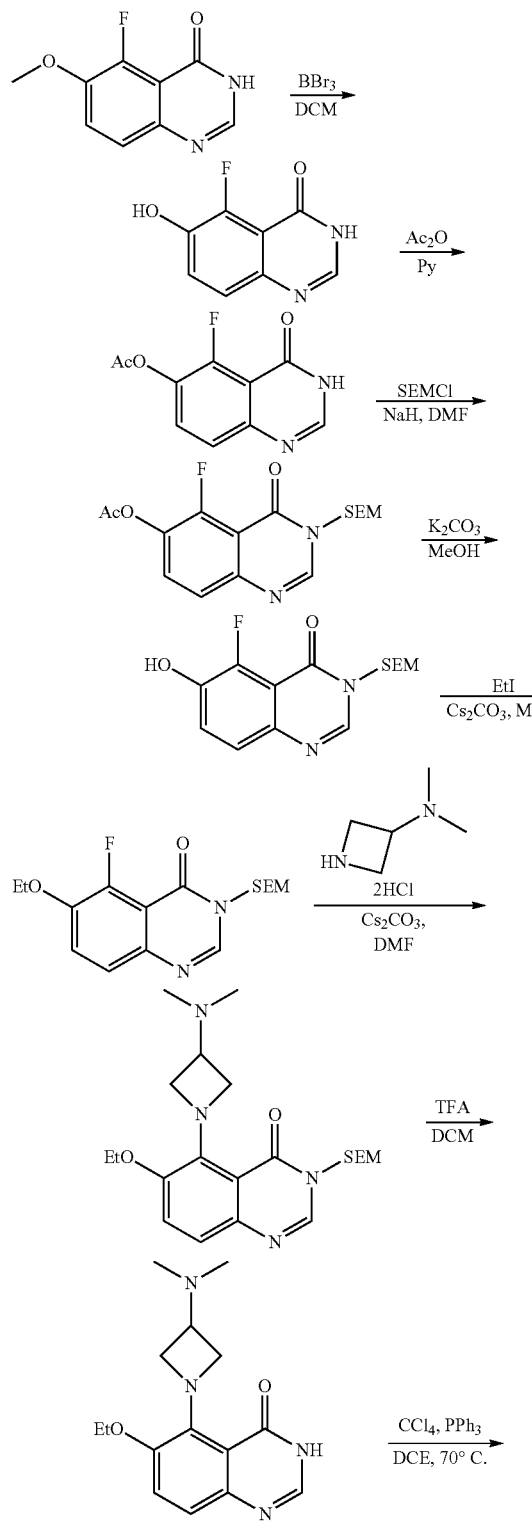

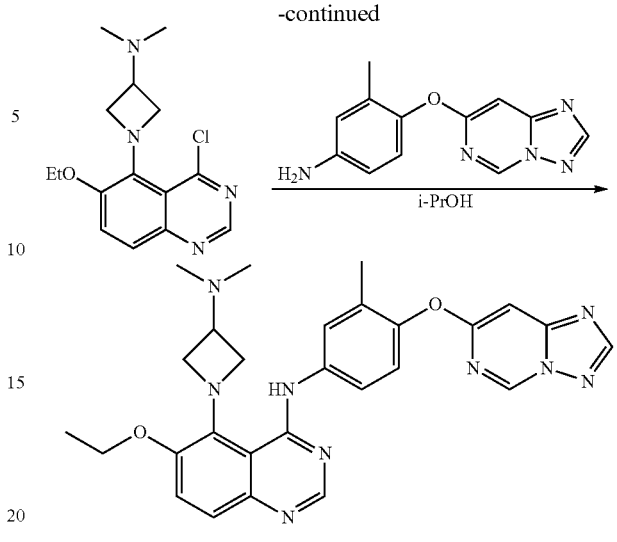

Step 1: 5-fluoro-6-hydroxyquinazolin-4(3H)-one

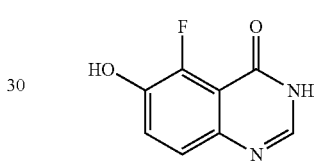

To a solution of 5-fluoro-6-methoxyquinazolin-4(3H)-one (1 g, 5.15 mmol) in anhydrous DCM (15 mL) stirred at room temperature under $N_2$, was added $BBr_3$ (6.5 g, 25.8 mmol) at 0° C. dropwise. The resulting mixture was stirred at room temperature for 48 hrs and the reaction was quenched with MeOH at 0° C. The solvent was evaporated to dryness to give the crude product (1 g) as a brown solid, which was used for next step without further purification. MS: 181 (M+H)$^+$.

Step 2: 5-fluoro-4-oxo-3,4-dihydroquinazolin-6-yl acetate

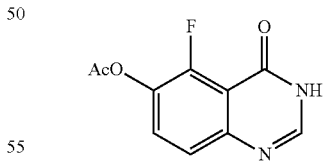

To a solution of 5-fluoro-6-hydroxyquinazolin-4(3H)-one (1 g, 5.5 mmol) in $Ac_2O$ (10 mL) stirred at room temperature, was added and pyridine (1 mL). The resulting mixture was stirred at 110° C. for 2 hrs. After cooled down, the crude mixture poured into ice water and extracted with DCM (50 mL). The organic phase was separated, washed with water and brine, dried over anhydrous $Na_2SO_4$, filtered and concentrated. The residue was purified by column chromatography on silica gel to give the desired product (560 mg, 45% yield for two steps) as a yellow solid. MS: 223 (M+H)$^+$.

Step 3: 5-fluoro-4-oxo-3-((2-(trimethylsilyl)ethoxy)methyl)-3,4-dihydroquinazolin-6-yl acetate

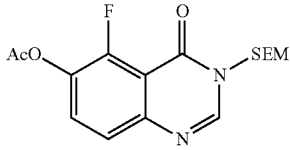 [SMILES: CC(=O)Oc1ccc2ncn(COCC[Si](C)(C)C)c(=O)c2c1F]

To a solution of 5-fluoro-4-oxo-3,4-dihydroquinazolin-6-yl acetate (560 mg, 2.52 mmol) in anhydrous DMF (10 mL) stirred at at 0° C. under nitrogen, was added NaH (151 mg, 3.78 mmol) portion-wise. The resulting mixture was stirred at 0° C. for 10 mins and then SEMCl (549 mg, 3.28 mmol) was added dropwise at 0° C. The resulting mixture was stirred at room temperature for another 30 mins and then poured into ice water. The resulting mixture was extracted with EtOAc (20 mL). The organic phase was separated, washed with water and brine, dried over anhydrous $Na_2SO_4$, filtered and concentrated to give the crude 5-fluoro-4-oxo-3-((2-(trimethylsilyl)ethoxy)methyl)-3,4-dihydroquinazolin-6-yl acetate (1 g) as a yellow solid. MS: 353 $(M+H)^+$.

Step 4: 5-fluoro-6-hydroxy-3-((2-(trimethylsilyl)ethoxy)methyl)quinazolin-4(3H)-one

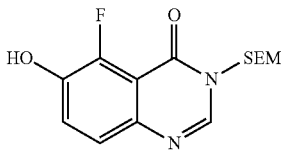 [SMILES: C[Si](C)(C)CCOCn1cnc2ccc(O)c(F)c2c1=O]

To a solution of 5-fluoro-4-oxo-3-((2-(trimethylsilyl)ethoxy)methyl)-3,4-dihydroquinazolin-6-yl acetate (1 g, 2.84 mmol) in MeOH (15 mL) stirred at room temperature, was added $K_2CO_3$ (1.2 g, 8.52 mml). The resulting mixture was stirred at room temperature for 16 hrs. The crude mixture was filtered, the filtrate was then concentrated. The residue was purified by column chromatography on silica gel to give the desired product (500 mg, 57% yield for two steps) as an off-white solid. MS: 311 $(M+H)^+$.

Step 5: 6-ethoxy-5-fluoro-3-((2-(trimethylsilyl)ethoxy)methyl)quinazolin-4(3H)-one

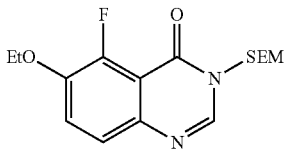 [SMILES: CCOc1ccc2ncn(COCC[Si](C)(C)C)c(=O)c2c1F]

To a mixture of 5-fluoro-6-hydroxy-3-((2-(trimethylsilyl)ethoxy)methyl)quinazolin-4(3H)-one (500 mg, 1.61 mmol) and $Cs_2CO_3$ (1.55 g, 4.83 mmol) in MeCN (10 mL) stirred at room temperature, was added EtI (502 mg, 3.22 mmol). The resulting mixture was stirred at 60° C. for 16 hrs. The crude mixture was filtered, washed with EtOAc (10 mL). The filtrate was poured into ice water, extracted with EtOAc (30 mL). The organic phase was separated, washed with water and brine, dried over anhydrous $Na_2SO_4$, filtered and concentrated to give the desired product (400 mg, 54% yield) as an off-white solid. MS: 339 $(M+H)^+$.

Step 6: 5-(3-(dimethylamino)azetidin-1-yl)-6-ethoxy-3-((2-(trimethylsilyl)ethoxy)methyl)quinazolin-4(3H)-one

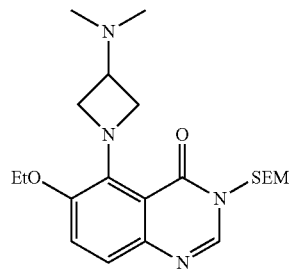 [SMILES: CCOc1ccc2ncn(COCC[Si](C)(C)C)c(=O)c2c1N1CC(N(C)C)C1]

To a mixture of N,N-dimethylazetidin-3-amine dihydrochloride (264 mg, 1.53 mmol) and $Cs_2CO_3$ (1.54 g, 4.72 mmol) in DMF (5 mL) stirred at room temperature, was added 6-ethoxy-5-fluoro-3-((2-(trimethylsilyl)ethoxy)methyl)quinazolin-4(3H)-one (400 mg, 1.18 mmol). The resulting mixture was stirred at 90° C. for 16 hrs. The crude mixture was filtered, washed with EtOAc (10 mL). The filtrate was poured into ice water and extracted with EtOAc (30 mL). The organic phase was separated, washed with water and brine, dried over anhydrous $Na_2SO_4$, filtered and concentrated. The residue was purified by column chromatography on silica gel to give the desired product (300 mg, 61% yield) as oil. MS: 419 $(M+H)^+$.

Step 7: 5-(3-(dimethylamino)azetidin-1-yl)-6-ethoxyquinazolin-4(3H)-one

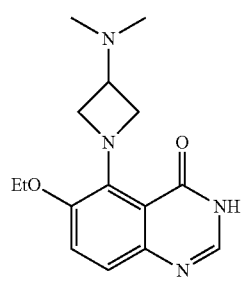 [SMILES: CCOc1ccc2nc[nH]c(=O)c2c1N1CC(N(C)C)C1]

To a solution of 5-(3-(dimethylamino)azetidin-1-yl)-6-ethoxy-3-((2-(trimethylsilyl)ethoxy)methyl)quinazolin-4(3H)-one (300 mg, 0.718 mmol) in DCM (4 mL) stirred at room temperature, was added in TFA (2 mL). The resulting mixture was stirred at room temperature for 4 hrs. The crude mixture was concentrated to dryness and the residue was basified with aq. $NaHCO_3$ to adjusted pH=9. The resulting mixture was extracted with DCM (15 mL), dried over anhydrous $Na_2SO_4$, filtered and concentrated to give the desired product (200 mg crude, 98% yield) as oil. MS: 289 $(M+H)^+$.

Step 8: 1-(4-chloro-6-ethoxyquinazolin-5-yl)-N,N-dimethylazetidin-3-amine

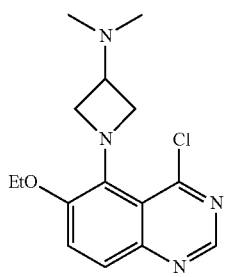 [SMILES: CCOc1ccc2ncnc(Cl)c2c1N1CC(N(C)C)C1]

To a solution of 5-(3-(dimethylamino)azetidin-1-yl)-6-ethoxyquinazolin-4(3H)-one (100 mg, 0.35 mmol) and triphenylphosphine (184 mg, 0.70 mmol) in 1,2-dichloroethane (5 mL) stirred at room temperature, was added carbon tetrachloride (267 mg, 1.75 mmol). The resulting mixture was heated to 70° C. overnight. After the reaction was cooled down and concentrated, the residue was purified by prep-TLC to afford the desired product (82 mg, 76% yield) as a yellow solid. LCMS: 307 (M+H)$^+$.

Step 9: N-(4-([1,2,4]triazolo[1,5-c]pyrimidin-7-yloxy)-3-methylphenyl)-5-(3-(dimethylamino)azetidin-1-yl)-6-ethoxyquinazolin-4-amine

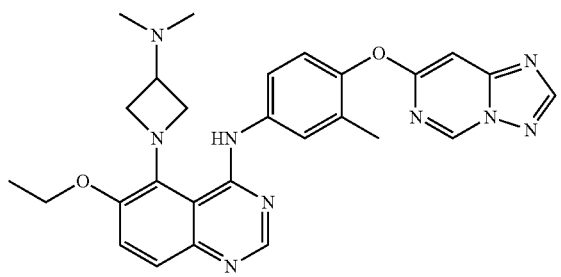 [SMILES: CCOc1ccc2ncnc(Nc3ccc(Oc4cc5ncnn5cn4)c(C)c3)c2c1N1CC(N(C)C)C1]

A mixture of 1-(4-chloro-6-ethoxyquinazolin-5-yl)-N,N-dimethylazetidin-3-amine (50 mg, 0.16 mmol) and 4-([1,2,4]triazolo[1,5-c]pyrimidin-7-yloxy)-3-methylaniline (39 mg, 0.16 mmol) in propan-2-ol (5 mL) was heated to 80° C. overnight. After cooled down, the crude mixture was quenched with aq. NaHCO$_3$ solution (10 mL), extracted with DCM (20 mL). The organic phase was washed with water and brine, dried over anhydrous Na$_2$SO$_4$, filtered and concentrated. The residue was purified by prep-TLC to afford the desired product (32 mg, 35% yield) as a white solid. MS: 511 (M+H)$^+$. $^1$H NMR (400 MHz, CDCl$_3$) δ 9.20 (d, J=1.2 Hz, 1H), 8.57 (s, 1H), 8.30 (d, J=12.9 Hz, 2H), 8.20 (s, 1H), 7.77 (s, 1H), 7.46 (d, J=9.3 Hz, 1H), 7.13 (d, J=8.7 Hz, 1H), 6.89 (s, 1H), 4.56 (q, J=11.3, 7.3 Hz, 2H), 4.35-4.25 (m, 2H), 3.79 (d, J=32.2 Hz, 2H), 3.17 (s, 1H), 2.27 (s, 9H), 1.60 (d, J=6.9 Hz, 3H).

Example 12

N-(4-([1,2,4]triazolo[4,3-c]pyrimidin-7-yloxy)-3-methylphenyl)-5-(3-(dimethylamino)azetidin-1-yl)-6-(2-fluoroethoxy)quinazolin-4-amine

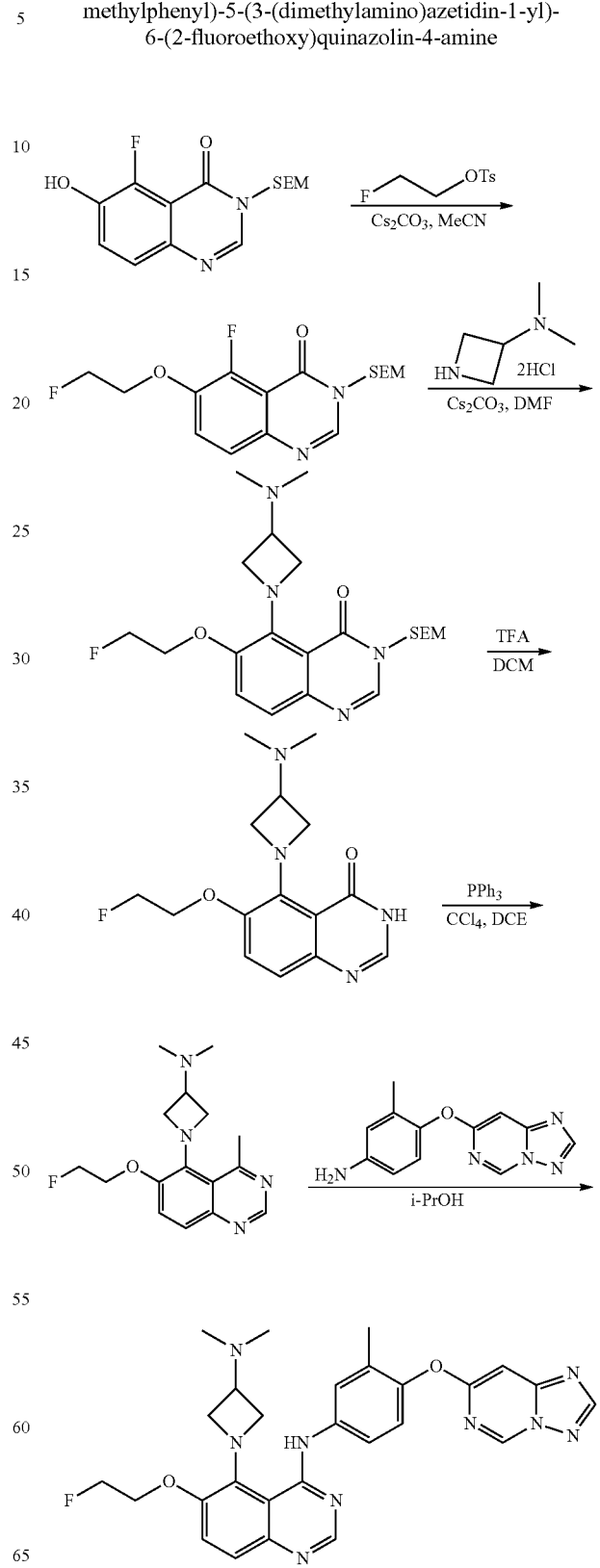

Step 1: 5-fluoro-6-(2-fluoroethoxy)-3-((2-(trimethylsilyl)ethoxy)methyl)quinazolin-4(3H)-one

To a solution of 5-fluoro-6-hydroxy-3-((2-(trimethyl silyl)ethoxy)methyl)quinazolin-4(3H)-one (140 mg, 0.45 mmol) and 2-fluoroethyl 4-methylbenzenesulfonate (196 mg, 0.9 mmol) in MeCN (5 mL) stirred at room temperature, was added $Cs_2CO_3$ (440 mg, 1.36 mmol). The resulting mixture was stirred at 60° C. for 16 hrs. The crude mixture was filtered, washed with EtOAc (10 mL). The filtrate was poured into ice water and extracted with EtOAc (20 mL). The organic phase was separated, washed with brine, dried over anhydrous $Na_2SO_4$, filtered and concentrated. The residue was purified by column chromatography on silica gel to give the desired product (140 mg, 87% yield) as an off-white solid. MS: 357 (M+H)+.

Step 2: 5-(3-(dimethylamino)azetidin-1-yl)-6-(2-fluoroethoxy)-3-((2-(trimethylsilyl)ethoxy)methyl)quinazolin-4(3H)-one

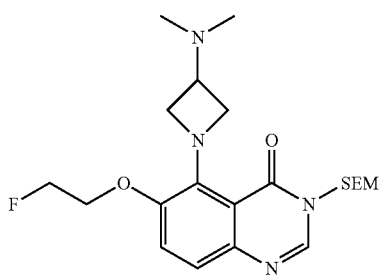 [SMILES: CN(C)C1CN(c2c(OCCF)ccc3ncn(COCC[Si](C)(C)C)c(=O)c23)C1]

To a solution of 5-fluoro-6-(2-fluoroethoxy)-3-((2-(trimethylsilyl)ethoxy)methyl)quinazolin-4(3H)-one (140 mg, 0.39 mmol) and N,N-dimethylazetidin-3-amine dihydrochloride (88 mg, 0.51 mmol) in DMF (5 mL) stirred at room temperature, was added $Cs_2CO_3$ (512 mg, 2.16 mmol). The resulting mixture was stirred at 90° C. for 16 hrs. The crude mixture was then filtered and washed with EtOAc. The filtrate was poured into ice water and extracted with EtOAc (20 mL). The organic phase was separated, washed with brine, dried over anhydrous $Na_2SO_4$, filtered and concentrated. The residue was purified by column chromatography on silica gel to give the desired product (100 mg, 58% yield) as an oil. MS: 437 (M+H)+.

Step 3: 5-(3-(dimethylamino)azetidin-1-yl)-6-(2-fluoroethoxy)quinazolin-4(3H)-one

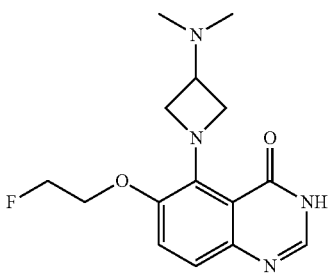 [SMILES: CN(C)C1CN(c2c(OCCF)ccc3nc[nH]c(=O)c23)C1]

To a solution of 5-(3-(dimethylamino)azetidin-1-yl)-6-(2-fluoroethoxy)-3-((2-(trimethylsilyl)ethoxy)methyl)quinazolin-4(3H)-one (100 mg, 0.23 mmol) in DCM (4 mL), was added TFA (2 mL). The resulting mixture was stirred at room temperature for 4 hrs. The crude mixture was concentrated to dryness. The residue was basified with aq. $NaHCO_3$ to adjusted pH=9 and extracted with DCM (15 mL). The organic layer was dried over anhydrous $Na_2SO_4$, filtered and concentrated to give the desired product (70 mg, 98% yield) as oil. MS: 307 (M+H)+.

Step 4: 1-(4-chloro-6-(2-fluoroethoxy)quinazolin-5-yl)-N,N-dimethylazetidin-3-amine

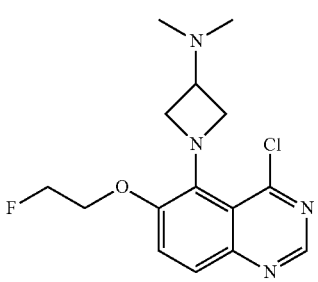 [SMILES: CN(C)C1CN(c2c(OCCF)ccc3ncnc(Cl)c23)C1]

To a solution of 5-(3-(dimethylamino)azetidin-1-yl)-6-(2-fluoroethoxy)quinazolin-4(3H)-one (70 mg, 0.227 mmol) and triphenylphosphine (119 mg, 0.454 mmol) in 1,2-dichloroethane (5 mL) stirred at room temperature, was added carbon tetrachloride (174 mg, 1.14 mmol). The resulting mixture was heated to 70° C. overnight. After the reaction was evaporated to dryness, the residue was purified by prep-TLC to afford the desired product (50 mg, 65% yield) as a yellow solid. LCMS: 325 (M+H)+.

Step 5: N-(4-([1,2,4]triazolo[1,5-c]pyrimidin-7-yloxy)-3-methylphenyl)-5-(3-(dimethylamino)azetidin-1-yl)-6-(2-fluoroethoxy)quinazolin-4-amine

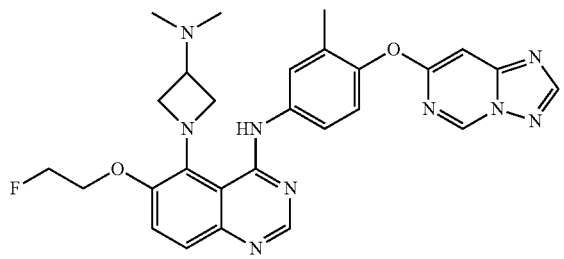 [SMILES: Cc1cc(Nc2ncnc3ccc(OCCF)c(N4CC(N(C)C)C4)c23)ccc1Oc1cc2ncnn2cn1]

A mixture of 1-(4-chloro-6-(2-fluoroethoxy)quinazolin-5-yl)-N,N-dimethylazetidin-3-amine (50 mg, 0.154 mmol) and 4-([1,2,4]triazolo[1,5-c]pyrimidin-7-yloxy)-3-methylaniline (37 mg, 0.154 mmol) in propan-2-ol (5 mL) was heated to 80° C. overnight. After cooled down, the crude mixture was quenched with aq.NaHCO₃ solution (10 mL) and extracted with DCM (20 mL). The organic phase was separated, washed with water and brine, dried over anhydrous Na₂SO₄, filtered and concentrated. The residue was purified by prep-TLC to afford the desired product (30 mg, 35% yield) as a white solid. MS: 530 (M+H)⁺. ¹H NMR (400 MHz, CDCl₃) δ 9.20 (d, J=1.3 Hz, 1H), 8.58 (s, 1H), 8.26 (d, J=44.0 Hz, 2H), 7.75 (d, J=9.2 Hz, 1H), 7.43 (d, J=9.3 Hz, 1H), 7.33 (d, J=15.9 Hz, 1H), 7.13 (d, J=8.7 Hz, 1H), 6.88 (s, 1H), 4.93 (d, J=47.8 Hz, 2H), 4.66-4.33 (m, 4H), 3.75 (s, 2H), 3.17 (s, 1H), 2.30 (d, J=20.1 Hz, 9H).

Example 17

(R)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine Example 18

(S)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine

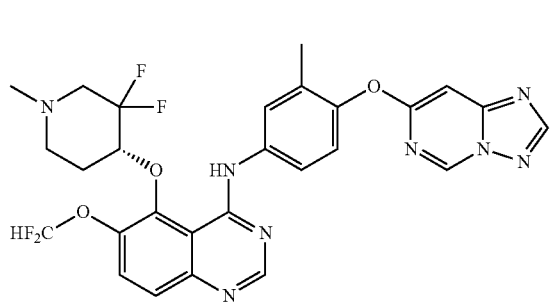

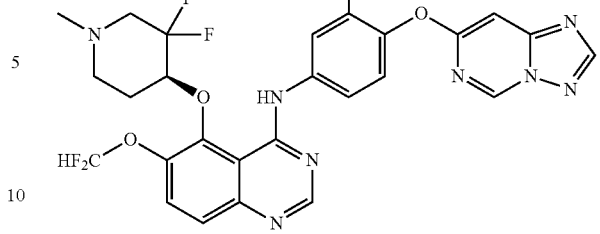

The racemic product was prepared using similar procedure as in Example 29 and 30 to give the desired product as a white solid, which was subsequently separated by chiral SFC to give two isomers.

(S)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine as a white solid. MS (ESI) m/z: 585 (M+H)+. ¹H NMR (400 MHz, CDCl₃) δ 9.87 (s, 1H), 9.13 (s, 1H), 8.59 (s, 1H), 8.25 (s, 1H), 7.75 (s, 1H), 7.70-7.59 (m, 2H), 7.53 (d, J=9.2 Hz, 1H), 7.04 (d, J=8.8 Hz, 1H), 6.82 (s, 1H), 6.54 (t, 1H), 4.80-4.58 (m, 1H), 3.25-3.04 (m, 1H), 2.96-2.69 (m, 2H), 2.39-2.22 (m, 4H), 2.18 (s, 3H), 2.15-1.94 (m, 2H).

(R)—N-(4-([1,2,4]triazolo[1,5-c]pyrimidin-7-yloxy)-3-methylphenyl)-5-((3,3-difluoro-1-methylpiperidin-4-yl)oxy)-6-(difluoromethoxy)quinazolin-4-amine as a white solid. MS (ESI) m/z: 585 (M+H)+. ¹H NMR (400 MHz, CDCl₃): δ 9.89 (s, 1H), 9.13 (s, 1H), 8.60 (s, 1H), 8.25 (s, 1H), 7.75 (s, 1H), 7.71-7.61 (m, 2H), 7.54 (d, J=9.2 Hz, 1H), 7.05 (d, J=8.8 Hz, 1H), 6.82 (s, 1H), 6.54 (t, 1H), 4.87-4.52 (m, 1H), 3.21-3.08 (m, 1H), 2.98-2.58 (m, 2H), 2.37-2.21 (m, 4H), 2.19 (s, 3H), 2.14-2.08 (m, 2H).

Example 21

N-(4-([1,2,4]triazolo[1,5-c]pyrimidin-7-yloxy)-3-methylphenyl)-5-(((R)-3,3-difluoro-1-methylpiperidin-4-yl)oxy)-6-(((S)-tetrahydrofuran-3-yl)oxy)quinazolin-4-amine Example 22

N-(4-([1,2,4]triazolo[1,5-c]pyrimidin-7-yloxy)-3-methylphenyl)-5-(((S)-3,3-difluoro-1-methylpiperidin-4-yl)oxy)-6-(((S)-tetrahydrofuran-3-yl)oxy)quinazolin-4-amine

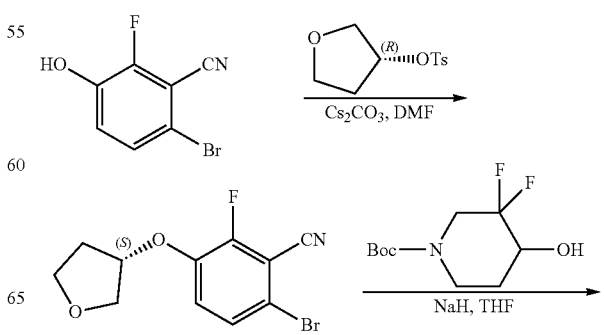

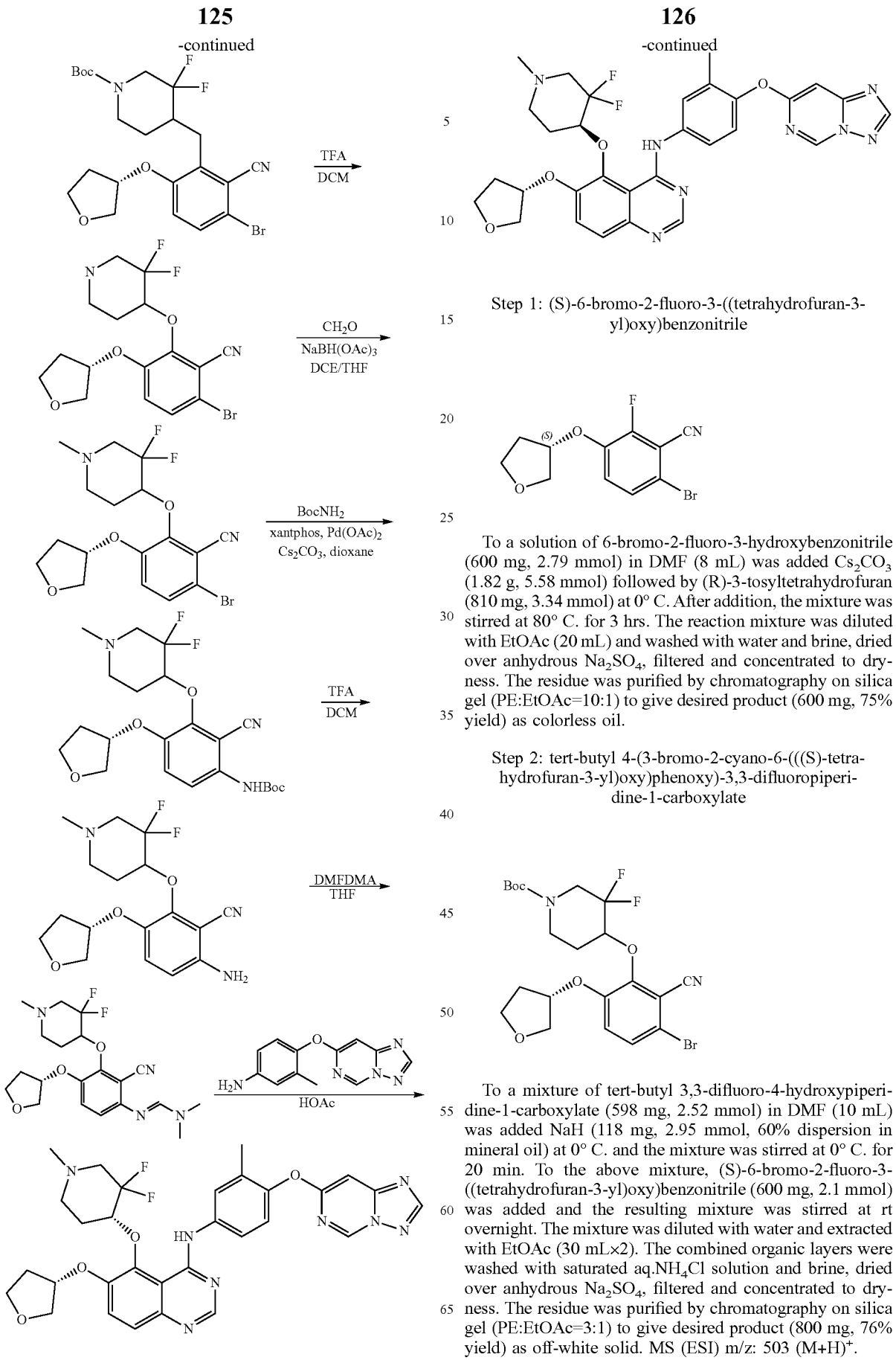

Step 1: (S)-6-bromo-2-fluoro-3-((tetrahydrofuran-3-yl)oxy)benzonitrile

To a solution of 6-bromo-2-fluoro-3-hydroxybenzonitrile (600 mg, 2.79 mmol) in DMF (8 mL) was added $Cs_2CO_3$ (1.82 g, 5.58 mmol) followed by (R)-3-tosyltetrahydrofuran (810 mg, 3.34 mmol) at 0° C. After addition, the mixture was stirred at 80° C. for 3 hrs. The reaction mixture was diluted with EtOAc (20 mL) and washed with water and brine, dried over anhydrous $Na_2SO_4$, filtered and concentrated to dryness. The residue was purified by chromatography on silica gel (PE:EtOAc=10:1) to give desired product (600 mg, 75% yield) as colorless oil.

Step 2: tert-butyl 4-(3-bromo-2-cyano-6-(((S)-tetrahydrofuran-3-yl)oxy)phenoxy)-3,3-difluoropiperidine-1-carboxylate To a mixture of tert-butyl 3,3-difluoro-4-hydroxypiperidine-1-carboxylate (598 mg, 2.52 mmol) in DMF (10 mL) was added NaH (118 mg, 2.95 mmol, 60% dispersion in mineral oil) at 0° C. and the mixture was stirred at 0° C. for 20 min. To the above mixture, (S)-6-bromo-2-fluoro-3-((tetrahydrofuran-3-yl)oxy)benzonitrile (600 mg, 2.1 mmol) was added and the resulting mixture was stirred at rt overnight. The mixture was diluted with water and extracted with EtOAc (30 mL×2). The combined organic layers were washed with saturated aq.$NH_4Cl$ solution and brine, dried over anhydrous $Na_2SO_4$, filtered and concentrated to dryness. The residue was purified by chromatography on silica gel (PE:EtOAc=3:1) to give desired product (800 mg, 76% yield) as off-white solid. MS (ESI) m/z: 503 $(M+H)^+$.

Step 3: 6-bromo-2-((3,3-difluoropiperidin-4-yl)oxy)-3-(((S)-tetrahydrofuran-3-yl)oxy)benzonitrile

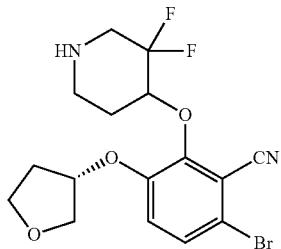 [SMILES: N#Cc1c(Br)ccc(O[C@H]2CCOC2)c1OC1CCNCC1(F)F]

To a solution of tert-butyl 4-(3-bromo-2-cyano-6-(((S)-tetrahydrofuran-3-yl)oxy)phenoxy)-3,3-difluoropiperidine-1-carboxylate (800 mg, 1.59 mmol) in DCM (4 mL) was added TFA (2 mL, 26.3 mmol). The reaction mixture was stirred at room temperature for 2 hrs. LCMS showed reaction was complete. The reaction mixture was concentrated to afford crude compound (800 mg) as a viscous oil, which was directly used for next step without further purification. MS (ESI) m/z: 403 (M+H)$^+$.

Step 4: 6-bromo-2-((3,3-difluoro-1-methylpiperidin-4-yl)oxy)-3-(((S)-tetrahydrofuran-3-yl)oxy)benzonitrile

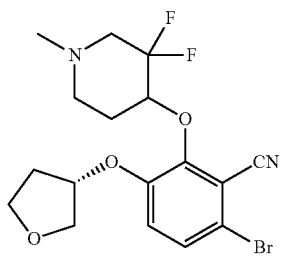 [SMILES: CN1CCC(Oc2c(O[C@H]3CCOC3)ccc(Br)c2C#N)C(F)(F)C1]

To a solution of 6-bromo-2-((3,3-difluoropiperidin-4-yl)oxy)-3-(((S)-tetrahydrofuran-3-yl)oxy)benzonitrile TFA salt (800 mg, 1.99 mmol) in DCE/THF (16/0.8 mL) was added formalin (2.3 mL). The mixture was stirred at room temperature for 1 hour. NaBH(OAc)$_3$ (843 mg, 3.98 mmol) was then added thereto. The mixture was stirred for another 2 hrs. LCMS showed reaction was complete. The reaction mixture was diluted with water (10 mL) and extracted with DCM/MeOH (10 mL×3, 10/1 v/v). The combined organic layers were dried over Na$_2$SO$_4$, filtered and concentrated to dryness. The residue was purified by chromatography on silica gel (DCM:MeOH=30:1) to give the title compound (700 mg, 84% yield for two steps) as yellow solid. MS (ESI) m/z: 417 (M+H)$^+$.

Step 5: tert-butyl (2-cyano-3-((3,3-difluoro-1-methylpiperidin-4-yl)oxy)-4-(((S)-tetrahydrofuran-3-yl)oxy)phenyl)carbamate

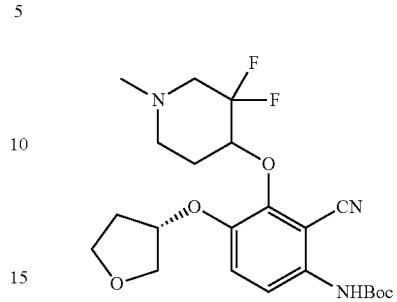

To a mixture of 6-bromo-2-((3,3-difluoro-1-methylpiperidin-4-yl)oxy)-3-(((S)-tetrahydrofuran-3-yl)oxy)benzonitrile (700 mg, 1.68 mmol) and tert-butyl carbamate (398 mg, 3.36 mmol) in 1,4-dioxane (15 mL) was added Cs$_2$CO$_3$ (1.09 g, 3.36 mmol). The mixture was degassed under N$_2$ atmosphere for three times and Pd(OAc)$_2$ (19 mg, 0.08 mmol) and Xantphos (97 mg, 0.16 mmol) was added. After addition, the mixture was degassed under N$_2$ atmosphere for two times and stirred at 90° C. under N$_2$ atmosphere overnight. The mixture was diluted with EtOAc (10 mL) and washed with water and brine, dried over Na$_2$SO$_4$, filtered and concentrated to give crude product, which was purified by silica gel chromatography (DCM:MeOH=30:1) to give desired product (602 mg, 78% yield) as white solid. MS (ESI) m/z: 454 (M+H)$^+$.

Step 6: 6-amino-2-((3,3-difluoro-1-methylpiperidin-4-yl)oxy)-3-(((S)-tetrahydrofuran-3-yl)oxy)benzonitrile

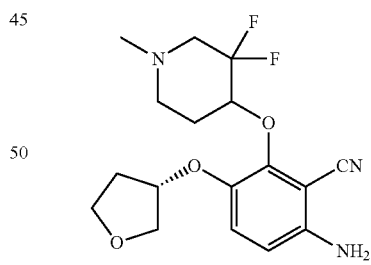

To a solution of tert-butyl (2-cyano-3-((3,3-difluoro-1-methylpiperidin-4-yl)oxy)-4-(((S)-tetrahydrofuran-3-yl)oxy)phenyl)carbamate (520 mg, 1.14 mmol) in DCM (3 mL) was added TFA (1 mL, 13.4 mmol). The reaction mixture was stirred at rt for 2 hrs. The mixture was concentrated to dryness and the residue was alkalified by adding saturated aq.NaHCO$_3$ solution to pH=8. The mixture was extracted with DCM (10 mL×2) and the combined organic layers were washed with brine, dried over Na$_2$SO$_4$, filtered and concentrated to dryness to give desired product (320 mg, 79% yield) as yellow oil. MS (ESI) m/z: 354 (M+H)$^+$.

Step 7: (E)-N'-(2-cyano-3-((3,3-difluoro-1-methylpiperidin-4-yl)oxy)-4-(((S)-tetrahydrofuran-3-yl)oxy)phenyl)-N,N-dimethylformimidamide

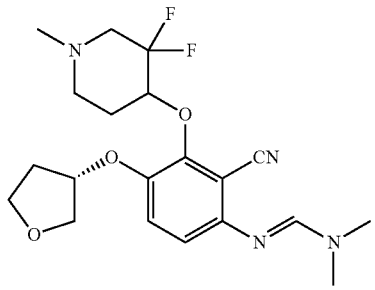 [SMILES: CN(C)/C=N/c1ccc(O[C@H]2CCOC2)c(OC2CCN(C)CC2(F)F)c1C#N]

To a solution of 6-amino-2-((3,3-difluoro-1-methylpiperidin-4-yl)oxy)-3-(((S)-tetrahydrofuran-3-yl)oxy)benzonitrile (320 mg, 0.91 mmol) in THF (2 mL) was added DMF-DMA (2 mL) and the mixture was stirred at 70° C. for 2 hrs. The mixture was diluted with EtOAc (10 mL), washed with water and brine, dried over $Na_2SO_4$, filtered and concentrated to give crude product, which was purified by silica gel chromatography (DCM:MeOH=20:1) to give desired product (180 mg, 49% yield) as yellow solid. MS (ESI) m/z: 409 $(M+H)^+$.

Step 8: N-(4-([1,2,4]triazolo[1,5-c]pyrimidin-7-yloxy)-3-methylphenyl)-5-(((R)-3,3-difluoro-1-methylpiperidin-4-yl)oxy)-6-(((S)-tetrahydrofuran-3-yl)oxy)quinazolin-4-amine and N-(4-([1,2,4]triazolo[1,5-c]pyrimidin-7-yloxy)-3-methylphenyl)-5-(((S)-3,3-difluoro-1-methylpiperidin-4-yl)oxy)-6-(((S)-tetrahydrofuran-3-yl)oxy)quinazolin-4-amine

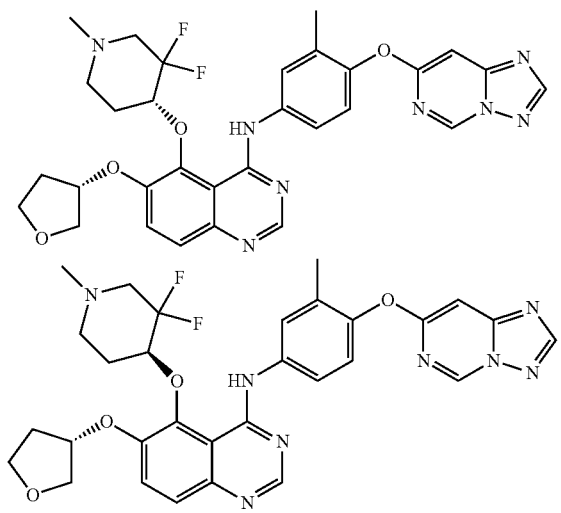

To a solution of (E)-N'-(2-cyano-3-((3,3-difluoro-1-methylpiperidin-4-yl)oxy)-4-(((S)-tetrahydrofuran-3-yl)oxy)phenyl)-N,N-dimethylformimidamide (180 mg, 0.44 mmol) in AcOH (2 mL) was added 4-([1,2,4]triazolo[1,5-c]pyrimidin-7-yloxy)-3-methylaniline (160 mg, 0.66 mmol) and the mixture was stirred at 100° C. for 5 hrs. The mixture was diluted with DCM (6 mL) and alkalified by adding saturated aq.$NaHCO_3$ solution to pH=8. The mixture was extracted with DCM (5 mL×2) and the combined organic layers were washed with brine, dried over $Na_2SO_4$, filtered and concentrated to dryness. The residue was purified by silica gel chromatography (DCM:MeOH=40:1 to 15:1) to give racemic product (90 mg, 34% yield) as white solid, which was subsequently separated by chiral SFC to give two diastereomers:

N-(4-([1,2,4]triazolo[1,5-c]pyrimidin-7-yloxy)-3-methylphenyl)-5-(((S)-3,3-difluoro-1-methylpiperidin-4-yl)oxy)-6-(((S)-tetrahydrofuran-3-yl)oxy)quinazolin-4-amine (30 mg, 67%) as light yellow solid. $^1$H-NMR (400 MHz, $CD_3OD$) δ 9.43 (s, 1H), 8.42 (d, J=3.4 Hz, 2H), 7.76 (dd, J=13.2, 10.8 Hz, 3H), 7.61 (d, J=9.2 Hz, 1H), 7.17 (d, J=8.4 Hz, 1H), 6.94 (s, 1H), 5.32 (s, 1H), 4.99 (s, 1H), 4.13-4.04 (m, 2H), 3.98-3.90 (m, 2H), 3.20 (s, 1H), 2.92 (d, J=12.8 Hz, 1H), 2.50-2.31 (m, 5H), 2.30-2.20 (m, 6H), 2.08 (t, J=12.0 Hz, 1H). MS (ESI) m/z: 605 $(M+H)^+$.

N-(4-([1,2,4]triazolo[4,3-c]pyrimidin-7-yloxy)-3-methylphenyl)-5-(((R)-3,3-difluoro-1-methylpiperidin-4-yl)oxy)-6-(((S)-tetrahydrofuran-3-yl)oxy)quinazolin-4-amine (35 mg, 78%) as light yellow solid. $^1$H NMR (400 MHz, $CD_3OD$) δ 9.44 (d, J=1.2 Hz, 1H), 8.43 (d, J=2.5 Hz, 2H), 7.83-7.71 (m, 3H), 7.61 (d, J=9.2 Hz, 1H), 7.18 (d, J=8.4 Hz, 1H), 6.94 (d, J=1.2 Hz, 1H), 5.34 (s, 1H), 4.93 (s, 1H), 4.13-4.03 (m, 2H), 4.02-3.91 (m, 2H), 3.17 (s, 1H), 2.94 (s, 1H), 2.45-2.30 (m, 6H), 2.28-2.18 (m, 5H), 2.06-2.04 (m, 1H). MS (ESI) m/z: 605 $(M+H)^+$.

SFC condition: Column: ChiralPak IA, 250×21.2 mm I.D., 5 μm; Mobile phase: A for CO2 and B for Methanol (0.1% $NH_4OH$); Gradient: B 40%; Flow rate: 55 mL/min; Column temperature: 35° C.

Example 29

(R)—N-(4-([1,2,4]triazolo[4,3-c]pyrimidin-7-yloxy)-3-methylphenyl)-5-((3,3-difluoro-1-methylpiperidin-4-yl)oxy)-6-isopropoxyquinazolin-4-amine Example 30

(S)—N-(4-([1,2,4]triazolo[4,3-c]pyrimidin-7-yloxy)-3-methylphenyl)-5-((3,3-difluoro-1-methylpiperidin-4-yl)oxy)-6-isopropoxyquinazolin-4-amine

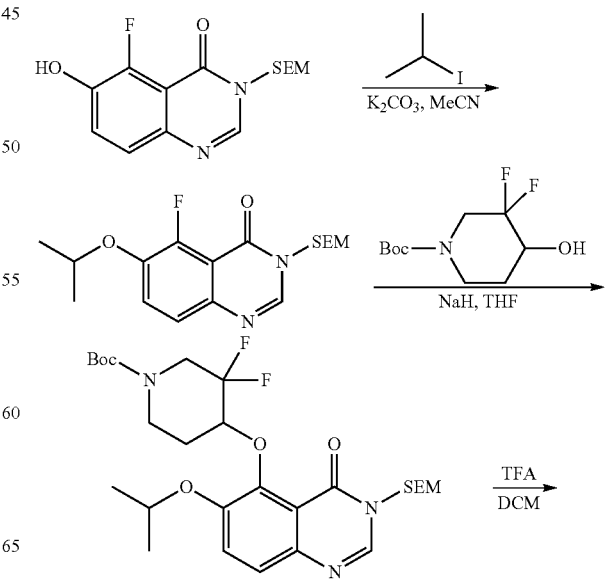

-continued

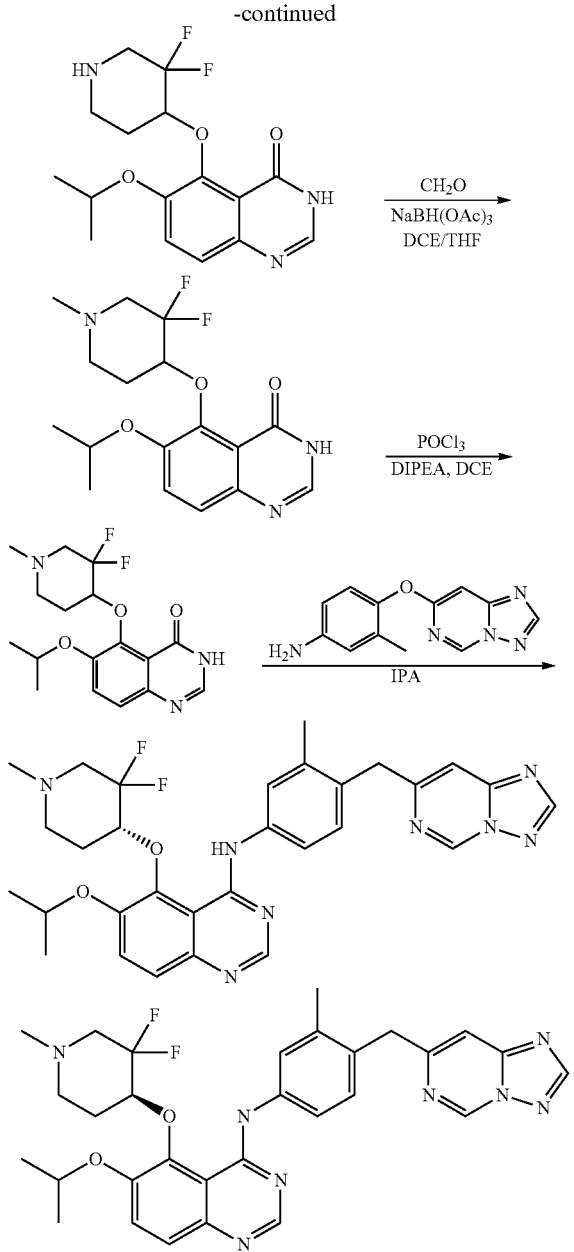

Step 1: 5-fluoro-6-isopropoxy-3-((2-(trimethylsilyl)ethoxy)methyl)quinazolin-4(3H)-one

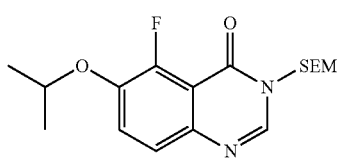 [SMILES: CC(C)Oc1ccc2ncn(COCC[Si](C)(C)C)c(=O)c2c1F]

To a solution of 5-fluoro-6-hydroxy-3-((2-(trimethyl silyl)ethoxy)methyl)quinazolin-4(3H)-one (450 mg, 1.45 mmol) in MeCN (6 mL) was added K$_2$CO$_3$ (600 mg, 4.35 mmol) followed by 2-iodopropane (0.43 mL, 4.35 mmol) at 0° C. After addition, the mixture was stirred at 90° C. for 12 hrs. The reaction mixture was diluted with EtOAc (10 mL) and washed with water and brine, dried over anhydrous Na$_2$SO$_4$, filtered and concentrated to dryness. The residue was purified by chromatography on silica gel (PE:EtOAc=4:1) to give desired product (380 mg, 75% yield) as off-white solid. LC/MS (ESI) m/z: 353 (M+H)$^+$.

Step 2: tert-butyl 3,3-difluoro-4-((6-isopropoxy-4-oxo-3-((2-(trimethylsilyl)ethoxy)methyl)-3,4-dihydroquinazolin-5-yl)oxy)piperidine-1-carboxylate

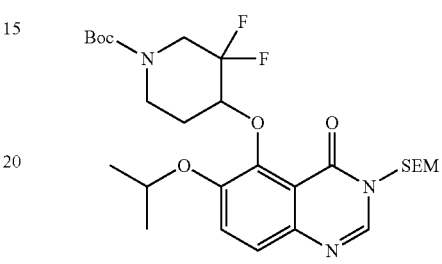

To a solution of tert-butyl 3,3-difluoro-4-hydroxypiperidine-1-carboxylate (307 mg, 1.29 mmol) in dry THF (8 mL) under N$_2$ was added NaH (60 mg, 1.51 mmol, 60% dispersion in mineral oil) in portions at 0° C. After addition, the mixture was stirred at this temperature for 0.5 hr. 5-fluoro-6-isopropoxy-3-((2-(trimethylsilyl)ethoxy)methyl)quinazolin-4(3H)-one (380 mg, 1.08 mmol) was then added to above solution. The reaction mixture was stirred at rt overnight. The mixture was diluted with water and extracted with EtOAc (10 mL×2). The combined organic layers were washed with saturated aq.NH$_4$Cl solution and brine, dried over anhydrous Na$_2$SO$_4$, filtered and concentrated to dryness. The residue was purified by chromatography on silica gel (PE:EtOAc=3:1) to give desired product (550 mg, 89% yield) as off-white solid. MS (ESI) m/z: 570 (M+H)$^+$.

Step 3: 5-((3,3-difluoropiperidin-4-yl)oxy)-6-isopropoxyquinazolin-4(3H)-one

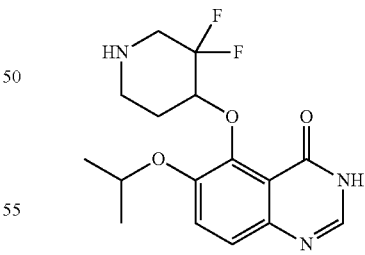

To a solution of tert-butyl 3,3-difluoro-4-((6-isopropoxy-4-oxo-3-((2-(trimethylsilyl)ethoxy)methyl)-3,4-dihydroquinazolin-5-yl)oxy)piperidine-1-carboxylate (550 mg, 0.96 mmol) in DCM (4 mL) was added TFA (2 mL, 26.9 mmol). The reaction mixture was stirred at rt for 2 hrs. LCMS showed reaction was complete. The reaction mixture was concentrated to afford crude compound (500 mg) as a viscous oil, which was directly used for next step steps without further purification. MS (ESI) m/z: 340 (M+H)$^+$.

Step 4: 5-((3,3-difluoro-1-methylpiperidin-4-yl)oxy)-6-isopropoxyquinazolin-4(3H)-one

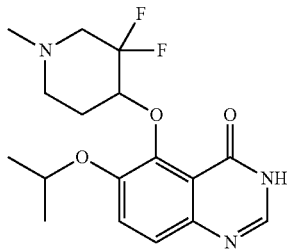 [SMILES: CC(C)Oc1ccc2nc[nH]c(=O)c2c1OC1CCN(C)CC1(F)F]

To a solution of 5-((3,3-difluoropiperidin-4-yl)oxy)-6-isopropoxyquinazolin-4(3H)-one TFA salt (500 mg, 1.47 mmol) in DCE/THF (10/0.5 mL) was added formalin (1.45 mL). The mixture was stirred at rt for 1 hr. NaBH(OAc)$_3$ (623 mg, 2.94 mmol) was then added thereto. The mixture was stirred for another 2 hrs. LCMS showed reaction was complete. The reaction mixture was diluted with water (10 mL) and extracted with DCM/MeOH (10 mL×3, 10/1 v/v). The organic layers were dried and filtered. The filtrate was concentrated and purified by chromatography on silica gel (DCM:MeOH=30:1) to give the title compound (270 mg, 50% yield for two steps) as yellow solid. MS (ESI) m/z: 372 (M+H)$^+$.

Step 5: 4-chloro-5-((3,3-difluoro-1-methylpiperidin-4-yl)oxy)-6-isopropoxyquinazoline

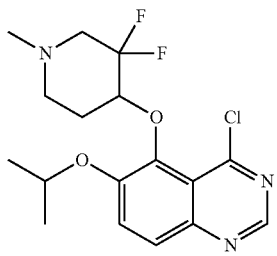 [SMILES: CC(C)Oc1ccc2ncnc(Cl)c2c1OC1CCN(C)CC1(F)F]

To a mixture of 5-((3,3-difluoro-1-methylpiperidin-4-yl)oxy)-6-isopropoxyquinazolin-4(3H)-one (230 mg, 0.65 mmol) in DCE (4 mL) was added DIPEA (0.54 mL, 3.25 mmol) and phosphorus oxychloride (0.3 mL, 3.25 mmol) at 0° C. The mixture was stirred at 90° C. for 4 hrs under N$_2$ atmosphere. LCMS showed the reaction was completed. The resulting mixture was cooled to 0° C., poured into ice water, and neutralized with saturated aqueous NaHCO$_3$ solution. The aqueous phase was extracted with DCM (10 mL×3). The combined organic layers were washed with water and brine, dried over anhydrous Na$_2$SO$_4$, filtered and concentrated to dryness to give desired product (230 mg, 95% yield) as brown solid. MS (ESI) m/z: 372 (M+H)$^+$.

Step 6: (R)—N-(4-([1,2,4]triazolo[4,3-c]pyrimidin-7-yloxy)-3-methylphenyl)-5-((3,3-difluoro-1-methylpiperidin-4-yl)oxy)-6-isopropoxyquinazolin-4-amine and (S)—N-(4-([1,2,4]triazolo[4,3-c]pyrimidin-7-yloxy)-3-methylphenyl)-5-((3,3-difluoro-1-methylpiperidin-4-yl)oxy)-6-isopropoxyquinazolin-4-amine

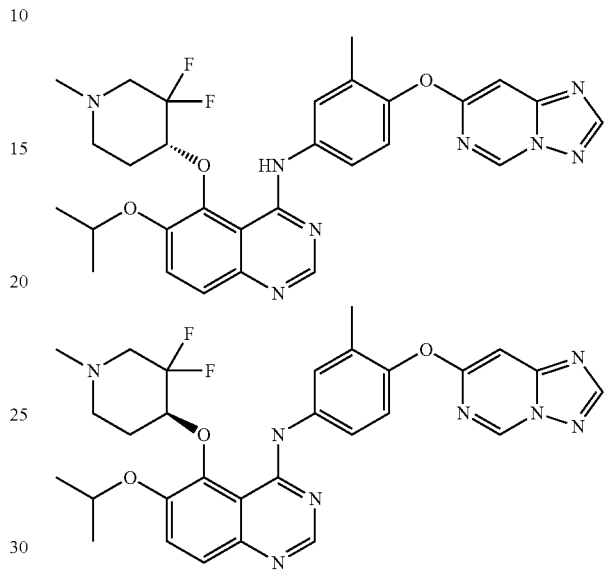

To a solution of 4-chloro-5-((3,3-difluoro-1-methylpiperidin-4-yl)oxy)-6-isopropoxyquinazoline (230 mg, 0.62 mmol) in propan-2-ol (4 mL) was added 4-([1,2,4]triazolo[1,5-c]pyrimidin-7-yloxy)-3-methylaniline (165 mg, 0.68 mmol). The reaction mixture was stirred at 90° C. under N$_2$ atmosphere. LCMS showed the reaction was complete. The reaction mixture was concentrated to remove propan-2-ol. The residue was dissolved in DCM (10 mL), basified with saturated aq.NaHCO$_3$ to pH=8, extracted with DCM:MeOH=10:1 (10 mL×3). The combined organic layers were washed with brine, dried over Na$_2$SO$_4$, filtered and concentrated to dryness. The residue was purified by silica gel chromatography (DCM:MeOH=40:1 to 15:1) to give racemic product (190 mg, 54% yield) as white solid, which was subsequently separated by chiral SFC to give two enantiomers:

(S)—N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine (50 mg, 53%) as light yellow solid. $^1$H NMR (400 MHz, CD$_3$OD) δ 9.43 (d, J=1.2 Hz, 1H), 8.42 (d, J=3.2 Hz, 2H), 7.84-7.71 (m, 3H), 7.58 (d, J=9.2 Hz, 1H), 7.17 (d, J=8.4 Hz, 1H), 6.93 (d, J=1.2 Hz, 1H), 5.06-4.93 (m, 1H), 4.84 (dt, J=12.0, 6.0 Hz, 1H), 3.26-3.15 (m, 1H), 2.94 (d, J=12.4 Hz, 1H), 2.44 (dd, J=29.0, 12.0 Hz, 1H), 2.34 (s, 3H), 2.25 (s, 3H), 2.15-2.03 (m, 1H), 1.44 (dd, J=13.6, 6.0 Hz, 6H), 1.20 (dd, J=30.8, 12.0 Hz, 2H). MS (ESI) m/z: 577 (M+H)$^+$.

(R)—N-(4-([1,2,4]triazolo[1,5-c]pyrimidin-7-yloxy)-3-methylphenyl)-5-((3,3-difluoro-1-methylpiperidin-4-yl)oxy)-6-isopropoxyquinazolin-4-amine (60 mg, 63%) as light yellow solid. $^1$H NMR (400 MHz, CD$_3$OD) δ 9.44 (d, J=1.2 Hz, 1H), 8.42 (d, J=2.8 Hz, 2H), 7.82-7.70 (m, 3H), 7.59 (d, J=9.2 Hz, 1H), 7.17 (d, J=8.4 Hz, 1H), 6.93 (d, J=1.2 Hz, 1H), 4.99 (dd, J=12.4, 8.1 Hz, 1H), 4.86-4.81 (m, 1H), 3.19 (s, 1H), 2.94 (d, J=11.8 Hz, 1H), 2.45 (dd, J=28.9, 12.3

Hz, 1H), 2.34 (s, 3H), 2.25 (s, 3H), 2.09 (d, J=11.9 Hz, 1H), 1.44 (dd, J=13.7, 6.0 Hz, 6H), 1.26-1.14 (m, 2H). MS (ESI) m/z: 577 (M+H)+.

SFC condition: Column: ChiralPak IA, 250×21.2 mm I.D., 5 μm; Mobile phase: A for CO$_2$ and B for Methanol (0.1% NH$_4$OH); Gradient: B 40%; Flow rate: 55 mL/min; Column temperature: 35° C.

Example 72

(R)—N-(4-([1,2,4]-triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine Example 73

(S)—N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine

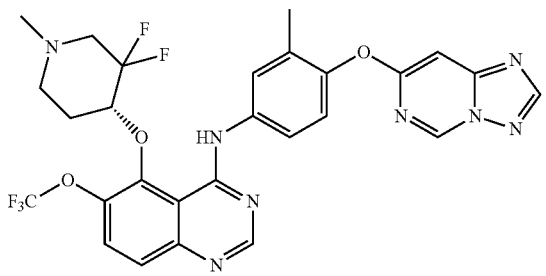

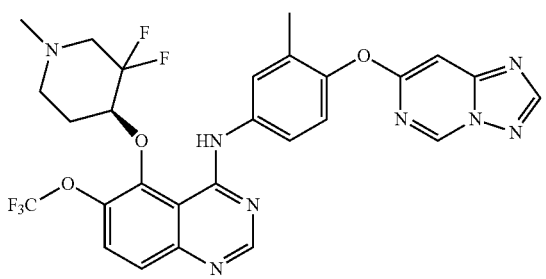

The racemic product was prepared using similar procedure as in Examples 21 and 22 to give the desired product as a yellow solid, which was subsequently separated by chiral SFC to give two isomers.

(R)—N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine as light yellow solid. $^1$H-NMR (400 MHz, CD$_3$OD) δ 9.43 (s, 1H), 8.57 (s, 1H), 8.42 (s, 1H), 7.91-7.73 (m, 3H), 7.69 (d, J=9.2 Hz, 1H), 7.19 (d, J=8.6 Hz, 1H), 6.95 (s, 1H), 4.87 (m, 1H), 3.20 (m, 1H), 2.93 (m, 1H), 2.49 (m, 1H), 2.34 (s, 3H), 2.26 (s, 4H), 2.18 (m, 2H). MS (ESI) m/z: 604 (M+H)+.

(S)—N-(4-([1,2,4]triazolo[1,5-c]pyrimidin-7-yloxy)-3-methylphenyl)-5-((3,3-difluoro-1-methylpiperidin-4-yl)oxy)-6-(trifluoromethoxy)quinazolin-4-amine as light yellow solid. $^1$H-NMR (400 MHz, CD$_3$OD) δ 9.43 (s, 1H), 8.57 (s, 1H), 8.42 (s, 1H), 7.83 (m, 3H), 7.69 (d, J=9.2 Hz, 1H), 7.19 (d, J=8.6 Hz, 1H), 6.95 (d, J=1.2 Hz, 1H), 4.86 (m, 1H), 3.22 (m, 1H), 2.93 (d, J=11.8 Hz, 1H), 2.49 (dm, 1H), 2.34 (s, 3H), 2.24 (m, 4H), 2.22-2.12 (m, 2H). MS (ESI) m/z: 604 (M+H)+.

Example 74

(R)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine Example 75

(S)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine

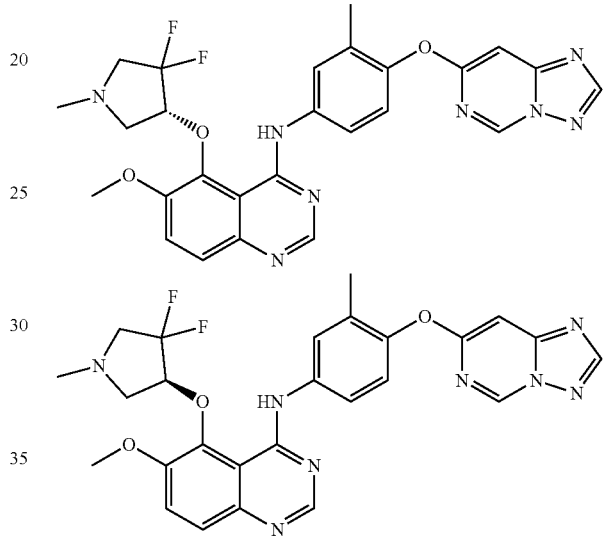

The racemic product was prepared using similar procedure as in Examples 21 and 22 to give the desired product as a yellow solid, which was subsequently separated by chiral SFC to give two isomers.

(S)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine as yellow solid. $^1$H-NMR (400 MHz, CD$_3$OD) δ 9.43 (d, J=1.0 Hz, 1H), 8.39 (t, J=7.7 Hz, 2H), 7.85-7.76 (m, 2H), 7.74 (d, J=9.3 Hz, 1H), 7.59 (d, J=9.2 Hz, 1H), 7.20-7.13 (m, 1H), 6.92 (d, J=1.0 Hz, 1H), 5.52-5.40 (m, 1H), 4.04 (s, 3H), 3.30-3.14 (m, 2H), 2.89-2.70 (m, 2H), 2.31 (s, 3H), 2.24 (s, 3H). MS (ESI) m/z: 535 (M+H)+.

(R)—N-(4-([1,2,4]triazolo[1,5-c]pyrimidin-7-yloxy)-3-methylphenyl)-5-((4,4-difluoro-1-methylpyrrolidin-3-yl)oxy)-6-methoxyquinazolin-4-amine. $^1$H-NMR (400 MHz, CD$_3$OD) δ 9.33 (d, J=1.0 Hz, 1H), 8.30 (d, J=8.3 Hz, 2H), 7.72-7.61 (m, 3H), 7.49 (d, J=9.2 Hz, 1H), 7.10-7.01 (m, 1H), 6.82 (d, J=1.0 Hz, 1H), 5.40-5.31 (m, 1H), 3.94 (s, 3H), 3.20-3.04 (m, 2H), 2.77-2.62 (m, 2H), 2.22 (s, 3H), 2.15 (s, 3H). MS (ESI) m/z: 535 (M+H)+. SFC condition: Column: ChiralPak OD, 250×21.2 mm I.D., 5 μm; Mobile phase: A for CO$_2$ and B for Methanol (0.1% NH$_4$OH); Gradient: B 40%; Flow rate: 50 mL/min; Column temperature: 35° C.

The following compounds were prepared according to the above described methods using different starting materials.

| Ex # | Structure | Name | MS m/z |
|---|---|---|---|
| 13 | 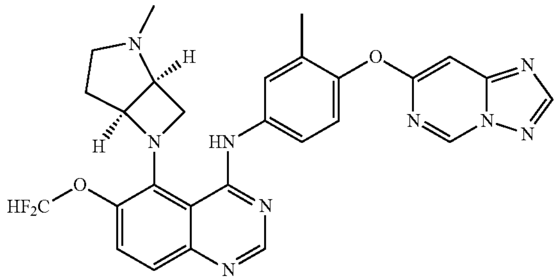 | N-(4-([1,2,4]triazolo[1,5-c]pyrimidin-7-yloxy)-3-methylphenyl)-6-(difluoromethoxy)-5-((1S,5S)-2-methyl-2,6-diazabicyclo[3.2.0]heptan-6-yl)quinazolin-4-amine | 546 (M + H)+ |
| 14 | 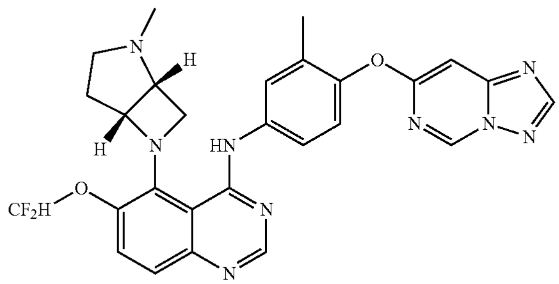 [SMILES: Cc1cc(Nc2ncnc3ccc(OC(F)F)c(N4C[C@@H]5[C@H]4CCN5C)c23)ccc1Oc1cc2ncnn2cn1] | N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine | 546 (M + H)+ |
| 19 | 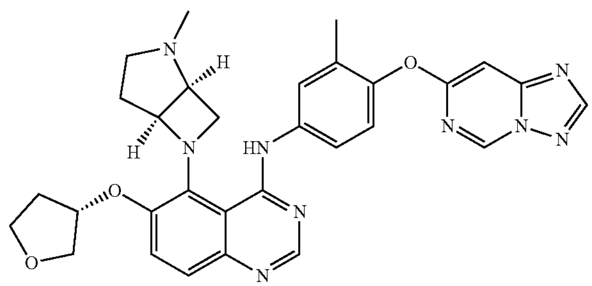 [SMILES: Cc1cc(Nc2ncnc3ccc(O[C@H]4CCOC4)c(N4C[C@H]5[C@@H]4CCN5C)c23)ccc1Oc1cc2ncnn2cn1] | N-(4-([1,2,4]triazolo[1,5-c]pyrimidin-7-yloxy)-3-methylphenyl)-5-((1S,5S)-2-methyl-2,6-diazabicyclo[3.2.0]heptan-6-yl)-6-(((S)-tetrahydrofuran-3-yl)oxy)quinazolin-4-amine | 566 (M + H)+ |
| 20 | 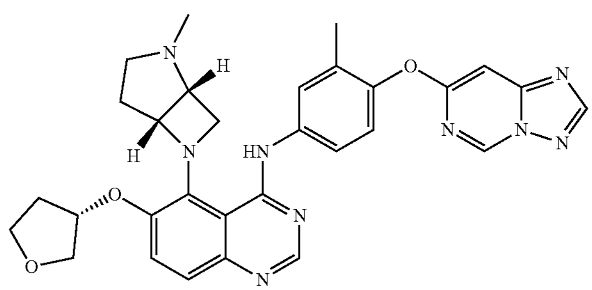 [SMILES: Cc1cc(Nc2ncnc3ccc(O[C@H]4CCOC4)c(N4C[C@@H]5[C@H]4CCN5C)c23)ccc1Oc1cc2ncnn2cn1] | N-(4-([1,2,4]triazolo[1,5-c]pyrimidin-7-yloxy)-3-methylphenyl)-5-((1R,5R)-2-methyl-2,6-diazabicyclo[3.2.0]heptan-6-yl)-6-(((S)-tetrahydrofuran-3-yl)oxy)quinazolin-4-amine | 566 (M + H)+ |
| 23 | 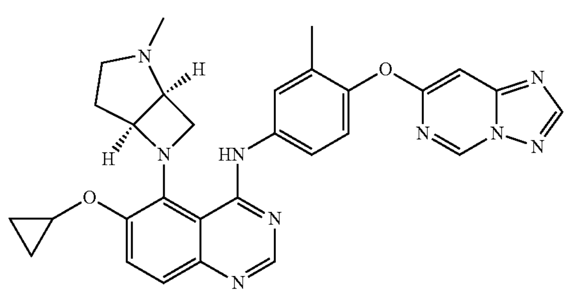 [SMILES: Cc1cc(Nc2ncnc3ccc(OC4CC4)c(N4C[C@H]5[C@@H]4CCN5C)c23)ccc1Oc1cc2ncnn2cn1] | N-(4-([1,2,4]triazolo[1,5-c]pyrimidin-7-yloxy)-3-methylphenyl)-6-cyclopropoxy-5-((1S,5S)-2-methyl-2,6-diazabicyclo[3.2.0]heptan-6-yl)quinazolin-4-amine | 536 (M + H)+ |

| Ex # | Structure | Name | MS m/z |
|---|---|---|---|
| 24 | 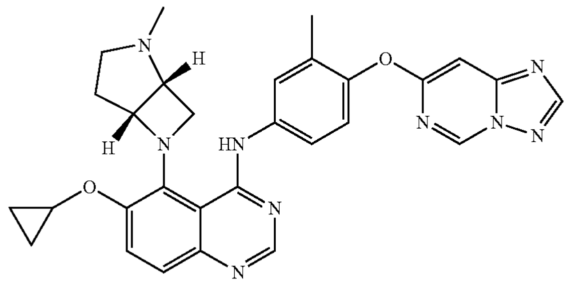 [SMILES: Cc1cc(Nc2ncnc3ccc(OC4CC4)c(N4C[C@@H]5[C@H]4CCN5C)c23)ccc1Oc1cc2ncnn2cn1] | N-(4-([1,2,4]triazolo[1,5-c]pyrimidin-7-yloxy)-3-methylphenyl)-6-cyclopropoxy-5-((1R,5R)-2-methyl-2,6-diazabicyclo[3.2.0]heptan-6-yl)quinazolin-4-amine | 536 (M + H)+ |
| 25 | 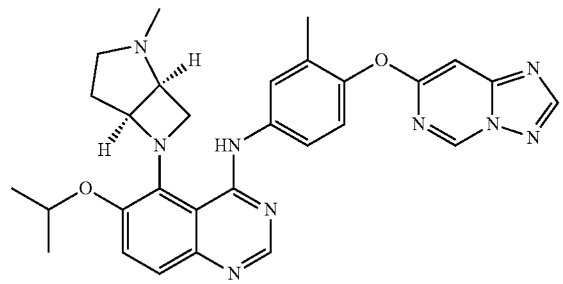 [SMILES: Cc1cc(Nc2ncnc3ccc(OC(C)C)c(N4C[C@H]5[C@@H]4CCN5C)c23)ccc1Oc1cc2ncnn2cn1] | N-(4-([1,2,4]triazolo[1,5-c]pyrimidin-7-yloxy)-3-methylphenyl)-6-isopropoxy-5-((1S,5S)-2-methyl-2,6-diazabicyclo[3.2.0]heptan-6-yl)quinazolin-4-amine | 538 (M + H)+ |
| 26 | 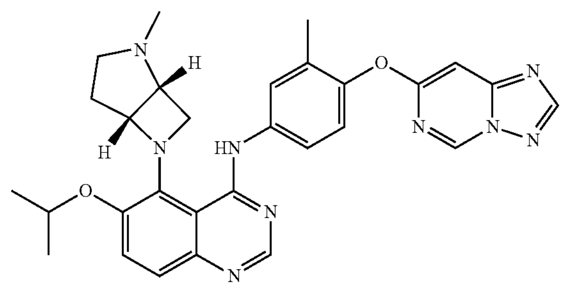 [SMILES: Cc1cc(Nc2ncnc3ccc(OC(C)C)c(N4C[C@@H]5[C@H]4CCN5C)c23)ccc1Oc1cc2ncnn2cn1] | N-(4-([1,2,4]triazolo[1,5-c]pyrimidin-7-yloxy)-3-methylphenyl)-6-isopropoxy-5-((1R,5R)-2-methyl-2,6-diazabicyclo[3.2.0]heptan-6-yl)quinazolin-4-amine | 538 (M + H)+ |
| 27 | 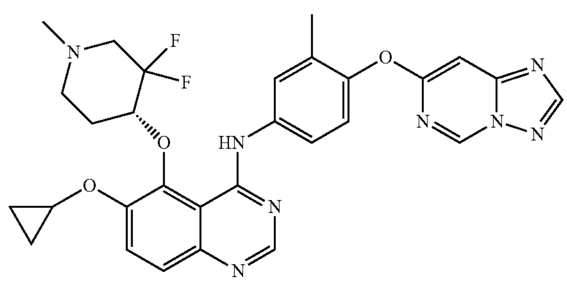 [SMILES: Cc1cc(Nc2ncnc3ccc(OC4CC4)c(O[C@@H]4CCN(C)CC4(F)F)c23)ccc1Oc1cc2ncnn2cn1] | (R)-N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine | 575 (M + H)+ |
| 28 | 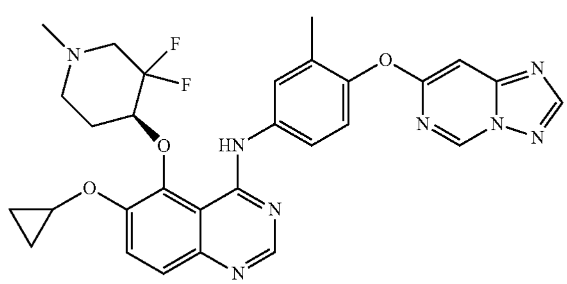 [SMILES: Cc1cc(Nc2ncnc3ccc(OC4CC4)c(O[C@H]4CCN(C)CC4(F)F)c23)ccc1Oc1cc2ncnn2cn1] | (S)-N-(4-([1,2,4]triazolo[1,5-c]pyrimidin-7-yloxy)-3-methylphenyl)-6-cyclopropoxy-5-((3,3-difluoro-1-methylpiperidin-4-yl)oxy)quinazolin-4-amine | 575 (M + H)+ |

| Ex # | Structure | Name | MS m/z |
|---|---|---|---|
| 88 | 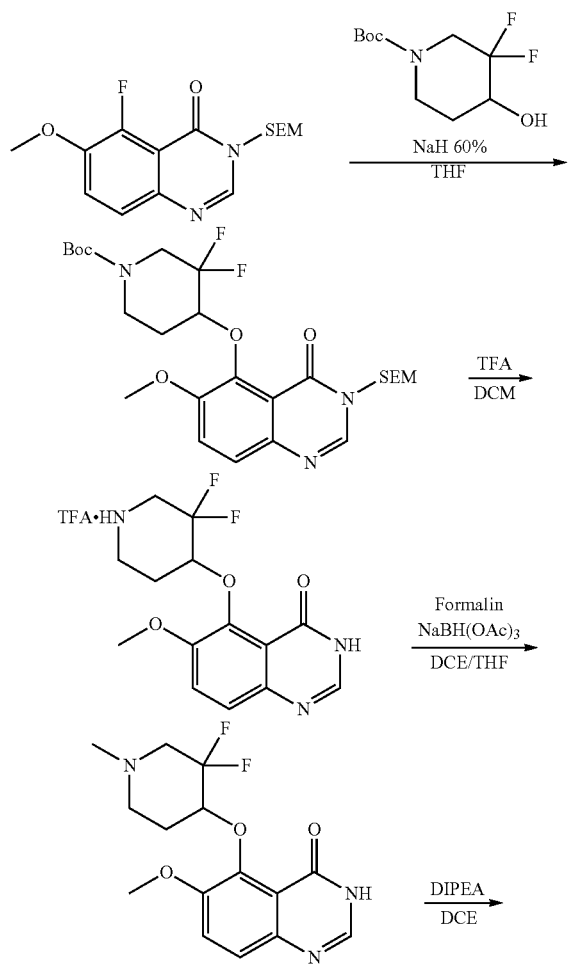 | 4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl 2,4-dimethylpiperazine-1-carboxylate | 675 (M + H)+ |

Example 31

(R)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine

Example 32

(S)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine

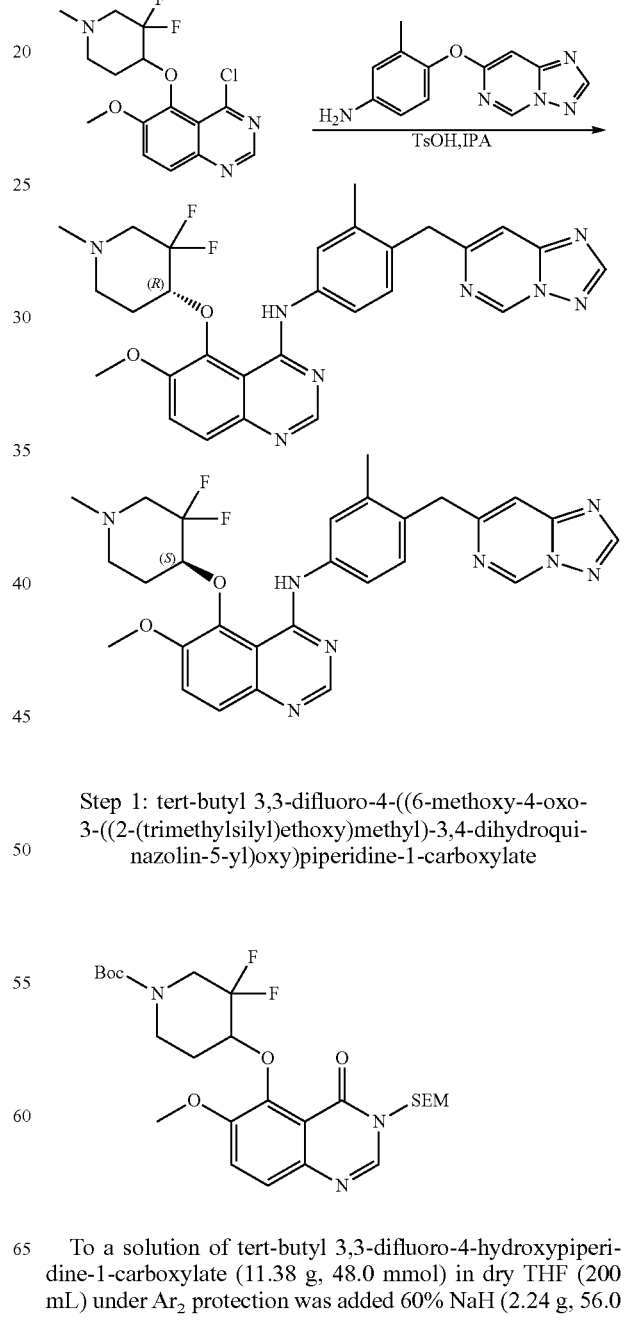

Step 1: tert-butyl 3,3-difluoro-4-((6-methoxy-4-oxo-3-((2-(trimethylsilyl)ethoxy)methyl)-3,4-dihydroquinazolin-5-yl)oxy)piperidine-1-carboxylate To a solution of tert-butyl 3,3-difluoro-4-hydroxypiperidine-1-carboxylate (11.38 g, 48.0 mmol) in dry THF (200 mL) under Ar₂ protection was added 60% NaH (2.24 g, 56.0 mmol) in batches at 0° C. After addition, the mixture was stirred at this temperature for 0.5 h. Then 5-fluoro-6-methoxy-3-((2-(trimethylsilyl)ethoxy)methyl)quinazolin-4(3H)-one (13 g, 40.0 mmol) was added to above solution. The reaction mixture was stirred at room temperature overnight. After quenched with H$_2$O (100 mL), the reaction was extracted with CH$_2$Cl$_2$ (150 mL×3). The combined organic layers were washed with brine, dried over anhydrous Na$_2$SO$_4$ and filtered. The filtrate was concentrated in vacuum and the purified by column chromatography (PE: EtOAc=10:1) to give the title compound (20 g, 92% yield) as a white solid. MS (ESI) m/z: 542.2 (M+H)$^+$.

Step 2: Synthesis of 5-((3,3-difluoropiperidin-4-yl)oxy)-6-methoxyquinazolin-4(3H)-one TFA Salt

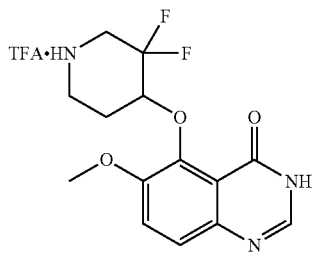

To a solution of tert-butyl 3,3-difluoro-4-((6-methoxy-4-oxo-3-((2-(trimethylsilyl)ethoxy)methyl)-3,4-dihydroquinazolin-5-yl)oxy)piperidine-1-carboxylate (20 g, 36.97 mmol) in DCM (150 mL) was added TFA (42.1 g, 369.7 mmol). The reaction mixture was stirred at room temperature for 3 h. When LCMS showed reaction was complete, the reaction mixture was concentrated to afford crude compound (12 g) as a yellow solid, which was used for next step without further purification. MS (ESI) m/z: 312.1 (M+H)$^+$.

Step 3: Synthesis of 5-((3,3-difluoro-1-methylpiperidin-4-yl)oxy)-6-methoxyquinazolin-4(3H)-one

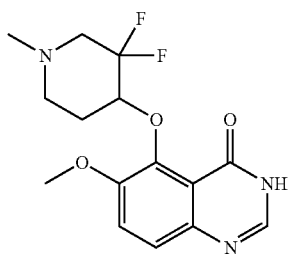 [SMILES: COc1ccc2nc[nH]c(=O)c2c1OC1CCN(C)CC1(F)F]

To a solution of 5-((3,3-difluoropiperidin-4-yl)oxy)-6-methoxyquinazolin-4(3H)-one TFA salt (12 g, 29.0 mmol) in DCE/THF (200 mL/10 mL) was added formalin (60 mL). The mixture was stirred at room temperature for 1 h and then NaBH(OAc)$_3$ (18.4 g, 86.8 mmol) was added thereto. The mixture was stirred for another 2 h. The reaction mixture was diluted with water (200 mL) and extracted with EtOAc (200 mL×3). The organic layers were washed with water (100 mL), dried over anhydrous Na$_2$SO$_4$ and filtered. The filtrate was concentrated and purified by column chromatography (CH$_2$Cl$_2$:MeOH=20:1) to give the title compound (8 g, 84% yield for two steps) as a yellow solid. MS (ESI) m/z: 326.1 (M+H)$^+$.

Step 4: Synthesis of 4-chloro-5-((3,3-difluoro-1-methylpiperidin-4-yl)oxy)-6-methoxyquinazoline

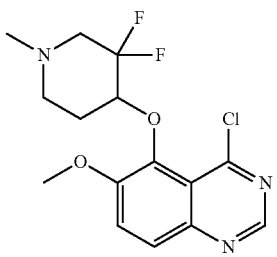 [SMILES: COc1ccc2ncnc(Cl)c2c1OC1CCN(C)CC1(F)F]

To a solution of 5-((3,3-difluoro-1-methylpiperidin-4-yl)oxy)-6-methoxyquinazolin-4(3H)-one (4.5 g, 13.8 mmol) and DIEA (8.9 g, 69 mmol) in DCE (120 mL) was added POCl$_3$ (8.5 g, 55.4 mmol) dropwise under Ar$_2$ protection. The reaction mixture was stirred at 95° C. for 3 h. Then the reaction mixture was cooled to room temperature and poured into ice water. The resulting mixture was slowly adjusted to pH=7-8 with NaHCO$_3$. After extraction with CH$_2$Cl$_2$:MeOH=20:1 (150 mL×2), the combined organic layers were dried with over anhydrous Na$_2$SO$_4$ and filtered. The filtrate was concentrated to dryness to give the title compound (4.3 g, 91% yield) as a brown solid. MS (ESI) m/z: 344.1 (M+H)$^+$.

Step 5: (R)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine and (S)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine

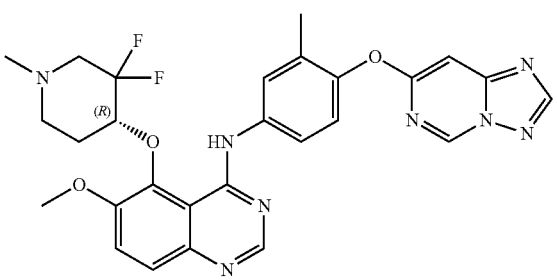

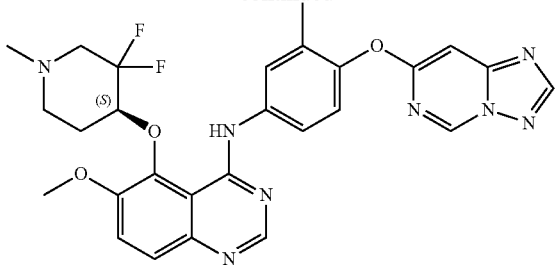

To a solution of 4-chloro-5-((3,3-difluoro-1-methylpiperidin-4-yl)oxy)-6-methoxyquinazoline (410 mg, 1.19 mmol) in Propan-2-ol (60 mL) was added TsOH.H$_2$O (68 mg, 0.36 mmol) and 4-([1,2,4]triazolo[1,5-c]pyrimidin-7-yloxy)-3-methylaniline (259 mg, 1.07 mmol). The resulting mixture was stirred at 100° C. under Ar$_2$ protection and concentrated. The residue was dissolved in H$_2$O (100 mL), basified with aq. NaHCO$_3$ to pH=7-8, extracted with DCM:MeOH=20:1 (100 mL×3). The combined organic layers were dried over anhydrous Na$_2$SO$_4$, filtered and concentrated. The residue was purified by column chromatography (DCM/MeOH=30/1) to give product (300 mg, 46% yield) as white solid. The racemic material was subsequently separated by chiral SFC to give two isomers:

(R)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine (Peak 1, retention time 6.241 min, ee: >99%) (100 mg, 67%) as a white solid. MS (ESI) m/z: 549.2 (M+H)$^+$. $^1$H NMR (400 MHz, CDCl$_3$) δ 10.04 (s, 1H), 9.20 (s, 1H), 8.61 (s, 1H), 8.33 (s, 1H), 7.88 (d, J=2.0 Hz, 1H), 7.79-7.76 (m, 1H) 7.69 (d, J=9.2 Hz, 1H), 7.53 (d, J=9.2 Hz, 1H), 7.11 (d, J=8.8 Hz, 1H), 6.90 (s, 1H), 4.84-4.79 (m, 1H), 4.03 (s, 3H), 3.22-3.21 (m, 1H), 2.93 (d, J=7.2 Hz, 1H), 2.38 (s, 3H), 2.41-2.34 (m, 1H), 2.34-2.27 (m, 1H), 2.19 (s, 3H), 2.16-2.10 (m, 2H).

(S)—N-(4-([1,2,4]triazolo[1,5-c]pyrimidin-7-yloxy)-3-methylphenyl)-5-((3,3-difluoro-1-methylpiperidin-4-yl)oxy)-6-methoxyquinazolin-4-amine (Peak 2, retention time 7.573 min, ee: >99%) (105 mg, 70%) as a white solid. MS (ESI) m/z: 549.2 (M+H)$^+$. $^1$H NMR (400 MHz, CDCl$_3$) δ 10.04 (s, 1H), 9.21 (s, 1H), 8.61 (s, 1H), 8.33 (s, 1H), 7.88 (d, J=2.4 Hz, 1H), 7.79-7.77 (m, 1H), 7.69 (d, J=9.2 Hz, 1H), 7.53 (d, J=9.2 Hz, 1H), 7.11 (d, J=8.8 Hz, 1H), 6.90 (s, 1H), 4.86-4.79 (m, 1H), 4.03 (s, 3H), 3.24-3.19 (m, 1H), 2.93 (d, J=7.6 Hz, 1H), 2.38 (s, 3H), 2.41-2.27 (m, 1H), 2.27 (s, 3H), 2.19-2.11 (m, 3H).

SFC condition: Column: AD 4.6×250 5um Mobile phase: A: CO$_2$ B: methanol (0.03% DEA) Gradient: hold 30% of B for 25 min Flow rate: 2.8 mL/min Column temp: 35° C.

Example 33

(R)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine Example 34

(S)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine

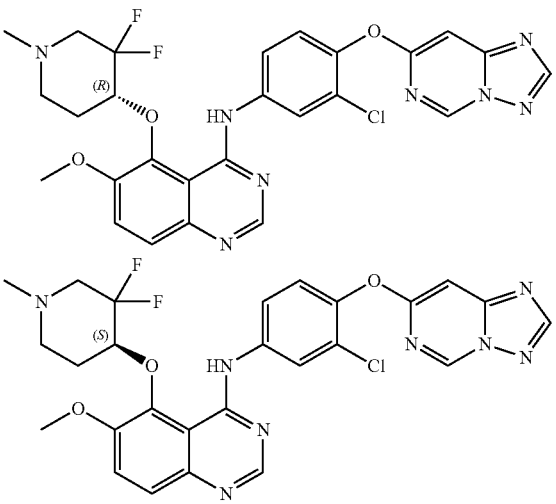

The racemate can be synthesized according to the procedure outline in Examples 31 and 32, which was subsequently separated by chiral SFC to give two isomers:

(R)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine (Peak 1, retention time 6.633 min) as a white solid. MS (ESI) m/z: 569.0 (M+H)$^+$. $^1$H NMR (400 MHz, DMSO-d$_6$) δ 10.12 (s, 1H), 9.69 (s, 1H), 8.62 (s, 1H), 8.54 (s, 1H), 8.33-8.32 (m, 1H), 7.86-7.84 (d, J=9.2 Hz, 1H), 7.73-7.65 (m, 2H), 7.47-7.42 (m, 2H), 4.92-4.84 (m, 1H), 4.01 (s, 3H), 3.18-3.13 (m, 2H), 2.82-2.79 (m, 1H), 3.23 (s, 3H), 2.16-2.09 (m, 2H), 1.98-1.92 (m, 1H).

(S)—N-(4-([1,2,4]triazolo[1,5-c]pyrimidin-7-yloxy)-3-chlorophenyl)-5-((3,3-difluoro-1-methylpiperidin-4-yl)oxy)-6-methoxyquinazolin-4-amine (Peak 2, retention time 7.309 min) as a white solid. MS (ESI) m/z: 569.0 (M+H)$^+$. $^1$H NMR (400 MHz, DMSO-d$_6$) δ 10.12 (s, 1H), 9.70-9.69 (d, J=1.2 Hz, 1H), 8.62 (s, 1H), 8.54 (s, 1H), 8.33-8.32 (d, J=2.4 Hz, 1H), 7.86-7.84 (d, J=9.2 Hz, 1H), 7.73-7.70 (m, 1H), 7.67-7.65 (d, J=9.2 Hz, 1H), 7.47-7.45 (d, J=8.8 Hz, 1H), 7.43-7.42 (d, J=0.8 Hz, 1H), 4.93-4.82 (m, 1H), 4.01 (s, 3H), 3.18-3.14 (m, 2H), 2.82-2.79 (d, J=11.6 Hz, 1H), 2.23 (s, 3H), 2.19-2.08 (m, 2H), 1.98-1.91 (m, 1H).

SFC condition: Column: AD-H 0.46 cm I.D.×15 cm L 254 nm Mobile phase: A: HEP B: EtOH (0.1% DEA) Gradient: hold 40% of B for 15 min Flow rate: 0.5 mL/min Column temp: 25° C.

The following compounds were prepared according to the above described methods using different starting materials.

| Ex # | Structure | Name | MS m/z |
|---|---|---|---|
| 15 | cis mixture | cis-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine | 531 (M + H)+ |
| 16 | trans mixture | trans-N-(4-([1,2,4]triazolo[1,5-c]pyrimidin-7-yloxy)-3-methylphenyl)-5-((3-fluoro-1-methylpiperidin-4-yl)oxy)-6-methoxyquinazolin-4-amine | 531 (M + H)+ |

Example 15

$^1$H NMR (400 MHz, DMSO-d$_6$) δ 10.04 (s, 1H), 9.65 (s, 1H), 8.58 (s, 1H), 8.49 (s, 1H), 7.79-7.78 (d, J=2.4 Hz, 1H), 7.73-7.70 (d, J=8.8 Hz, 1H), 7.20-7.18 (m, 1H), 7.14 (s, 1H), 6.96-6.95 (d, J=2.0 Hz, 1H), 6.86-6.85 (d, J=2.0 Hz, 1H), 5.23-5.10 (m, 1H), 5.05-4.99 (m, 1H), 3.91 (s, 3H), 3.15-3.09 (m, 1H), 2.80-2.77 (d, J=10.8 Hz, 1H), 2.43-2.30 (m, 2H), 2.22 (s, 3H), 2.17 s, 3H), 2.04-2.00 (m, 2H).

Example 16

$^1$H NMR (400 MHz, DMSO-d$_6$) δ 9.82 (s, 1H), 9.67-9.66 (d, J=1.2 Hz 1H), 8.58 (s, 1H), 8.47 (s, 1H), 7.79-7.78 (d, J=2.4 Hz, 1H), 7.73-7.70 (m, 1H), 7.20-7.18 (d, J=8.8 Hz, 1H), 7.14-7.13 (d, J=1.2 Hz, 1H), 6.92-6.91 (d, J=2.0 Hz, 1H), 6.85-6.84 (d, J=2.4 Hz, 1H), 5.16-4.99 (m, 1H), 4.89-4.83 (m, 1H), 3.91 (s, 3H), 3.19-3.14 (m, 1H), 2.76-2.73 (m, 1H), 2.35-2.30 (m, 2H), 2.27 (s, 3H), 2.24 (m, 1H), 2.19 (s, 3H). 1.91-1.83 (m, 1H).

Example 35

N-(4-([1,2,4]triazolo[1,5-c]pyrimidin-7-yloxy)-3-methylphenyl)-5-((3,3-difluoro-1-(methyl-d3)piperidin-4-yl)oxy)-6-methoxyquinazolin-4-amine

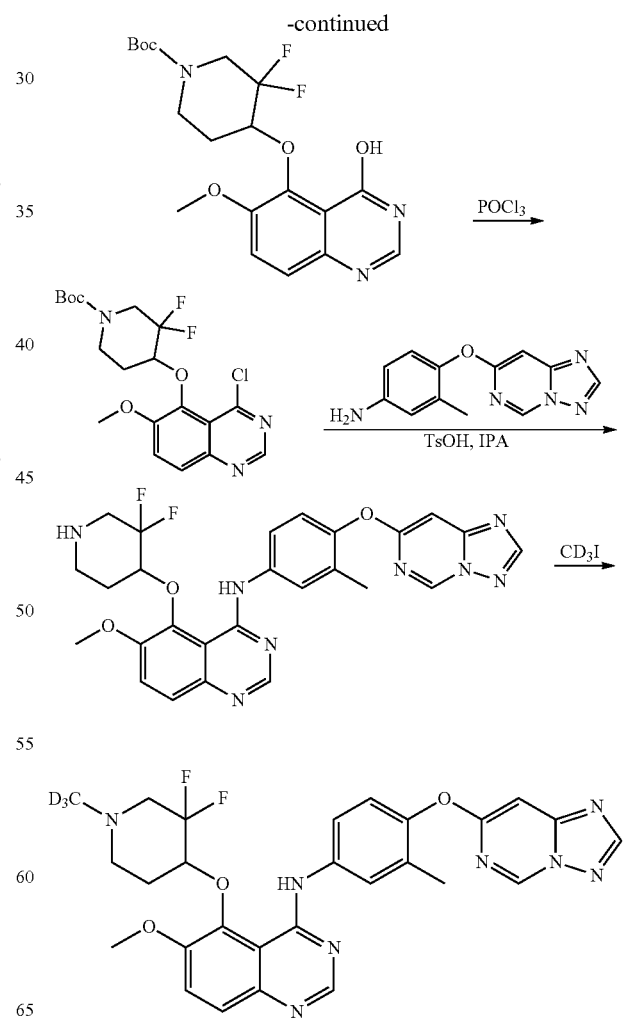

149

Step 1: tert-butyl 3,3-difluoro-4-((6-methoxy-4-oxo-3,4-dihydroquinazolin-5-yl)oxy)piperidine-1-carboxylate

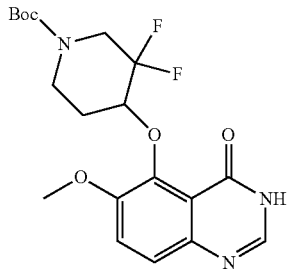 [SMILES: COc1ccc2nc[nH]c(=O)c2c1OC1CCN(C(=O)OC(C)(C)C)CC1(F)F]

To a solution of 5-((3,3-difluoropiperidin-4-yl)oxy)-6-methoxyquinazolin-4(3H)-one (1.4 g, 4.50 mmol) in DCM (20 mL) was added Et$_3$N (909 mg, 9.0 mmol) and Boc$_2$O (1.08 g, 4.95 mmol) at 0° C., and then the resulting mixture was stirred at room temperature for 18 h. When LCMS indicated the reaction was complete, the reaction mixture was diluted with DCM (50 mL) and washed with brine (20 mL). The organic layer was separated and concentrated in vacuum. The residue was triturated with n-hexane at 0° C. and the precipitate was filtered to give the desired product as a pale white solid (1.2 g, 64% yield). MS (ESI) m/z: 412.1 (M+H)$^+$.

Step 2: tert-butyl 4-((4-chloro-6-methoxyquinazolin-5-yl)oxy)-3,3-difluoropiperidine-1-carboxylate

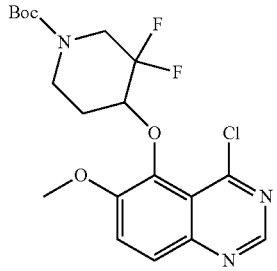 [SMILES: COc1ccc2ncnc(Cl)c2c1OC1CCN(C(=O)OC(C)(C)C)CC1(F)F]

To a solution of tert-butyl 3,3-difluoro-4-((6-methoxy-4-oxo-3,4-dihydroquinazolin-5-yl)oxy)piperidine-1-carboxylate (1.2 g, 2.92 mmol) in DCE (20 mL) was added Et$_3$N (3767 mg, 29.2 mmol) and POCl$_3$ (1.12 g, 7.30 mmol) at room temperature and then the resulting mixture was stirred at 90° C. for 4 h under Ar$_2$ protection. When LCMS indicated the reaction was complete, the reaction mixture was cooled to 0° C., poured into ice water, and neutralized with saturated aqueous NaHCO$_3$ solution. The aqueous phase was extracted with DCM (50 mL×3) and the combined organic layers were washed with saturated aqueous NaHCO$_3$ solution (20 mL) and brine (20 mL). The organic layer was dried over anhydrous Na$_2$SO$_4$ and concentrated in vacuum to give the desired product as a brown solid (0.8 g, 63% yield). MS (ESI) m/z: 430.0 (M+H)$^+$.

150

Step 3: N-(4-([1,2,4]triazolo[1,5-c]pyrimidin-7-yloxy)-3-methylphenyl)-5-((3,3-difluoropiperidin-4-yl)oxy)-6-methoxyquinazolin-4-amine (Example 76)

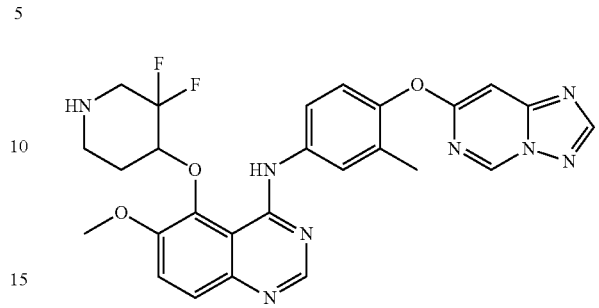

A mixture of tert-butyl 4-((4-chloro-6-methoxyquinazolin-5-yl)oxy)-3,3-difluoropiperidine-1-carboxylate (200 mg, 0.47 mmol), 4-([1,2,4]triazolo[1,5-c]pyrimidin-7-yloxy)-3-methylaniline (112 mg, 0.47 mmol) and TsOH.H$_2$O (18 mg, 0.09 mmol) in IPA (10 mL) was stirred at 100° C. for 16 h under Ar$_2$ protection. When LCMS indicated the reaction was complete, the reaction mixture was cooled to 0° C. Then 4M HCl-dioxane (1 mL) was added thereto and the mixture was stirred at 0° C. for 2 h and neutralized with saturated aqueous NaHCO$_3$ solution. The aqueous phase was extracted with DCM (30 mL×3). The combined organic layer was washed with brine (20 mL). The organic layer was dried over anhydrous Na$_2$SO$_4$ and concentrated in vacuum. The residue was purified by Prep-HPLC to give the desired product as a white solid (100 mg, 38% yield). MS (ESI) m/z: 535 (M+H)$^+$.

$^1$H NMR (400 MHz, DMSO-d$_6$) δ 10.07 (s, 1H), 9.66 (d, J=1.2 Hz, 1H), 8.58 (s, 1H), 8.46 (s, 1H), 7.80 (d, J=9.2 Hz, 2H), 7.71 (dd, J=8.8, 2.4 Hz, 1H), 7.61 (d, J=9.2 Hz, 1H), 5.04-4.91 (m, 1H), 4.00 (s, 3H), 3.16 (t, J=11.3 Hz, 1H), 2.94 (d, J=12.2 Hz, 1H), 2.82 (dd, J=32.6, 14.0 Hz, 1H), 2.56 (t, J=12.5 Hz, 1H), 2.19 (s, 3H), 2.09 (d, J=12.7 Hz, 1H), 1.78 (dt, J=11.8, 8.1 Hz, 1H).

Step 4: N-(4-([1,2,4]triazolo[1,5-c]pyrimidin-7-yloxy)-3-methylphenyl)-5-((3,3-difluoro-1-(methyl-d3)piperidin-4-yl)oxy)-6-methoxyquinazolin-4-amine

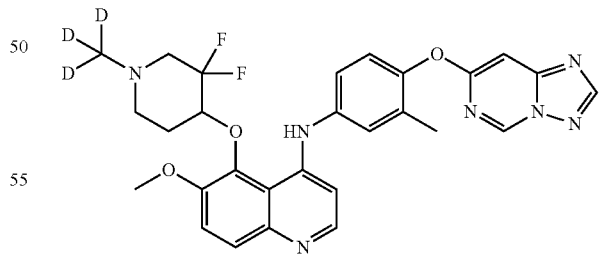

To a solution of N-(4-([1,2,4]triazolo[1,5-c]pyrimidin-7-yloxy)-3-methylphenyl)-5-((3,3-difluoropiperidin-4-yl)oxy)-6-methoxyquinazolin-4-amine (100 mg, 0.18 mmol) in THF (5 mL) was added Et$_3$N (36 mg, 0.36 mmol) and CD$_3$I (130 mg, 0.90 mmol) at room temperature, and then the resulting mixture was stirred at room temperature for 4 h under Ar$_2$. LCMS indicated the reaction was complete and the reaction mixture was poured into ice water, and neutralized with saturated aqueous NaHCO₃ solution. The aqueous phase was extracted with DCM (50 mL×2) and the combined organic layer was washed with brine (20 mL). The organic layer was dried over anhydrous Na$_2$SO$_4$ and concentrated in vacuum. The residue was purified by Prep-HPLC to give the desired product as a white solid (20 mg, 20% yield). MS (ESI) m/z: 552.2 (M+H)$^+$. $^1$H NMR (400 MHz, CDCl$_3$) δ:10.03 (s, 1H), 9.20 (d, J=1.2 Hz, 1H), 8.59 (s, 1H), 8.32 (s, 1H), 7.86 (s, 1H), 7.75-7.78 (m, 1H), 7.68 (d, J=9.2 Hz, 1H), 7.51 (d, J=9.2 Hz, 1H), 7.10 (d, J=8.8 Hz, 1H), 6.88 (d, J=1.2 Hz, 1H), 4.77-4.84 (m, 1H), 4.01 (s, 3H), 3.17-3.23 (m, 1H), 2.91-2.93 (m, 1H), 2.28-2.39 (m, 1H), 2.25 (s, 3H), 2.13 (d, J=6.4 Hz, 3H).

The following compounds were prepared according to the above described methods using different starting materials.

| Ex # | Structure | Name | MS m/z |
|---|---|---|---|
| 78 | 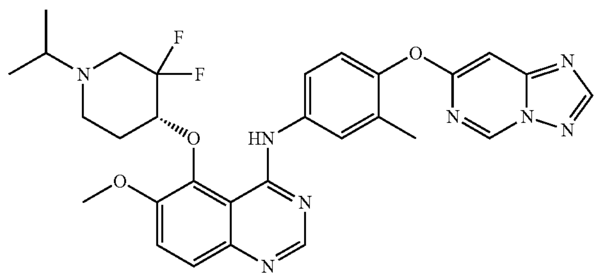 [SMILES: COc1ccc2ncnc(Nc3ccc(Oc4cc5ncnn5cn4)c(C)c3)c2c1O[C@@H]1CCN(C(C)C)CC1(F)F] | (R)-N-(4-([1,2,4]triazolo[1,5-c]pyrimidin-7-yloxy)-3-methylphenyl)-5-((3,3-difluoro-1-isopropylpiperidin-4-yl)oxy)-6-methoxyquinazolin-4-amine | 577 (M + H)$^+$ |
| 79 | 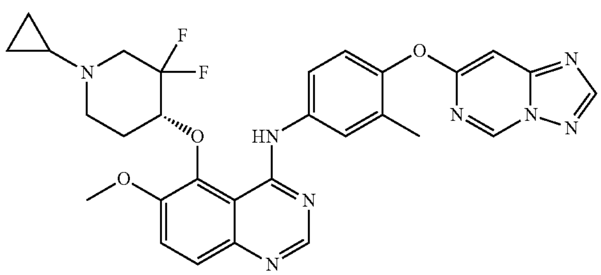 [SMILES: COc1ccc2ncnc(Nc3ccc(Oc4cc5ncnn5cn4)c(C)c3)c2c1O[C@@H]1CCN(C2CC2)CC1(F)F] | (R)-N-(4-([1,2,4]triazolo[1,5-c]pyrimidin-7-yloxy)-3-methylphenyl)-5-((1-cyclopropyl-3,3-difluoropiperidin-4-yl)oxy)-6-methoxyquinazolin-4-amine | 575 (M + H)$^+$ |

Example 78

Yellow solid. $^1$H NMR (400 MHz, CD$_3$OD) δ 9.43 (d, J=1.2 Hz, 1H), 8.41 (d, J=4.8 Hz, 2H), 7.81-7.74 (m, 3H), 7.61 (d, J=9.2 Hz, 1H), 7.17 (d, J=8.8 Hz, 1H), 6.93 (d, J=1.2 Hz, 1H), 4.97-4.88 (m, 1H), 4.05 (s, 3H), 3.21-3.13 (m, 1H), 2.97-2.82 (m, 2H), 2.64-2.51 (m, 1H), 2.47-2.39 (m, 1H), 2.25 (s, 4H), 2.06-1.95 (m, 1H), 1.05 (t, J=6.8 Hz, 6H). MS (ESI) m/z: 577 (M+H)$^+$.

Example 79

Yellow solid. $^1$H NMR (400 MHz, CD$_3$OD) δ 9.43 (d, J=1.2 Hz, 1H), 8.41 (d, J=5.6 Hz, 2H), 7.80-7.70 (m, 3H), 7.61 (d, J=9.2 Hz, 1H), 7.17 (d, J=8.8 Hz, 1H), 6.93 (d, J=1.2 Hz, 1H), 5.01-4.90 (m, 1H), 4.05 (s, 3H), 3.29-3.25 (m, 1H), 3.13-3.07 (m, 1H), 2.72-2.59 (m, 1H), 2.52-2.43 (m, 1H), 2.24 (s, 3H), 2.23-2.18 (m, 1H), 2.03-1.92 (m, 1H), 1.81-1.75 (m, 1H), 0.52-0.39 (m, 4H). MS (ESI) m/z: 575 (M+H)$^+$.

Example 36
(R)—N-(4-([1,2,4]-triazolo[1,5-c]pyrimidin-7-yloxy)-3-methylphenyl)-5-((3,3-difluoro-1-methylpiperidin-4-yl)oxy)-6-(methoxy-d3)quinazolin-4-amine
Example 37
(S)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine
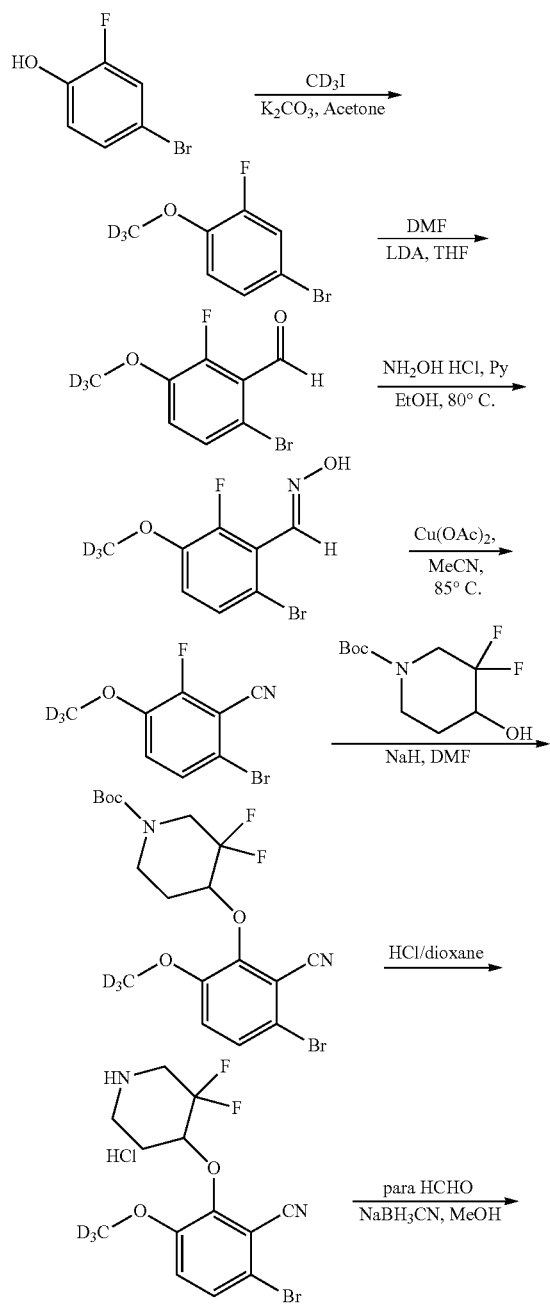
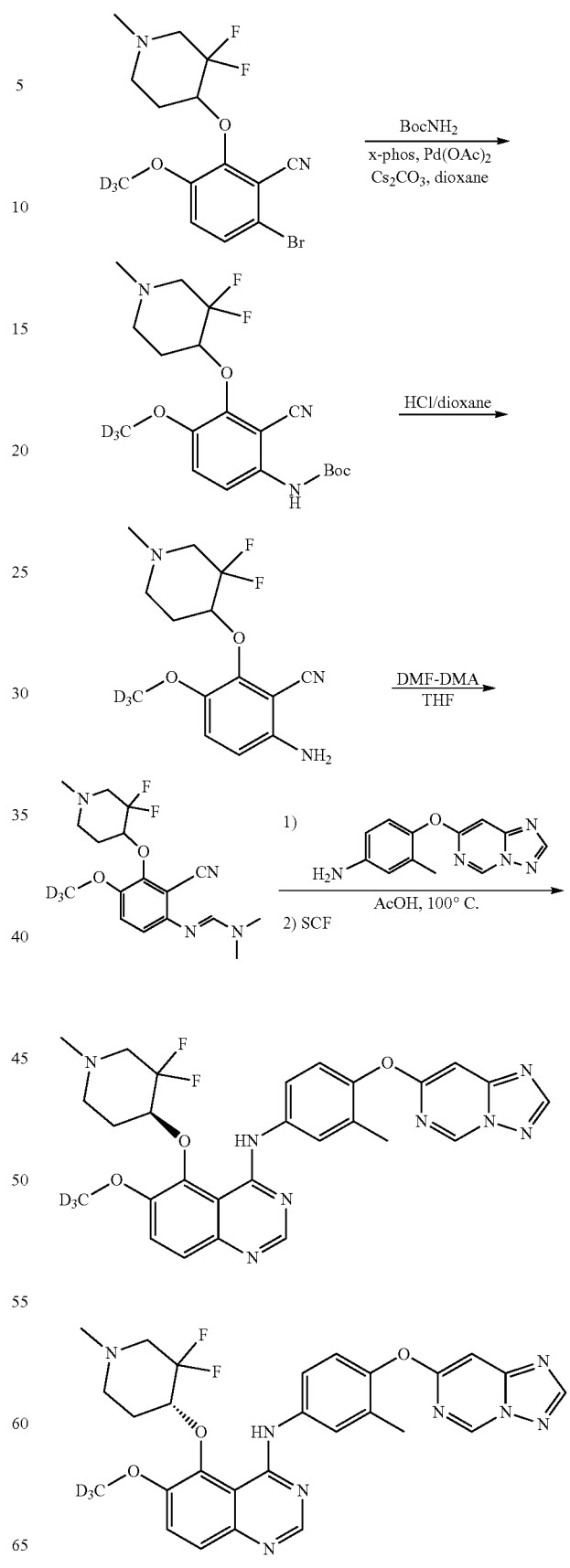

Step 1: 4-bromo-2-fluoro-1-(methoxy-d3)-benzene

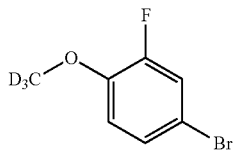

To a solution of 4-bromo-2-fluorophenol (6 g, 31.6 mmol) in acetone (60 mL) was added K₂CO₃ (8.72 g, 63.2 mmol) at 0° C. followed by CD₃I (5.5 g, 37.9 mmol). After addition, the mixture was stirred at room temperature for 2 hrs. The reaction mixture was diluted with EtOAc (100 mL) and washed with water and brine, dried over anhydrous Na₂SO₄, filtered and concentrated to dryness. The residue was purified by chromatography on silica gel (PE:EtOAc=50:1) to give desired product (6 g, 92% yield) as colorless oil.

Step 2: 6-bromo-2-fluoro-3-(methoxy-d3)-benzaldehyde

To a solution of 4-bromo-2-fluoro-1-(methoxy-d3)-benzene (6 g, 29.1 mmol) in THF (60 mL) was added LDA (18.9 mL, 37.83 mmol, 2 M in THF) drop-wise at −78° C. under N₂ atmosphere and the mixture was stirred at −78° C. for 0.5 hr. DMF (4.14 g, 56.7 mmol) was added to the mixture dropwise at −70° C. and the resulting mixture was stirred at room temperature for 1 hr under N₂ atmosphere. The mixture was quenched with saturated aq.NH₄Cl solution (10 mL) at 0° C. and extracted with EtOAc (30 mL×2). The combined organic layers were washed with brine, dried over anhydrous Na₂SO₄, filtered and concentrated to dryness. The residue was purified by chromatography on silica gel (PE:EtOAc=30:1) to give desired product (2.8 g, 41% yield) as yellow solid. ¹H-NMR (400 MHz, DMSO-d₆) δ 10.18 (s, 1H), 7.57 (d, J=8.9 Hz, 1H), 7.42 (t, J=8.8 Hz, 1H).

Step 3: (E)-6-bromo-2-fluoro-3-(methoxy-d3)-benzaldehyde oxime

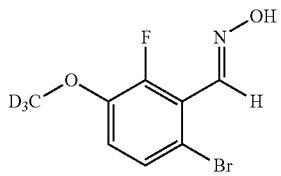 [SMILES: [2H]C([2H])([2H])Oc1ccc(Br)c(/C=N/O)c1F]

To a mixture of 6-bromo-2-fluoro-3-(methoxy-d₃)-benzaldehyde (2.65 g, 11.2 mmol) in EtOH (3 mL) was added pyridine (1.15 g, 14.6 mmol) followed by hydroxylamine hydrochloride (938 mg, 13.5 mmol) at 0° C. After addition, the mixture was stirred at 80° C. for 1 hr. The mixture was diluted with water (30 mL) and extracted with EtOAc (50 mL×2). The combined organic layers were washed with water and brine, dried with anhydrous Na₂SO₄, filtered and concentrated to dryness to give desired product (2.5 g, 89% yield) as white solid. MS (ESI) m/z: 251/253 (M+H)⁺.

Step 4: 6-bromo-2-fluoro-3-(methoxy-d3)-benzonitrile

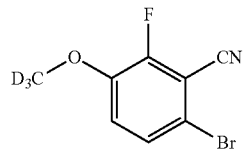 [SMILES: [2H]C([2H])([2H])Oc1ccc(Br)c(C#N)c1F]

To a mixture of (E)-6-bromo-2-fluoro-3-(methoxy-d₃)-benzaldehyde oxime (2.5 g, 10.0 mmol) in MeCN (30 mL) was added Cu(OAc)₂ (200 mg, 1.0 mmol) and the reaction was stirred at 85° C. for 16 hrs. The mixture was diluted with water and extracted with EtOAc (20 mL×2). The combined organic layers were washed with water and brine, dried over anhydrous Na₂SO₄, filtered and concentrated to dryness. The residues was purified by chromatography on silica gel (PE:EtOAc=20:1) to give desired product (2.2 g, 96% yield) as yellow solid.

Step 5: tert-butyl 4-(3-bromo-2-cyano-6-(methoxy-d3)-phenoxy)-3,3-difluoropiperidine-1-carboxylate

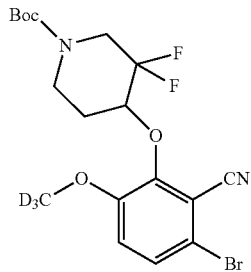 [SMILES: [2H]C([2H])([2H])Oc1ccc(Br)c(C#N)c1OC1CCN(C(=O)OC(C)(C)C)CC1(F)F]

To a mixture of tert-butyl 3,3-difluoro-4-hydroxypiperidine-1-carboxylate (1.02 g, 4.3 mmol) in DMF (20 mL) was added NaH (224 mg, 5.59 mmol, 60% dispersion in mineral oil) at 0° C. and the mixture was stirred at 0° C. for 10 mins. To the above mixture, 6-bromo-2-fluoro-3-(methoxy-d₃)-benzonitrile (1 g, 4.3 mmol) was added and the resulting mixture was stirred at room temperature for 3 hrs. The mixture was diluted with water and extracted with EtOAc (30 mL×2). The combined organic layers were washed with saturated aq.NH₄Cl solution and brine, dried over anhydrous Na₂SO₄, filtered and concentrated to dryness. The residue was purified by chromatography on silica gel (eluted with PE:EtOAc=10:1) to give desired product (1.3 g, 67% yield) as yellow solid. MS (ESI) m/z: 450/452 (M+H)⁺.

Step 6: 6-bromo-2-((3,3-difluoropiperidin-4-yl)oxy)-3-methoxybenzonitrile hydrochloride

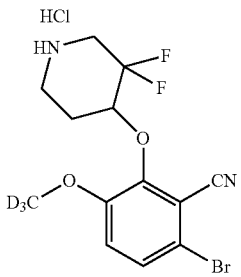 [SMILES: Cl ; [2H]C([2H])([2H])Oc1ccc(Br)c(C#N)c1OC1CCNCC1(F)F]

A solution of tert-butyl 4-(3-bromo-2-cyano-6-(methoxy-d3)-phenoxy)-3,3-difluoropiperidine-1-carboxylate (1.3 g, 2.9 mmol) in HCl/1,4-dioxane (10 mL, 4 M) was stirred at room temperature for 1 hr. The mixture was concentrated to dryness to give 6-bromo-2-((3,3-difluoropiperidin-4-yl)oxy)-3-methoxybenzonitrile hydrochloride (1.3 g, 100% yield) as white solid, which was directly used for next step without purification. MS (ESI) m/z: 350/352 (M+H)$^+$.

Step 7: 6-bromo-2-((3,3-difluoro-1-methylpiperidin-4-yl)oxy)-3-(methoxy-d3)-benzonitrile

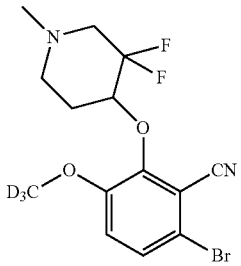 [SMILES: [2H]C([2H])([2H])Oc1ccc(Br)c(C#N)c1OC1CCN(C)CC1(F)F]

To a mixture of 6-bromo-2-((3,3-difluoropiperidin-4-yl)oxy)-3-methoxybenzonitrile hydrochloride (650 mg, 1.43 mmol) in MeOH (10 mL) was added paraformaldehyde (429 mg, 14.3 mmol) followed by AcOH (26 mg, 0.43 mmol) and sodium cyanoborohydride (270 mg, 4.29 mmol) at 0° C. After addition, the mixture was stirred at 70° C. overnight. The mixture was diluted with water and extracted with EtOAc (20 mL×2). The combined organic layers were washed with brine, dried over anhydrous Na$_2$SO$_4$, filtered and concentrated to dryness. The residue was purified by chromatography on silica gel (PE:EtOAc=6:1) to give desired product (500 mg, 96% yield) as yellow solid. MS (ESI) m/z: 364/366 (M+H)$^+$.

Step 8: tert-butyl (2-cyano-3-((3,3-difluoro-1-methylpiperidin-4-yl)oxy)-4-(methoxy-d3)-phenyl)carbamate To a mixture of 6-bromo-2-((3,3-difluoro-1-methylpiperidin-4-yl)oxy)-3-(methoxy-d$_3$)-benzonitrile (500 mg, 1.38 mmol) and tert-Butyl carbamate (71 mg, 2.75 mmol) in 1,4-dioxane (5 mL) was added Cs$_2$CO$_3$ (1.35 g, 4.14 mmol). The mixture was degassed under N$_2$ atmosphere for three times and Pd(OAc)$_2$ (31.4 mg, 0.14 mmol) and Xant-phos (133.3 mg, 0.28 mmol) was added. After addition, the mixture was degassed under N$_2$ atmosphere for three times and stirred at 90° C. overnight. The mixture was diluted with EtOAc (10 mL) and washed with water and brine, dried over anhydrous Na$_2$SO$_4$, filtered and concentrated to give crude product, which was purified by silica gel chromatography (PE:EtOAc=5:1) to give desired product (380 mg, 69% yield) as yellow solid. MS (ESI) m/z: 401 (M+H)$^+$.

Step 9: 6-amino-2-((3,3-difluoro-1-methylpiperidin-4-yl)oxy)-3-(methoxy-d3)-benzonitrile A solution of tert-butyl (2-cyano-3-((3,3-difluoro-1-methylpiperidin-4-yl)oxy)-4-(methoxy-d$_3$)-phenyl)carbamate (380 mg, 0.95 mmol) in HCl/1,4-dioxane (5 mL, 4 M) was stirred at room temperature for 1 hr. The mixture was concentrated to dryness and the residue was alkalified by adding saturated aq.NaHCO$_3$ solution to pH=8. The mixture was extracted with DCM (10 mL×2) and the combined organic layers were washed with brine, dried over anhydrous Na$_2$SO$_4$, filtered and concentrated to dryness to give desired product (280 mg, 98% yield) as yellow oil. MS (ESI) m/z: 301 (M+H)$^+$.

Step 10: (E)-N'-(2-cyano-3-((3,3-difluoro-1-methylpiperidin-4-yl)oxy)-4-(methoxy-d3)-phenyl)-N,N-dimethylformimidamide

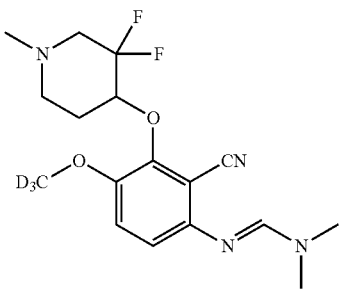

To a solution of 6-amino-2-((3,3-difluoro-1-methylpiperidin-4-yl)oxy)-3-(methoxy-d₃)-benzonitrile (280 mg, 0.93 mmol) in THF (3 mL) was added DMF-DMA (3 mL) and the mixture was stirred at 70° C. for 2 hrs. The mixture was diluted with EtOAc (10 mL), washed with water and brine, dried over anhydrous Na₂SO₄, filtered and concentrated to give crude product, which was purified by silica gel chromatography (PE:EtOAc=2:1) to give desired product (300 mg, 91% yield) as yellow oil. MS (ESI) m/z: 356 (M+H)⁺.

Step 11: (R)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine and (S)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine

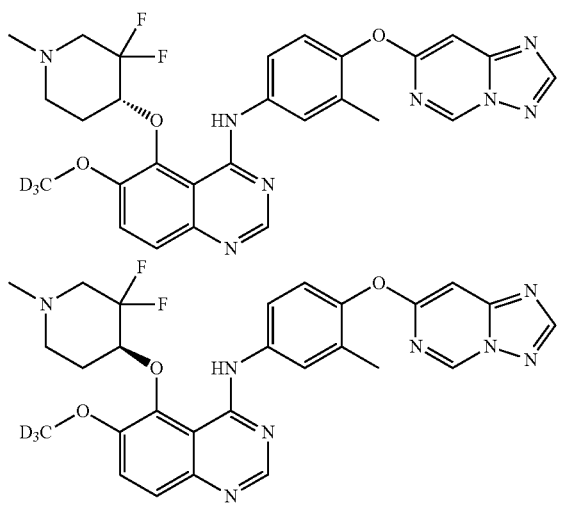

To a solution of (E)-N'-(2-cyano-3-((3,3-difluoro-1-methylpiperidin-4-yl)oxy)-4-(methoxy-d3)-phenyl)-N,N-dimethylformimidamide (150 mg, 0.42 mmol) in AcOH (3 mL) was added 4-([1,2,4]triazolo[1,5-c]pyrimidin-7-yloxy)-3-methylaniline (152 mg, 0.63 mmol) and the mixture was stirred at 100° C. for 5 hrs. The mixture was diluted with EtOAc (10 mL) and alkalified by adding saturated aq.NaHCO₃ solution to pH=8. The mixture was extracted with EtOAc (20 mL×2) and the combined organic layers were washed with brine, dried over anhydrous Na₂SO₄, filtered and concentrated to dryness. The residue was purified by silica gel chromatography (DCM:MeOH=40:1 to 15:1) to give racemic product (90 mg, yield 38.9%) as white solid, which was subsequently separated by chiral SFC to give two enantiomers:

(R)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine (peak 1, retention time: 5.41 min) (28 mg, 12% yield) as light yellow solid. ¹H-NMR (400 MHz, CD₃OD) δ 9.43 (s, 1H), 8.41 (d, J=4.5 Hz, 2H), 7.77 (dd, J=9.6, 4.6 Hz, 3H), 7.61 (d, J=9.2 Hz, 1H), 7.17 (d, J=8.5 Hz, 1H), 6.93 (d, J=1.0 Hz, 1H), 5.00-4.91 (m, 1H), 3.21-3.12 (m, 1H), 2.99-2.85 (m, 1H), 2.46 (dd, J=29.6, 13.0 Hz, 1H), 2.33 (s, 3H), 2.32-2.27 (m, 1H), 2.25 (s, 4H), 2.14-2.06 (m, 1H). MS (ESI) m/z: 552 (M+H)⁺.

(S)—N-(4-([1,2,4]triazolo[1,5-c]pyrimidin-7-yloxy)-3-methylphenyl)-5-((3,3-difluoro-1-methylpiperidin-4-yl)oxy)-6-(methoxy-d3)quinazolin-4-amine (peak 2, retention time: 6.32 min) (30 mg, 13% yield) as light yellow solid. ¹H-NMR (400 MHz, CD₃OD) δ 9.43 (s, 1H), 8.41 (d, J=4.6 Hz, 2H), 7.77 (dd, J=9.6, 4.4 Hz, 3H), 7.61 (d, J=9.2 Hz, 1H), 7.17 (d, J=8.4 Hz, 1H), 6.93 (s, 1H), 5.05-4.89 (m, 1H), 3.16 (d, J=12.0 Hz, 1H), 2.92 (d, J=11.3 Hz, 1H), 2.46 (dd, J=29.5, 12.7 Hz, 1H), 2.33 (s, 3H), 2.29 (d, J=13.1 Hz, 2H), 2.25 (s, 3H), 2.08 (t, J=14.1 Hz, 1H). MS (ESI) m/z: 552 (M+H)⁺.

SFC condition: Column: ChiralPak AS, 250×21.2 mm I.D., 5 μm; Mobile phase: A for CO₂ and B for Methanol (0.1% NH₄OH); Gradient: B 40%; Flow rate: 50 mL/min; Column temperature: 35° C.

Example 77

(R)—N-(4-([1,2,4]triazolo[1,5-c]pyrimidin-7-yloxy)-3-methylphenyl)-5-((3,3-difluoro-1-(methyl-d3)piperidin-4-yl)oxy)-6-(methoxy-d3)quinazolin-4-amine

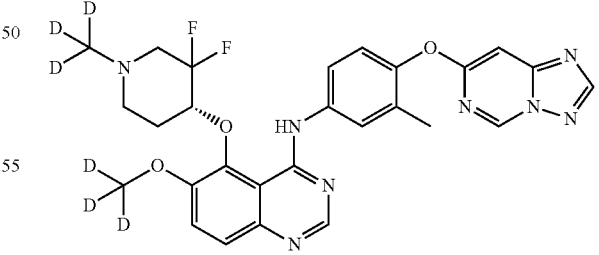

The title compound can be synthesized according to the procedure outline in Examples 36 and 37 as white solid. ¹H NMR (400 MHz, CD₃OD) δ 9.43 (s, 1H), 8.41 (d, J=3.8 Hz, 2H), 7.77 (m, 3H), 7.62 (d, J=9.2 Hz, 1H), 7.17 (d, J=8.5 Hz, 1H), 6.93 (s, 1H), 5.01-4.90 (m, 1H), 3.17 (m, 1H), 2.92 (d, J=12.4 Hz, 1H), 2.46 (m, 1H), 2.36-2.16 (m, 5H), 2.07 (m, 1H). MS (ESI) m/z: 555 (M+H)⁺.

Example 38

N-(4-([1,2,4]triazolo[1,5-c]pyrimidin-7-yloxy)-3-methylphenyl)-6-methoxy-5-(8-methyl-5-oxa-2,8-diazaspiro[3.5]nonan-2-yl)quinazolin-4-amine

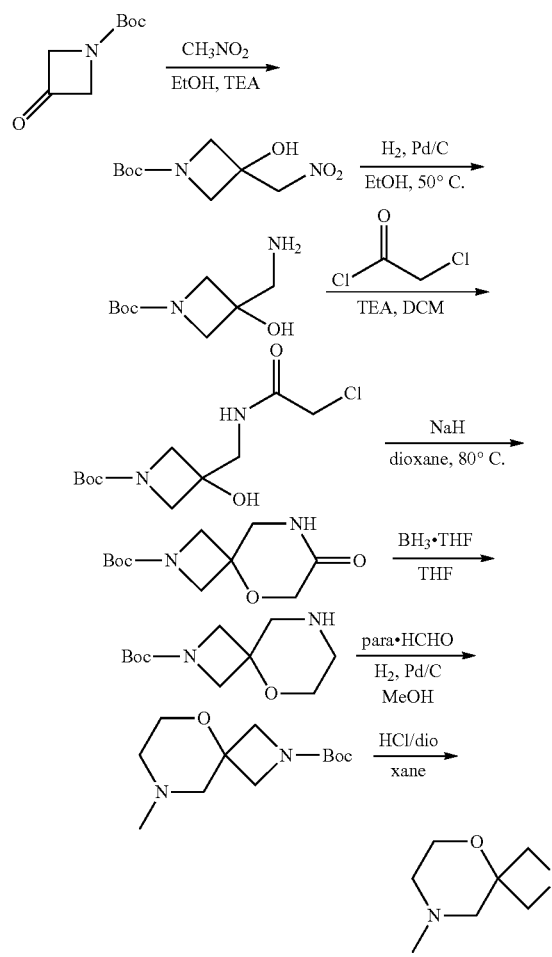

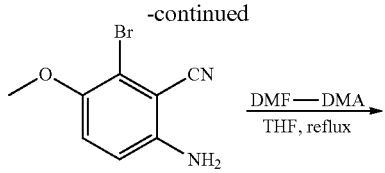

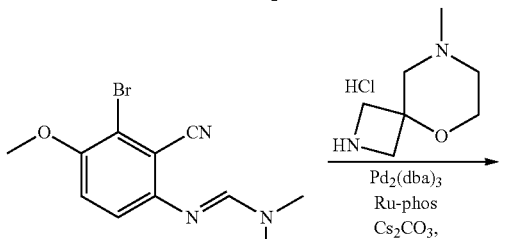

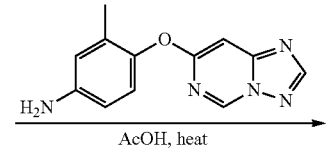

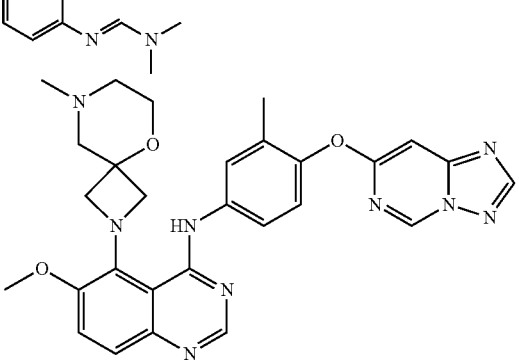

Step 1: tert-butyl 3-hydroxy-3-(nitromethyl)azetidine-1-carboxylate

To a solution of tert-butyl 3-oxoazetidine-1-carboxylate (16.0 g, 0.09 mol) in EtOH (150 mL) was added Et₃N (0.95 g, 9.40 mmol) and nitromethane (21.7 g, 0.36 mol). The mixture was stirred at room temperature for 16 hrs and concentrated to dryness to give desired product (20 g crude) as yellow oil, which was directly used for next step without further purification. MS (ESI) m/z: 233 (M+H)⁺.

Step 2: tert-butyl 3-(aminomethyl)-3-hydroxyazetidine-1-carboxylate

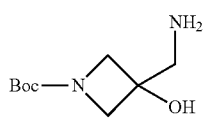

To a solution of tert-butyl 3-hydroxy-3-(nitromethyl)azetidine-1-carboxylate (20 g, 0.09 mol) in EtOH (200 mL) was added Pd/C (2 g, 10% wt) and the reaction mixture was degassed under N$_2$ atmosphere for three times and stirred under that 50° C. for 16 hrs. The mixture was filtered and the filtrate was concentrated to dryness. The residue was purified by silica gel chromatography (DCM:MeOH=50:1) to give desired product (13.0 g, 75% yield) as colorless oil. MS (ESI) m/z: 103 (M+H-100)$^+$.

Step 3: tert-butyl 3-((2-chloroacetamido)methyl)-3-hydroxyazetidine-1-carboxylate

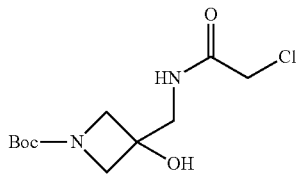 [SMILES: CC(C)(C)OC(=O)N1CC(O)(CNC(=O)CCl)C1]

To a solution of tert-butyl 3-(aminomethyl)-3-hydroxyazetidine-1-carboxylate (13.0 g, 0.06 mol) in DCM (150 mL) was added Et$_3$N (8.5 g, 0.08 mol) followed by drop-wise addition of 2-chloroacetyl chloride (8.7 g, 0.07 mol) at 0° C. The mixture was stirred at room temperature for 2 hrs and quenched with water. The resulting mixture was extracted with DCM (150 mL), washed with aq. NH$_4$Cl and brine, dried over anhydrous Na$_2$SO$_4$, filtered and concentrated to dryness. The residue was purified by silica gel chromatography (DCM:MeOH=50:1) to give desired product (14.0 g, 79% yield) as yellow oil. MS (ESI) m/z: 279 (M+H)$^+$.

Step 4: tert-butyl 7-oxo-5-oxa-2,8-diazaspiro[3.5]nonane-2-carboxylate

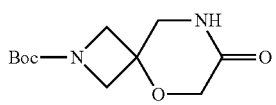

To a solution of tert-butyl 3-((2-chloroacetamido)methyl)-3-hydroxyazetidine-1-carboxylate (7.0 g, 25.2 mmol) in 1,4-dioxane (100 mL) was added NaH (1.76 g, 44.1 mmol, 60% dispersion in mineral oil) in portions at 0° C. The mixture was stirred at 80° C. for 16 hrs and quenched with ice-water. The mixture was extracted with EtOAc (50 mL), washed with saturated aq. NH$_4$Cl solution and brine, dried over anhydrous Na$_2$SO$_4$, filtered and concentrated to dryness. The residue was purified by silica gel chromatography (DCM:MeOH=100:1) to give desired product (2.7 g, 44% yield) as yellow oil. MS (ESI) m/z: 243 (M+H)$^+$.

Step 5: Synthesis of tert-butyl 5-oxa-2,8-diazaspiro[3.5]nonane-2-carboxylate

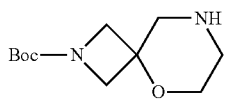

To a solution of tert-butyl 7-oxo-5-oxa-2,8-diazaspiro[3.5]nonane-2-carboxylate (2.7 g, 11.2 mmol) in THF (30 mL) was added borane-tetrahydrofuran complex (33.6 mL, 33.6 mmol) dropwise at 0° C. and the mixture was stirred at 25° C. for 16 hrs. The mixture was quenched with MeOH (10 mL) at 0° C. and stirred at 70° C. for 5 hrs. The resulting mixture was concentrated to dryness and the residue was purified by silica gel chromatography (DCM:MeOH=25:1) to give desired product (2.3 g, 90% yield) as yellow oil. MS (ESI) m/z: 229 (M+H)$^+$.

Step 6: Synthesis of tert-butyl 8-methyl-5-oxa-2,8-diazaspiro[3.5]nonane-2-carboxylate

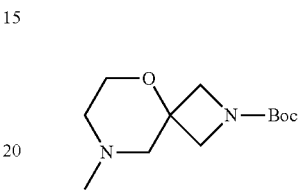

To a degassed mixture of tert-butyl 5-oxa-2,8-diazaspiro[3.5]nonane-2-carboxylate (2.3 g, 10.1 mmol) and paraformaldehyde (1.52 g, 50.5 mmol) in MeOH (25 mL) was added Pd/C (150 mg, 10% wt) and the mixture was degassed under N$_2$ atmosphere for three times and stirred under a H$_2$ balloon at 25° C. for 16 hrs. The mixture was filtered and the filtrate was concentrated to dryness to give desired product (2.0 g, 82% yield) as colorless oil. MS (ESI) m/z: 243 (M+H)$^+$.

Step 7: Synthesis of 8-methyl-5-oxa-2,8-diazaspiro[3.5]nonane hydrochloride

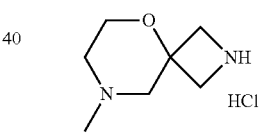

A solution of tert-butyl 8-methyl-5-oxa-2,8-diazaspiro[3.5]nonane-2-carboxylate (1.3 g, 5.3 mmol) in HCl/1,4-dioxane (10 mL, 4M) was stirred at room temperature for 1 hr. The mixture was concentrated to dryness to give desired product (1.1 g, yield 100%) as light yellow solid, which was directly used for next step without purification. MS (ESI) m/z: 143 (M+H)$^+$.

Step 8: 3-methoxy-6-((4-methoxybenzyl)amino)-2-nitrobenzonitrile

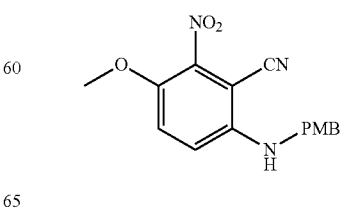

To a solution of 6-fluoro-3-methoxy-2-nitrobenzonitrile (5.4 g, 27.5 mmol) in DMSO (50 mL) was added 4-methoxybenzylamine (4.5 g, 33 mmol) followed by DBU (5.86 g, 38.5 mmol) at 0° C. After addition, the mixture was stirred at room temperature for 16 hrs. The mixture was diluted with EtOAc (100 mL), washed with water and brine, dried over anhydrous $Na_2SO_4$, filtered and concentrated to dryness. The residue was purified by silica gel chromatography (PE:EtOAc=5:1 to 3:1) to give desired product (4.5 g, 52% yield) as orange solid. MS (ESI) m/z: 314 (M+H)$^+$. $^1$H-NMR (400 MHz, CDCl$_3$) δ 7.25-7.27 (d, J=8.4 Hz, 2H), 7.17-7.19 (d, J=9.2 Hz, 1H), 6.91-6.93 (d, J=8.8 Hz, 2H), 6.79-6.82 (d, J=9.6 Hz, 1H), 4.39 (s, 2H), 3.86 (s, 3H), 3.83 (s, 3H).

Step 9: 2-amino-3-methoxy-6-((4-methoxybenzyl)amino)benzonitrile

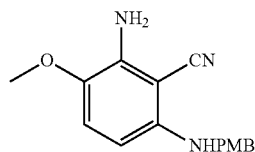

To a solution of 3-methoxy-6-((4-methoxybenzyl)amino)-2-nitrobenzonitrile (3.5 g, 11.2 mmol) in THF (50 mL) was added Pd/C (500 mg, 10% wt) and the mixture was degassed under $N_2$ for three times and stirred under a $H_2$ balloon at room temperature for 5 hrs. The mixture was filtered and the filtrate was concentrated to dryness to give desired product (2.3 g, 73% yield) as brown solid, which was directly used for next step without further purification. MS (ESI) m/z: 284 (M+H)$^+$.

Step 10: 2-bromo-3-methoxy-6-((4-methoxybenzyl)amino)benzonitrile

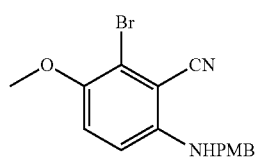

To a solution of 2-amino-3-methoxy-6-((4-methoxybenzyl)amino)benzonitrile (2.2 g, 7.77 mmol) in aq. HBr (20 mL, 40% wt) was added NaNO$_2$ (805 mg, 11.7 mmol) in water (2 mL) at 0° C. After stirred at 0° C. for 1 hr, the mixture was added drop-wise to a solution of CuBr (2.2 g, 15.55 mmol) in HBr (20 mL, 40% wt) at 10° C. and the resulting mixture was stirred at room temperature for 1 hr. The mixture was basified with NH$_4$OH and extracted with EtOAc (20 mL×2). The combined organic layers were washed with brine, dried over anhydrous Na$_2$SO$_4$, filtered and evaporated to dryness. The residue was purified by silica gel chromatography (PE:EtOAc=10:1 to 2:1) to give desired product (700 mg, 26% yield) as yellow solid. MS (ESI) m/z: 347/349 (M+H)$^+$.

Step 11: 6-amino-2-bromo-3-methoxybenzonitrile

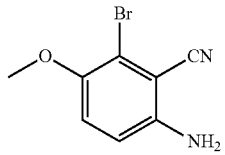

To a solution of 2-bromo-3-methoxy-6-((4-methoxybenzyl)amino)benzonitrile (700 mg, 2.02 mmol) in DCM (3 mL) was added TFA (3 mL) at 0° C. and the reaction was stirred at room temperature for 1 hr. The mixture was concentrated to dryness and the residue was dissolved in DCM (10 mL), washed with saturated aq. NaHCO$_3$ solution and brine, dried over anhydrous Na$_2$SO$_4$, filtered and evaporated to dryness to give desired product (500 mg crude) as red solid, which was directly used to the next reaction without purification. MS (ESI) m/z: 227/229 (M+H)$^+$.

Step 12: (E)-N'-(3-bromo-2-cyano-4-methoxyphenyl)-N,N-dimethylformimidamide

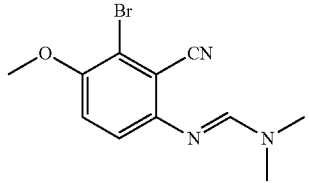

To a solution of 6-amino-2-bromo-3-methoxybenzonitrile (500 mg, 2.02 mmol) in THF (5 mL) was added DMF-DMA (5 mL) and the mixture was stirred at 70° C. for 16 hrs. The mixture was diluted with EtOAc (10 mL) and washed with water and brine successively, dried over anhydrous Na$_2$SO$_4$, filtered and concentrated to give crude product, which was purified by silica gel chromatography (PE:acetone=5:1) to give desired product (390 mg, 69% yield for two steps) as yellow oil. MS (ESI) m/z: 282/284 (M+H)$^+$.

Step 13: (E)-N'-(2-cyano-4-methoxy-3-(8-methyl-5-oxa-2,8-diazaspiro[3.5]nonan-2-yl)phenyl)-N,N-dimethylformimidamide

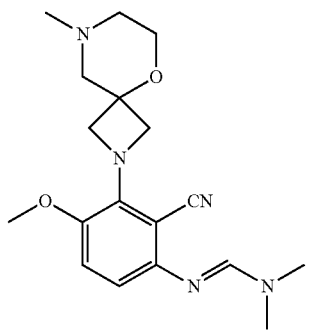

To a mixture of (E)-N'-(3-bromo-2-cyano-4-methoxyphenyl)-N,N-dimethylformimidamide (300 mg, 1.07 mmol) and 8-methyl-5-oxa-2,8-diazaspiro[3.5]nonane (227 mg, 1.60 mmol) in 1,4-dioxane (10 mL) was added Cs$_2$CO$_3$ (1.04 g, 3.20 mmol), Pd$_2$(dba)$_3$ (98 mg, 0.11 mmol) and Ru-phos (100 mg, 0.21 mmol). After addition, the mixture was degassed under N$_2$ atmosphere for three times and stirred at 100° C. under N$_2$ atmosphere for 16 hrs. The mixture was diluted with EtOAc (10 mL) and washed with water and brine, dried over anhydrous Na$_2$SO$_4$, filtered and concentrated to dryness. The residue was purified by silica gel chromatography (PE:acetone=1:1) to give desired product (260 mg, 71% yield) as yellow solid. MS (ESI) m/z: 344 (M+H)$^+$.

Step 14: N-(4-([1,2,4]triazolo[1,5-c]pyrimidin-7-yloxy)-3-methylphenyl)-6-methoxy-5-(8-methyl-5-oxa-2,8-diazaspiro[3.5]nonan-2-yl)quinazolin-4-amine

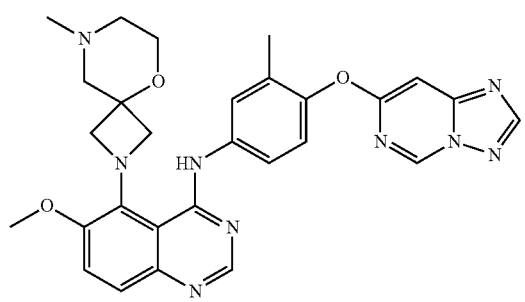

To a solution of (E)-N'-(2-cyano-4-methoxy-3-(8-methyl-5-oxa-2,8-diazaspiro[3.5]nonan-2-yl)phenyl)-N,N-dimethylformimidamide (260 mg, 0.76 mmol) in CH$_3$CN (3 mL) was added AcOH (3 mL) and 4-([1,2,4]triazolo[1,5-c]pyrimidin-7-yloxy)-3-methylaniline (183 mg, 0.76 mmol). After addition, the mixture was stirred at 100° C. under N$_2$ atmosphere for 8 hrs. The mixture was evaporated to dryness. The residue was dissolved in DCM (10 mL), washed with saturated aq. NaHCO$_3$ solution and brine, dried over anhydrous Na$_2$SO$_4$, filtered and concentrated to dryness. The residue was purified by prep-HPLC (10%~100% acetonitrile in water with 0.1% formic acid) to give desired product (37 mg, 9.1% yield) as white solid. MS (ESI) m/z: 540 (M+H)$^+$. $^1$H-NMR (400 MHz, DMSO-d$_6$) δ9.66 (s, 1H), 8.57 (s, 1H), 8.45 (s, 1H), 8.10 (s, 1H), 7.89 (s, 1H), 7.75-7.70 (m, 2H), 7.22-7.20 (m, 1H), 7.11 (s, 1H), 4.18 (m, 2H), 4.06 (s, 3H), 3.82-3.80 (m, 4H), 2.62 (s, 2H), 2.35 (s, 2H), 2.25 (s, 3H), 2.19 (s, 3H).

Example 39

N-(4-([1,2,4]triazolo[1,5-c]pyrimidin-7-yloxy)-3-methylphenyl)-5-((3R,4S)-3-(dimethylamino)-4-fluoropyrrolidin-1-yl)-6-methoxyquinazolin-4-amine

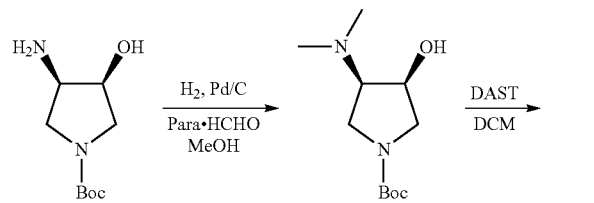

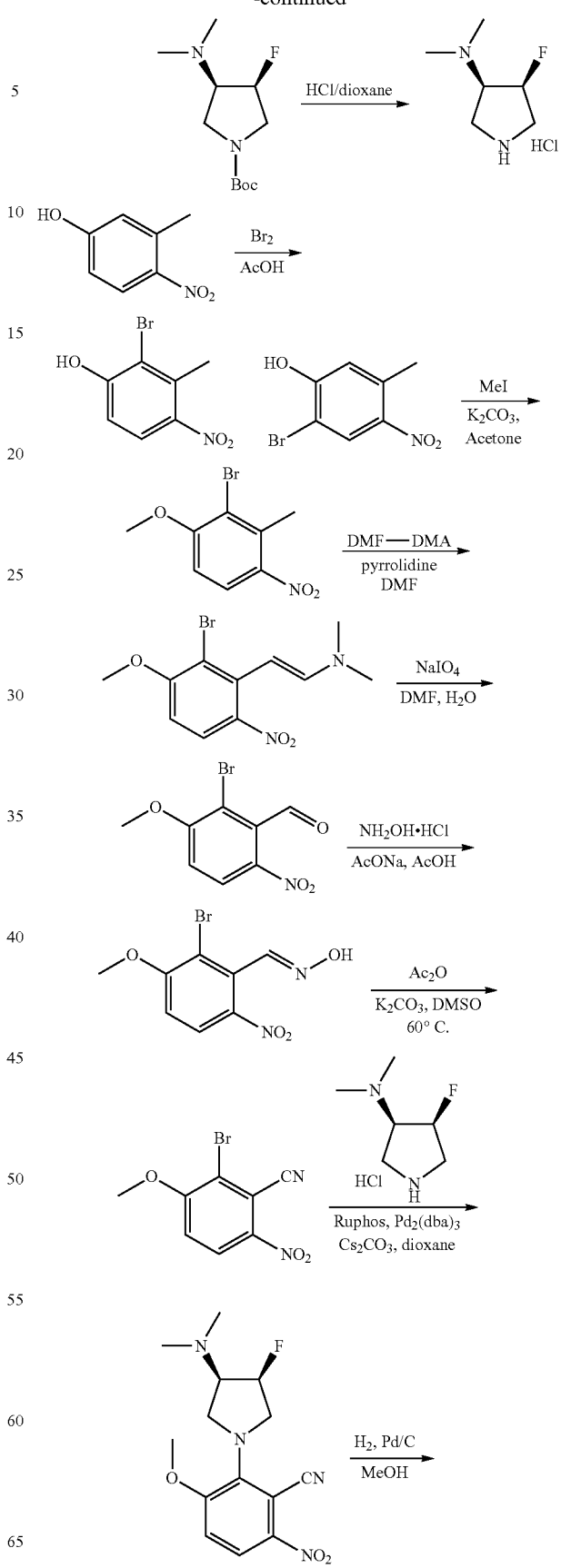

-continued

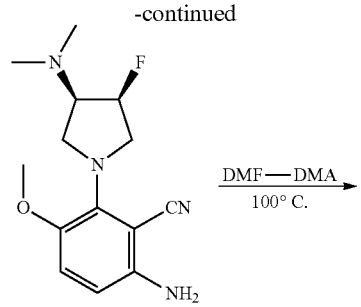

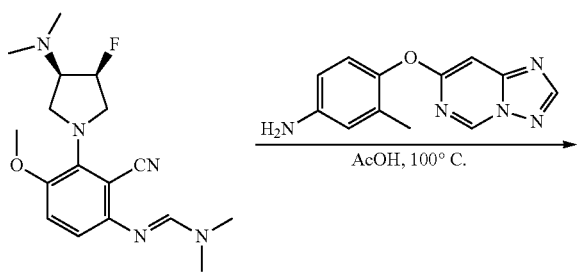

Step 1: (3R,4S)-tert-butyl 3-(dimethylamino)-4-hydroxypyrrolidine-1-carboxylate

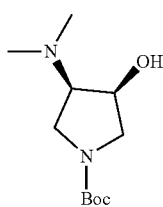 [SMILES: CN(C)[C@@H]1CN(C(=O)OC(C)(C)C)C[C@@H]1O]

To a degassed mixture of tert-butyl (3R,4S)-3-amino-4-hydroxypyrrolidine-1-carboxylate (1 g, 4.95 mmol) and paraformaldehyde (1.49 g, 49.5 mmol) in MeOH (25 mL) was added Pd(OH)$_2$ (500 mg, 10% wt) and the mixture was degassed under N$_2$ atmosphere for three times and stirred under a H$_2$ balloon at 25° C. for 16 hrs. The mixture was filtered and the filtrate was concentrated to dryness to give desired product (950 mg, 84% yield) as colorless oil. MS (ESI) m/z: 231 (M+H)$^+$.

Step 2: (3R,4S)-tert-butyl 3-(dimethylamino)-4-fluoropyrrolidine-1-carboxylate

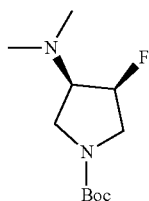 [SMILES: CN(C)[C@@H]1CN(C(=O)OC(C)(C)C)C[C@@H]1F]

To a mixture of (3R,4S)-tert-butyl 3-(dimethylamino)-4-hydroxypyrrolidine-1-carboxylate (500 mg, 2.17 mmol) in DCM (3 mL) was added DAST (83 mg, 3.26 mmol) dropwise at −78° C. After addition, the mixture was stirred at room temperature for 16 hrs and quenched by saturated aq. NaHCO$_3$ solution (10 mL). The resulting mixture was extracted with DCM (10 mL×2). The organic phases were washed with water and brine, dried over anhydrous Na$_2$SO$_4$, filtered and concentrated to dryness. The residue was purified by column chromatography on silica gel (DCM:MeOH=60:1) to give desired product (460 mg, 92% yield) as light yellow oil. MS (ESI) m/z: 233 (M+H)$^+$.

Step 3: (3R,4S)-4-fluoro-N,N-dimethylpyrrolidin-3-amine hydrochloride

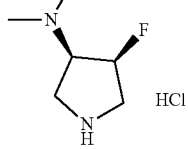

A solution of (3R,4S)-tert-butyl 3-(dimethylamino)-4-fluoropyrrolidine-1-carboxylate (460 mg, 1.98 mmol) in HCl/1,4-dioxane (10 mL, 4M) was stirred at room temperature for 1 hr. The mixture was concentrated to dryness to give desired product (430 mg, 100% yield) as white solid, which was directly used to the next reaction without further purification. MS (ESI) m/z: 133 (M+H)$^+$.

Step 4: 2-bromo-3-methyl-4-nitrophenol

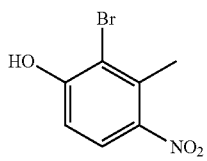

To a solution of 3-methyl-4-nitrophenol (25 g, 0.149 mol) in AcOH (200 mL) was added a solution of Br$_2$ (26.3 g, 0.164 mol) in AcOH (50 mL) dropwise at 15° C. After addition, the mixture was stirred at room temperature for 16 hrs. After TLC (PE:DCM=1:1) showed the reaction was complete, the reaction mixture was poured into ice-water and the slurry was filtered. The filter cake was washed with water twice and dried under reduced pressure to give a mixture of 2-bromo-3-methyl-4-nitrophenol and 2-bromo-5-methyl-4-nitrophenol (28 g, 76% yield) as brown solid, which was directly used to the next reaction without purification.

Step 5:
2-bromo-1-methoxy-3-methyl-4-nitrobenzene (3)

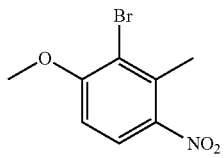

To a mixture of 2-bromo-3-methyl-4-nitrophenol and 2-bromo-5-methyl-4-nitrophenol (28 g, 0.114 mol) in acetone (300 mL) was added $K_2CO_3$ (23.6 g, 0.171 mol) followed by MeI (19.4 g, 0.136 mol) at 0° C. After addition, the reaction was stirred at 35° C. for 3 hrs. The mixture was filtered and the filtrate was diluted with EtOAc, washed with water and brine, dried and concentrated to dryness. The residue was purified by silica gel chromatography (PE:EtOAc=15:1 to 5:1) to give a mixture of 2-bromo-1-methoxy-3-methyl-4-nitrobenzene and 1-bromo-2-methoxy-4-methyl-5-nitrobenzene (12.3 g, 44% yield) as yellow solid.

Step 6: (E)-2-(2-bromo-3-methoxy-6-nitrophenyl)-N,N-dimethylethenamine

To a mixture of 2-bromo-1-methoxy-3-methyl-4-nitrobenzene and 1-bromo-2-methoxy-4-methyl-5-nitrobenzene (12 g, 48.8 mmol) in DMF (100 mL) was added pyrrolidine (3.5 g, 48.8 mmol) followed by DMF-DMA (17.4 g, 0.15 mol) and the resulting mixture was stirred at 100° C. under $N_2$ atmosphere for 16 hrs. The mixture was concentrated to dryness and the residue was diluted with EtOAc, washed with water and brine, dried and concentrated to dryness to give a mixture of (E)-2-(2-bromo-3-methoxy-6-nitrophenyl)-N,N-dimethylethenamine and (E)-2-(4-bromo-5-methoxy-2-nitrophenyl)-N,N-dimethylethen-1-amine (15.5 g, crude) as dark oil, which was directly used to the next reaction without purification.

Step 7: 2-bromo-3-methoxy-6-nitrobenzaldehyde

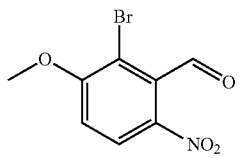

To a stirred solution of $NaIO_4$ (31.2 g, 0.146 mol) in water/DMF (300 mL/100 mL) was added a mixture of (E)-2-(2-bromo-3-methoxy-6-nitrophenyl)-N,N-dimethylethenamine and (E)-2-(4-bromo-5-methoxy-2-nitrophenyl)-N,N-dimethylethen-1-amine (15.5 g, 48.8 mmol) in DMF (50 mL) dropwise at 0° C. After addition, the mixture was stirred at 0° C. for 3 hrs. The mixture was diluted with EtOAc and washed with water and brine, dried over anhydrous $Na_2SO_4$, filtered and concentrated to dryness. The residue was purified by silica gel chromatography (PE:EtOAc=10:1 to 5:1) to desire product (4.6 g, 36% yield) as yellow solid.

Step 8:
(E/Z)-2-bromo-3-methoxy-6-nitrobenzaldehyde oxime

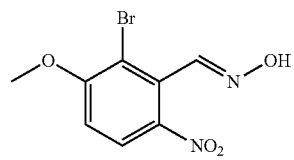

To a solution of 2-bromo-3-methoxy-6-nitrobenzaldehyde (4 g, 15.4 mmol) in AcOH (30 mL) was added Hydroxylamine hydrochloride (1.28 g, 18.4 mmol) and AcONa (1.64 g, 20 mmol). The mixture was stirred 100° C. for 2 hrs and then concentrated to dryness. The residue was dissolved in EtOAc, washed with water and brine, dried and concentrated to dryness to give desire product (4.3 g, 100% yield) as yellow oil. MS (ESI) m/z: 275/277 $(M+H)^+$.

Step 9: 2-bromo-3-methoxy-6-nitrobenzonitrile

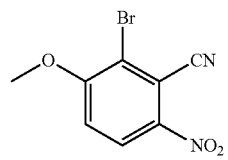

To a solution of (E/Z)-2-bromo-3-methoxy-6-nitrobenzaldehyde oxime (4.3 g, 15.4 mmol) in DMSO (100 mL) was added $K_2CO_3$ (4.25 g, 30.8 mmol) followed by $Ac_2O$ (3.1 g, 30.8 mmol) and the mixture was stirred at 60° C. under $N_2$ atmosphere for 16 hrs. The mixture was diluted with EtOAc, washed with water and brine, and concentrated to dryness. The residue was purified by silica gel chromatography (PE:EtOAc=10:1 to 3:1) to give desire product (3.8 g, 91% yield) as yellow solid.

Step 10: 2-((3R,4S)-3-(dimethylamino)-4-fluoropyrrolidin-1-yl)-3-methoxy-6-nitrobenzonitrile

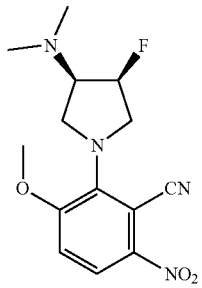 [SMILES: COc1ccc([N+](=O)[O-])c(C#N)c1N1C[C@@H](N(C)C)[C@@H](F)C1]

To a mixture of 2-bromo-3-methoxy-6-nitrobenzonitrile (150 mg, 0.59 mmol) and (3R,4S)-4-fluoro-N,N-dimethylpyrrolidin-3-amine hydrochloride (178 mg, 0.77 mmol) in 1,4-dioxane (5 mL) was added $Cs_2CO_3$ (587 mg, 1.77 mmol) followed by $Pd_2(dba)_3$ (54.9 mg, 0.06 mmol) and Ru-phos (55.9 mg, 0.12 mmol) under $N_2$ atmosphere. After addition, the mixture was degassed under $N_2$ atmosphere for three times and stirred at 90° C. under $N_2$ atmosphere overnight. The mixture was diluted with EtOAc (20 mL) and washed with water and brine, dried over anhydrous $Na_2SO_4$, filtered and concentrated to give crude product, which was purified by silica gel chromatography (PE:EtOAc=3:1) to give desired product (160 mg, 88% yield) as yellow oil. MS (ESI) m/z: 309 $(M+H)^+$.

Step 11: 6-amino-2-((3R,4S)-3-(dimethylamino)-4-fluoropyrrolidin-1-yl)-3-methoxybenzonitrile

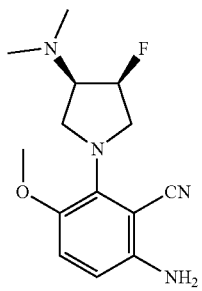 [SMILES: COc1ccc(N)c(C#N)c1N1C[C@@H](N(C)C)[C@@H](F)C1]

To a mixture of 2-((3R,4S)-3-(dimethylamino)-4-fluoropyrrolidin-1-yl)-3-methoxy-6-nitrobenzonitrile (160 mg, 0.52 mmol) in MeOH (3 mL) and EtOAc (3 mL) was added Pd/C (30 mg, 10% wt). The mixture was degassed under $N_2$ atmosphere for three times and stirred under a $H_2$ balloon at 25° C. for 2 hrs. The mixture was filtered and the filtrate was concentrated to dryness to give desired product (100 mg 69% yield) as yellow oil. MS (ESI) m/z: 279 $(M+H)^+$.

Step 12: (E)-N'-(2-cyano-3-((3R,4S)-3-(dimethylamino)-4-fluoropyrrolidin-1-yl)-4-methoxyphenyl)-N,N-dimethylformimidamide

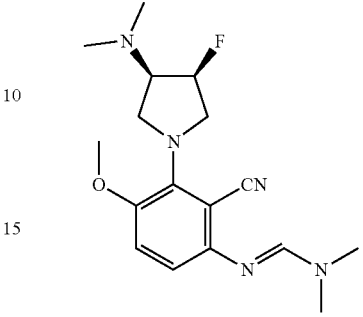

A solution of 6-amino-2-((3R,4S)-3-(dimethylamino)-4-fluoropyrrolidin-1-yl)-3-methoxybenzonitrile (100 mg, 0.36 mmol) in THF (2 mL) was added DMF-DMA (2 mL) and the mixture was stirred at 70° C. for 2 hrs. The mixture was diluted with EtOAc (20 mL), washed with water and brine, dried over anhydrous $Na_2SO_4$, filtered and concentrated to give crude product, which was purified by silica gel chromatography (PE:EtOAc=1:1) to give desired product (100 mg, 83% yield) as yellow oil. MS (ESI) m/z: 334 $(M+H)^+$.

Step 13: N-(4-([1,2,4]triazolo[1,5-c]pyrimidin-7-yloxy)-3-methylphenyl)-5-((3R,4S)-3-(dimethylamino)-4-fluoropyrrolidin-1-yl)-6-methoxyquinazolin-4-amine

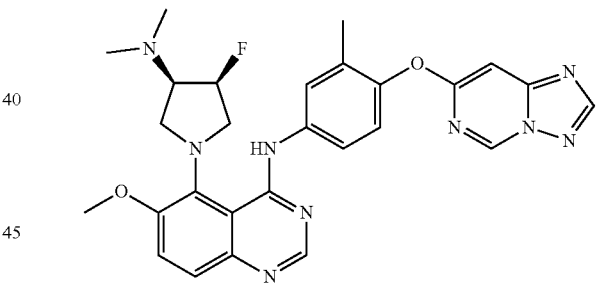

To a solution of (E)-N'-(2-cyano-3-((3R,4S)-3-(dimethylamino)-4-fluoropyrrolidin-1-yl)-4-methoxyphenyl)-N,N-dimethylformimidamide (100 mg, 0.30 mmol) in AcOH (3 mL) was added 4-([1,2,4]triazolo[1,5-c]pyrimidin-7-yloxy)-3-methylaniline (108 mg, 0.45 mmol) and the mixture was stirred at 100° C. for 16 hrs. The mixture was diluted with EtOAc (10 mL) and alkalified by adding saturated aq. $NaHCO_3$ solution to pH=8. The mixture was extracted with EtOAc (10 mL×2) and the combined organic layers were washed with brine, dried over anhydrous $Na_2SO_4$, filtered and concentrated to dryness. The residue was purified by column chromatography on silica gel (DCM:MeOH=50:1 to 15:1) to give desired product (30 mg, 19% yield) as white solid. MS (ESI) m/z: 530 $(M+H)^+$. $^1$H-NMR (400 MHz, DMSO-$d_6$) δ 13.25 (s, 1H), 9.43 (d, J=1.2 Hz, 1H), 8.58 (s, 1H), 8.46 (s, 1H), 7.81-7.87 (m, 2H), 7.75-7.77 (m, 2H), 7.18-7.20 (d, J=8.4 Hz, 1H), 7.12 (d, J=1.2 Hz, 1H), 5.32-5.56 (m, 1H), 3.94-4.04 (m, 1H), 4.00 (s, 3H), 3.38-3.53 (m, 4H), 2.26-2.29 (br, 6H), 2.17 (s, 3H).

Example 40

N-(4-([1,2,4]triazolo[1,5-c]pyrimidin-7-yloxy)-3-methylphenyl)-5-((3R,4R)-3-(dimethylamino)-4-fluoropyrrolidin-1-yl)-6-methoxyquinazolin-4-amine

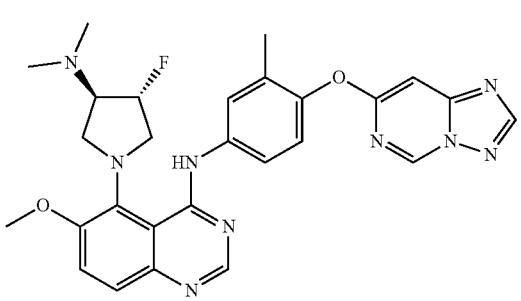 [SMILES: COc1ccc2ncnc(Nc3ccc(Oc4cc5ncnn5cn4)c(C)c3)c2c1N1C[C@@H](F)[C@H](N(C)C)C1]

This material can be synthesized according to the procedure outline in Example 39 to give the desired product as a white solid. MS (ESI) m/z: 530 (M+H)$^+$. $^1$H-NMR (400 MHz, DMSO-d$_6$) δ 13.15 (s, 1H), 9.66 (d, J=1.1 Hz, 1H), 8.58 (s, 1H), 8.45 (d, J=5.4 Hz, 1H), 7.87 (d, J=2.0 Hz, 1H), 7.85-7.78 (m, 1H), 7.76 (d, J=5.9 Hz, 2H), 7.20-7.06 (m, 2H), 5.50-5.35 (m, 1H), 4.12-3.90 (m, 4H), 3.57-3.39 (m, 2H), 3.28-3.09 (m, 1H), 2.30 (t, J=13.0 Hz, 6H), 2.17 (s, 3H).

Example 41

N-(4-([1,2,4]triazolo[1,5-c]pyrimidin-7-yloxy)-3-methylphenyl)-6-methoxy-5-(5-methyl-8-oxa-2,5-diazaspiro[3.5]nonan-2-yl)quinazolin-4-amine

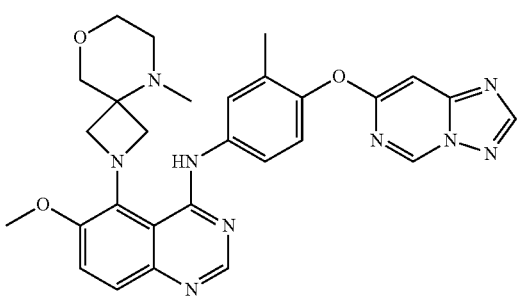 [SMILES: COc1ccc2ncnc(Nc3ccc(Oc4cc5ncnn5cn4)c(C)c3)c2c1N1CC2(COCCN2C)C1]

This material can be synthesized according to the procedure outline in Example 39 to give the desired product as a light yellow solid. MS (ESI) m/z: 540 (M+H)$^+$. $^1$H-NMR (400 MHz, DMSO-d$_6$) δ 13.29 (s, 1H), 9.67 (d, J=1.2 Hz, 1H), 8.58 (s, 1H), 8.36 (s, 1H), 7.79 (d, J=9.3 Hz, 1H), 7.72-7.67 (m, 3H), 7.21-7.18 (m, 1H), 7.16 (d, J=1.1 Hz, 1H), 4.59-4.21 (m, 2H), 4.05 (s, 3H), 3.86-3.83 (m, 2H), 3.82-3.65 (m, 2H), 3.65-3.61 (m, 2H), 2.58 (s, 3H), 2.54-2.51 (m, 2H), 2.18 (s, 3H).

Example 42

N-(4-([1,2,4]triazolo[1,5-c]pyrimidin-7-yloxy)-3-methylphenyl)-6-methoxy-5-(4-methylhexahydropyrrolo[3,4-b][1,4]oxazin-6(2H)-yl)quinazolin-4-amine

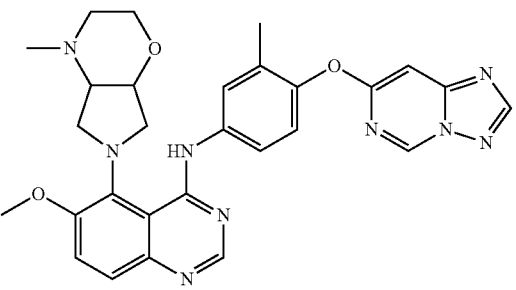 [SMILES: COc1ccc2ncnc(Nc3ccc(Oc4cc5ncnn5cn4)c(C)c3)c2c1N1CC2OCCN(C)C2C1]

This material can be synthesized according to the procedure outline in Example 39 to give the desired product as a yellow solid. MS (ESI) m/z: 540 (M+H)$^+$. $^1$H-NMR (400 MHz, CD$_3$OD) δ 9.43 (s, 1H), 8.39-8.41 (d, J=8.0 Hz, 2H), 7.99-8.02 (dd, J=8.4, 2.4 Hz, 1H), 7.94-7.95 (d, J=2.4 Hz, 1H), 7.73 (s, 2H), 7.14-7.16 (d, J=8.4 Hz, 1H), 6.89 (s, 1H), 4.31-4.33 (m, 1H), 4.06 (s, 3H), 3.98-4.01 (m, 1H), 3.76-3.81 (m, 2H), 3.67-3.72 (m, 1H), 3.60-3.66 (m, 2H), 3.25-3.27 (m, 1H), 2.80-2.87 (m, 1H), 2.54-2.57 (m, 1H), 2.40 (s, 3H), 2.24 (s, 3H).

Example 43

(S)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine

Example 44

(R)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine

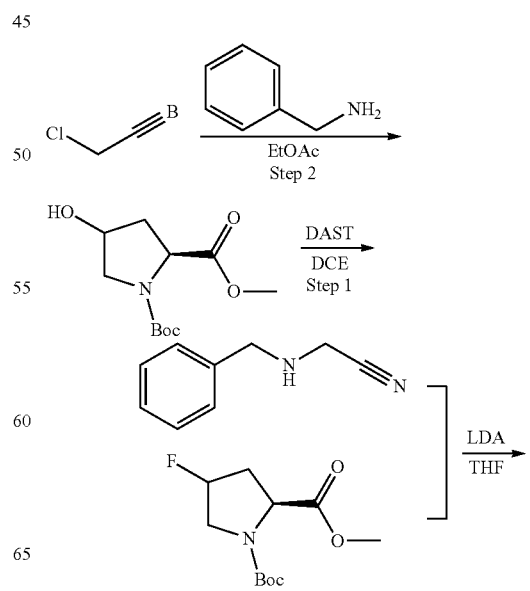

177
-continued

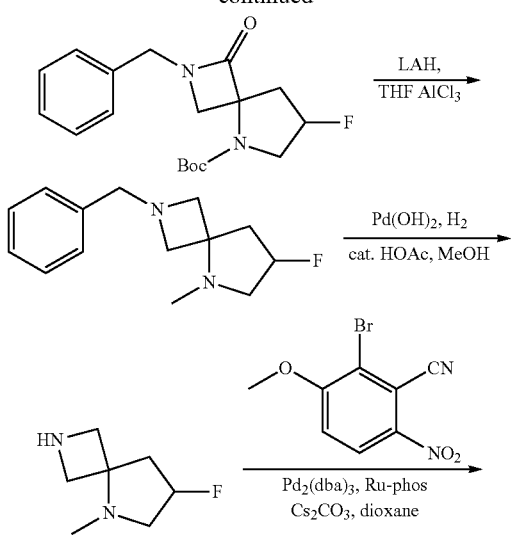

178
-continued

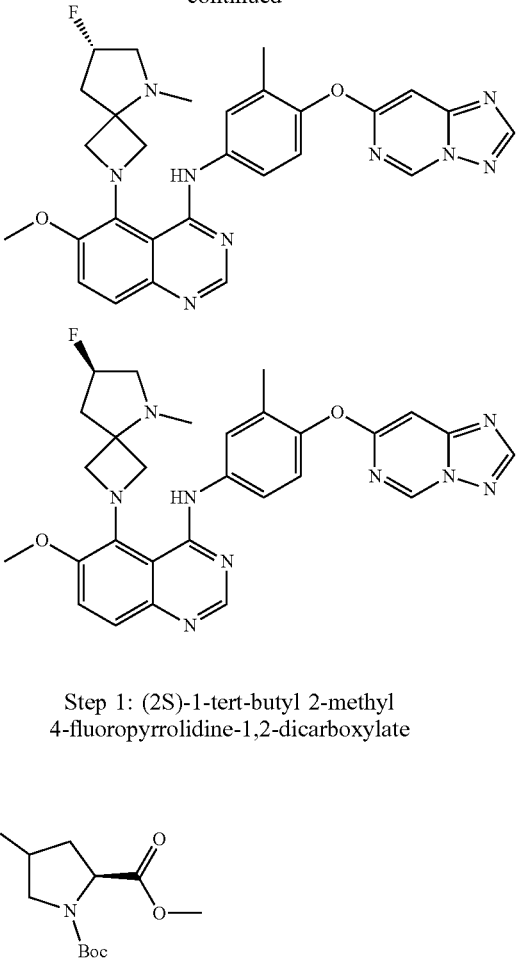

Step 1: (2S)-1-tert-butyl 2-methyl 4-fluoropyrrolidine-1,2-dicarboxylate

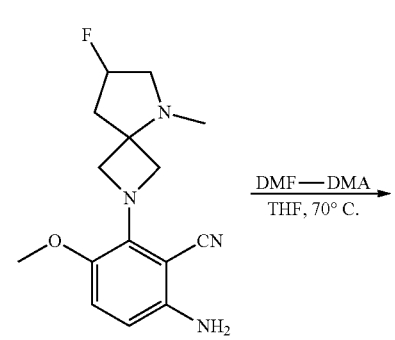

To a solution of 1-(tert-butyl) 2-methyl (2S)-4-hydroxy-pyrrolidine-1,2-dicarboxylate (8 g, 32.7 mmol) in DCE (100 mL) was added DAST (7.89 g, 48.9 mmol) dropwise at 0° C. and the mixture was stirred at 25° C. for 5 hrs. The mixture was quenched by ice-cooled saturated aq. NaHCO$_3$ solution and extracted with DCM (100 mL). The organic phase was washed with water and brine, dried over anhydrous Na$_2$SO$_4$, filtered and concentrated to dryness. The residue was purified by column chromatography on silica gel (DCM:MeOH=60:1) to give desired product (6.0 g, 74% yield) as light yellow oil. MS (ESI) m/z: 248 (M+H)$^+$.

Step 2: 2-(benzylamino)acetonitrile

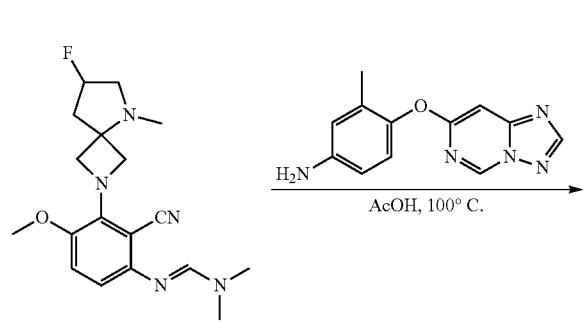

To a solution of 2-chloroacetonitrile (15 g, 0.2 mol) in EtOAc (60 ml) was added benzylamine (43.9 g, 0.4 mol) and the mixture was stirred at 45° C. for 0.5 hr. The mixture was filtered and the filtrate was concentrated to dryness. The residue was purified by column chromatography on silica gel (PE:EtOAc=5:1) to give 2-(benzylamino)acetonitrile (29 g, 99% yield) as light yellow oil. MS (ESI) m/z: 147 (M+H)$^+$.

Step 3: tert-butyl 2-benzyl-7-fluoro-1-oxo-2,5-diazaspiro[3.4]octane-5-carboxylate

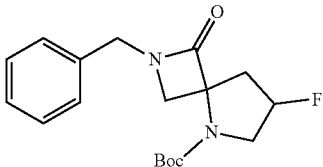 [SMILES: CC(C)(C)OC(=O)N1CC(F)CC12CN(Cc1ccccc1)C2=O]

To a solution of 2-(benzylamino)acetonitrile (2 g, 13.7 mmol) in anhydrous THF (20 mL) was added LDA (23.9 mL, 47.9 mmol, 1M) dropwise at −78° C. After addition, the reaction mixture was stirred at this temperature for 60 min followed by drop-wise addition of a solution of 1-(tert-butyl)-2-methyl (2S)-4-fluoropyrrolidine-1,2-dicarboxylate (6.76 g, 27.4 mmol) in THF (20 mL). The reaction mixture was stirred at −78° C. to room temperature overnight. The resulting mixture was quenched with saturated aq. NH$_4$Cl solution (40 mL) and extracted with EtOAc (30 mL×2). The combined organic layers were washed with brine, dried over anhydrous Na$_2$SO$_4$, filtered and concentrated under vacuum to give crude product, which was purified by flash chromatography (silica gel, 0-20% EtOAc in PE) to give desired product (2.4 g, 53% yield) as a yellow solid. MS (ESI) m/z 335 (M+H)$^+$.

Step 4: 2-benzyl-7-fluoro-5-methyl-2,5-diazaspiro[3.4]octane

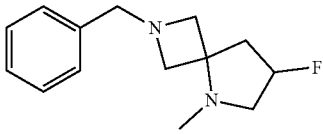 [SMILES: CN1CC(F)CC12CN(Cc1ccccc1)C2]

To a suspension of LiAlH$_4$ (816 mg, 21.5 mmol) in anhydrous THF (50 mL) was added aluminum trichloride (2.83 g, 21.5 mmol) in portions at 0° C. After addition, the mixture was stirred at this temperature for 30 min followed by addition of tert-butyl 2-benzyl-7-fluoro-1-oxo-2,5-diazaspiro[3.4]octane-5-carboxylate (2.4 g, 7.16 mmol). The reaction mixture was stirred at room temperature overnight. The resulting mixture was quenched by aq.NaOH solution (1 mL, 15% wt) and water (1 mL, 3 mL). The slurry was filtered and the filter cake was washed with dichloromethane twice, the combined filtrate was dried over anhydrous Na$_2$SO$_4$, filtered and concentrated to give desired product (700 mg, 42% yield) as yellow oil. MS (ESI) m/z: 235 (M+1)$^+$.

Step 5: 2-benzyl-7-fluoro-5-methyl-2,5-diazaspiro[3.4]octane

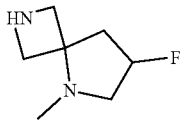

A solution of 2-benzyl-7-fluoro-5-methyl-2,5-diazaspiro[3.4]octane (700 mg, 2.97 mmol) and cat. HOAc (0.1 mL) in methanol (20 mL) was degassed three times under N$_2$ atmosphere, and Pd(OH)$_2$ (100 mg, 10% wt) was added. The mixture was degassed again and stirred under a H$_2$ balloon at room temperature overnight. The reaction was filtered and the filtrate was concentrated to dryness to give desired product (350 mg, 81% yield) as light yellow oil. MS (ESI) m/z: 145 (M+1)$^+$.

Step 6-9: (S)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine and (R)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine

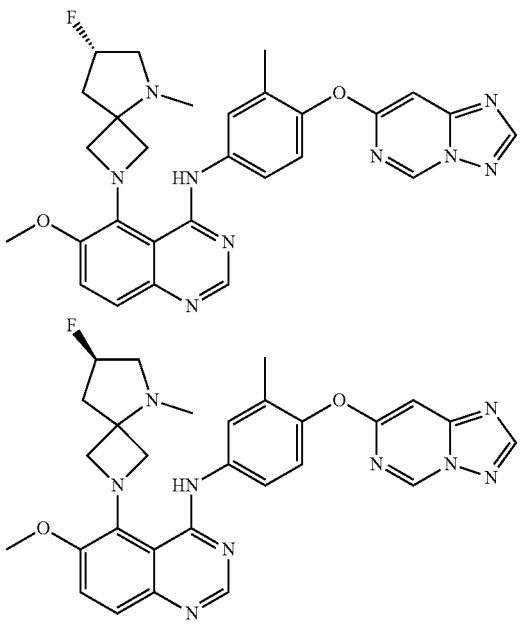

The racemic N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine (60 mg) as white solid was prepared in a similar fashion to Example 39, which was separated by chiral SFC to give arbitrarily assigned:

(S)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine (peak 1, retention time: 4.02 min) (22 mg, 9.4% yield) as light yellow solid. MS (ESI) m/z: 542 (M+H)$^+$. $^1$H-NMR (400 MHz, CD$_3$OD) δ 9.42 (s, 1H), 8.41 (s, 1H), 8.29 (s, 1H), 7.67-7.74 (m, 5H), 7.18-7.20 (d, J=8.8 Hz, 1H), 5.14-5.28 (m, 1H), 4.09-4.29 (m, 2H), 4.11 (s, 3H), 3.41-3.69 (m, 2H), 2.91-3.16 (m, 2H), 2.56-2.71 (m, 2H), 2.70 (s, 3H), 2.25 (s, 3H).

(R)—N-(4-([1,2,4]triazolo[1,5-c]pyrimidin-7-yloxy)-3-methylphenyl)-5-(7-fluoro-5-methyl-2,5-diazaspiro[3.4]octan-2-yl)-6-methoxyquinazolin-4-amine (peak 2, retention time: 4.51 min) (9 mg, 3.8% yield) as light yellow solid. MS (ESI) m/z: 542 (M+H)$^+$. $^1$H-NMR (400 MHz, DMSO-d$_6$) δ 9.43 (s, 1H), 8.42 (s, 1H), 8.32 (s, 1H), 7.67-7.74 (m, 4H), 7.21-7.23 (d, J=8.8 Hz, 1H), 6.96 (s, 1H), 5.14-5.28 (m, 1H), 4.10-4.31 (m, 2H), 4.13 (s, 3H), 3.42-3.70 (m, 2H), 2.91-3.12 (m, 2H), 2.56-2.71 (m, 2H), 2.72 (s, 3H), 2.26 (s, 3H).

SFC condition: Column: ChiralPak AS, 250×21.2 mm I.D., 5 μm; Mobile phase: A for $CO_2$ and B for Methanol (0.1% $NH_4OH$); Gradient: B 30%; Flow rate: 55 mL/min; Column temperature: 35° C.

Example 45

N-(4-([1,2,4]triazolo[1,5-c]pyrimidin-7-yloxy)-3-methylphenyl)-6-methoxy-5-((1S,5S)-2-methyl-2,6-diazabicyclo[3.2.0]heptan-6-yl)quinazolin-4-amine Example 46

N-(4-([1,2,4]triazolo[1,5-c]pyrimidin-7-yloxy)-3-methylphenyl)-6-methoxy-5-((1R,5R)-2-methyl-2,6-diazabicyclo[3.2.0]heptan-6-yl)quinazolin-4-amine

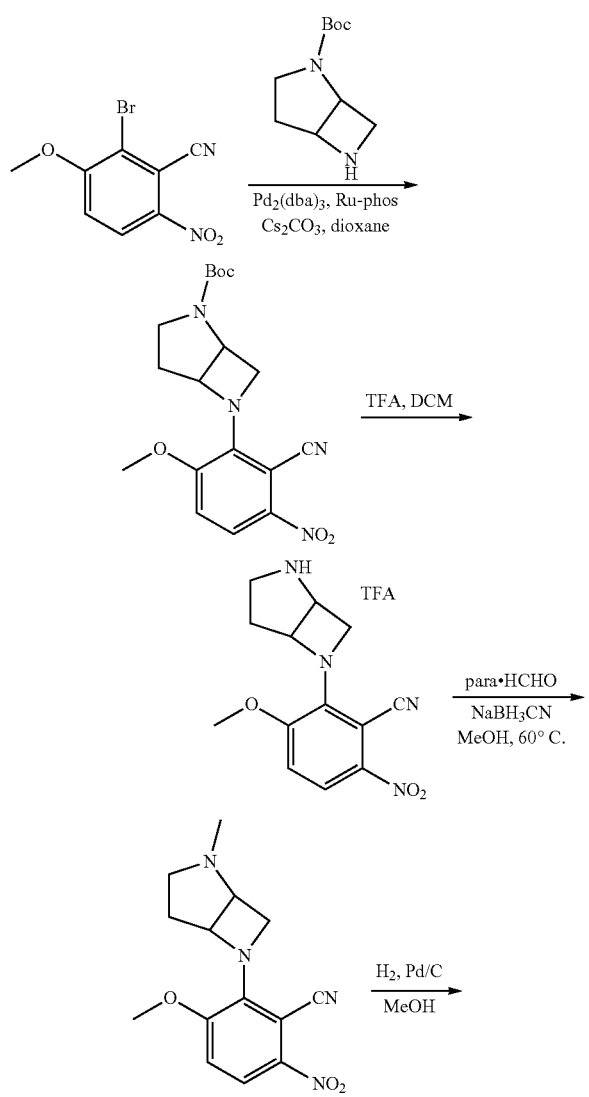

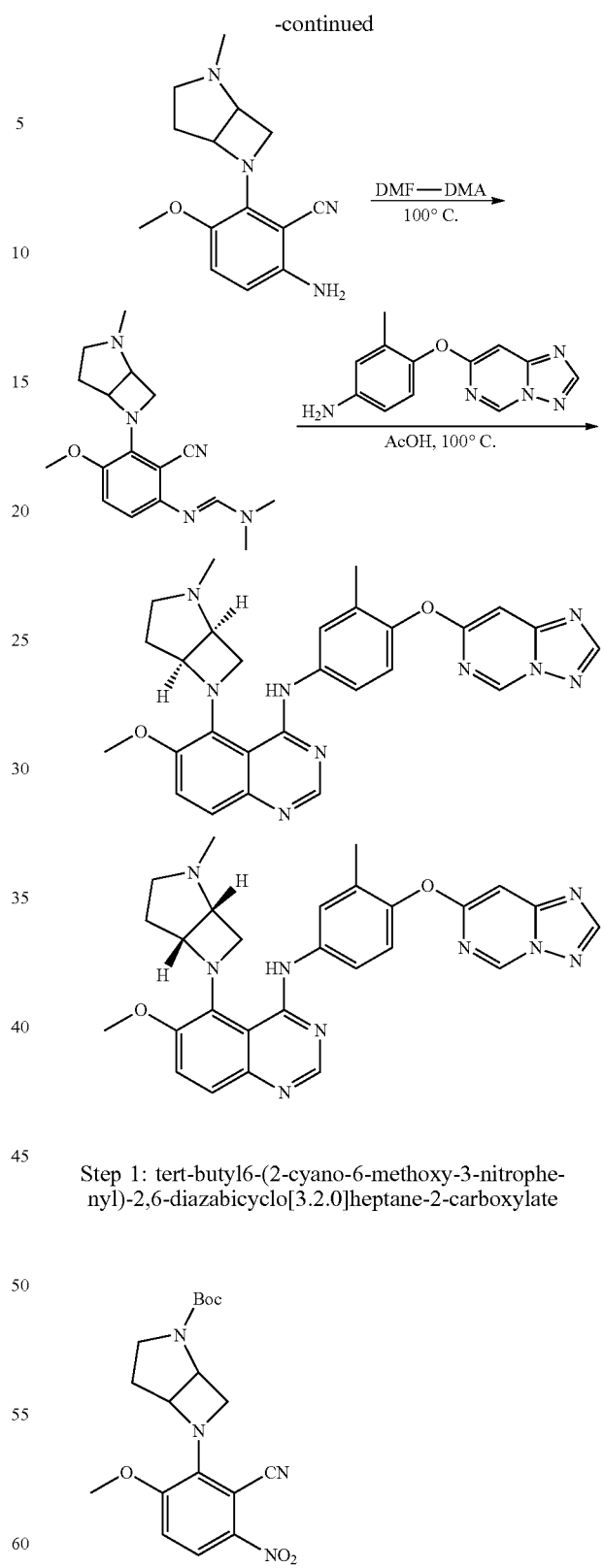

Step 1: tert-butyl6-(2-cyano-6-methoxy-3-nitrophenyl)-2,6-diazabicyclo[3.2.0]heptane-2-carboxylate To a mixture of 2-bromo-3-methoxy-6-nitrobenzonitrile (1.5 g, 5.83 mmol) and tert-butyl 2,6-diazabicyclo[3.2.0]heptane-2-carboxylate (1.3 g, 6.55 mmol) in degassed 1,4-dioxane (30 mL) was added $Cs_2CO_3$ (3.3 g, 10 mmol) followed by $Pd_2(dba)_3$ (320 mg, 0.35 mmol) and RuPhos (196 mg, 0.52 mmol) under N₂ atmosphere. After addition, the mixture was degassed under N₂ atmosphere for three times and stirred under N₂ atmosphere at 100° C. for 16 hrs. TLC (PE:EtOAc=2:1) showed the reaction was complete. The mixture was diluted with EtOAc (50 mL) and washed with water (30 mL) and brine (20 mL), dried over anhydrous Na₂SO₄, filtered and concentrated under vacuum to give crude product, which was purified by silica gel chromatography (PE:EtOAc=5:1 to 3:1) to give desired product (1.6 g, 73% yield) as an orange solid. MS (ESI) m/z: 375 (M+H)⁺.

Step 2: 2-(2,6-diazabicyclo[3.2.0]heptan-6-yl)-3-methoxy-6-nitrobenzonitrile TFA Salt

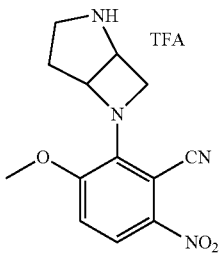 [SMILES: COc1ccc([N+](=O)[O-])c(C#N)c1N1CC2NCCC21]

To a solution of tert-butyl 6-(2-cyano-6-methoxy-3-nitrophenyl)-2,6-diazabicyclo[3.2.0]heptane-2-carboxylate (1.6 g, 4.27 mmol) in DCM (10 mL) was added TFA (10 mL) at 0° C. and the reaction mixture was stirred at room temperature for 2 hrs. The mixture was concentrated to dryness and the residue was co-evaporated with toluene for three times. The residue was dried in vacuum to give desired product (2.4 g) as brown oil, which was directly used for next reaction without purification. MS (ESI) m/z: 275 (M+H)⁺.

Step 3: 3-methoxy-2-(2-methyl-2,6-diazabicyclo[3.2.0]heptan-6-yl)-6-nitrobenzonitrile

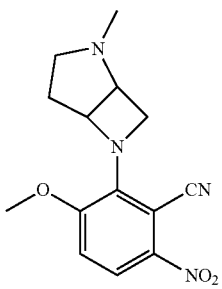 [SMILES: COc1ccc([N+](=O)[O-])c(C#N)c1N1CC2C1CCN2C]

To as solution of 2-(2,6-diazabicyclo[3.2.0]heptan-6-yl)-3-methoxy-6-nitrobenzonitrile TFA salt (1.6 g, 2.84 mmol) in MeOH (20 mL) was added para. HCHO (430 mg, 14.2 mmol) followed by NaBH₃CN (536 mg, 8.52 mmol) at 0° C. and the mixture was stirred at 50° C. for two hrs. The reaction was quenched with 1N aq. HCl (10 mL) and diluted with EtOAc (30 mL). The mixture was washed with water (20 mL) and brine (20 mL), dried over anhydrous Na₂SO₄, filtered and concentrated to dryness. The residue was purified by silica gel chromatography (DCM:MeOH=40:1) to give desired product (760 mg, 93% yield) as yellow syrup. MS (ESI) m/z: 289 (M+H)⁺.

Step 4-6: N-(4-([1,2,4]triazolo[1,5-c]pyrimidin-7-yloxy)-3-methylphenyl)-6-methoxy-5-((1S,5S)-2-methyl-2,6-diazabicyclo[3.2.0]heptan-6-yl)quinazolin-4-amine and N-(4-([1,2,4]triazolo[1,5-c]pyrimidin-7-yloxy)-3-methylphenyl)-6-methoxy-5-((1R,5R)-2-methyl-2,6-diazabicyclo[3.2.0]heptan-6-yl)quinazolin-4-amine

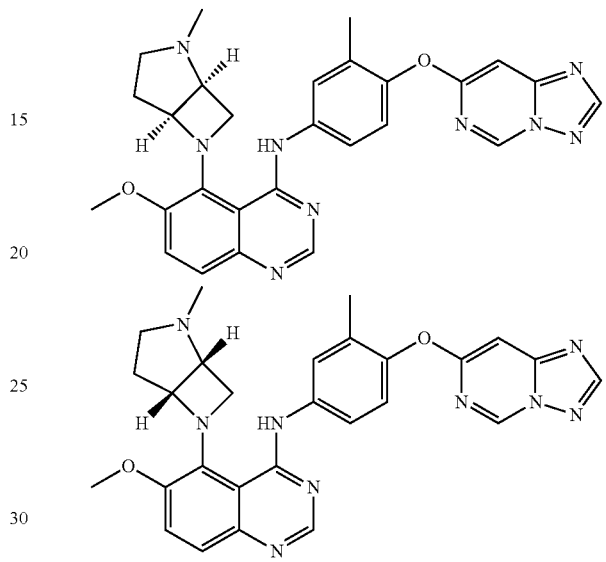

The racemic N-(4-([1,2,4]triazolo[1,5-c]pyrimidin-7-yloxy)-3-methylphenyl)-6-methoxy-5-(2-methyl-2,6-diazabicyclo[3.2.0]heptan-6-yl)quinazolin-4-amine (95 mg) as yellow solid was prepared in a similar fashion to Example 39, which was separated by chiral SFC to give the enantiomers:

N-(4-([1,2,4]triazolo[1,5-c]pyrimidin-7-yloxy)-3-methylphenyl)-6-methoxy-5-((1S,5S)-2-methyl-2,6-diazabicyclo[3.2.0]heptan-6-yl)quinazolin-4-amine (peak 1, retention time: 6.86 min) (35 mg, 4.8% yield) as light yellow solid. MS (ESI) m/z: 510 (M+H)⁺. ¹H-NMR (400 MHz, DMSO-d₆) δ 13.69 (s, 1H), 9.67 (s, 1H), 8.58 (s, 1H), 8.39 (s, 1H), 7.82-7.84 (m, 2H), 7.78-7.80 (d, J=9.2 Hz, 1H), 7.69-7.72 (d, J=9.2 Hz, 1H), 7.20-7.22 (d, J=9.2 Hz, 1H), 7.16 (s, 1H), 4.90-4.93 (t, 1H), 4.10-4.11 (m, 1H), 4.09 (s, 3H), 3.98-4.01 (m, 1H), 3.83-3.88 (m, 2H), 3.07-3.13 (m, 1H), 2.96-3.01 (m, 1H), 2.42 (s, 3H), 2.22 (s, 3H), 1.90-1.94 (m, 1H), 1.71-1.75 (m, 1H).

N-(4-([1,2,4]triazolo[1,5-c]pyrimidin-7-yloxy)-3-methylphenyl)-6-methoxy-5-((1R,5R)-2-methyl-2,6-diazabicyclo[3.2.0]heptan-6-yl)quinazolin-4-amine (peak 2, retention time: 8.31 min) (35 mg, 4.8% yield) as light yellow solid. MS (ESI) m/z: 510 (M+H)⁺. ¹H-NMR (400 MHz, DMSO-d₆) δ 13.69 (s, 1H), 9.67 (s, 1H), 8.58 (s, 1H), 8.39 (s, 1H), 7.81-7.84 (m, 2H), 7.78-7.80 (d, J=9.2 Hz, 1H), 7.69-7.72 (d, J=9.2 Hz, 1H), 7.20-7.22 (d, J=9.2 Hz, 1H), 7.16 (s, 1H), 4.90-4.93 (t, 1H), 4.10-4.11 (m, 1H), 4.09 (s, 3H), 3.98-4.01 (m, 1H), 3.84-3.88 (m, 2H), 3.07-3.11 (m, 1H), 2.97-3.01 (m, 1H), 2.42 (s, 3H), 2.22 (s, 3H), 1.90-1.94 (m, 1H), 1.71-1.75 (m, 1H).

SFC condition: Column: ChiralPak AS, 250×21.2 mm I.D., 5 μm; Mobile phase: A for CO₂ and B for Methanol (0.1% NH₄OH); Gradient: B 40%; Flow rate: 50 mL/min; Column temperature: 35° C.

Example 47
(R)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine
Example 48
(S)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine
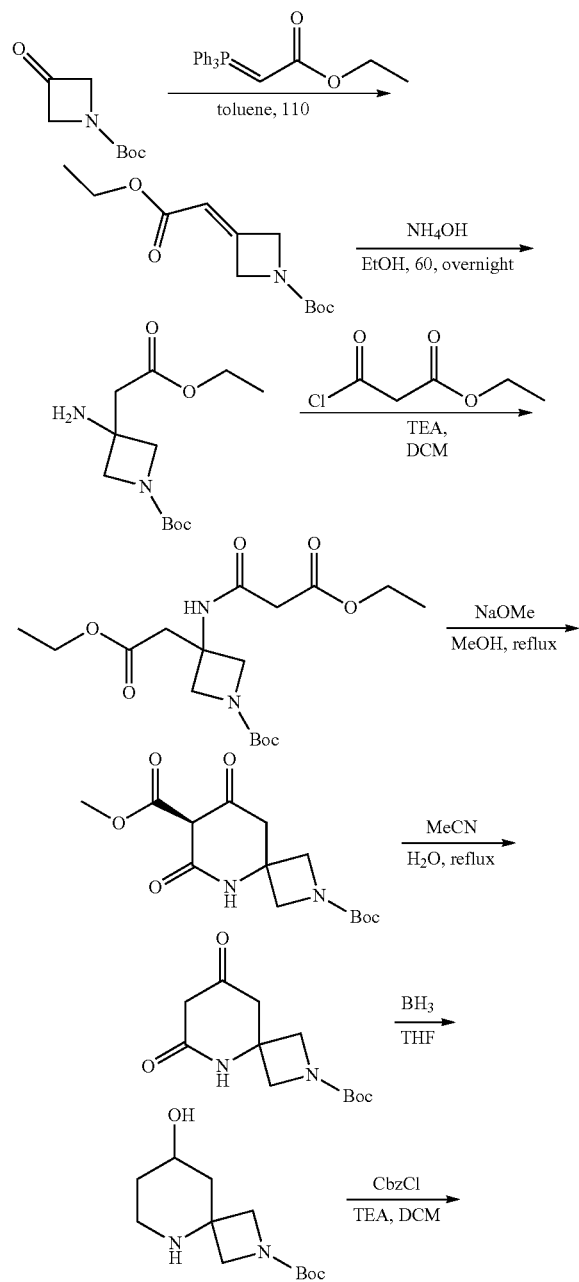
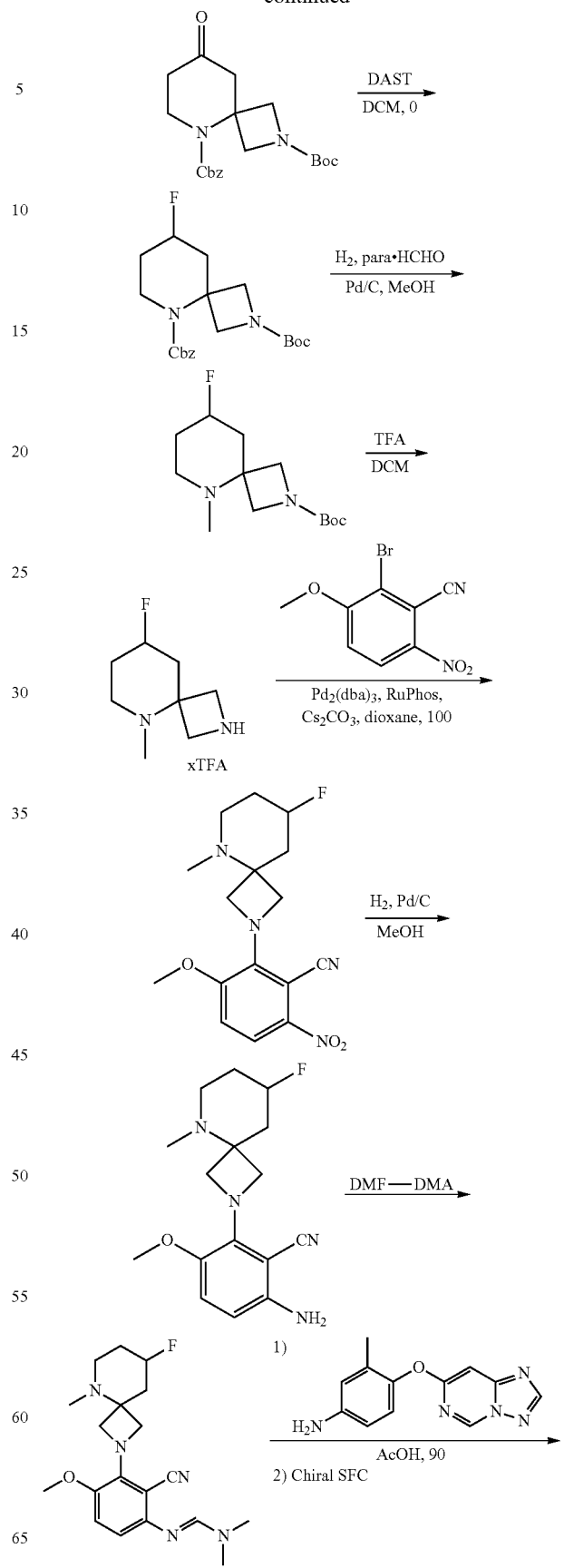

-continued

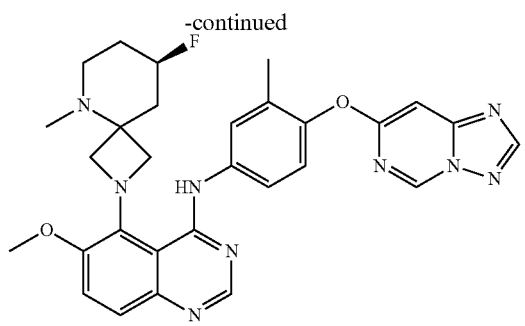

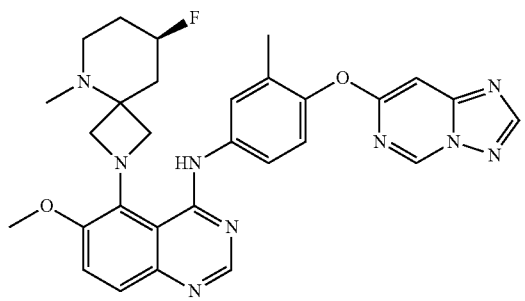

Step 1: tert-butyl 3-(2-ethoxy-2-oxoethylidene)azetidine-1-carboxylate

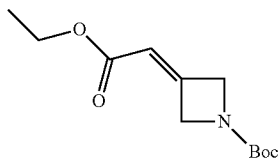 [SMILES: CCOC(=O)C=C1CN(C(=O)OC(C)(C)C)C1]

To a solution of tert-butyl 3-oxoazetidine-1-carboxylate (15 g, 87.6 mmol) in toluene (300 mL) was added ethyl 2-(triphenyl-λ-phosphanylidene)acetate (33.5 g, 96.4 mmol) and the resulting mixture was stirred at 110° C. for 5 hrs. After cooled down to room temperature, the reaction mixture was concentrated to about 50 mL and filtered. The filtrate was concentrated to dryness and the residue was purified by flash chromatography (silica gel, 0-30% EtOAc in PE) to give desired product (20 g, 95% yield) as a colorless liquid. MS (ESI) m/z: 242 (M+H)$^+$.

Step 2: tert-butyl 3-amino-3-(2-ethoxy-2-oxoethyl)azetidine-1-carboxylate

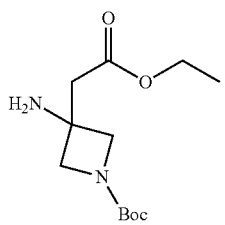 [SMILES: CCOC(=O)CC1(N)CN(C(=O)OC(C)(C)C)C1]

To a solution of tert-butyl 3-(2-ethoxy-2-oxoethylidene)azetidine-1-carboxylate (20 g, 82.9 mmol) in EtOH (130 mL) was added NH$_4$OH (130 mL, 30% wt) and the mixture was stirred at 60° C. for 16 hrs. The mixture was concentrated to dryness and the residue was diluted with EtOAc (100 mL×2), washed with water (100 mL) and brine (100 mL), dried over anhydrous Na$_2$SO$_4$, filtered and concentrated to dryness. The residue was purified by flash chromatography (silica gel, 50%-100% EtOAc in PE) to give desired product (15 g, 70% yield) as light yellow liquid. MS (ESI) m/z: 259 (M+H)$^+$.

Step 3: tert-butyl 3-(2-ethoxy-2-oxoethyl)-3-(3-ethoxy-3-oxopropanamido)azetidine-1-carboxylate

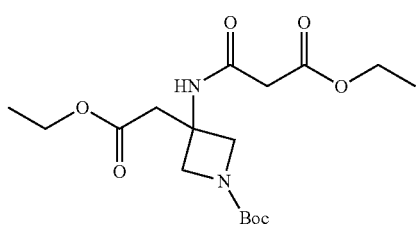 [SMILES: CCOC(=O)CC(=O)NC1(CC(=O)OCC)CN(C(=O)OC(C)(C)C)C1]

To a solution of tert-butyl 3-amino-3-(2-ethoxy-2-oxoethyl)azetidine-1-carboxylate (18.6 g, 72 mmol) in anhydrous DCM (300 mL) was added TEA (15 mL 110 mmol), followed by drop-wise addition of a solution of ethyl 3-chloro-3-oxopropanoate (14.4 g, 95.62 mmol) in DCM (50 mL) at 0° C. and the resulting mixture was stirred at room temperature for 4 hrs. The reaction was quenched saturated aq. NaHCO$_3$ solution (100 mL) at 0° C. and the layers were separated. The aqueous layer was extracted with DCM (100 mL×2) and the combined organic layers were washed with brine, dried over anhydrous Na$_2$SO$_4$, filtered and concentrated to dryness to give desired product (26 g, 97% yield) as a light yellow oil, which was directly used for next step without purification. MS (ESI) m/z: 373 (M+H)$^+$.

Step 4: 2-(tert-butyl) 7-methyl(S)-6,8-dioxo-2,5-diazaspiro[3.5]nonane-2,7-dicarboxylate

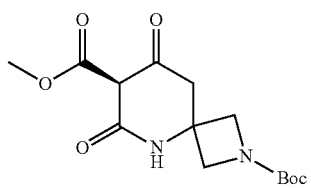 [SMILES: COC(=O)[C@H]1C(=O)CC2(CN(C(=O)OC(C)(C)C)C2)NC1=O]

To a solution of tert-butyl 3-(2-ethoxy-2-oxoethyl)-3-(3-ethoxy-3-oxopropanamido)azetidine-1-carboxylate (26 g, 69.86 mmol) in MeOH (100 mL) was added sodium methanolate (100 mL, 5.4 M in MeOH) and the reaction mixture was stirred at 80° C. for 4 hrs. The mixture was concentrated to dryness and the residue was poured into ice-cooled saturated aq. NH$_4$Cl solution and extracted with EtOAc (150 mL×2). The combined organic layers were washed with brine, dried over anhydrous Na$_2$SO$_4$, filtered and concentrated to dryness. The residue was purified by flash chromatography (silica gel, 0-70% EtOAc in PE) to give desired product (18.6 g, 85% yield) as light yellow oil. MS (ESI) m/z: 313 (M+H)$^+$.

Step 5: tert-butyl 6,8-dioxo-2,5-diazaspiro[3.5]nonane-2-carboxylate

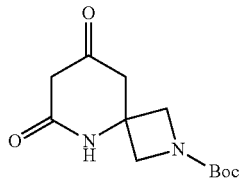 [SMILES: CC(C)(C)OC(=O)N1CC2(CC(=O)CC(=O)N2)C1]

A solution of (S)-2-tert-butyl 7-methyl 6,8-dioxo-2,5-diazaspiro[3.5]nonane-2,7-dicarboxylate (18.6 g, 59.59 mmol) in MeCN (304 mL) and water (34 mL) was stirred at 100° C. for 4 hrs. The mixture was concentrated under reduced pressure to give desired product (14.5 g, 96% yield) as light yellow oil. MS (ESI) m/z: 255 (M+H)$^+$.

Step 6: tert-butyl 8-hydroxy-2,5-diazaspiro[3.5]nonane-2-carboxylate

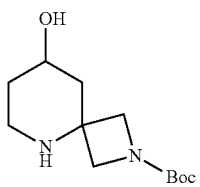 [SMILES: CC(C)(C)OC(=O)N1CC2(CC(O)CCN2)C1]

To a solution of tert-butyl 6,8-dioxo-2,5-diazaspiro[3.5]nonane-2-carboxylate (14.5 g, 57 mmol) in anhydrous THF (150 mL) was added borane-tetrahydrofuran complex (228 mL, 1M in THF) dropwise at 0° C., and the resulting mixture was stirred at room temperature overnight. The reaction was quenched with MeOH (100 mL) at 0° C. and the mixture was concentrated to dryness. The residue was purified by flash chromatography (silica gel, 0-30% MeOH in DCM) to give desired product (4.5 g, 33% yield) as light yellow oil. MS (ESI) m/z: 243 (M+H)$^+$.

Step 7: 5-benzyl 2-(tert-butyl) 8-hydroxy-2,5-diazaspiro[3.5]nonane-2,5-dicarboxylate

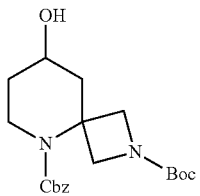

To a solution of tert-butyl 8-hydroxy-2,5-diazaspiro[3.5]nonane-2-carboxylate (2.7 g, 11.14 mmol) in anhydrous DCM (120 mL) was added TEA (3.1 mL, 22.28 mmol), followed by drop-wise addition of benzyl chloroformate (2.85 g, 16.71 mmol) at 0° C. and the mixture was stirred at room temperature for 3 hrs. The reaction was quenched with ice water and the organic layers were separated. The aqueous layer was extracted with DCM (100 mL×2) and the combined organic layers was washed with brine, dried over anhydrous Na$_2$SO$_4$, filtered and concentrated to dryness. The residue was purified by flash chromatography (silica gel, 0-100% EtOAc in PE) to give desired product (1.5 g, 36% yield) as colorless oil. MS (ESI) m/z: 377 (M+H)$^+$.

Step 8: 5-benzyl 2-(tert-butyl) 8-fluoro-2,5-diazaspiro[3.5]nonane-2,5-dicarboxylate

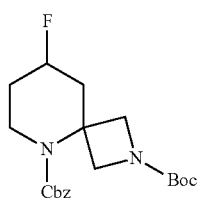 [SMILES: CC(C)(C)OC(=O)N1CC2(CC(F)CCN2C(=O)OCc2ccccc2)C1]

To a solution of 5-benzyl 2-(tert-butyl) 8-hydroxy-2,5-diazaspiro[3.5]nonane2,5-dicarboxylate (1.5 g, 3.98 mmol) in anhydrous DCM (150 mL) was added DAST (964 mg, 5.98 mmol) in anhydrous DCM (7 mL) dropwise at 0° C. and the mixture was stirred at 0° C. for 1 hr. The reaction was quenched with saturated aq. NaHCO$_3$ solution (100 mL) at 0° C. and the layers were separated. The aqueous layer was extracted with DCM (50 mL×2) and the combined organic layers were washed with brine, dried over anhydrous Na$_2$SO$_4$, filtered and concentrated to dryness. The residue was purified by flash chromatography (silica gel, 0-40% EtOAc in PE) to give desired product (600 mg, 40% yield) as colorless oil. MS (ESI) m/z: 379 (M+H)$^+$.

Step 9: tert-butyl 8-fluoro-5-methyl-2,5-diazaspiro[3.5]nonane-2-carboxylate

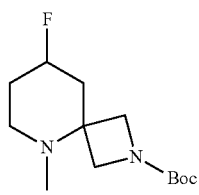 [SMILES: CN1CCC(F)CC12CN(C(=O)OC(C)(C)C)C2]

To a mixture of 5-benzyl 2-(tert-butyl) 8-fluoro-2,5-diazaspiro[3.5]nonane-2,5-dicarboxylate (590 mg, 1.56 mmol) and paraformaldehyde (1.4 g, 15.6 mmol) in MeOH (50 mL) was added Pd/C (100 mg, 5% wt). The mixture was degassed under N$_2$ atmosphere for three times and stirred under a H$_2$ balloon at room temperature for 16 hrs. The mixture was filtered and the filtrate was concentrated to dryness. The residue was purified by flash chromatography (silica gel, 0-15% MeOH in DCM) to give desired product (300 mg, 75% yield) as colorless oil. MS (ESI) m/z: 259 (M+H)$^+$.

191

Step 10: 8-fluoro-5-methyl-2,5-diazaspiro[3.5]nona-netrifluoroacetic acid salt

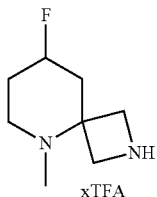

xTFA

To a solution of tert-butyl 8-fluoro-5-methyl-2,5-diazaspiro[3.5]nonane-2-carboxylate (258 mg, 1 mmol) in anhydrous DCM (5 mL) was added TFA (1 mL) and the mixture was stirred at 0° C. for 2 hrs. The mixture was concentrated to dryness and the residue was co-evaporated with toluene twice, dried under vacuum to give desired product (380 mg, 98% yield) as yellow solid. LC-MS (ESI) m/z: 159 (M+H)$^+$.

Step 11-14: (R)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine and (S)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine

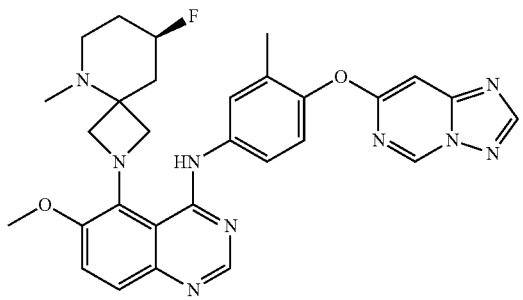

192

The racemic N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine (49 mg) as a light yellow solid was prepared in a similar fashion to Example 39, which was separated by chiral SFC to give arbitrarily assigned:

(R)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine (peak 1, retention time: 15.71 min) (11 mg, 22% yield) as a light yellow solid. MS (ESI) m/z: 556 (M+H)$^+$. $^1$H-NMR (400 MHz, DMSO-d$_6$) δ 9.67 (s, 1H), 8.57 (s, 1H), 8.40 (s, 1H), 8.07-8.08 (m, 1H), 7.77-7.79 (m, 1H), 7.75-7.77 (d, J=9.2 Hz, 1H), 7.69-7.71 (d, J=9.2 Hz, 1H), 7.17-7.20 (d, J=8.8 Hz, 1H), 7.11 (s, 1H), 4.75-4.80 (br, 1H), 4.01-4.14 (m, 4H), 4.06 (s, 3H), 2.91-2.95 (m, 1H), 2.66-2.71 (m, 1H), 2.28-2.33 (m, 1H), 2.18 (s, 3H), 2.09-2.14 (m, 1H), 1.66-1.88 (m, 2H).

(S)—N-(4-([1,2,4]triazolo[1,5-c]pyrimidin-7-yloxy)-3-methylphenyl)-5-(8-fluoro-5-methyl-2,5-diazaspiro[3.5]nonan-2-yl)-6-methoxyquinazolin-4-amine (peak 2, retention time: 18.43 min) (12 mg, 24% yield) as a light yellow solid. MS (ESI) m/z: 556 (M+H)$^+$. $^1$H-NMR (400 MHz, DMSO-d$_6$) δ 9.67 (s, 1H), 8.58 (s, 1H), 8.41 (s, 1H), 8.07-8.08 (m, 1H), 7.77-7.79 (m, 1H), 7.76-7.78 (d, J=9.2 Hz, 1H), 7.69-7.71 (d, J=9.2 Hz, 1H), 7.18-7.20 (d, J=8.8 Hz, 1H), 7.11 (s, 1H), 4.75-4.80 (br, 1H), 4.02-4.13 (m, 4H), 4.06 (s, 3H), 2.91-2.95 (m, 1H), 2.66-2.71 (m, 1H), 2.28-2.33 (m, 1H), 2.18 (s, 3H), 2.09-2.14 (m, 1H), 1.84-1.91 (m, 1H), 1.68-1.73 (m, 1H).

SFC condition: Column: ChiralPak AS, 250×21.2 mm I.D., 5 µm; Mobile phase: A for CO$_2$ and B for Methanol (0.1% NH$_4$OH); Gradient: B 35%; Flow rate: 55 mL/min; Column temperature: 35° C.

The following compounds were prepared according to the above described methods using different starting materials.

| Ex # | Structure | Name | MS m/z |
|---|---|---|---|
| 49 | 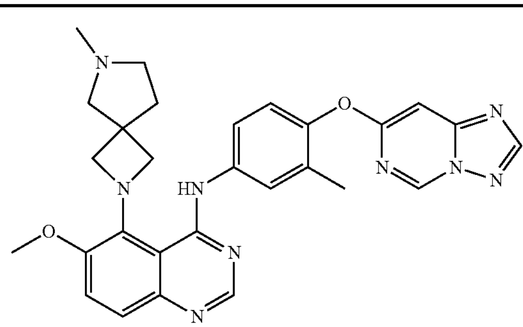 | N-(4-([1,2,4]triazolo[1,5-c]pyrimidin-7-yloxy)-3-methylphenyl)-6-methoxy-5-(6-methyl-2,6-diazaspiro[3.4]octan-2-yl)quinazolin-4-amine | 524 (M + H)$^+$ |

-continued

| Ex # | Structure | Name | MS m/z |
|---|---|---|---|
| 50 | 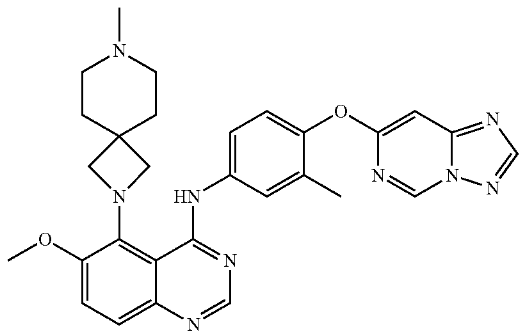 [SMILES: COc1ccc2ncnc(Nc3ccc(Oc4cc5ncnn5cn4)c(C)c3)c2c1N1CC2(CCN(C)CC2)C1] | N-(4-([1,2,4]triazolo[1,5-c]pyrimidin-7-yloxy)-3-methylphenyl)-6-methoxy-5-(7-methyl-2,7-diazaspiro[3.5]nonan-2-yl)quinazolin-4-amine | 538 (M + H)+ |
| 56 | 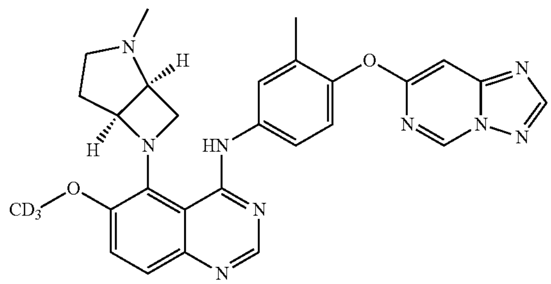 [SMILES: [2H]C([2H])([2H])Oc1ccc2ncnc(Nc3ccc(Oc4cc5ncnn5cn4)c(C)c3)c2c1N1C[C@H]2[C@@H]1CCN2C] | N-(4-([1,2,4]triazolo[1,5-c]pyrimidin-7-yloxy)-3-methylphenyl)-6-(methoxy-d3)-5-((1S,5S)-2-methyl-2,6-diazabicyclo[3.2.0]heptan-6-yl)quinazolin-4-amine | 513 (M + H)+ |
| 57 | 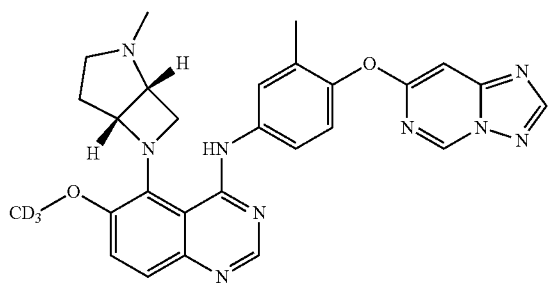 [SMILES: [2H]C([2H])([2H])Oc1ccc2ncnc(Nc3ccc(Oc4cc5ncnn5cn4)c(C)c3)c2c1N1C[C@@H]2[C@H]1CCN2C] | N-(4-([1,2,4]triazolo[1,5-c]pyrimidin-7-yloxy)-3-methylphenyl)-6-(methoxy-d3)-5-((1R,5R)-2-methyl-2,6-diazabicyclo[3.2.0]heptan-6-yl)quinazolin-4-amine | 513 (M + H)+ |
| 58 | 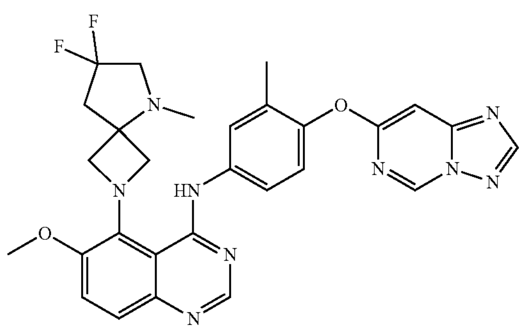 [SMILES: COc1ccc2ncnc(Nc3ccc(Oc4cc5ncnn5cn4)c(C)c3)c2c1N1CC2(C1)CC(F)(F)CN2C] | N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-methoxyquinazolin-4-amine | 560 (M + H)+ |
| 59 | 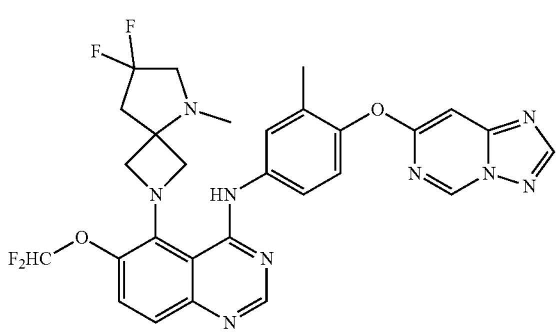 [SMILES: Cc1cc(Nc2ncnc3ccc(OC(F)F)c(N4CC5(C4)CC(F)(F)CN5C)c23)ccc1Oc1cc2ncnn2cn1] | N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(difluoromethoxy)quinazolin-4-amine | 596 (M + H)+ |

-continued

| Ex # | Structure | Name | MS m/z |
|---|---|---|---|
| 60 | 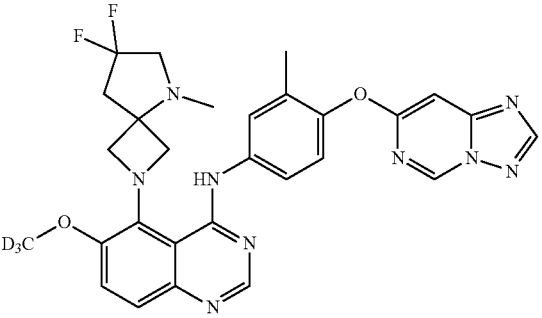 [SMILES: [2H]C([2H])([2H])Oc1ccc2ncnc(Nc3ccc(Oc4cc5ncnn5cn4)c(C)c3)c2c1N1CC2(C1)CC(F)(F)CN2C] | N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-(methoxy-d3)quinazolin-4-amine | 563 (M + H)+ |
| 61 | 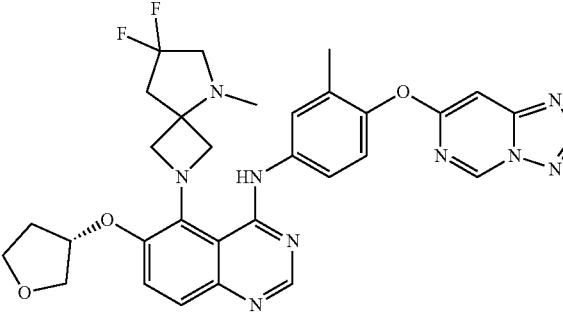 | (S)-N-(4-([1,2,4]triazolo[1,5-c]pyrimidin-7-yloxy)-3-methylphenyl)-5-(7,7-difluoro-5-methyl-2,5-diazaspiro[3.4]octan-2-yl)-6-((tetrahydrofuran-3-yl)oxy)quinazolin-4-amine | 616 (M + H)+ |
| 62 | 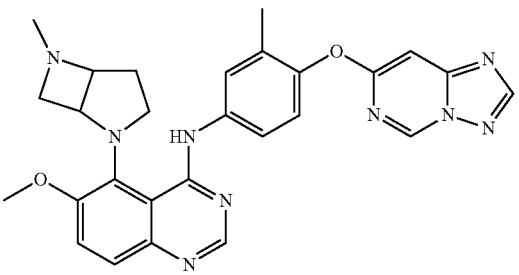 [SMILES: COc1ccc2ncnc(Nc3ccc(Oc4cc5ncnn5cn4)c(C)c3)c2c1N1CCC2C1CN2C] | N-(4-([1,2,4]triazolo[1,5-c]pyrimidin-7-yloxy)-3-methylphenyl)-6-methoxy-5-(6-methyl-2,6-diazabicyclo[3.2.0]heptan-2-yl)quinazolin-4-amine | 510 (M + H)+ |
| 63 | 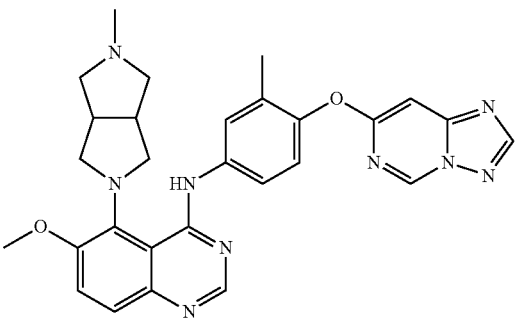 [SMILES: COc1ccc2ncnc(Nc3ccc(Oc4cc5ncnn5cn4)c(C)c3)c2c1N1CC2CN(C)CC2C1] | N-(4-([1,2,4]triazolo[1,5-c]pyrimidin-7-yloxy)-3-methylphenyl)-6-methoxy-5-(5-methylhexahydropyrrolo[3,4-c]pyrrol-2(1H)-yl)quinazolin-4-amine | 524 (M + H)+ |
| 64 | 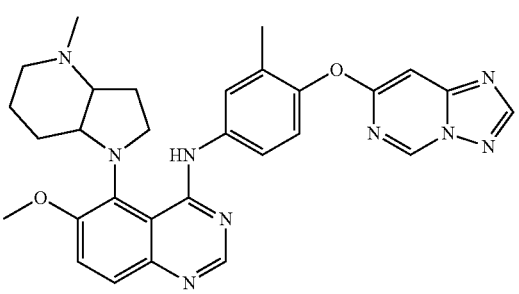 [SMILES: COc1ccc2ncnc(Nc3ccc(Oc4cc5ncnn5cn4)c(C)c3)c2c1N1CCC2C1CCCN2C] | N-(4-([1,2,4]triazolo[1,5-c]pyrimidin-7-yloxy)-3-methylphenyl)-6-methoxy-5-(4-methyloctahydro-1H-pyrrolo[3,2-b]pyridin-1-yl)quinazolin-4-amine | 538 (M + H)+ |

-continued

| Ex # | Structure | Name | MS m/z |
|---|---|---|---|
| 65 | 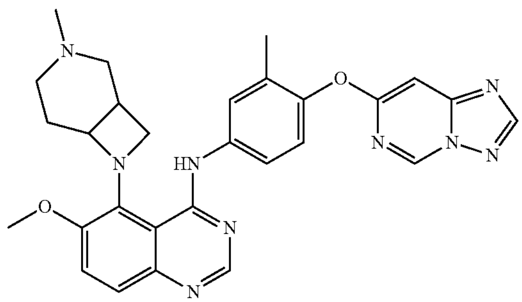 [SMILES: COc1ccc2ncnc(Nc3ccc(Oc4cc5ncnn5cn4)c(C)c3)c2c1N1CC2CN(C)CCC21] | N-(4-([1,2,4]triazolo[1,5-c]pyrimidin-7-yloxy)-3-methylphenyl)-6-methoxy-5-(3-methyl-3,7-diazabicyclo[4.2.0]octan-7-yl)quinazolin-4-amine | 524 (M + H)+ |
| 66 | 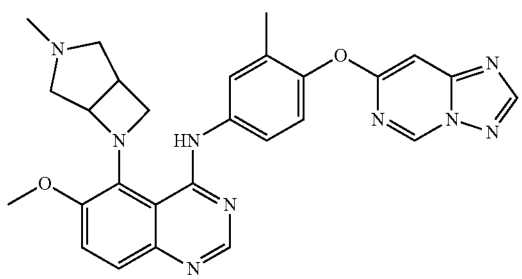 [SMILES: COc1ccc2ncnc(Nc3ccc(Oc4cc5ncnn5cn4)c(C)c3)c2c1N1CC2CN(C)CC21] | N-(4-([1,2,4]triazolo[1,5-c]pyrimidin-7-yloxy)-3-methylphenyl)-6-methoxy-5-(3-methyl-3,6-diazabicyclo[3.2.0]heptan-6-yl)quinazolin-4-amine | 510 (M + H)+ |
| 67 | 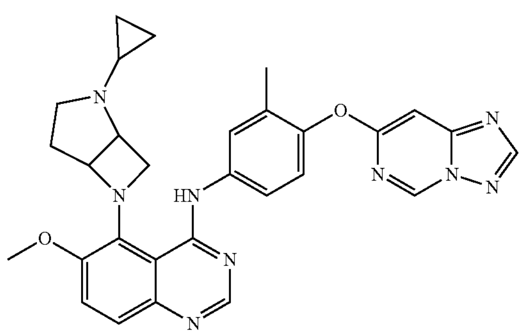 [SMILES: COc1ccc2ncnc(Nc3ccc(Oc4cc5ncnn5cn4)c(C)c3)c2c1N1CC2C1CCN2C1CC1] | N-(4-([1,2,4]triazolo[1,5-c]pyrimidin-7-yloxy)-3-methylphenyl)-5-(2-cyclopropyl-2,6-diazabicyclo[3.2.0]heptan-6-yl)-6-methoxyquinazolin-4-amine | 536 (M + H)+ |
| 68 | 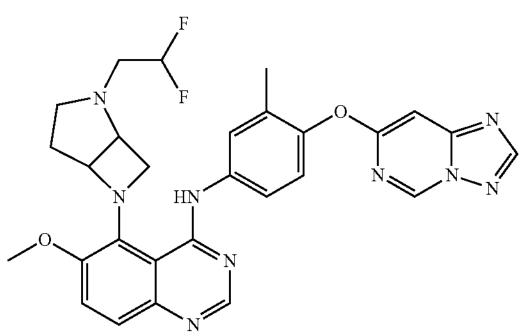 [SMILES: COc1ccc2ncnc(Nc3ccc(Oc4cc5ncnn5cn4)c(C)c3)c2c1N1CC2C1CCN2CC(F)F] | N-(4-([1,2,4]triazolo[1,5-c]pyrimidin-7-yloxy)-3-methylphenyl)-5-(2-(2,2-difluoroethyl)-2,6-diazabicyclo[3.2.0]heptan-6-yl)-6-methoxyquinazolin-4-amine | 560 (M + H) |
| 69 | 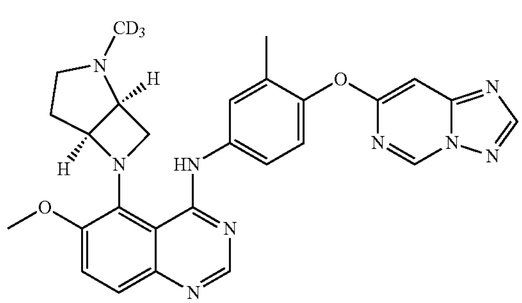 [SMILES: [2H]C([2H])([2H])N1CC[C@H]2[C@@H]1CN2c1c(OC)ccc2ncnc(Nc3ccc(Oc4cc5ncnn5cn4)c(C)c3)c12] | N-(4-([1,2,4]triazolo[1,5-c]pyrimidin-7-yloxy)-3-methylphenyl)-6-methoxy-5-((1S,5S)-2-(methyl-d3)-2,6-diazabicyclo[3.2.0]heptan-6-yl)quinazolin-4-amine | 513 (M + H)+ |

| Ex # | Structure | Name | MS m/z |
|---|---|---|---|
| 70 | 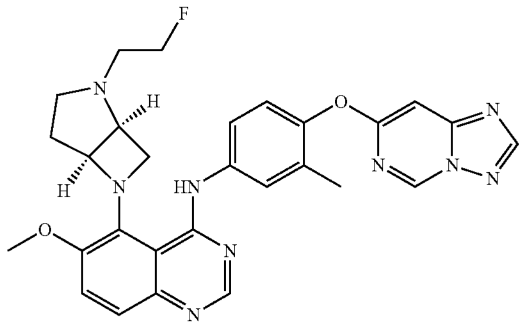 [SMILES: COc1ccc2ncnc(Nc3ccc(Oc4cc5ncnn5cn4)c(C)c3)c2c1N1C[C@H]2[C@@H]1CCN2CCF] | N-(4-([1,2,4]triazolo[1,5-c]pyrimidin-7-yloxy)-3-methylphenyl)-5-((1S,5S)-2-(2-fluoroethyl)-2,6-diazabicyclo[3.2.0]heptan-6-yl)-6-methoxyquinazolin-4-amine | 542 (M + H) |
| 71 | 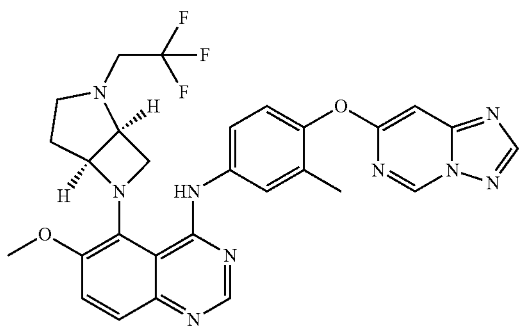 [SMILES: COc1ccc2ncnc(Nc3ccc(Oc4cc5ncnn5cn4)c(C)c3)c2c1N1C[C@H]2[C@@H]1CCN2CC(F)(F)F] | N-(4-([1,2,4]triazolo[1,5-c]pyrimidin-7-yloxy)-3-methylphenyl)-6-methoxy-5-((1S,5S)-2-(2,2,2-trifluoroethyl)-2,6-diazabicyclo[3.2.0]heptan-6-yl)quinazolin-4-amine | 578 (M + H) |

Example 67

$^1$H-NMR (400 MHz, CD$_3$OD) δ 9.44 (d, J=1.2 Hz, 1H), 8.42 (d, J=2.8 Hz, 2H), 7.82-7.70 (m, 3H), 7.59 (d, J=9.2 Hz, 1H), 7.17 (d, J=8.4 Hz, 1H), 6.93 (d, J=1.2 Hz, 1H), 4.99 (dd, J=12.4, 8.1 Hz, 1H), 4.86-4.81 (m, 1H), 3.19 (s, 1H), 2.94 (d, J=11.8 Hz, 1H), 2.45 (dd, J=28.9, 12.3 Hz, 1H), 2.34 (s, 3H), 2.25 (s, 3H), 2.09 (d, J=11.9 Hz, 1H), 1.44 (dd, J=13.7, 6.0 Hz, 6H), 1.26-1.14 (m, 2H).

Example 68

Yellow solid. $^1$H-NMR (400 MHz, CD$_3$OD) δ 9.44 (s, 1H), 8.42 (s, 1H), 8.32 (s, 1H), 7.81 (s, 1H), 7.81-7.70 (m, 3H), 7.21 (d, J=8.5 Hz, 1H), 6.95 (s, 1H), 6.17-5.81 (m, 1H), 5.06 (t, J=5.9 Hz, 1H), 4.28 (t, J=7.4 Hz, 1H), 4.14 (s, 3H), 4.10 (d, J=7.3 Hz, 1H), 4.04-3.92 (m, 1H), 3.25-2.99 (m, 4H), 2.27 (s, 3H), 2.11-1.99 (m, 1H), 1.90-1.79 (m, 1H).

Example 70

Light yellow solid. $^1$H-NMR (400 MHz, CD$_3$OD) δ 9.44 (s, 1H), 8.42 (s, 1H), 8.32 (s, 1H), 7.89-7.67 (m, 4H), 7.20 (d, J=8.6 Hz, 1H), 6.95 (s, 1H), 5.05 (t, J=6.0 Hz, 1H), 4.66 (t, J=4.8 Hz, 1H), 4.54 (t, J=4.8 Hz, 1H), 4.31 (d, J=4.4 Hz, 1H), 4.14 (s, 3H), 4.10-3.96 (m, 2H), 3.28-3.17 (m, 2H), 3.13-2.98 (m, 2H), 2.26 (s, 3H), 2.07 (dd, J=13.6, 4.8 Hz, 1H), 1.90-1.81 (m, 1H).

Example 51

(S)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine

Example 52

(R)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine

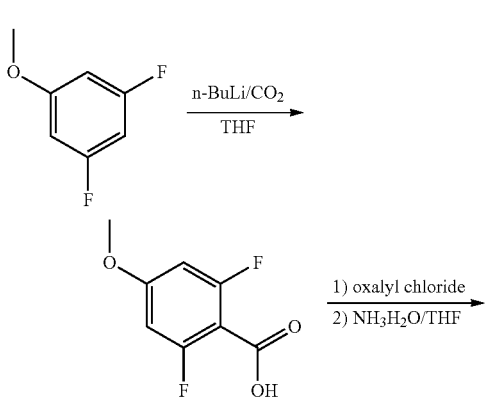

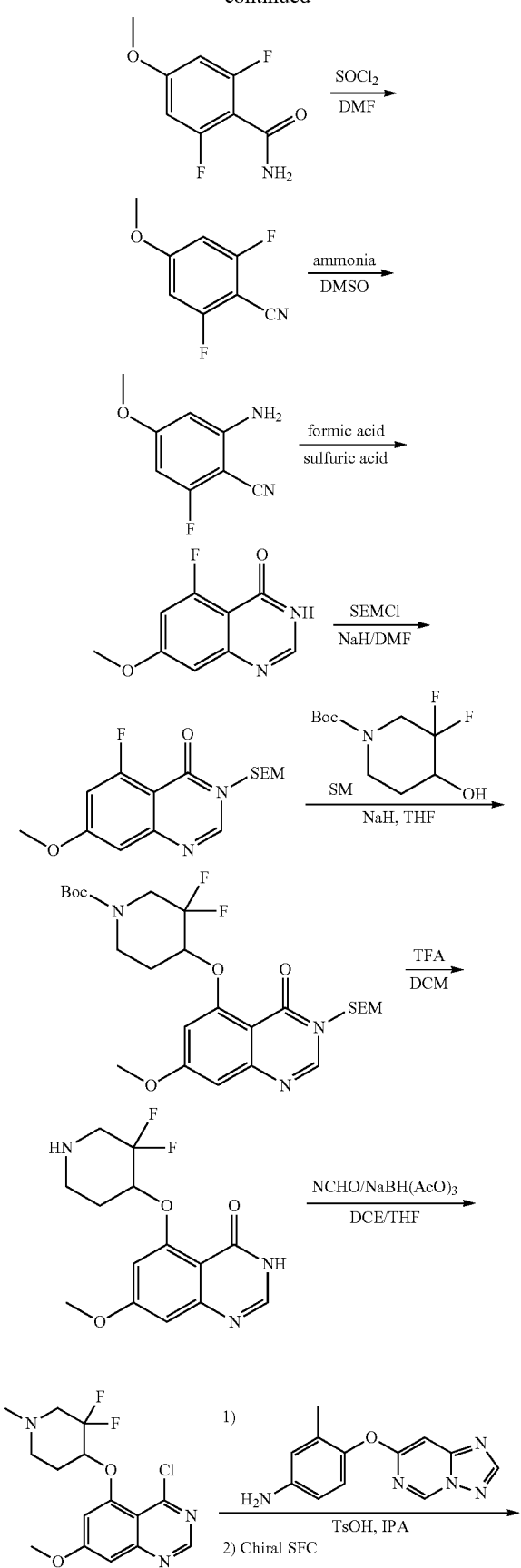

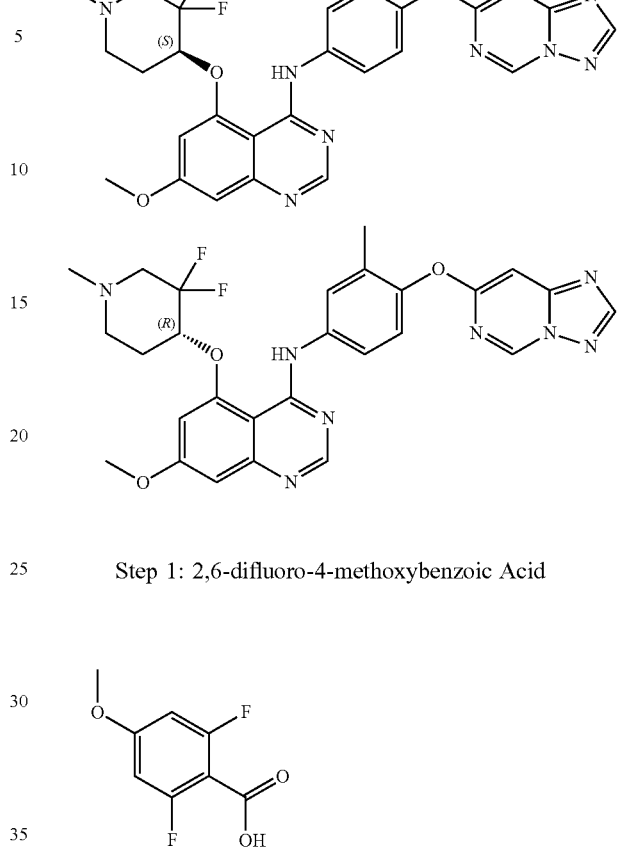

Step 1: 2,6-difluoro-4-methoxybenzoic Acid

To a solution of 1,3-difluoro-5-methoxybenzene (40.0 g, 277.7 mmol) in THF (250 mL) was added n-BuLi (120 mL, 361.1 mmol) dropwise at −78° C. with $N_2$ protected. After addition, the resulting mixture was stirred for 1 h at −78° C. Then dry ice (61 g, 1.39 mol) was added and the reaction mixture was allowed to room temperature and stirred for 10 min. Then the reaction mixture was added 1 N HCl at 0° C. and extracted with EA/THF (200 mL×3). The combined organic layers were dried over anhydrous $Na_2SO_4$, filtered and concentrated to give crude product. The crude product was triturated in PE/EA=25:1 and filtered to give product (40 g, 77% yield) as off-white solid. $^1H$ NMR (400 MHz, DMSO-$d_6$): δ 13.42 (brs, 1H), 8.85 (s, 1H), 8.80 (s, 1H), 3.80 (s, 3H).

Step 2: 2,6-difluoro-4-methoxybenzamide

To a solution of 2,6-difluoro-4-methoxybenzoic acid (45.0 g, 240 mmol) in $CH_2Cl_2$ (120 mL) was added DMF (0.1 mL) and oxalyl chloride (50 mL, 840 mmol) dropwise.

The reaction mixture was stirred for 30 min and then concentrated to give a residue. The residue was dissolved in DCM (120 mL) and then was added into a mixture of NH₄OH/THF (200 mL/200 mL) slowly. After addition the resulting mixture was stirred at room temperature for 2 h. The reaction mixture was concentrated, re-dissolved in water and extracted with DCM (300 mL×3). The combined organic phases were washed with brine, dried over anhydrous Na₂SO₄ and filtered. The filtrate was concentrated. The residue was triturated in PE/EA (20:1, 500 mL) and filtered to give the product (32 g, 72% yield) as a yellow solid. MS (ESI) m/z: 188.2 (M+H)⁺.

Step 3: 2,6-difluoro-4-methoxybenzonitrile

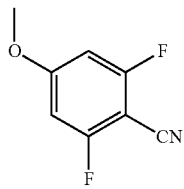

To a solution of 2,6-difluoro-4-methoxybenzamide (55 g, 294.1 mmol) in DMF (300 mL) was added a mixture of SOCl₂ (350 g) in DMF at 0° C. The resulting mixture was stirred at room temperature overnight. The reaction mixture was poured into ice-water (1 L) and extracted with EtOAc (1 L×3). The combined organic layer was dried over anhydrous Na₂SO₄ and filtered. The filtrate was concentrated. The residue was purified by silica gel chromatography (PE/EtOAc=5/1) to give the product (45 g, 91% yield) as a white solid. MS (ESI) m/z: 170.1 (M+H)⁺.

Step 4: 2-amino-6-fluoro-4-methoxybenzonitrile

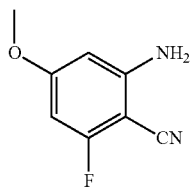

To a solution of 2,6-difluoro-4-methoxybenzonitrile (45 g, 266.3 mmol) in DMSO (400 mL) was added DHP (1.0 mL, 12.40 mmol). Then ammonia was bubbled through the reaction mixture about 10 min and then the reaction mixture was sealed. After stirred at 80° C. overnight, the reaction mixture was diluted with water (300 mL) and extracted with EtOAc (300 mL×3). The combined organic layer was washed with water (300 mL×3) and brine (300 mL), dried over anhydrous Na₂SO₄, filtered and concentrated to give a residue. The residue was purified by silica gel chromatography (PE/EtOAc=1/3) to give the product (40 g, 91% yield) as a white solid. MS (ESI) m/z: 167.1 (M+H)⁺.

Step 5: 5-fluoro-7-methoxyquinazolin-4(3H)-one

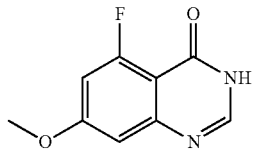

To a solution of 2-amino-6-fluoro-4-methoxybenzonitrile (60 g, 361.1 mmol) in HCOOH (500 mL) was added H₂SO₄ (3.0 g, 27.6 mmol) under N₂. The reaction mixture was stirred at 100° C. for 3 h. After cooled to room temperature, the mixture was poured into ice water (2 L) and the pH of the mixture was adjusted to 5-6. The precipitate was filtered and washed with water and EtOAc. The solid was triturated in EtOAc and filtered to give product (55 g, 78% yield) as yellow solid. ¹H NMR (400 MHz, CDCl₃) δ 12.13 (brs, 1H), 8.03 (d, J=3.2 Hz, 1H), 6.96-6.90 (m, 2H), 3.89 (s, 3H).

Step 6: 5-fluoro-7-methoxy-3-((2-(trimethylsilyl)ethoxy)methyl)quinazolin-4(3H)-one

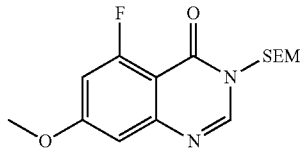 [SMILES: COc1cc(F)c2c(=O)n(COCC[Si](C)(C)C)cnc2c1]

To a suspension of NaH (17.0 g, 425.2 mmol) in DMF (600 mL) was added 5-fluoro-7-methoxyquinazolin-4(3H)-one (55.0 g, 283.5 mmol) at 0° C. under N₂. The mixture was stirred at 0° C. for 30 min. Then to the mixture was added (2-(chloromethoxy)ethyl)trimethylsilane (71.0 g, 425.2 mmol) at 0° C. The resulting mixture was warmed to room temperature and stirred overnight. LCMS showed the reaction was complete. The reaction mixture was quenched with ice water (500 mL) and extracted with EtOAc (500 mL×3). The combined organic layer was washed with water (500 mL×3) and brine (500 mL), dried over anhydrous Na₂SO₄, filtered and concentrated to give a residue. The residue was purified by silica gel chromatography (PE/EtOAc=3/1) to give the product (47.0 g, 58% yield) as a white solid. MS (ESI) m/z: 325.1 (M+H)⁺.

Step 7: tert-butyl 3,3-difluoro-4-((7-methoxy-4-oxo-3-((2-(trimethylsilyl)ethoxy)methyl)-3,4-dihydroquinazolin-5-yl)oxy)piperidine-1-carboxylate

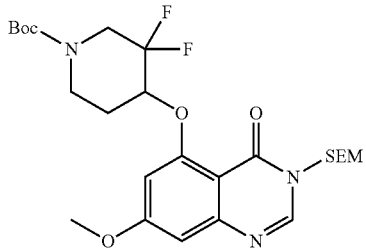 [SMILES: COc1cc(OC2CCN(C(=O)OC(C)(C)C)CC2(F)F)c2c(=O)n(COCC[Si](C)(C)C)cnc2c1]

To a suspension of NaH (60%, 3.44 g, 86.1 mmol) in THF (250 mL) was added tert-butyl 3,3-difluoro-4-hydroxypiperidine-1-carboxylate (16.8 g, 70.7 mmol) at 0° C. under $N_2$. The mixture was stirred at 0° C. for 30 min. Then to the mixture was added 5-fluoro-7-methoxy-3-((2-(trimethylsilyl)ethoxy)methyl)quinazolin-4(3H)-one (20.0 g, 61.5 mmol) at 0° C. The reaction mixture was stirred for 4 h. LCMS showed the reaction was complete. The reaction mixture was quenched with ice water and extracted with EtOAc (200 mL×2). The combined organic layer was dried over anhydrous $Na_2SO_4$, filtered and concentrated to give a residue. The residue was purified by silica gel chromatography (PE/EtOAc=2/1) to give the product (30.0 g, 90% yield) as a white solid. MS (ESI) m/z: 542.3 (M+H)$^+$.

Step 8: 5-((3,3-difluoropiperidin-4-yl)oxy)-7-methoxyquinazolin-4(3H)-one

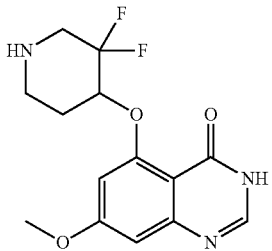 [SMILES: COc1cc(OC2CCNCC2(F)F)c2c(=O)[nH]cnc2c1]

To a solution of tert-butyl 3,3-difluoro-4-((7-methoxy-4-oxo-3,4-dihydroquinazolin-5-yl)oxy)piperidine-1-carboxylate (30.0 g, 55.4 mmol) in DCM (150 mL) was added TFA (63 g, 554 mmol). The reaction was stirred at room temperature overnight. LC-MS showed reaction was complete. The reaction mixture was concentrated to afford crude product. The residue was dissolved in DCM (300 mL), washed with sat. aq. $Na_2CO_3$, and then the organic layer was separated. The aqueous layer was extracted with DCM/MeOH (20/1, 50 mL×3). The combined organic layers were washed with brine and dried over anhydrous $Na_2SO_4$, filtered and concentrated to give crude product (17 g, 99% yield) as a yellow solid. MS (ESI) m/z: 312.1 (M+H)$^+$.

Step 9: 5-((3,3-difluoro-1-methylpiperidin-4-yl)oxy)-7-methoxyquinazolin-4(3H)-one

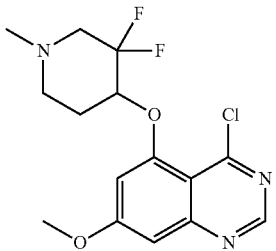 [SMILES: COc1cc(OC2CCN(C)CC2(F)F)c2c(Cl)ncnc2c1]

To a solution of 5-((3,3-difluoropiperidin-4-yl)oxy)-7-methoxyquinazolin-4(3H)-one (1.66 g, 4.04 mmol) in a mixture of DCE (30 mL) and THF (5 mL) was added aq. HCHO (1.5 mL) at 0° C. and stirred for 2 h. Then NaBH(AcO)$_3$ (2.0 g, 9.54 mmol) was added at 0° C. and the mixture was stirred at 0° C. for another 2 h. LC-MS showed reaction was complete. The reaction mixture was concentrated and diluted with water (100 mL). The mixture was extracted with DCM:MeOH (10:1, 200 mL×5). The combined organics were washed with brine (300 mL), dried over anhydrous $Na_2SO_4$, filtered. The filtrate was concentrated to dryness and the residue was purified by silica gel chromatography (DCM/MeOH=10/1) to afford product as a white solid (1.15 g, 74% yield). MS (ESI) m/z: 326.2 (M+H)$^+$. $^1$H NMR (400 MHz, CDCl$_3$) δ 10.98 (br, 1H), 7.92 (s, 1H), 6.82 (d, J=2.4 Hz, 1H), 6.60 (d, J=2.0 Hz, 1H), 4.66-4.62 (m, 1H), 3.91 (s, 3H), 3.14-3.04 (m, 1H), 2.90-2.83 (m, 1H), 2.73-2.66 (m, 1H), 2.59-2.56 (m, 1H), 2.41 (s, 3H), 2.18-2.16 (m, 2H).

Step 10: (S)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine and (R)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine

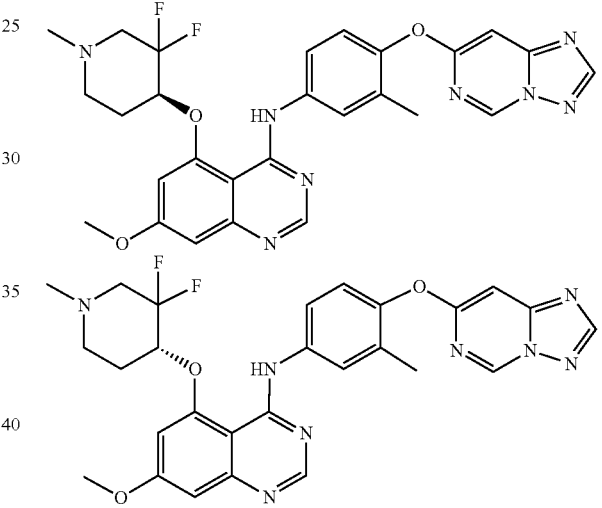

To a solution of 4-chloro-5-((3,3-difluoro-1-methylpiperidin-4-yl)oxy)-7-methoxyquinazoline (130 mg, 0.38 mmol) and 4-([1,2,4]triazolo[1,5-c]pyrimidin-7-yloxy)-3-methylaniline (74 mg, 0.30 mmol) in iPrOH (15 mL) was added TsOH (66 mg, 0.38 mmol). The resulting mixture was stirred at 90° C. for 5 hrs. LC-MS showed the reaction was complete. The reaction mixture was concentrated to remove iPrOH. The residue was dissolved in DCM (50 mL) and washed with sat.aq. NaHCO$_3$ and brine, dried over anhydrous $Na_2SO_4$, filtered and concentrated to give a residue. The residue was purified by prep-TLC (DCM/MeOH=20/1) two times to give product (65 mg, 39% yield) as white solid, which was separated by chiral SFC to give the enantiomers:

(S)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine (Peak 1, retention time 6.339 min, ee: 91.43%) (9 mg, 5.35% yield) as a white solid. MS (ESI) m/z: 549.2 (M+H)$^+$. $^1$HNMR (400 MHz, CDCl$_3$) δ9.82 (s, 1H), 9.20 (s, 1H), 8.60 (s, 1H), 8.32-8.27 (m, 1H), 7.79-7.73 (m, 2H), 7.10 (d, J=8.8 Hz, 1H), 6.98 (s, 1H), 6.90 (s, 1H), 6.52 (s, 1H), 4.59-4.65 (m, 1H), 3.94 (s, 3H), 3.27-3.24 (m, 1H), 2.98-2.95 (m, 1H), 2.58-2.48 (m, 1H), 2.43 (s, 3H), 2.37-2.25 (m, 2H), 2.19 (s, 3H), 2.19-2.13 (m, 1H).

(R)—N-(4-([1,2,4]triazolo[1,5-c]pyrimidin-7-yloxy)-3-methylphenyl)-5-((3,3-difluoro-1-methylpiperidin-4-yl)oxy)-7-methoxyquinazolin-4-amine (Peak 2, retention time 9.068 min, ee: 100%) (9 mg, 5.35% yield) as a white solid. MS (ESI) m/z: 549.2 (M+H)+. $^1$HNMR (400 MHz, CDCl$_3$): δ 9.74 (s, 1H), 9.11 (s, 1H), 8.51 (s, 1H), 8.23-8.16 (m, 1H), 7.69 (d, J=2.0 Hz, 1H), 7.65-7.62 (m, 1H), 7.04-6.99 (m, 1H), 6.91 (d, J=2.0 Hz, 1H), 6.81 (s, 1H), 6.43 (d, J=2.0 Hz, 1H), 4.57-4.50 (m, 1H), 3.84 (s, 3H), 3.17-3.12 (m, 1H), 2.88-2.85 (m, 1H), 2.49-2.39 (m, 1H), 2.33 (s, 3H), 2.27-2.16 (m, 2H), 2.18 (s, 3H), 2.15-2.03 (m, 1H).

SFC condition: Column: OD 4.6×250 5 um Mobile phase: A: CO$_2$ B: methanol Gradient: hold 40% of B for 15 min Flow rate: 1.8 mL/min Column temp: 35° C.

The following compound was prepared according to the above described methods using different starting materials.

| Ex # | Structure | Name | MS m/z |
|---|---|---|---|
| 53 | 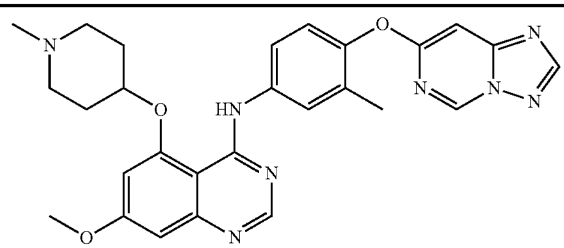 | N-(4-([1,2,4]triazolo[1,5-c]pyrimidin-7-yloxy)-3-methylphenyl)-7-methoxy-5-((1-methylpiperidin-4-yl)oxy)quinazolin-4-amine | 513 (M + H)+ |

$^1$H NMR (400 MHz, CDCl$_3$) δ 9.88 (s, 1H), 9.19 (d, J=1.2 Hz, 1H), 8.56 (s, 1H), 8.31 (s, 1H), 7.72 (d, J=2.0 Hz, 1H), 7.63-7.66 (m, 1H), 7.10 (d, J=8.4 Hz, 1H), 6.88 (d, J=0.8 Hz, 1H), 6.84 (d, J=2.4 Hz, 1H), 6.51 (d, J=2.4 Hz, 1H), 4.57-4.61 (m, 1H), 4.03 (s, 3H), 2.83-2.86 (m, 2H), 2.17-2.38 (m, 12H).

Example 54

N4-(4-([1,2,4]triazolo[1,5-c]pyrimidin-7-yloxy)-3-methylphenyl)-N6-(4,4-dimethyl-4,5-dihydrooxazol-2-yl)-5-(3-(dimethylamino)azetidin-1-yl)quinazoline-4,6-diamine

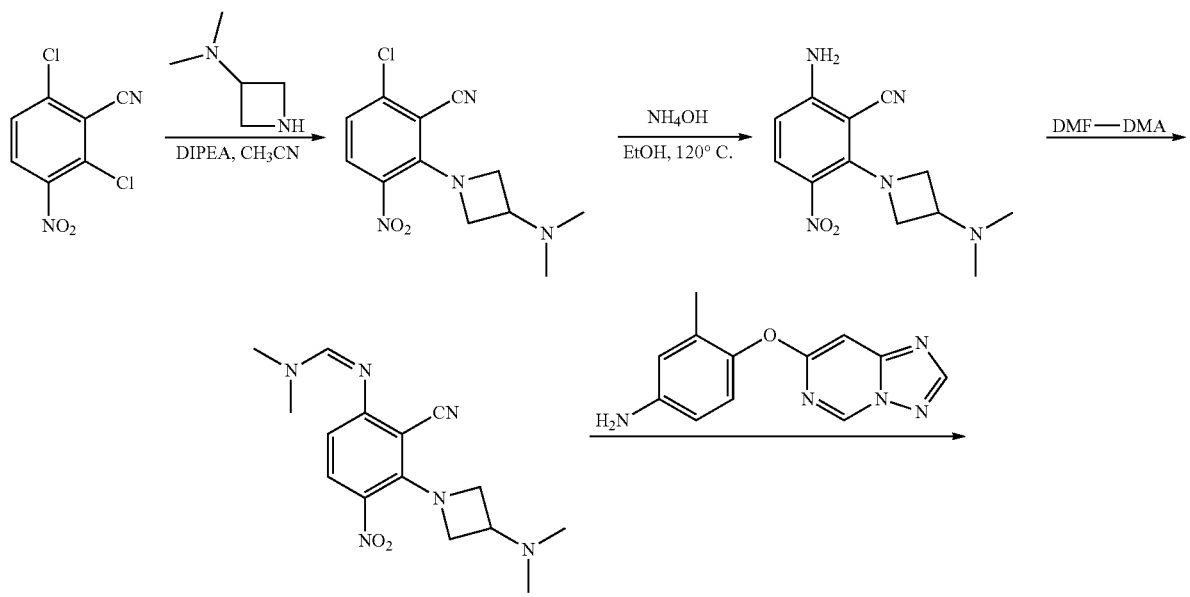

-continued
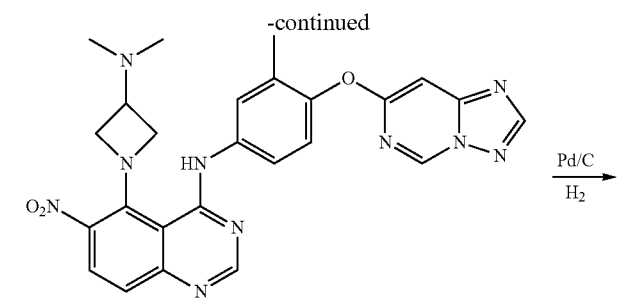
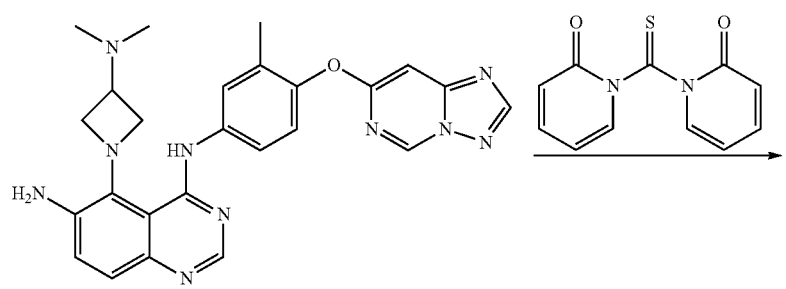
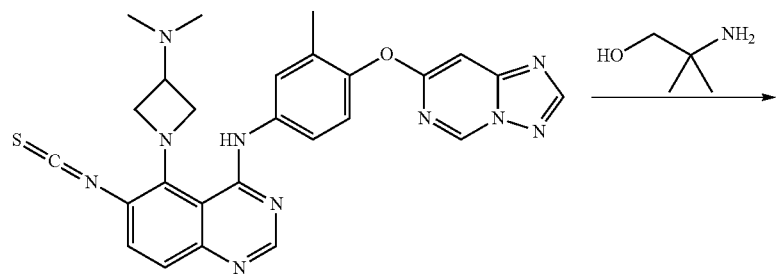
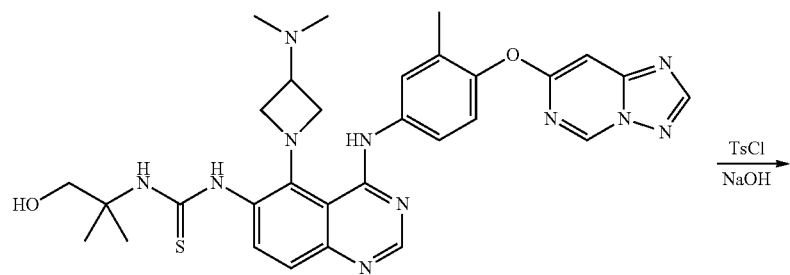
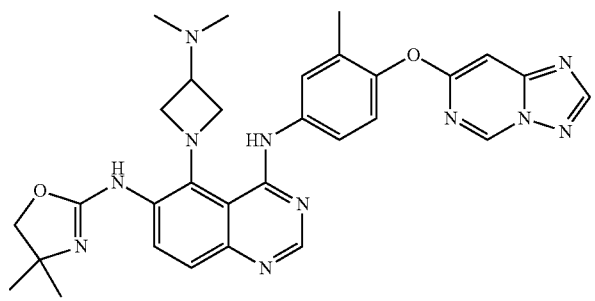

Step 1: 6-chloro-2-(3-(dimethylamino)azetidin-1-yl)-3-nitrobenzonitrile

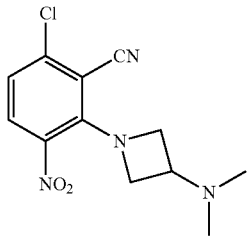 [SMILES: CN(C)C1CN(c2c([N+](=O)[O-])ccc(Cl)c2C#N)C1]

To a solution of 2,6-dichloro-3-nitrobenzonitrile (5.0 g, 23.0 mmol) in MeCN (40 mL) was stirred at 0° C., was added a solution of N,N-dimethylazetidin-3-amine dihydrochloride (2.1 g, 21.0 mmol) and DIPEA (7.8 g, 63.0 mmol) in MeCN (40 mL) dropwise in 20 min. The resulting mixture was then stirred at room temperature for 4 h and then poured into ice water. The precipitate was collected by filtration. The solid was washed with water and dried in vacuum to give the desired product (5 g, 98% yield) as a yellow solid. MS: m/z 281 (M+H)$^+$.

Step 2: 6-amino-2-(3-(dimethylamino)azetidin-1-yl)-3-nitrobenzonitrile

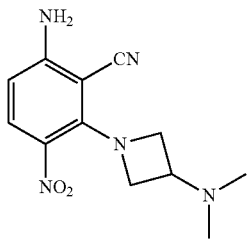 [SMILES: CN(C)C1CN(c2c([N+](=O)[O-])ccc(N)c2C#N)C1]

To a solution of 6-chloro-2-(3-(dimethylamino)azetidin-1-yl)-3-nitrobenzonitrile (5 g, 17.9 mmol) in EtOH (100 mL) stirred at room temperature, was added 37% ammonia (30 mL), the resulting mixture was stirred at 120° C. for 12 hrs. After cooled down, the crude mixture was evaporated to dryness, the residue was purified by column chromatography on silica gel (EtOAc:PE=1:2) to give desired product (2 g, 43% yield) as a yellow solid. MS: m/z 262 (M+H)$^+$.

Step 3: (Z)—N'-(2-cyano-3-(3-(dimethylamino)azetidin-1-yl)-4-nitrophenyl)-N,N-dimethylformimidamide

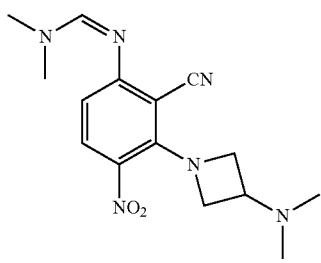

A mixture of 6-amino-2-(3-(dimethylamino)azetidin-1-yl)-3-nitrobenzonitrile (300 mg, 1.1 mmol) and DMF-DMA (3 mL) in EtOH (30 mL) was stirred at 80° C. for 4 hrs. After cooled down, the crude mixture was evaporated to dryness to give desired product (310 mg) as a yellow solid, which was used for next step without further purification. MS: m/z 317 (M+H)$^+$.

Step 4: N-(4-([1,2,4]triazolo[1,5-c]pyrimidin-7-yloxy)-3-methylphenyl)-5-(3-(dimethylamino)azetidin-1-yl)-6-nitroquinazolin-4-amine

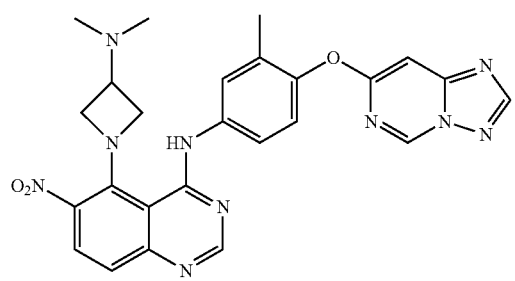

To a solution of (Z)—N'-(2-cyano-3-(3-(dimethylamino)azetidin-1-yl)-4-nitrophenyl)-N,N-dimethylformimidamide (300 mg, 1 mmol) in HOAc (10 mL) stirred at room temperature, was added 4-([1,2,4]triazolo[1,5-c]pyrimidin-7-yloxy)-3-methylaniline (241 mg, 1 mmol), the resulting mixture was stirred at 50° C. for 12 hrs. The crude mixture was then concentrated to dryness, the residue was purified by column chromatography on silica gel (DCM:MeOH=20:1) to give desired product (220 mg, 45% yield for two steps) as a yellow solid. MS: m/z 513 (M+H)$^+$.

Step 5: N4-(4-([1,2,4]triazolo[1,5-c]pyrimidin-7-yloxy)-3-methylphenyl)-5-(3-(dimethylamino)azetidin-1-yl)quinazoline-4,6-diamine

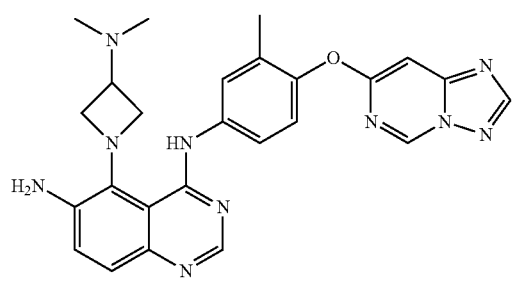 [SMILES: Cc1cc(Nc2ncnc3ccc([N+](=O)[O-])c(N4CC(N(C)C)C4)c23)ccc1Oc1cc2ncnn2cn1]

To a solution of N-(4-([1,2,4]triazolo[1,5-c]pyrimidin-7-yloxy)-3-methylphenyl)-5-(3-(dimethylamino)azetidin-1-yl)-6-nitroquinazolin-4-amine (220 mg, 0.4 mmol) in MeOH (50 mL), was added 10% Pd/C (20 mg). The resulting mixture was stirred under H$_2$ atmosphere at room temperature for 12 hrs. The catalyst was filtered off through Celite and the filtrate was evaporated to dryness to give desired product (190 mg, 92% yield) as a yellow solid, which was used for next step without further purification. MS: m/z 483 (M+H)$^+$.

Step 6: N-(4-([1,2,4]triazolo[1,5-c]pyrimidin-7-yloxy)-3-methylphenyl)-5-(3-(dimethylamino)azetidin-1-yl)-6-isothiocyanatoquinazolin-4-amine

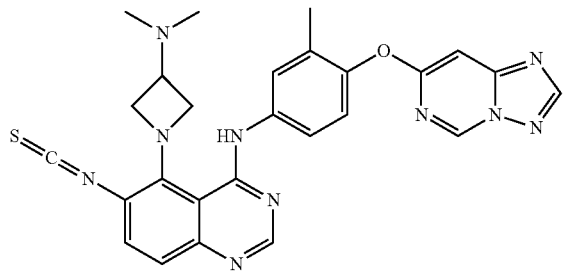 [SMILES: Cc1cc(Nc2ncnc3ccc(N=C=S)c(N4CC(N(C)C)C4)c23)ccc1Oc1cc2ncnn2cn1]

To a solution of N4-(4-([1,2,4]triazolo[1,5-c]pyrimidin-7-yloxy)-3-methylphenyl)-5-(3-(dimethylamino)azetidin-1-yl)quinazoline-4,6-diamine (110 mg, 0.2 mmol) and Et₃N (41 mg, 0.4 mmol) in PhMe (10 mL) stirred at room temperature under nitrogen, was added 1,1'-thiocarbonylbis(pyridin-2(1H)-one) (47 mg, 0.2 mmol). The resulting mixture was heated to 110° C. under nitrogen for 2 hrs. After cooled down, the crude mixture was diluted with EtOAc (20 mL), washed with water and brine, filtered and concentrated to give desired product (70 mg, 59% yield). LCMS: m/z 525 (M+H)⁺.

Step 7: 1-(4-((4-([1,2,4]triazolo[1,5-c]pyrimidin-7-yloxy)-3-methylphenyl)amino)-5-(3-(dimethylamino)azetidin-1-yl)quinazolin-6-yl)-3-(1-hydroxy-2-methylpropan-2-yl)thiourea

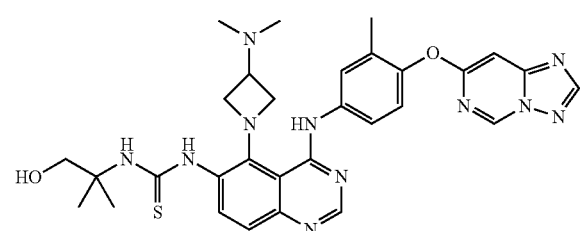

To a solution of N-(4-([1,2,4]triazolo[1,5-c]pyrimidin-7-yloxy)-3-methylphenyl)-5-(3-(dimethylamino)azetidin-1-yl)-6-isothiocyanatoquinazolin-4-amine (70 mg, 0.1 mmol) in 1,4-dioxane (20 mL) stirred at room temperature, was added 2-amino-2-methylpropan-1-ol (18 mg, 0.2 mmol). The resulting mixture was stirred at 60° C. for 2 hrs. The crude mixture was then poured into ice water, extracted with EtOAc (100 mL). The organic phase was separated, washed with water and brine, dried over anhydrous Na₂SO₄, filtered and concentrated. The residue was purified by column chromatography on silica gel (DCM:MeOH=20:1) to give desired product (40 mg, 49% yield) as a yellow solid. MS: m/z 614 (M+H)⁺.

Step 8: N4-(4-([1,2,4]triazolo[1,5-c]pyrimidin-7-yloxy)-3-methylphenyl)-N6-(4,4-dimethyl-4,5-dihydrooxazol-2-yl)-5-(3-(dimethylamino)azetidin-1-yl)quinazoline-4,6-diamine

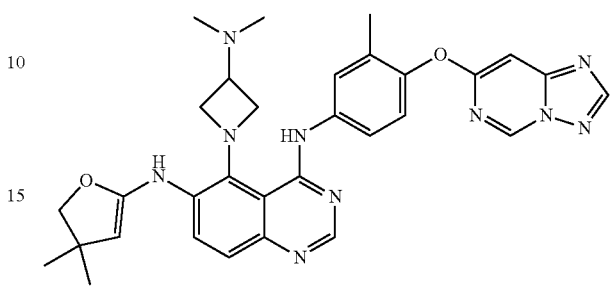

To a solution of 1-(4-((4-([1,2,4]triazolo[1,5-c]pyrimidin-7-yloxy)-3-methylphenyl)amino)-5-(3-(dimethylamino)azetidin-1-yl)quinazolin-6-yl)-3-(1-hydroxy-2-methylpropan-2-yl)thiourea (20 mg, 0.03 mmol) in THF (3 mL) were added TsCl (6 mg, 0.03 mmol) and NaOH (3 mg, 0.06 mmol). The mixture was stirred at room temperature under nitrogen for 16 hrs and then filtered. After the filtrate was concentrated, the residue was purified by prep-TLC to give desired product (10 mg, 53% yield) as a yellow solid. MS: 580 (M+H)⁺. ¹H NMR (400 MHz, CD₃OD) δ 9.43 (d, J=1.2 Hz, 1H), 8.41 (s, 1H), 8.35 (s, 1H), 7.95 (d, J=19.3 Hz, 2H), 7.53 (t, J=6.9 Hz, 2H), 7.17 (d, J=8.7 Hz, 1H), 6.90 (d, J=1.2 Hz, 1H), 4.23 (s, 6H), 3.51 (s, 1H), 2.38 (s, 6H), 2.26 (s, 3H), 1.40 (s, 6H).

Example 55

N-(4-([1,2,4]triazolo[1,5-c]pyrimidin-7-yloxy)-3-methylphenyl)-5-(8-methyl-5-oxa-2,8-diazaspiro[3.5]nonan-2-yl)quinazolin-4-amine

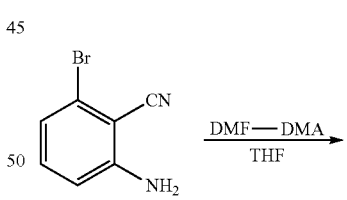

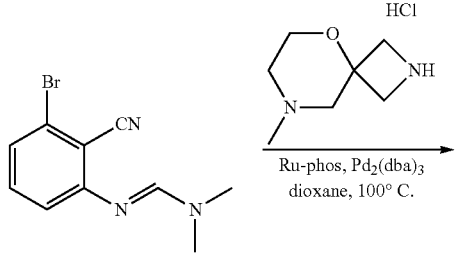

-continued

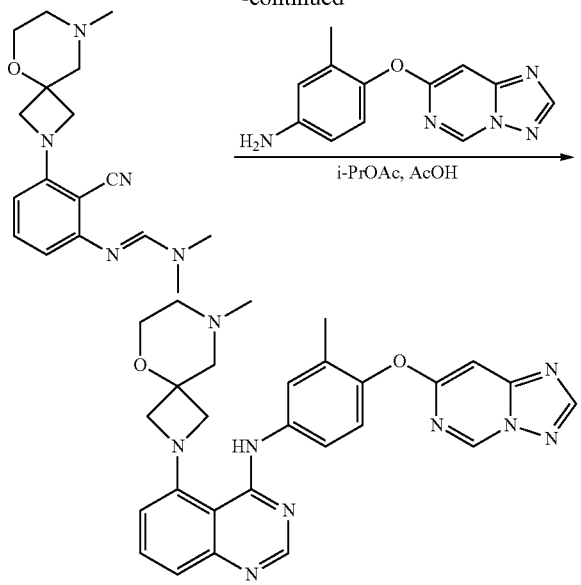

Step 1: (E)-N'-(3-bromo-2-cyanophenyl)-N,N-dimethylformimidamide

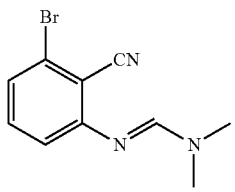

To a solution of 2-amino-6-bromobenzonitrile (2.0 g, 10.2 mmol) in THF (10 mL) was added DMF-DMA (10 mL) and the mixture was stirred at 70° C. for 2 hrs. The mixture was diluted with EtOAc (10 mL) and washed with water and brine, dried over anhydrous $Na_2SO_4$, filtered and concentrated to give crude product, which was purified by silica gel chromatography (PE:EtOAc=2:1) to give desired product (2.0 g, 78% yield) as yellow oil. MS (ESI) m/z: 252/254 $(M+H)^+$.

Step 2: (E)-N'-(2-cyano-3-(8-methyl-5-oxa-2,8-diazaspiro[3.5]nonan-2-yl)phenyl)-N,N-dimethylformimidamide

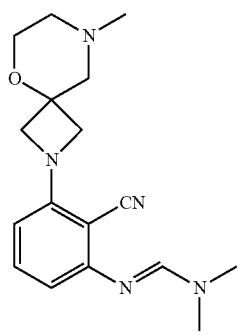 [SMILES: CN(C)/C=N/c1cccc(N2CC3(CN(C)CCO3)C2)c1C#N]

To a mixture of (E)-N'-(3-bromo-2-cyanophenyl)-N,N-dimethylformimidamide (150 mg, 0.60 mmol) and 8-methyl-5-oxa-2,8-diazaspiro[3.5]nonane hydrochloride (127.8 mg, 0.90 mmol) in 1,4-dioxane (5 mL) was added $Cs_2CO_3$ (587 mg, 1.80 mmol) followed by $Pd_2(dba)_3$ (54.9 mg, 0.06 mmol) and Ru-phos (55.9 mg, 0.12 mmol). The mixture was degassed under $N_2$ atmosphere for three times and stirred at 90° C. under $N_2$ atmosphere overnight. The mixture was diluted with EtOAc (10 mL) and washed with water and brine, dried over anhydrous $Na_2SO_4$, filtered and concentrated to give crude product, which was purified by silica gel chromatography (PE:EtOAc=5:1) to give crude product (150 mg, 80% yield) as yellow oil. MS (ESI) m/z: 314 $(M+H)^+$.

Step 3: N-(4-([1,2,4]triazolo[1,5-c]pyrimidin-7-yloxy)-3-methylphenyl)-5-(8-methyl-5-oxa-2,8-diazaspiro[3.5]nonan-2-yl)quinazolin-4-amine

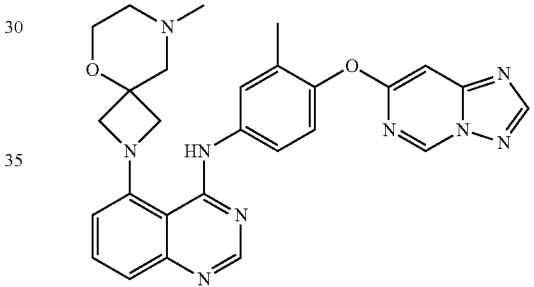

To a solution of (E)-N'-(2-cyano-3-(8-methyl-5-oxa-2,8-diazaspiro[3.5]nonan-2-yl)phenyl)-N,N-dimethylformimidamide (50 mg, 0.16 mmol) in i-PrOAc (3 mL) and AcOH (1 mL) was added 4-([1,2,4]triazolo[1,5-c]pyrimidin-7-yloxy)-3-methylaniline (38.7 mg, 0.16 mmol) and the mixture was stirred at 100° C. for 16 hrs. The mixture was diluted with EtOAc (10 mL) and alkalified by adding saturated aq. $NaHCO_3$ solution to pH=8. The mixture was extracted with EtOAc (20 mL×2) and the combined organic layers were washed with brine, dried over anhydrous $Na_2SO_4$, filtered and concentrated to dryness. The residue was purified by silica gel chromatography (DCM:MeOH=80:1 to 20:1) to give desired product (80.0 mg, 34% yield) as white solid. MS (ESI) m/z: 510 $(M+H)^+$. $^1$H-NMR (400 MHz, $CD_3OD$) δ 9.42 (d, J=1.1 Hz, 1H), 8.48 (s, 1H), 8.41 (s, 1H), 7.92-7.92 (m, 2H), 7.75 (t, J=8.1 Hz, 1H), 7.45 (d, J=7.7 Hz, 1H), 7.33 (d, J=7.7 Hz, 1H), 7.18 (d, J=8.5 Hz, 1H), 6.93 (d, J=1.1 Hz, 1H), 3.94 (d, J=8.4 Hz, 2H), 3.89-3.73 (m, 4H), 2.74 (s, 3H), 2.49-2.42 (m, 2H), 2.32 (d, J=8.6 Hz, 3H), 2.25 (s, 3H).

Example 80
1-(4-(4-(4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one
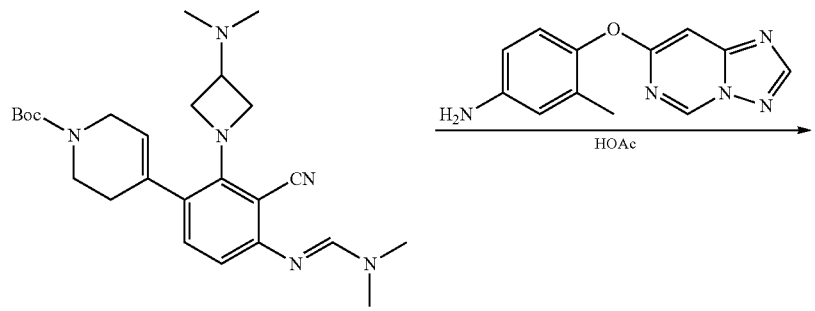
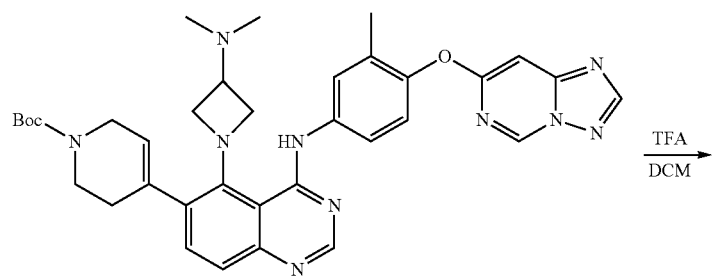
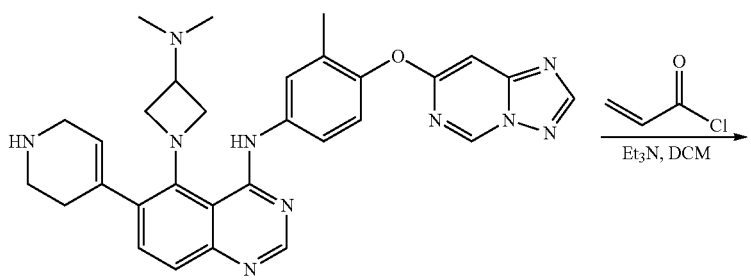
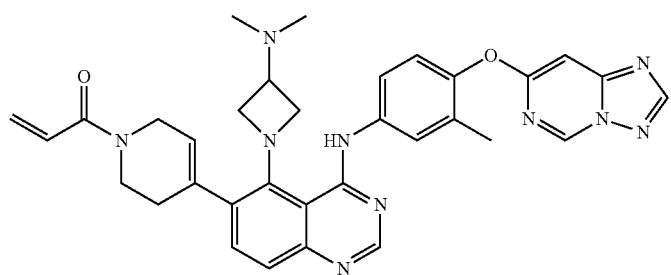

Step 1: tert-butyl 4-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridine-1(2H)-carboxylate

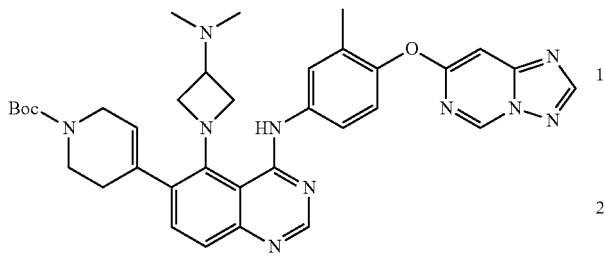

To a solution of tert-butyl (E)-4-(3-cyano-2-(3-(dimethylamino)azetidin-1-yl)-4-(((dimethylamino)methylene)amino)phenyl)-3,6-dihydropyridine-1(2H)-carboxylate (300 mg, 0.66 mmol) in AcOH (5 mL) was added 4-([1,2,4]triazolo[1,5-c]pyrimidin-7-yloxy)-3-methylaniline (240 mg, 1.00 mmol) and the mixture was stirred at 100° C. for 5 hrs. The mixture was concentrated to dryness and the residue was dissolved in EtOAc and washed with aq. NaHCO₃ and brine, dried over anhydrous Na₂SO₄, filtered and concentrated to dryness. The residue was purified by silica gel chromatography (DCM:MeOH=60:1 to 20:1) to give desired product (260 mg, 61% yield) as yellow solid. MS (ESI) m/z: 649 (M+H)⁺.

Step 2: N-(4-([1,2,4]triazolo[1,5-c]pyrimidin-7-yloxy)-3-methylphenyl)-5-(3-(dimethylamino)azetidin-1-yl)-6-(1,2,3,6-tetrahydropyridin-4-yl)quinazolin-4-amine

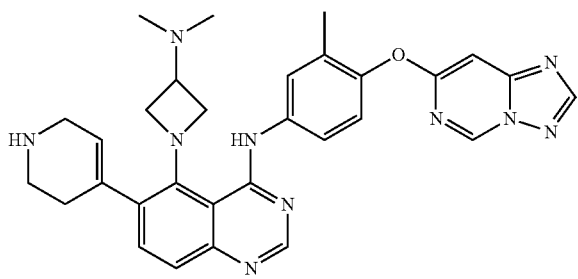 [SMILES: Cc1cc(Nc2ncnc3ccc(C4=CCNCC4)c(N4CC(N(C)C)C4)c23)ccc1Oc1cc2ncnn2cn1]

To a solution of tert-butyl 4-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridine-1(2H)-carboxylate (260 mg, 0.40 mmol) in DCM (4 mL) was added TFA (2 mL) at 0° C. and the reaction mixture was stirred at rt for 2 hrs. The mixture was concentrated to dryness and the residue was dissolved in DCM (10 mL), washed with saturated aq. NaHCO₃ solution and brine, dried over Na₂SO₄, filtered and evaporated to dryness to give desired product (190 mg, 86% yield) as red solid, which was directly used for next step without purification. MS (ESI) m/z: 549 (M+H)⁺.

Step 3: 1-(4-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one To a solution of N-(4-([1,2,4]triazolo[4,3-a]pyrimidin-7-yloxy)-3-methylphenyl)-5-(3-(dimethylamino)azetidin-1-yl)-6-(1,2,3,6-tetrahydropyridin-4-yl)quinazolin-4-amine (100 mg, 0.18 mmol) in DCM (5 mL) was added TEA (55 mg, 0.55 mmol) at 0° C., followed by drop-wise addition of acryloyl chloride (13 mg, 0.15 mmol). The reaction mixture was stirred at room temperature for 1 hr, quenched with water, extracted with DCM (10 mL×3), washed with saturated aq.NaHCO₃ solution and brine, dried over Na₂SO₄, filtered and evaporated to dryness. The residue was purified by prep-TLC (DCM:MeOH=10:1) to give desired product (20.0 mg, 18% yield) as yellow solid. $^1$H NMR (400 MHz, CD₃OD) δ 9.44 (d, J=1.1 Hz, 1H), 8.42 (d, J=1.5 Hz, 2H), 7.93-7.75 (m, 2H), 7.54 (d, J=8.6 Hz, 1H), 7.27 (d, J=8.5 Hz, 1H), 7.20 (d, J=8.7 Hz, 1H), 7.02-6.64 (m, 2H), 6.27 (d, J=17.1 Hz, 1H), 5.81 (m, 2H), 4.39 (m, 2H), 4.10 (m, 2H), 3.96 (m, 2H), 3.79 (m, 2H), 3.10 (m, 1H), 2.73 (m, 2H), 2.27 (s, 3H), 2.16 (s, 6H). MS (ESI) m/z: 603 (M+H)⁺.

The following compounds were prepared according to the above described methods using different starting materials.

| Ex # | Structure | Name | MS m/z |
|---|---|---|---|
| 82 | 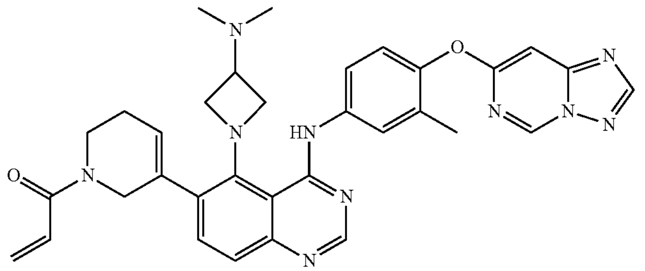 [SMILES: C=CC(=O)N1CCC=C(c2ccc3ncnc(Nc4ccc(Oc5cc6ncnn6cn5)c(C)c4)c3c2N2CC(N(C)C)C2)C1] | 1-(5-(4-((4-([1,2,4]triazolo[1,5-c]pyrimidin-7-yloxy)-3-methylphenyl)amino)-5-(3-(dimethylamino)azetidin-1-yl)quinazolin-6-yl)-3,6-dihydropyridin-1(2H)-yl)prop-2-en-1-one | 603 (M + H)+ |
| 83 | 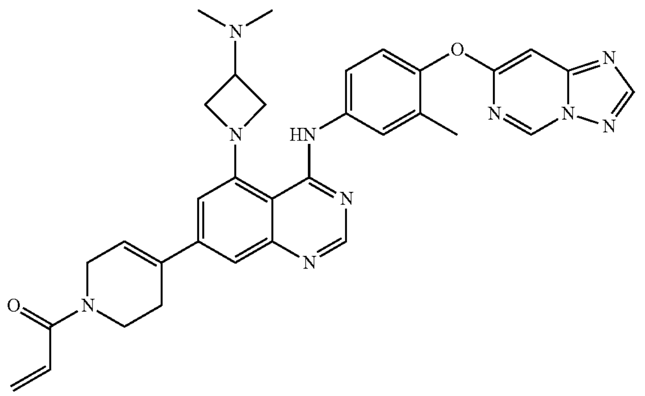 [SMILES: C=CC(=O)N1CC=C(c2cc(N3CC(N(C)C)C3)c3c(Nc4ccc(Oc5cc6ncnn6cn5)c(C)c4)ncnc3c2)CC1] | 1-(4-(4-((4-([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one | 603 (M + H)+ |
| 84 | 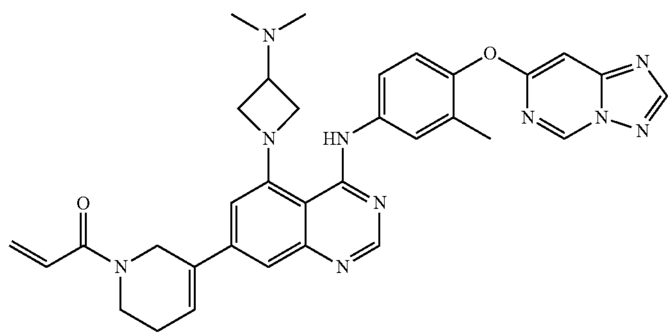 [SMILES: C=CC(=O)N1CCC=C(c2cc(N3CC(N(C)C)C3)c3c(Nc4ccc(Oc5cc6ncnn6cn5)c(C)c4)ncnc3c2)C1] | 1-(5-(4-((4-([1,2,4]triazolo[1,5-c]pyrimidin-7-yloxy)-3-methylphenyl)amino)-5-(3-(dimethylamino)azetidin-1-yl)quinazolin-7-yl)-3,6-dihydropyridin-1(2H)-yl)prop-2-en-1-one | 603 (M + H)+ |
| 85 | 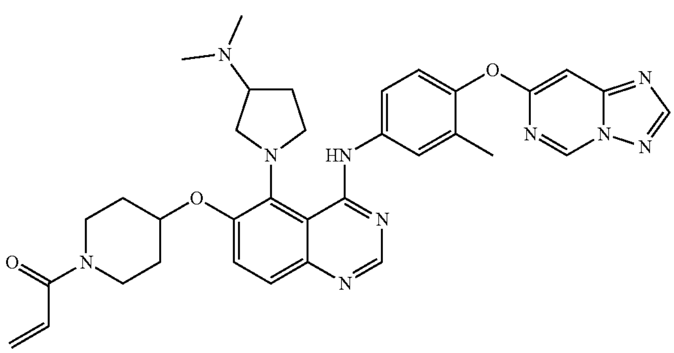 [SMILES: C=CC(=O)N1CCC(Oc2ccc3ncnc(Nc4ccc(Oc5cc6ncnn6cn5)c(C)c4)c3c2N2CCC(N(C)C)C2)CC1] | 1-(4-((4-((4-([1,2,4]triazolo[1,5-c]pyrimidin-7-yloxy)-3-methylphenyl)amino)-5-(3-(dimethylamino)pyrrolidin-1-yl)quinazolin-6-yl)oxy)piperidin-1-yl)prop-2-en-1-one | 635 (M + H)+ |

Example 82

Yellow solid. 1H NMR (400 MHz, CDCl3) δ 9.14 (d, J=1.1 Hz, 1H), 8.56 (s, 1H), 8.26 (s, 1H), 7.89 (s, 2H), 7.43-7.29 (m, 2H), 7.07 (d, J=8.8 Hz, 1H), 6.82 (s, 1H), 6.65-6.55 (m, 1H), 6.31 (d, J=16.7 Hz, 1H), 5.82 (s, 1H), 5.71 (dd, J=10.5, 1.7 Hz, 1H), 4.37 (d, J=37.7 Hz, 2H), 4.05 (s, 2H), 3.94-3.57 (m, 5H), 2.94 (s, 1H), 2.39 (s, 2H), 2.21 (s, 3H), 2.09 (s, 6H).

Example 83

Yellow solid. 1H NMR (400 MHz, CD3OD) δ 9.43 (s, 1H), 8.44 (d, J=15.6 Hz, 2H), 7.85 (m, 2H), 7.55-7.36 (m, 2H), 7.20 (d, J=8.7 Hz, 1H), 6.98-6.70 (m, 2H), 6.49 (m, 1H), 6.27 (m, 1H), 5.80 (d, J=10.5 Hz, 1H), 4.39 (m, 2H), 4.10 (t, J=7.3 Hz, 2H), 3.93 (m, 2H), 3.83 (t, J=7.0 Hz, 2H), 3.36 (m, 1H), 2.74 (m, 2H), 2.28 (m, 9H).

223
Example 84
Yellow solid. $^1$H NMR (400 MHz, CD$_3$OD) δ 9.44 (s, 1H), 8.43 (m, 2H), 8.00-7.77 (m, 2H), 7.43 (m, 2H), 7.21 (d, J=8.7 Hz, 1H), 7.01-6.77 (m, 2H), 6.64 (m, 1H), 6.33-6.19 (m, 1H), 5.80 (m, 1H), 4.60 (m, 3H), 4.11 (t, J=7.3 Hz, 2H), 3.84 (m, 4H), 2.51 (m, 2H), 2.28 (m, 9H).
224
Example 81
(R)-1-(4-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-3,6-dihydropyridin-1(2H)-yl)prop-2-en-1-one
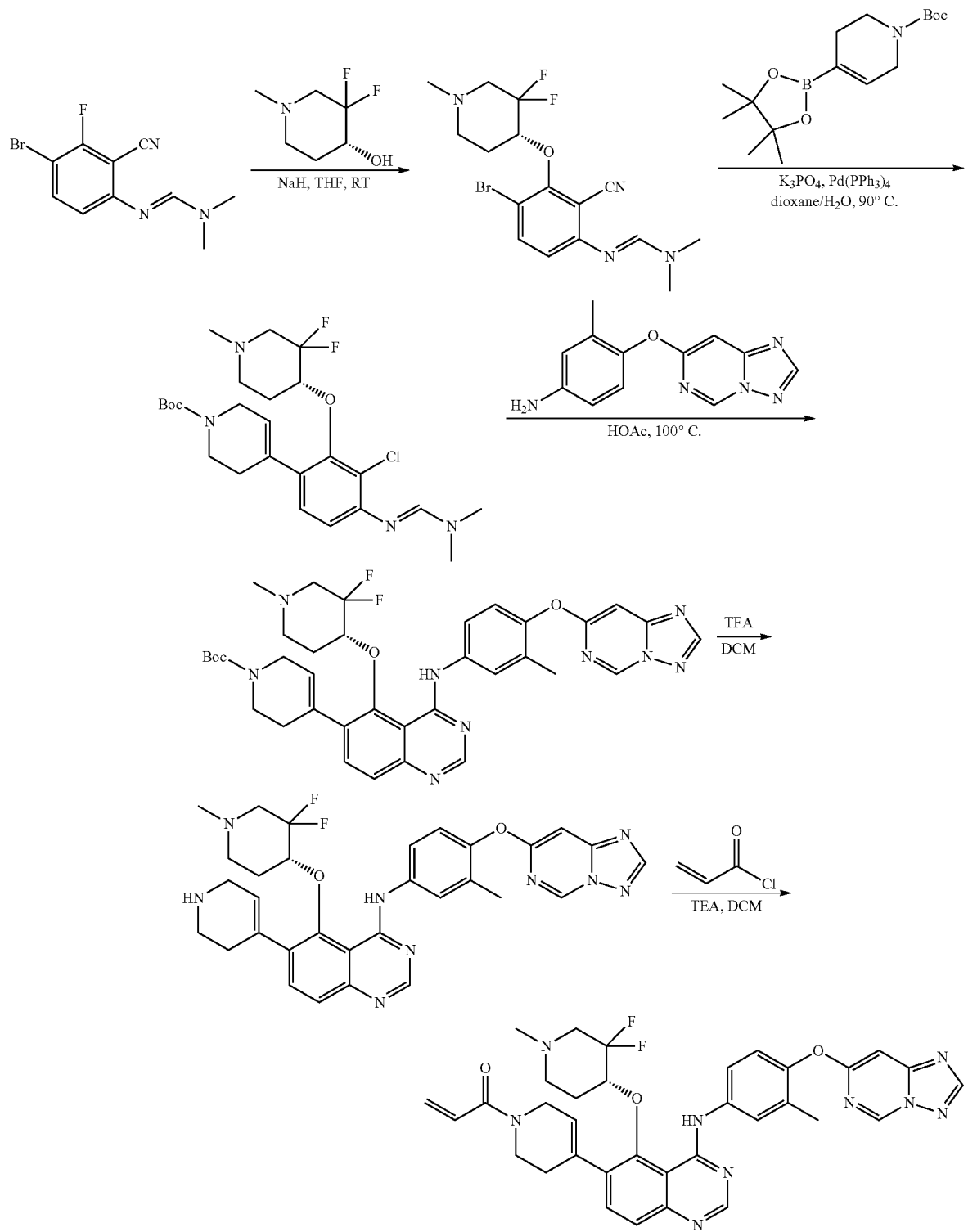

Step 1: (R,E)-N'-(4-bromo-2-cyano-3-((3,3-difluoro-1-methylpiperidin-4-yl)oxy)phenyl)-N,N-dimethyl-formimidamide

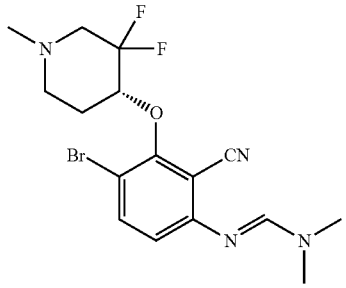

To a solution of (R)-3,3-difluoro-1-methylpiperidin-4-ol (337 mg, 2.2 mmol) in dry THF (1 mL) was added NaH (103 mg, 2.55 mmol, 60% dispersion in mineral oil) at 0° C. and the mixture was stirred at 0° C. for 30 min. To the above mixture, (E)-N'-(4-bromo-2-cyano-3-fluorophenyl)-N,N-dimethylformimidamide (460 mg, 1.7 mmol) was added and the resulting mixture was stirred at rt overnight. The mixture was diluted with water and extracted with EtOAc (10 mL×2). The combined organic layers were washed with saturated aq. NH$_4$Cl solution and brine, dried over anhydrous Na$_2$SO$_4$, filtered and concentrated to dryness. The residue was purified by chromatography on silica gel (PE:EtOAc=10:1) to give desired product (524 mg, 76% yield) as a white solid. MS (ESI) m/z: 401 (M+H)$^+$.

Step 2: tert-butyl (R,E)-4-(3-cyano-2-((3,3-difluoro-1-methylpiperidin-4-yl)oxy)-4-(((dimethylamino)methylene)amino)phenyl)-3,6-dihydropyridine-1(2H)-carboxylate

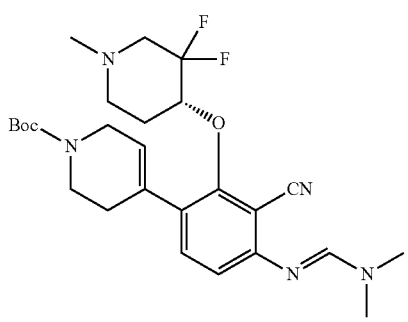 [SMILES: CN(C)/C=N/c1ccc(C2=CCN(C(=O)OC(C)(C)C)CC2)c(O[C@@H]2CCN(C)CC2(F)F)c1C#N]

To a solution of (R,E)-N'-(4-bromo-2-cyano-3-((3,3-difluoro-1-methylpiperidin-4-yl)oxy)phenyl)-N,N-dimethylformimidamide (524 mg, 1.3 mmol) in degassed 1,4-dioxane (10 mL) and water (2 mL) was added tert-butyl 4-(4,4,5,5-tetramethyl-1,3,2-dioxaborolan-2-yl)-5,6-dihydropyridine-1(2H)-carboxylate (526 mg, 1.7 mmol), followed by K$_3$PO$_4$ (555 mg, 2.6 mmol) and Pd(PPh$_3$)$_4$ (151 mg, 0.13 mmol) under N$_2$ atmosphere, after addition, the mixture was degassed under N$_2$ atmosphere for three times and stirred under N$_2$ atmosphere at 90° C. for 2 hrs. The mixture was diluted with EtOAc and washed with water and brine, dried over anhydrous Na$_2$SO$_4$, filtered and concentrated to dryness. The residue was purified by chromatography on silica gel (PE:EtOAc=10:1) to give desired product (611 mg, 93% yield) as white solid. MS (ESI) m/z: 504 (M+H)$^+$.

Steps 3-5: (R)-1-(4-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-3,6-dihydropyridin-1(2H)-yl)prop-2-en-1-one

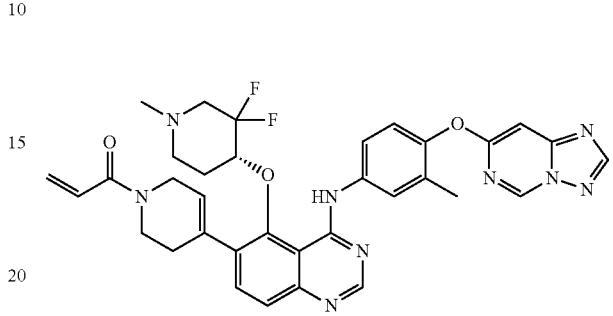

The title product was prepared in a similar fashion to Example 80 as white solid. $^1$H NMR (400 MHz, CD$_3$OD) δ 9.43 (d, J=1.2 Hz, 1H), 8.51 (s, 1H), 8.42 (s, 1H), 7.84-7.70 (m, 3H), 7.60 (d, J=8.6 Hz, 1H), 7.18 (d, J=8.6 Hz, 1H), 6.94 (d, J=1.2 Hz, 1H), 6.93-6.78 (m, 1H), 6.33-6.24 (m, 1H), 6.15 (d, J=11.2 Hz, 1H), 5.82 (d, J=10.6 Hz, 1H), 4.66-4.51 (m, 1H), 4.43-4.31 (m, 2H), 4.04-3.84 (m, 2H), 3.21-3.15 (m, 1H), 2.95-2.78 (m, 2H), 2.59-2.50 (m, 1H), 2.46-2.33 (m, 1H), 2.28 (s, 3H), 2.25 (s, 3H), 2.12-1.98 (m, 2H), 1.84-1.75 (m, 1H). MS (ESI) m/z: 654 (M+H)+.

Example 86

(R)-4-((4-([1,2,4]triazolo[1,5-c]pyrimidin-7-yloxy)-3-methylphenyl)amino)-5-((3,3-difluoro-1-methylpiperidin-4-yl)oxy)-6-methoxyquinoline-3-carbonitrile

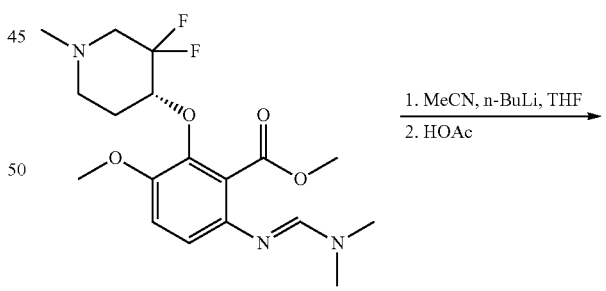

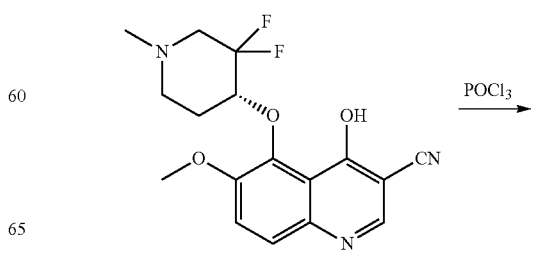

-continued

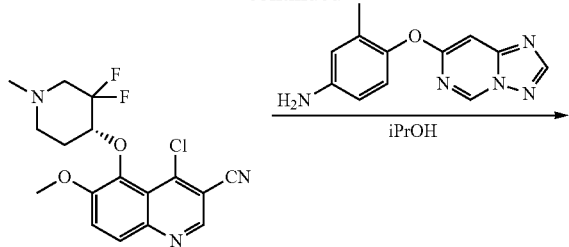

Step 1: (R)-5-((3,3-difluoro-1-methylpiperidin-4-yl)oxy)-4-hydroxy-6-methoxyquinoline-3-carbonitrile

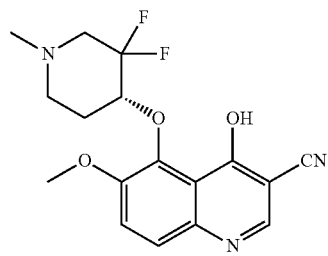 [SMILES: COc1ccc2ncc(C#N)c(O)c2c1O[C@@H]1CCN(C)CC1(F)F]

To a solution of CH$_3$CN (177 mg, 4.3 mmol) in THF (3 mL) was added n-BuLi (2.1 mL, 3.6 mmol) drop-wisely at −78° C. and the mixture was stirred at this temperature for 20 minutes. To the above slurry a solution of (R)-(6-amino-2-((3,3-difluoro-1-methylpiperidin-4-yl)oxy)-3-methoxyphenyl) (11-oxidanyl)methanone (600 mg, 1.54 mmol) in THF (6 mL) was added and the resulting mixture was stirred at rt overnight. AcOH (0.1 mL) was added and the mixture was stirred for another 1 hr. The mixture was diluted with EtOAc (10 mL), washed with water and brine, dried over Na$_2$SO$_4$, filtered and concentrated to give crude product, which was purified by silica gel chromatography (DCM:MeOH=20:1) to give desired product (400 mg, 74% yield) as yellow oil. MS (ESI) m/z: 350 (M+H)$^+$.

Steps 2-3: (R)-4-((4-([1,2,4]triazolo[1,5-c]pyrimidin-7-yloxy)-3-methylphenyl)amino)-5-((3,3-difluoro-1-methylpiperidin-4-yl)oxy)-6-methoxyquinoline-3-carbonitrile

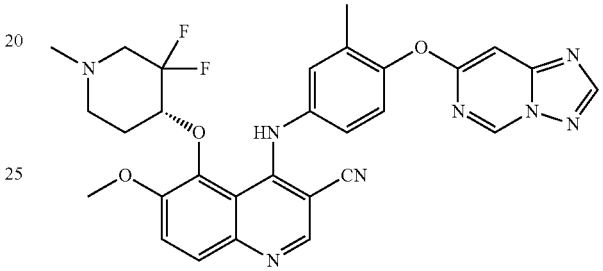

The crude product was prepared in a similar fashion to Examples 31 and 32, which was purified by column chromatography (DCM:MeOH=30:1) to give the title product as white solid. $^1$H-NMR (400 MHz, CD$_3$OD) δ 9.46 (s, 1H), 8.40 (s, 1H), 8.31 (s, 1H), 7.74 (s, 2H), 7.41 (d, J=2.3 Hz, 1H), 7.34 (dd, J=8.5, 2.5 Hz, 1H), 7.24 (d, J=8.5 Hz, 1H), 6.98 (d, J=1.2 Hz, 1H), 4.93 (m, 1H), 4.06 (s, 3H), 3.22-3.11 (m, 1H), 2.97-2.87 (m, 1H), 2.45 (m, 1H), 2.33 (s, 3H), 2.25 (s, 3H), 2.22-2.27 (m, 2H), 2.10-1.98 (m, 1H). MS (ESI) m/z: 573 (M+H)$^+$.

The following compounds were prepared according to the above described methods using different starting materials.

| Ex # | Structure | Name | MS m/z |
|---|---|---|---|
| 87 | 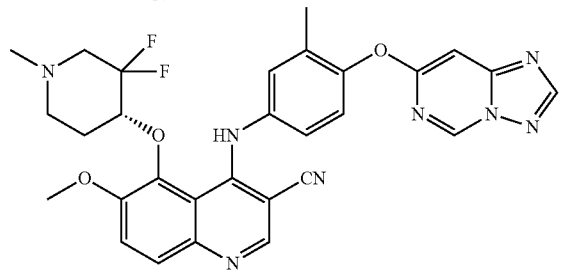 [SMILES: COc1ccc2ncc(C#N)c(Nc3ccc(Oc4cc5ncnn5cn4)c(C)c3)c2c1O[C@@H]1CCN(C)CC1(F)F] | (R)-4-((4-([1,2,4]triazolo[1,5-c]pyrimidin-7-yloxy)-3-methylphenyl)amino)-5-((3,3-difluoro-1-methylpiperidin-4-yl)oxy)-7-methoxyquinoline-3-carbonitrile | 573 (M + H)$^+$ |
| 89 | 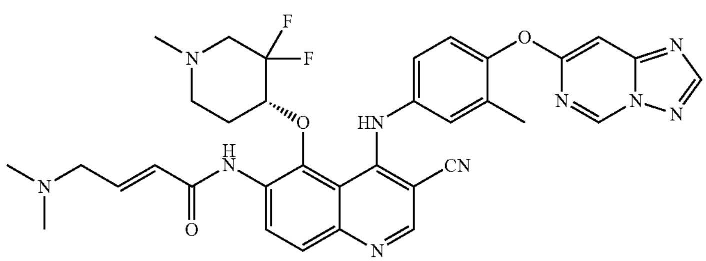 [SMILES: Cc1cc(Nc2c(C#N)cnc3ccc(NC(=O)/C=C/CN(C)C)c(O[C@@H]4CCN(C)CC4(F)F)c23)ccc1Oc1cc2ncnn2cn1] | (R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)quinolin-6-yl)-4-(dimethylamino)but-2-enamide | 669 (M + H)$^+$ |

| Ex # | Structure | Name | MS m/z |
|---|---|---|---|
| 90 | 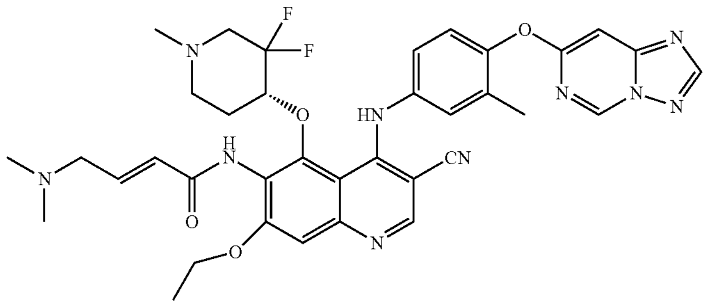 [SMILES: CCOc1cc2ncc(C#N)c(Nc3ccc(Oc4cc5ncnn5cn4)c(C)c3)c2c(O[C@@H]2CCN(C)CC2(F)F)c1NC(=O)/C=C/CN(C)C] | (R,E)-N-(4-((4-([1,2,4]triazolo[1,5-c]pyrimidin-7-yloxy)-3-methylphenyl)amino)-3-cyano-5-((3,3-difluoro-1-methylpiperidin-4-yl)oxy)-7-ethoxyquinolin-6-yl)-4-(dimethylamino)but-2-enamide | 713 (M + H)+ |
| 93 | 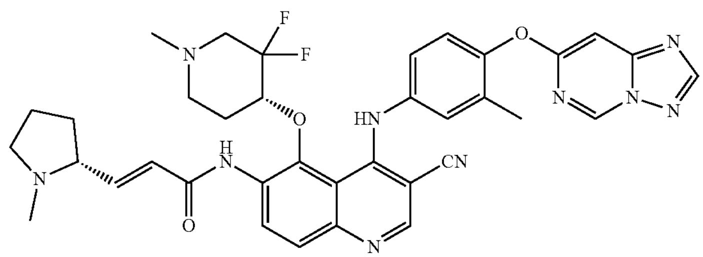 [SMILES: Cc1cc(Nc2c(C#N)cnc3ccc(NC(=O)/C=C/[C@H]4CCCN4C)c(O[C@@H]4CCN(C)CC4(F)F)c23)ccc1Oc1cc2ncnn2cn1] | (E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)quinolin-6-yl)-3-((R)-1-methylpyrrolidin-2-yl)acrylamide | 695 (M + H)+ |
| 94 | 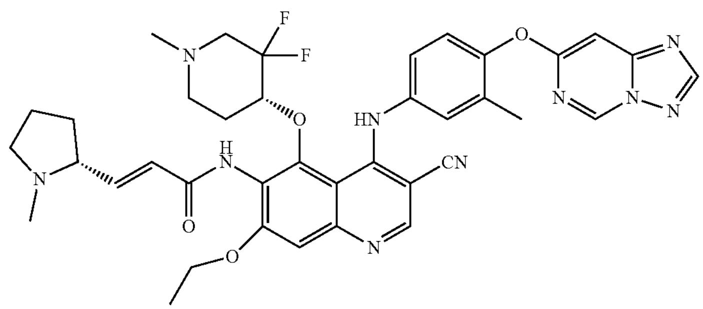 [SMILES: CCOc1cc2ncc(C#N)c(Nc3ccc(Oc4cc5ncnn5cn4)c(C)c3)c2c(O[C@@H]2CCN(C)CC2(F)F)c1NC(=O)/C=C/[C@H]1CCCN1C] | (E)-N-(4-((4-([1,2,4]triazolo[1,5-c]pyrimidin-7-yloxy)-3-methylphenyl)amino)-3-cyano-5-(((R)-3,3-difluoro-1-methylpiperidin-4-yl)oxy)-7-ethoxyquinolin-6-yl)-3-((R)-1-methylpyrrolidin-2-yl)acrylamide | 739 (M + H)+ |

Example 87

White solid. $^1$H-NMR (400 MHz, CD$_3$OD) δ 9.47 (d, J=1.1 Hz, 1H), 8.40 (d, J=11.6 Hz, 2H), 7.38 (d, J=2.3 Hz, 1H), 7.31 (dd, J=8.5, 2.5 Hz, 1H), 7.24 (d, J=8.5 Hz, 1H), 7.01-6.93 (m, 3H), 5.17-5.03 (m, 1H), 3.97 (s, 3H), 3.14 (t, J=10.5 Hz, 1H), 2.87 (d, J=12.1 Hz, 1H), 2.61 (dd, J=28.0, 11.4 Hz, 1H), 2.43 (t, J=10.2 Hz, 2H), 2.36 (s, 3H), 2.25 (s, 3H), 2.01 (d, J=11.4 Hz, 1H).

Example 92

(R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)-4-(dimethylamino)but-2-enamide

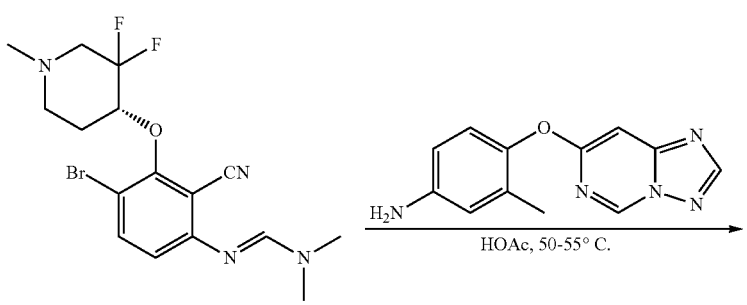

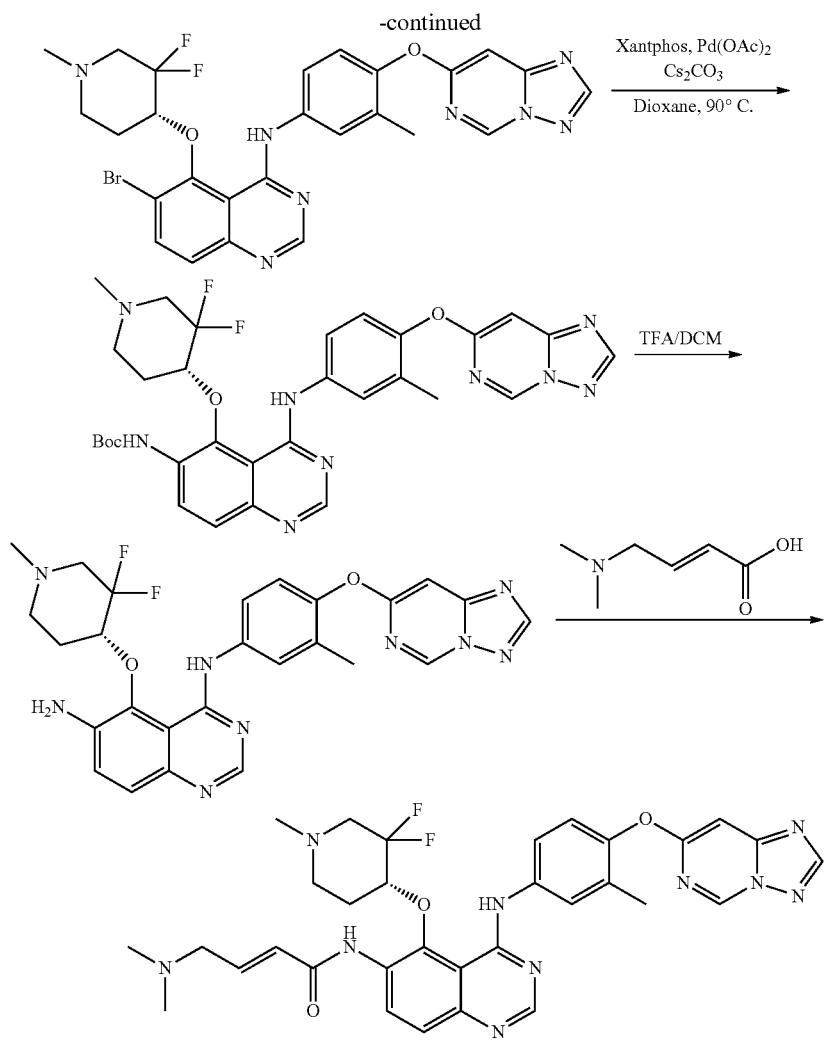

Step 1: (R)—N-(4-([1,2,4]triazolo[1,5-c]pyrimidin-7-yloxy)-3-methylphenyl)-6-bromo-5-((3,3-difluoro-1-methylpiperidin-4-yl)oxy)quinazolin-4-amine

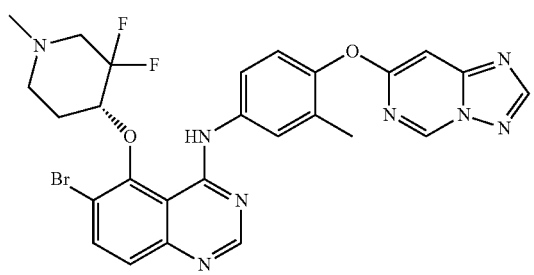 [SMILES: Cc1cc(Nc2ncnc3ccc(Br)c(O[C@@H]4CCN(C)CC4(F)F)c23)ccc1Oc1cc2ncnn2cn1]

To the solution of (R,E)-N'-(4-bromo-2-cyano-3-((3,3-difluoro-1-methylpiperidin-4-yl)oxy)phenyl)-N,N-dimethylformimidamide (5.0 g, 12.5 mmol) in AcOH (50 mL) was added 4-([1,2,4]triazolo[1,5-c]pyrimidin-7-yloxy)-3-methylaniline (4.5 g, 18.7 mmol). The mixture was heated to 50-55° C. and stirred for 3 hours. TLC showed most of the reactant consumed. The solvent was removed under reduced pressure, and the residue was dissolved in EA (100 mL). The solution was washed with NaHCO$_3$ solution (50 mL). Then the organic layer was removed under reduced pressure. The residue was purified by column chromatograph (MeOH/DCM=1/20) to give desired product (3.2 g, 43% yield). MS (ESI) m/z: 597 (M+H)$^+$.

Step 2: (R)-tert-butyl(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl)carbamate

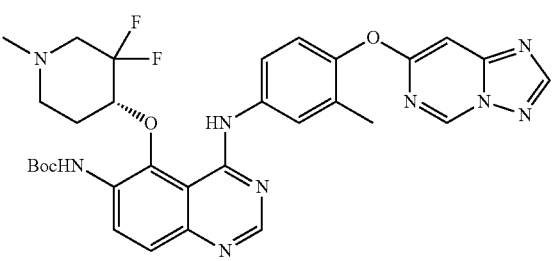 [SMILES: Cc1cc(Nc2ncnc3ccc(NC(=O)OC(C)(C)C)c(O[C@@H]4CCN(C)CC4(F)F)c23)ccc1Oc1cc2ncnn2cn1]

The mixture of (R)—N-(4-([1,2,4]triazolo[1,5-c]pyrimidin-7-yloxy)-3-methylphenyl)-6-bromo-5-((3,3-difluoro-1- methylpiperidin-4-yl)oxy)quinazolin-4-amine (3.0 g, 5.0 mmol), NH₂Boc (1.18 g, 10.0 mmol), Cs₂CO₃ (3.28 g, 10 mmol), Xantphos (1.74 g, 3.0 mmol) and Pd(OAc)₂ (0.68 g, 3.0 mmol) in dioxane (60 mL) was degassed under N₂ atmosphere for 3 times and stirred at 80-90° C. for 2 h under N₂ atmosphere. TLC showed most of the reactant consumed. The mixture was cooled down to r.t. The solid was filtrated, and the filtrate was diluted by EA (100 mL). It was washed with water (50 mL×2), dried by anhydrous Na₂SO₄. Then the solvent was removed to give crude desired product (4.3 g) as a solid. MS (ESI) m/z: 634 (M+H)⁺.

Step 3: (R)—N4-(4-([1,2,4]triazolo[1,5-c]pyrimidin-7-yloxy)-3-methylphenyl)-5-((3,3-difluoro-1-methylpiperidin-4-yl)oxy)quinazoline-4,6-diamine

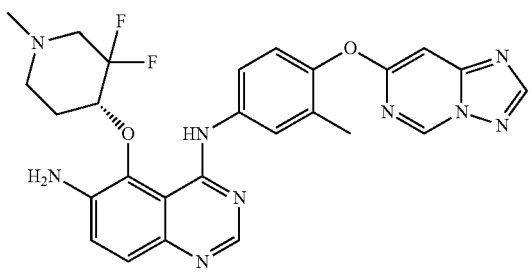 [SMILES: Cc1cc(Nc2ncnc3ccc(N)c(O[C@@H]4CCN(C)CC4(F)F)c23)ccc1Oc1cc2ncnn2cn1]

To the solution of crude (R)-tert-butyl(4-((4-([1,2,4]triazolo[1,5-c]pyrimidin-7-yloxy)-3-methylphenyl)amino)-5-((3,3-difluoro-1-methylpiperidin-4-yl)oxy)quinazolin-6-yl) carbamate (3.9 g) in DCM (100 mL) in ice-water was added TFA (25 mL). It was kept stirring at r.t. for 2-3 h. TLC showed that the reaction complete. The solvent was removed, and the residue was diluted by sat. NaHCO₃ (50 mL). It was extracted by EA (100 mL×2), and the solvent was removed. The residue was purified by column chromatograph (DCM/MeOH=50/1) to give desired product (1.0 g, 30% yield) as a yellow solid. MS (ESI) m/z: 534 (M+H)⁺.

Step 4: (R,E)-N-(4-O-([1,2,4]triazolo[1,5-c]pyrimidin-7-yloxy)-3-methylphenyl)amino)-5-((3,3-difluoro-1-methylpiperidin-4yl)oxy)quinazolin-6-yl)-4-(dimetjylamino)but-2-enamide

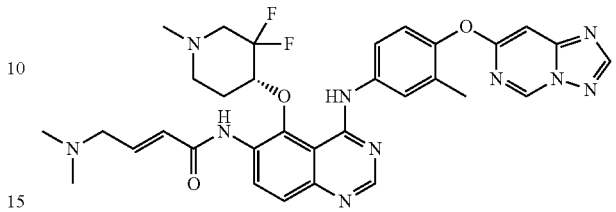

To a solution of 4-(Dimethylamino)-2-butenoic acid hydrochloride (100 mg, 0.6 mmol) in THF (3 mL) was added DMF (0.1 mL) and oxalyl chloride (76 mg, 0.5 mmol at 0° C. The mixture was stirred at 20° C. for 1.5 hr. The mixture was concentrated to give 4-(Dimethylamino)but-2-enoyl chloride (130 mg). To a solution of (R)—N4-(4-([1,2,4]triazolo[1,5-c]pyrimidin-7-yloxy)-3-methylphenyl)-5-((3,3-difluoro-1-methylpiperidin-4-yl)oxy)quinazoline-4,6-diamine (100 mg, 0.19 mmol) in THF (3 mL) were added DIPEA (129 mg, 1 mmol) and the above suspension of 4-(Dimethylamino)but-2-enoyl chloride (130 mg) in THF (3 mL) at 0° C. The mixture was stirred at 20° C. for 1 hour, then quenched with aq.NaHCO₃ (10 mL). It was extracted with EtOAc (10 mL×2), washed with water and brine, dried over anhydrous Na₂SO₄, filtered and concentrated to give crude product. The crude product was purified by silica gel column chromatography (MeOH:DCM=1:20) to give desired product (28 mg, 22% yield) as yellow solid. MS (ESI) m/z: 645 (M+H)⁺. ¹H NMR (400 MHz, DMSO-d₆) δ 10.06 (s, 1H), 9.90 (s, 1H), 9.66 (d, J=1.2 Hz, 1H), 8.58 (s, 2H), 7.90 (d, J=9.0 Hz, 1H), 7.81 (s, 1H), 7.71 (d, J=8.5 Hz, 1H), 7.61 (d, J=8.9 Hz, 1H), 7.20 (dd, J=19.5, 4.9 Hz, 2H), 6.82 (dt, J=15.4, 6.0 Hz, 1H), 6.40 (d, J=15.6 Hz, 1H), 4.46 (s, 1H), 3.11 (s, 2H), 2.89-2.64 (m, 2H), 2.25-2.14 (m, 14H), 1.98 (d, J=8.6 Hz, 2H).

The following compounds were prepared according to the above described methods using different starting materials.

| Ex # | Structure | Name | MS m/z |
|---|---|---|---|
| 91 | 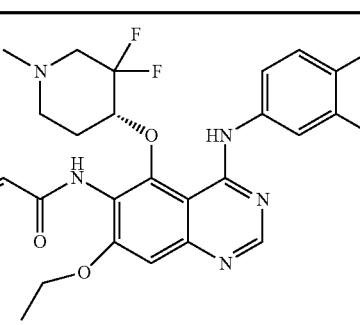 | (R,E)-N-(4-((4-([1,2,4]triazolo[1,5-c]pyrimidin-7-yloxy)-3-methylphenyl)amino)-5-((3,3-difluoro-1-methylpiperidin-4-yl)oxy)-7-ethoxyquinazolin-6-yl)-4-(dimethylamino)but-2-enamide | 689 (M + H)⁺ |

| Ex # | Structure | Name | MS m/z |
|---|---|---|---|
| 95 | 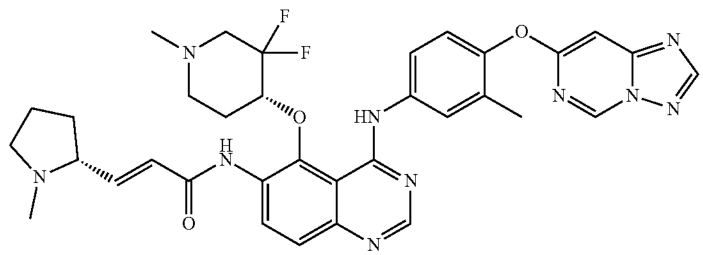 [SMILES: Cc1cc(Nc2ncnc3ccc(NC(=O)/C=C/[C@H]4CCCN4C)c(O[C@@H]4CCN(C)CC4(F)F)c23)ccc1Oc1cc2ncnn2cn1] | (E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)quinazolin-6-yl)-3-((R)-1-methylpyrrolidin-2-yl)acrylamide | 671 (M + H)+ |
| 96 | 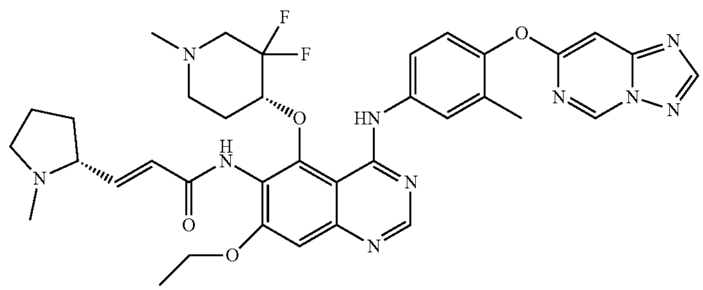 [SMILES: CCOc1cc2ncnc(Nc3ccc(Oc4cc5ncnn5cn4)c(C)c3)c2c(O[C@@H]2CCN(C)CC2(F)F)c1NC(=O)/C=C/[C@H]1CCCN1C] | (E)-N-(4-((4-([1,2,4]triazolo[1,5-c]pyrimidin-7-yloxy)-3-methylphenyl)amino)-5-(((R)-3,3-difluoro-1-methylpiperidin-4-yl)oxy)-7-ethoxyquinazolin-6-yl)-3-((R)-1-methylpyrrolidin-2-yl)acrylamide | 715 (M + H)+ |
| 97 | 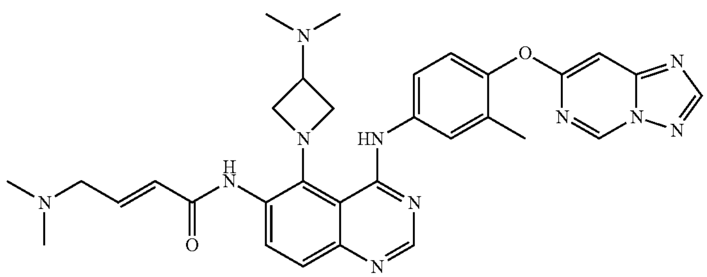 [SMILES: Cc1cc(Nc2ncnc3ccc(NC(=O)/C=C/CN(C)C)c(N4CC(N(C)C)C4)c23)ccc1Oc1cc2ncnn2cn1] | (E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-4-(dimethylamino)but-2-enamide | 594 (M + H)+ |
| 98 | 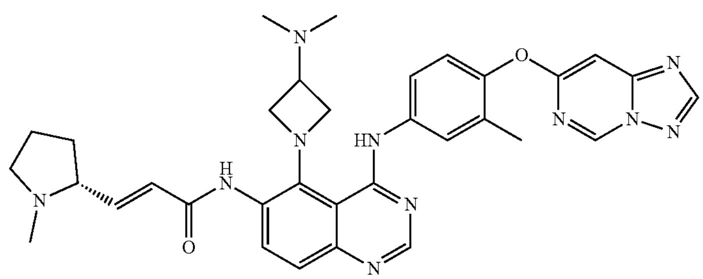 [SMILES: Cc1cc(Nc2ncnc3ccc(NC(=O)/C=C/[C@H]4CCCN4C)c(N4CC(N(C)C)C4)c23)ccc1Oc1cc2ncnn2cn1] | (R,E)-N-(4-((4-([1,2,4]triazolo[1,5-c]pyrimidin-7-yloxy)-3-methylphenyl)amino)-5-(3-(dimethylamino)azetidin-1-yl)quinazolin-6-yl)-3-(1-methylpyrrolidin-2-yl)acrylamide | 620 (M + H)+ |

Example 99

(R)—N-(4-([1,2,4]triazolo[1,5-c]pyrimidin-7-yloxy)-3-methylphenyl)-5-((3,3-difluoro-1-methylpiperidin-4-yl)oxy)-6,7-dimethoxyquinazolin-4-amine

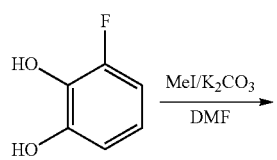

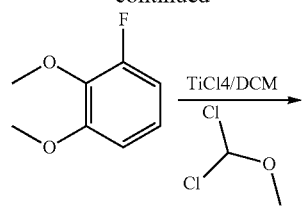

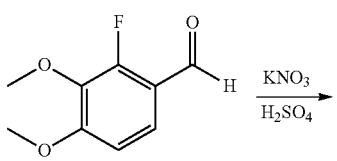

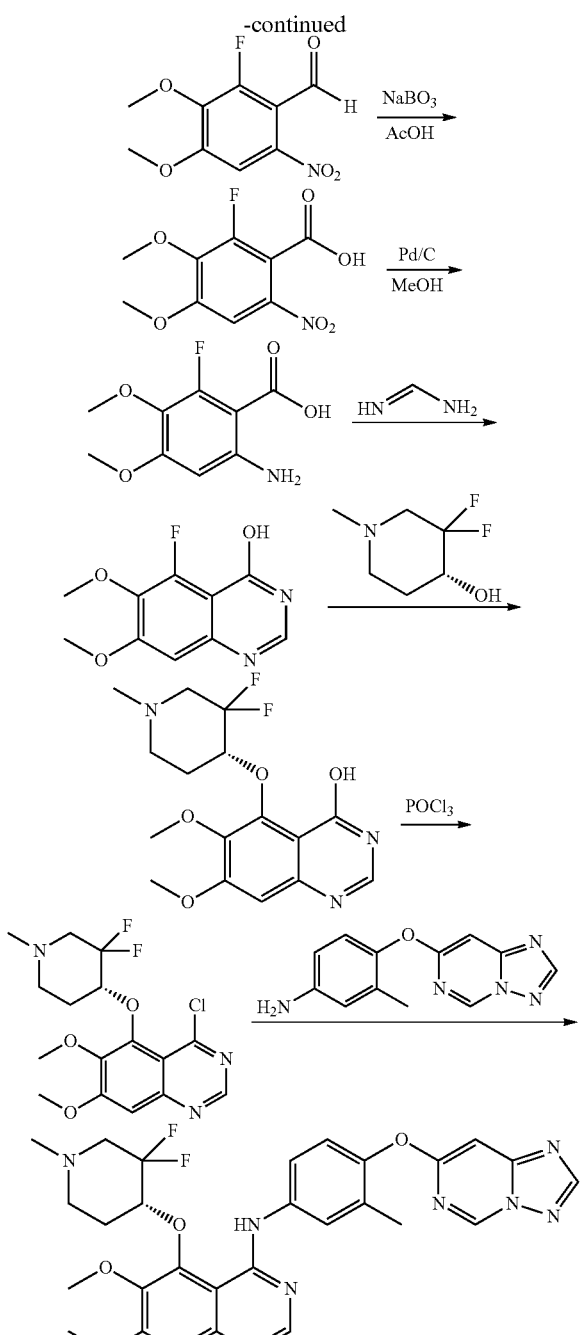

Step 1: 1-fluoro-2,3-dimethoxybenzene

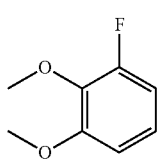

After dissolving 3-fluorobenzene-1,2-diol (20.0 g, 156.1 mmol) in DMF (200 mL), methyl iodide (55.4 g, 390.3 mmol) and potassium carbonate (54.0 g, 390.3 mmol) were added while stirring under ice batch. The mixture was stirred at r.t. for 18 hours. Then water (600 mL) was added and extraction was performed with diethyl ether (400 mL×2). Then the combined organic layers were washed with brine (400 mL) and dried with anhydrous Na$_2$SO$_4$, filtered and concentrated to dryness to give desired product (23 g, 94% yield) as a light yellow liquid.

Step 2: 2-fluoro-3,4-dimethoxybenzaldehyde

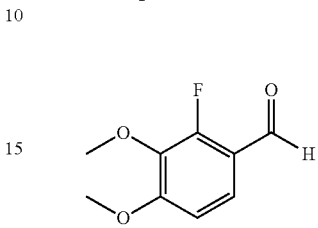

At 0° C., a solution of titanium tetrachloride (23.3 mL, 211.2 mmol) in anhydrous DCM (40 mL) was added dropwise over 30 min to a solution of 1-fluoro-2,3-dimethoxybenzene (20.0 g, 128.1 mmol) in anhydrous DCM (120 mL) under a nitrogen atmosphere. To the resulting solution was added a solution of dichloromethyl methyl ether (12.8 mL, 140.8 mmol) in anhydrous DCM (20 mL) drop wise over 15 min whereupon the reaction mixture turned red. Stirring at 0° C. was continued for 30 min before the reaction solution was allowed to warm to rt. After stirring for another 5 h the reaction mixture was poured onto 200 g of crushed ice. The organic layer was separated, and the aqueous phase was extracted with DCM. dried with anhydrous Na$_2$SO$_4$, filtered and concentrated to dryness. The residues was purified by column chromatography on silica gel (PE:EtOAc=20:1) to give desired product (16.05 g, 70% yield) as a yellow solid. MS (ESI) m/z: 185 (M+H)$^+$.

Step 3: 2-fluoro-3,4-dimethoxy-6-nitrobenzaldehyde

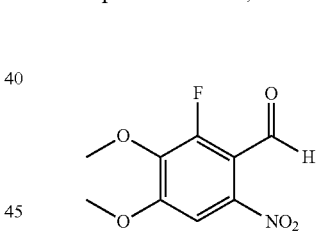

Potassium nitrate (2.8 g, 27.4 mmol) was added dropwise to 2-fluoro-3,4-dimethoxybenzaldehyde (4.2 g, 22.8 mol) in concentrated sulfuric acid (30 mL, 562.9 mmol) at 0° C. The resulting solution was stirred at rt for 18 h. The reaction mixture was poured into ice water. The precipitate was collected by filtration, washed with ice water (75 mL) and dried under vacuum to afford the title compound as a brown solid (3.2 g, 61% yield). MS (ESI) m/z: 230 (M+H)$^+$.

Step 4: 2-fluoro-3,4-dimethoxy-6-nitrobenzoic Acid

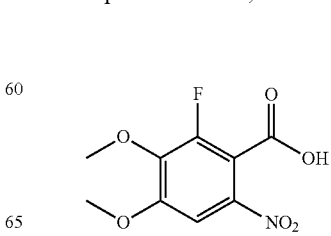

Sodium perborate (4.3 g, 27.9 mmol) was added portion wise to 2-fluoro-3,4-dimethoxy-6-nitrobenzaldehyde (3.2 g, 14.0 mmol) in acetic acid (45 mL) over a period of 2 min. The resulting mixture was stirred at 50° C. for 2 days. The reaction mixture was evaporated to dryness and the residue was dissolved in DCM (200 mL), and washed sequentially with water (200 mL×2). The aqueous layer was separated, frozen and lyophilized to afford the title compound as yellow solid (3.0 g, 85% yield).

Step 5: 6-amino-2-fluoro-3,4-dimethoxybenzoic acid

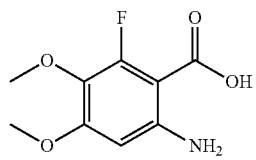 [SMILES: COc1cc([N+](=O)[O-])c(C(=O)O)c(F)c1OC]

Pd/C (0.3 g, 5% on carbon) was added to 2-fluoro-3,4-dimethoxy-6-nitrobenzoic acid (3.0 g, 12.2 mmol) in MeOH (30 mL). The reaction mixture was stirred at rt with $H_2$ (balloon, 1 atm) for 15 h. The reaction mixture was filtered and concentrated to dryness. The residue was purified by column chromatography on silica gel (DCM:MeOH=20:1) to give desired product (2.2 g, 83% yield) as a solid.

Steps 6-9: (R)—N-(4-([1,2,4]triazolo[1,5-c]pyrimidin-7-yloxy)-3-methylphenyl)-5-((3,3-difluoro-1-methylpiperidin-4-yl)oxy)-6,7-dimethoxyquinazolin-4-amine

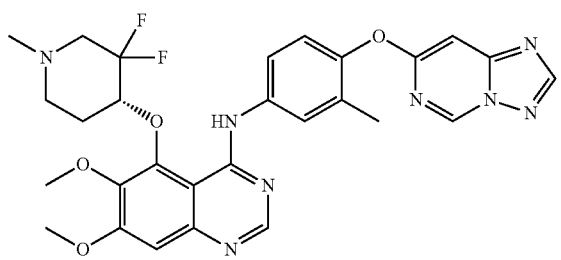 [SMILES: COc1cc2ncnc(Nc3ccc(Oc4cc5ncnn5cn4)c(C)c3)c2c(O[C@@H]2CCN(C)CC2(F)F)c1OC]

The crude product was prepared in a similar fashion to Examples 31 and 32, which was purified by column chromatography (DCM/MeOH=30/1) to give desired product (80 mg, 74% yield) as white solid. MS (ESI) m/z: 579 (M+H)$^+$.

$^1$H NMR (400 MHz, CDCl$_3$) δ 10.31 (s, 1H), 9.19 (d, J=1.2 Hz, 1H), 8.59 (s, 1H), 8.33 (s, 1H), 7.74 (d, J=12.9 Hz, 1H), 7.70-7.57 (m, 2H), 7.13 (d, J=8.7 Hz, 1H), 6.92 (d, J=1.2 Hz, 1H), 5.07-4.87 (m, 1H), 4.09 (s, 3H), 3.94 (s, 3H), 3.22 (d, J=2.3 Hz, 2H), 2.94 (d, J=11.2 Hz, 2H), 2.36 (s, 3H), 2.26 (s, 3H), 2.16 (s, 2H).

Example 100

Biological Assays

Assay a) BT474 Cellular Assay (HER2 Inhibition)

Inhibition of phosphor HER2 was determined by enzyme-linked immunosorbent assay (ELISA) in BT474 cells. BT474 cell line was purchased from ATCC (catalog number HTB-20). Human Phospho-ErbB2 ELISA kit was purchased from R&D systems (catalog number DYC1768).

Day 1:

When the cells reach 70-90% confluence, cells were trypsinized and re-suspended. 5000 cells per well were seeded to a 384-well plate. The plate was incubated at 37° C. with 5% CO$_2$ for 24 hours. ELISA plate was coated with 2 µg/ml capture antibody, which was incubated at 4° C. overnight.

Day 2:

25 nl compounds was dosed by Echo from source plate and the 384-well plate was incubated at 37° C. for 2 hours. 30 µl lysis buffer was added to each well and the 384-well plate was shaken softly at 4° C. for 30 minutes. The ELISA plate was washed, blocked and incubated at room temperature for 1-2 hours. The blocked ELISA plate was washed and 20 µl cell lysate was transferred from the 384-well plate to the ELISA plate, which was incubated overnight at 4° C.

Day 3:

The ELISA plate was washed 3 times. 25 µl/well detection antibody was added (diluted 1 by 2000 in 1% BSA in PBS). After 2 hours of incubation with detection antibody, the ELISA plate was washed 3 times, 25 µl/well TMB substrate was added and incubated for 10-15 minutes before stop solution was added. Absorbance at 450 nm and 570 nm was read within 30 minutes after adding the stop solution.

The compounds synthesized in Examples 1-68 are tested in BT474 cellular assay as described above. The IC$_{50}$ results are provided in Table 1 for some exemplary compounds. For the other Example compounds for which the results are not shown, all have an IC$_{50}$ result of no more than 1000 nM. Some have an IC$_{50}$ result no more than 300 nM, some no more than 200 nM, or no more than 100 nM, or even no more than 50 nM.

Assay b) NCI H838 Cellular Assay (Wt-EGFR Inhibition)

Inhibition of phosphor wt-EGFR was determined by enzyme-linked immunosorbent assay (ELISA) in NCI H838 cells (ATCC, catalog number CRL-5844). Human Phospho-EGFR DuoSet IC ELISA kit was purchased from R&D systems (catalog number DYC1095).

Day 1:

When the cells reach 70-90% confluence, cells were trypsinized and re-suspended. 5000 cells per well were seeded to a 384-well plate. The plate was incubated at 37° C. with 5% CO$_2$ for 24 hours.

Day 2:

Cell culture medium was replaced with 40 µL FBS-Free RPMI1640. After 2 hours of starvation, the 384-well plate was dosed with 40 nL of compounds by Echo from source plate and the 384-well plate was incubated at 37° C. with 5% CO$_2$ for 2 hours. After 2 hours of incubation with compounds, EGF (final concentration at 100 ng/ml) was added to the plate which was incubated at 37° C. with 5% CO$_2$ for 5-10 minutes. Medium was discarded from the plate and 30 µl/well lysis buffer was added to the plate which was incubated at 4° C. for 10 minutes. The cell lysates can be stored at −80° C. in cell plates but must be thawed at room temperature for at least 30 minutes prior to use and continuing the assay. ELISA plate was coated by diluting capture antibody to 4 µg/ml with PBS, and 25 µl/well was dispensed to 384 well UltraCruz® ELISA Plate, which was incubated at 4° C. overnight.

Day 3:

After the plates were washed three times with 100 µl/well of wash buffer, the plates were blocked by adding 75 µl of Block Buffer to each well and incubated at room temperature for 3 hours. After the plates were washed three times with 100 µl/well of wash buffer, 20 µl cell lysate was transferred to the blocked ELISA plate which was incubated for 2 hours at room temperature. After the plates were washed three times with 100 µl/well of wash buffer, 25 µl/well detection antibody (dilute 1 in 900 in assay buffer) was added the plate which was incubated for 2 hours, protected from light. After washed three times, 25 µl/well TMB substrate was added to the ELISA plate which was incubated for about 10-15 min, protected from light before addition of 25 µl/well stop solution. Absorbance was read at 450 nm and 570 nm within 30 minutes.

Results of exemplary compounds of the present disclosure in assays a) and b) are shown in Table 1. From Table 1, it can be found that the compounds of the present disclosure not only have good inhibition of HER2, they are also very selective for HER2 over wt-EGFR. For the other Example compounds for which the results are not shown, all have an $IC_{50}$ against HER2 of no more than 1000 nM. Some of these compounds have an $IC_{50}$ against HER2 of no more than 500 nM, some no more than 400 nM, some no more than 300 nM, some no more than 200 nM, or no more than 100 nM, or no more than 50 nM, or no more than 40 nM, or no more than 30 nM, or no more than 20 nM, or no more than 10 nM, or even no more than 5 nM. In addition, some of the Example compounds for which the results are not shown show $IC_{50}$ against wt-EGFR of more than 0.5 µM, more than 1 µM, some more than 2 µM, more than 3 µM, more than 4 µM, more than 6 µM, more than 8 µM, or even more than 10 µM.

TABLE 1

HER2 and wt-EGFR inhibition data for exemplary compounds in assays a)-b)

| Example | BT474 $IC_{50}$(nM) | H838 $IC_{50}$ (µM) |
|---|---|---|
| 1 | 9.2 | 2.8 |
| 2 | 27 | N/A |
| 3 | 31 | 0.33 |
| 4 | 105 | >10 |
| 5 | 82 | N/A |
| 11 | 13 | 6.7 |
| 12 | 26 | 0.18 |
| 17 | 35 | N/A |
| 18 | 48 | N/A |
| 21 | 15 | N/A |
| 22 | 21 | N/A |
| 29 | 9.3 | N/A |
| 30 | 20 | N/A |
| 31 | 9.5 | 12 |
| 32 | 16 | 4.8 |
| 33 | 8 | 0.40 |
| 34 | 18 | 6.3 |
| 35 | 16 | 1.28 |
| 36 | 11 | 0.44 |
| 37 | 12 | >10 |
| 38 | 37 | >10 |
| 39 | 94 | >10 |
| 40 | 63 | >10 |
| 41 | 35 | 2.26 |
| 42 | 58 | >10 |
| 43 | 24 | 2.03 |
| 44 | 5 | 0.234 |
| 45 | 2.5 | 6.6 |
| 46 | 7.3 | 0.215 |
| 47 | 4.1 | 4.54 |
| 48 | 6.7 | 0.364 |
| 51 | 176 | 0.183 |
| 52 | 182 | 0.80 |
| 54 | 190 | >10 |
| 55 | 912 | >10 |
| 67 | 17 | N/A |

TABLE 1-continued

HER2 and wt-EGFR inhibition data for exemplary compounds in assays a)-b)

| Example | BT474 $IC_{50}$(nM) | H838 $IC_{50}$ (µM) |
|---|---|---|
| 68 | 6.4 | N/A |
| 72 | 51 | N/A |
| 73 | 145 | N/A |
| 74 | 9.9 | N/A |
| 75 | 13 | N/A |
| 76 | 11 | N/A |
| 77 | 14 | N/A |
| 78 | 11 | N/A |
| 79 | 9.8 | N/A |
| 80 | 390 | N/A |
| 81 | 225 | N/A |
| 82 | 179 | N/A |
| 84 | 207 | N/A |
| 86 | 208 | N/A |
| 92 | 267 | N/A |
| 95 | 48 | N/A |
| 99 | 170 | N/A |

Example 101

DMPK and hERG Inhibition Studies

DMPK and hERG inhibition studies were carried out with the compounds of the present disclosure as well as Reference compound 1 (2-chloro-$N^4$-(5-((1-methylpiperidin-4-yl)oxy)quinazolin-4-yl)-$N^1$-(pyridin-2-ylmethyl)benzene-1,4-diamine), Reference compound 2 (Neratinib) and Reference compound 3 (ARRY-380, N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine) using the following assays: c): MDCK-MDR1 Pgp assessment, d) Caco-2 BCRP assessment, e) mouse SOA study for brain penetration (Brain Kp) and f) hERG inhibition assessment.

Assay c): MDCK-MDR1 Pgp Assessment

Efflux transport mediated by P-glycoprotein (Pgp) was assessed by MDCK-MDR1 cells. The final concentrations of test compounds and control compound were at 1 µM. The multi-well insert plate was incubated at 37° C. for 2 hours.

Assay d): Caco-2 BCRP Assessment

Caco-2 cells were used to study efflux transport mediated by BCRP. Rate of drug transport by BCRP was determined in the presence and absence of novobiocin, a strong inhibitor of BCRP, which was added to both apical and basolateral compartment sat a final concentration of 30 µM. The final concentrations of test compounds and control compound were at 1 µM. The multi-well insert plate was incubated at 37° C. for 2 hours. Efflux ratio (−inhibitor/+inhibitor)>2 was considered to be a BCRP substrate.

Assay e) Mouse SOA Study for Brain Penetration

Six non-fasted male balb/c mice (6-8 weeks, 20-25 g) were orally administered at 10 mg/kg, using a suspension formulation of 1% methylcellulose (MC) in deionized water. Brain and blood samples were collected at 0.25, 0.5, 1, 2, 4, 7 hours after dose. Plasma was obtained by centrifuging the blood samples for 5 min at 4000 g and 4° C. Brain tissue was homogenized following addition of four times the volume of phosphate-buffered saline (pH 7.4). Quantification of the compound in plasma and brain was undertaken by LC-MS/MS. Area under the curve (AUC) was determined from 0 to 7 hours in the brain tissue and plasma.

Total brain to plasma concentration ratio $K_p$ was determined using the equation:

Brain $K_p$=AUC0-7 hr brain/AUC0-7 hr plasma

Unbound brain to plasma ratio was determined using the equation:

Brain $K_{p,uu}=K_p*fu,brain/fu,plasma$

Unbound fraction (fu, plasma) and unbound fraction (fu, brain) were obtained from in vitro equilibrium dialysis by using plasma and brain homogenate, respectively.

Assay f): hERG Inhibition

Inhibition of hERG channel was conducted in HEK 293 cell line stably expressing hERG channel by manual patch clamp.

The compounds synthesized in Examples 1-99 are tested in the above assays c)-f) for DMPK and hERG inhibition studies. Results of exemplary compounds of Examples 17, 31 and 45 and Reference compounds 1-3 in assay a), b), c) and d) are shown in Table 3.

TABLE 3

Results of exemplary compounds of Examples 31, 33 and 36 and Reference compounds 1-3 in assay a)-d)

| | Reference Comp. 1 | Reference Comp. 2 | Reference Comp. 3 | Example 31 | Example 33 | Example 36 |
|---|---|---|---|---|---|---|
| PgpER | 0.57 | >18.6 | 23.8 | 1.3 | 0.6 | 0.81 |
| BCRP ER | 1.1 | 1.4 | 2.1 | 0.68 | 1.3 | 1.8 |
| Mouse $K_{pu,u}$ | Not determined | Too low to calculate | Too low to calculate | 0.26 | 0.24 | 0.19 |
| hERG(IC$_{50}$) | <2 µM | >10 µM | >10 µM | 18 µM | 13.3 µM | >10 µM |

From Table 3, it is shown that Reference compound 1 is a strong hERG inhibitor with IC$_{50}$<2 µM. In contrast, compounds of Examples 31, 33 and 36 do not show hERG liability. Furthermore, Reference compounds 2 and 3 are strong Pgp substrates and not brain penetrable in vivo with $K_{pu,u}$ that are too low to calculate. In contrast, compounds of Examples 31, 33 and 36 are not Pgp or BCRP substrates, and are further confirmed to be brain penetrable in mouse SOA study.

For the other Example compounds for which the results are not shown, all are expected to be capable of brain penetration, are not not Pgp or BCRP substrates and are not hERG inhibitor. For some of the Example compounds, the results for PgpER, BCRP ER, Mouse $K_{pu,u}$ and hERG are comparable or even slightly better than those of the exemplary compounds of Examples 31, 33 and 36.

The foregoing description is considered as illustrative only of the principles of the present disclosure. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise", "comprising", "include", "including", and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula (I):

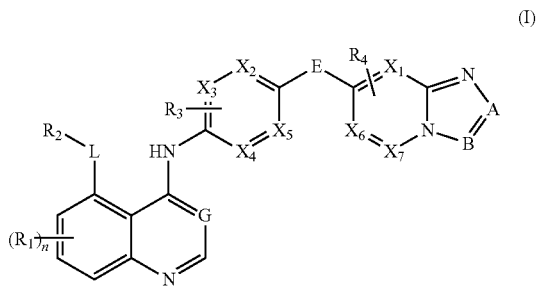

(I)

or a pharmaceutically acceptable salt thereof, wherein:
G is C(R$_5$) or N;
A is CH or N;
B is CH or N;
X$_1$, X$_2$, X$_3$, X$_4$, X$_5$, X$_6$, and X$_7$ are each independently CH or N, with the provision that X$_6$ is N and X$_7$ is CH, or Xe is CH and X$_7$ is N;
E is O, NH, or S;
L is selected from the group consisting of O, S and N(R$_6$);
R$_1$ is each independently selected from the group consisting of hydrogen, halogen, cyano, nitro, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, N(R$_7$)(R$_8$), and O(R$_9$), wherein said cycloalkyl and heterocyclyl are optionally substituted with one or more groups independently selected from the group consisting of halogen, cyano, nitro, hydroxyl, carboxy, carbamoyl, acyl, alkyl, alkenyl, alkynyl, and haloalkyl;
R$_2$ is selected from the group consisting of alkyl, saturated or partially unsaturated cycloalkyl, saturated or partially unsaturated heterocyclyl, wherein said alkyl, cycloalkyl, and heterocyclyl are optionally substituted with one or more groups independently selected from the group consisting of halogen, cyano, nitro, hydroxyl, carboxy, carbamoyl, alkyl, alkenyl, alkynyl, haloalkyl, saturated or partially unsaturated cycloalkyl, and N(R$_{10}$)(R$_{11}$);
R$_6$ is hydrogen or alkyl; or
when L is N(R$_6$), R$_2$ and R$_5$ together with the nitrogen atom to which they are attached form a 3 to 10 membered saturated or partially unsaturated heterocyclyl ring optionally containing one or more additional heteroatoms selected from N, O and S, wherein said 3 to 10 membered heterocyclyl ring is optionally substituted with one or more groups independently selected from the group consisting of halogen, cyano, nitro, carboxy, carbamoyl, alkyl, alkenyl, alkynyl, haloalkyl, saturated and partially unsaturated cycloalkyl, and N(R$_{10}$)(R$_{11}$);

R$_3$ and R$_4$ are each independently selected from the group consisting of hydrogen, halogen, cyano, nitro, alkyl, alkenyl, alkynyl and alkoxyl;

R$_5$ is selected from the group consisting of hydrogen, halogen and cyano;

R$_7$ and R$_8$ are each independently selected from the group consisting of hydrogen, alkyl, alkenyl, alkynyl, heteroalkyl, heteroalkenyl, heteroalkynyl, acyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, acyl, cycloalkyl, heterocyclyl, cycloalkylalkyl, aryl, arylalkyl, heteroaryl, heteroarylalkyl, and heterocyclylalkyl are optionally substituted with one or more groups independently selected from the group consisting of alkyl, alkenyl, alkynyl, heteroalkyl, heteroalkenyl, heteroalkynyl, alkylamino, saturated and partially unsaturated cycloalkyl, saturated and partially unsaturated heterocyclyl optionally substituted by alkyl, aryl, and heteroaryl; or R$_7$ and R$_8$ together with the atom to which they are attached form a 3 to 10 membered saturated or partially unsaturated heterocyclyl ring optionally containing one or more additional heteroatoms selected from N, O, S, SO, SO$_2$ and NR$_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

R$_9$ is selected from the group consisting of alkyl, alkenyl, alkynyl, acyl, saturated or partially unsaturated cycloalkyl, saturated or partially unsaturated heterocyclyl, wherein said alkyl, alkenyl, alkynyl, acyl, cycloalkyl, heterocyclyl are optionally substituted by one or more groups independently selected from the group consisting of halogen, alkyl, alkenyl, alkynyl, alkoxyl, acyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

R$_{10}$ and R$_{11}$ are each independently selected from the group consisting of hydrogen, alkyl, alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl, arylalkyl, heteroaryl, heteroarylalkyl, or heterocyclylalkyl, wherein said alkyl, alkenyl, alkynyl, cycloalkyl, heterocyclyl, cycloalkylalkyl, aryl, arylalkyl, heteroaryl, heteroarylalkyl, and heterocyclylalkyl are optionally substituted with one or more groups independently selected from alkyl, alkenyl, alkynyl, heteroalkyl, heteroalkenyl, heteroalkynyl, saturated and partially unsaturated cycloalkyl, saturated and partially unsaturated heterocyclyl, aryl, and heteroaryl; or R$_{10}$ and R$_{11}$ together with the atom to which they are attached form a 3 to 10 membered saturated or partially unsaturated heterocyclyl ring optionally containing one or more additional heteroatoms selected from N, O, S, SO, SO$_2$ and NR$_{12}$, wherein said heterocyclyl ring is optionally substituted with one or more groups independently selected from the group consisting of oxo, halogen, alkyl, alkenyl, alkynyl, saturated and partially unsaturated cycloalkyl, saturated and partially unsaturated heterocyclyl, cycloalkylalkyl, cyano, nitro, haloalkyl, haloalkoxy, azido, aryl, heteroaryl, arylalkyl, heteroarylalkyl, and heterocyclylalkyl;

R$_{12}$ is selected from the group consisting of hydrogen, alkyl, saturated or partially unsaturated cycloalkyl, saturated or partially unsaturated heterocyclyl, aryl, arylalkyl, heteroaryl, heteroarylalkyl, or heterocyclylalkyl, wherein said alkyl, cycloalkyl, heterocyclyl, aryl, arylalkyl, heteroaryl, heteroarylalkyl, and heterocyclylalkyl are optionally substituted with one or more groups independently selected from halogen, alkyl, alkenyl, alkynyl, saturated and partially unsaturated cycloalkyl, saturated and partially unsaturated heterocyclyl, cycloalkylalkyl, cyano, nitro, aryl, heteroaryl, arylalkyl, heteroarylalkyl, and heterocyclylalkyl;

n is 0, 1 or 2.

2. The compound or a pharmaceutically acceptable salt thereof, as claimed in claim 1, wherein the compound has a formula of:

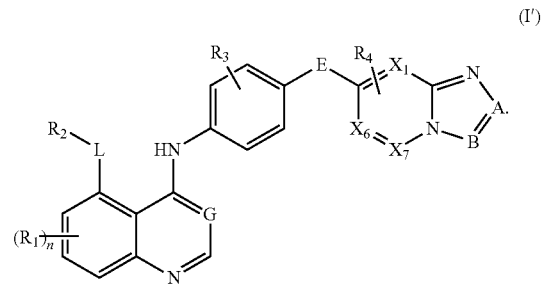

(I')

3. The compound or a pharmaceutically acceptable salt thereof, as claimed in claim 1, wherein X$_1$ is CH.

4. The compound or a pharmaceutically acceptable salt thereof, as claimed in claim 1, wherein one or two of X$_2$, X$_3$, X$_4$, and X$_5$ is N.

5. The compound or a pharmaceutically acceptable salt thereof, as claimed in claim 1, wherein G is N, optionally, A is CH and B is N, optionally, E is O.

6. The compound or a pharmaceutically acceptable salt thereof, as claimed in claim 1, wherein R$_1$ is selected from hydrogen, N(R$_7$)(R$_8$), O(R$_9$), or saturated or partially unsaturated hetercyclyl optionally substituted by acyl.

7. The compound or a pharmaceutically acceptable salt thereof, as claimed in claim 1, wherein L is N(R$_5$), and R$_2$ and R$_6$ together with the nitrogen atom to which they are attached form a 3 to 10 membered saturated or partially unsaturated heterocyclyl ring optionally containing one or more additional heteroatoms selected from N, O and S, wherein said heterocyclyl ring is optionally substituted with one or more groups independently selected from the group consisting of halogen, alkyl, haloalkyl, saturated and partially unsaturated cycloalkyl, and N(R$_{10}$)(R$_{11}$).

8. The compound or a pharmaceutically acceptable salt thereof, as claimed in claim 7, wherein R$_2$ and R$_6$ together with the nitrogen atom to which they are attached form:

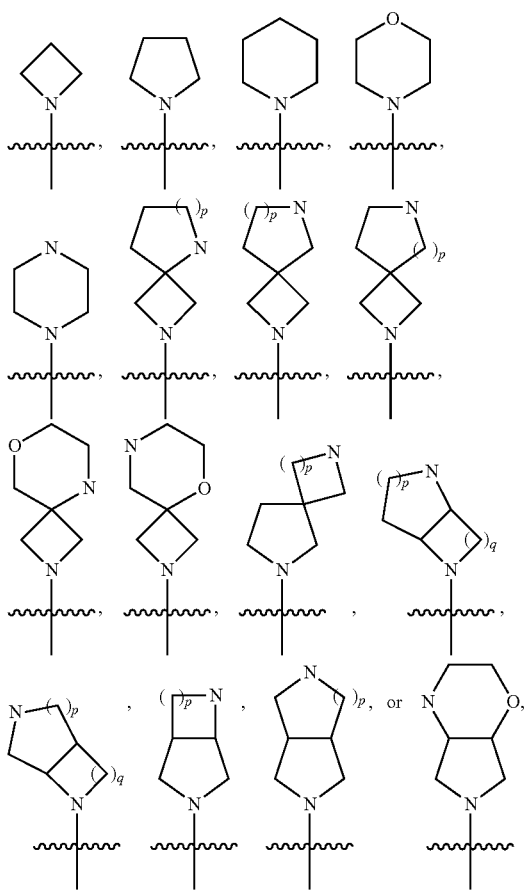

each of which is optionally substituted with one or more groups independently selected from the group consisting of halogen, alkyl, haloalkyl, saturated and partially unsaturated cycloalkyl, $N(R_{10})(R_{11})$, wherein p is 1, 2 or 3, and q is 1, 2 or 3.

9. The compound or a pharmaceutically acceptable salt thereof, as claimed in claim 1, wherein L is O, and $R_2$ is selected from saturated or partially unsaturated cycloalkyl and saturated or partially unsaturated heterocyclyl, wherein said cycloalkyl and heterocyclyl are optionally substituted with one or more groups independently selected from the group consisting of halogen, alkyl, and $N(R_{10})(R_{11})$.

10. The compound or a pharmaceutically acceptable salt thereof, as claimed in claim 1, wherein $R_3$ is selected from halogen or alkyl.

11. The compound or a pharmaceutically acceptable salt thereof, as claimed in claim 1, wherein $R_4$ is hydrogen.

12. The compound or a pharmaceutically acceptable salt thereof, as claimed in claim 1, wherein:
G is N;
A is CH;
B is N;
$X_1$ is CH;
$X_6$ is N;
$X_7$ is CH;
E is O;
L is selected from O or $N(R_6)$;
$R_1$ is $O(R_9)$, $N(R_7)(R_8)$, or partially unsaturated heterocyclyl optionally substituted by acyl;
$R_2$ is selected from $C_{4-6}$ saturated cycloalkyl or 5 to 6 membered saturated heterocyclyl, wherein said $C_{4-6}$ saturated cycloalkyl and 5 to 6 membered saturated heterocyclyl are optionally substituted with one or more groups independently selected from the group consisting of halogen, alkyl, and $N(R_{10})(R_{11})$, or;
$R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$;
$R_3$ is selected from halogen or alkyl;
$R_4$ and $R_5$ are hydrogen;
$R_7$ and $R_8$ are each independently selected from hydrogen, acyl, or saturated or partially unsaturated heterocyclyl, wherein said acyl and heterocyclyl are optionally substituted with one or more groups selected from alkyl, alkylamino, saturated and partially unsaturated heterocyclyl;
$R_9$ is selected from the group consisting of alkyl, acyl, $C_{3-7}$ saturated or partially unsaturated cycloalkyl, and 4 to 6 membered saturated or partially unsaturated heterocyclyl, wherein said alkyl, acyl, cycloalkyl, and heterocyclyl are optionally substituted by one or more groups independently selected from halogen, alkyl, acyl, and alkoxyl;
$R_{10}$ and $R_{11}$ are alkyl; and
n is 1.

13. The compound or a pharmaceutically acceptable salt thereof, as claimed in claim 1, wherein the compound has a formula selected from the group consisting of:

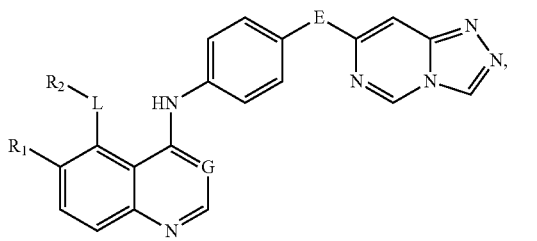

(IVa)

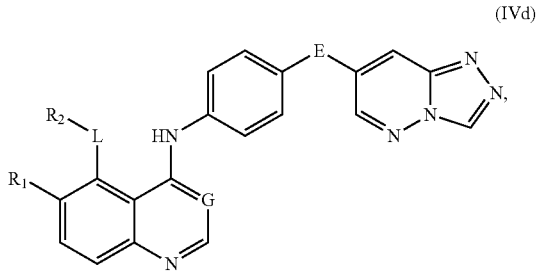

(IVd)

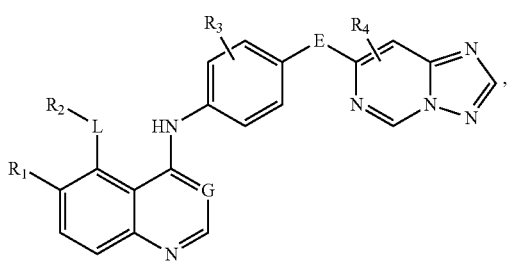

(IVb)

(IVe)
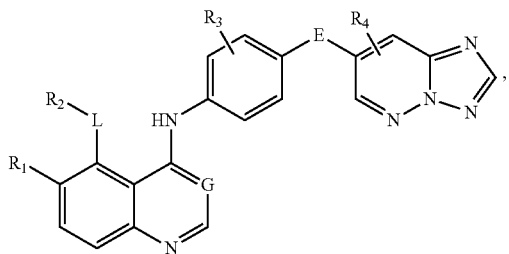
(IVc)
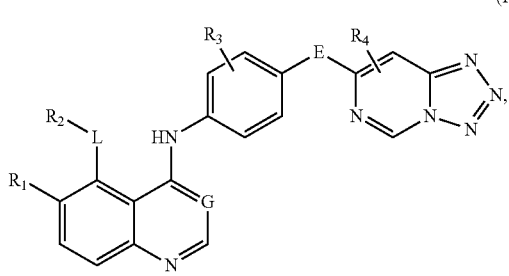
(IVf)
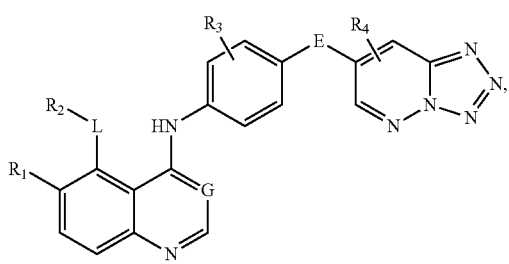
(Va)
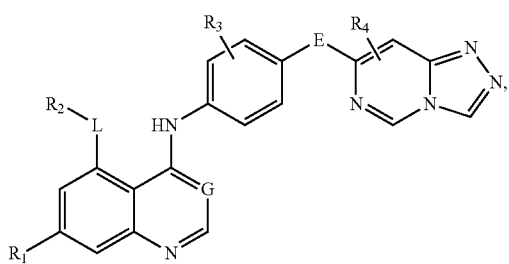
(Vd)
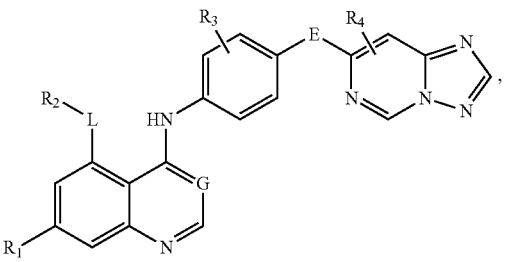
(Vb)
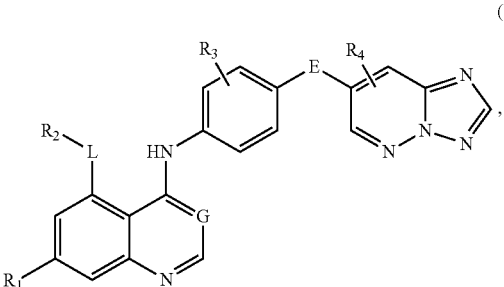
(Ve)
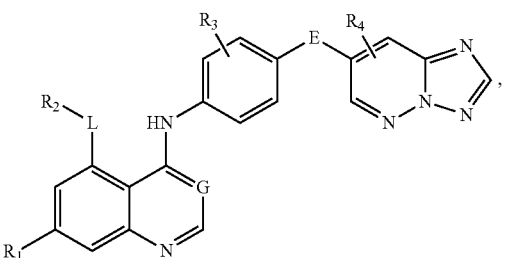
(Vc)
and
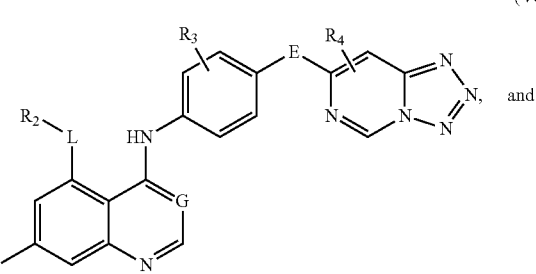
(Vf)
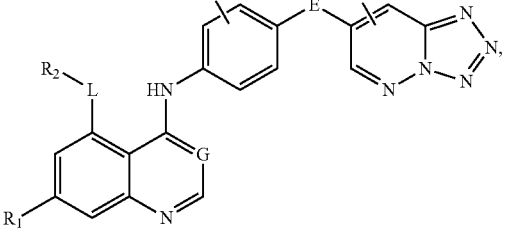
14. The compound as claimed in claim 1, selected from the group consisting of:
1
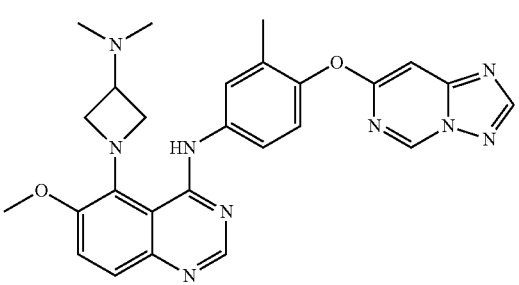

-continued
2
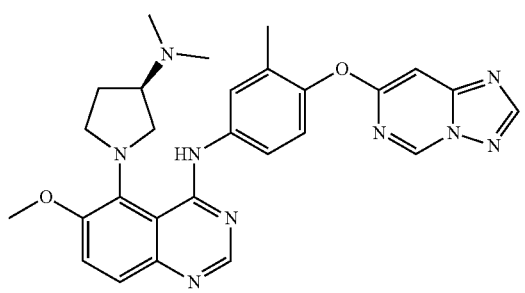
3
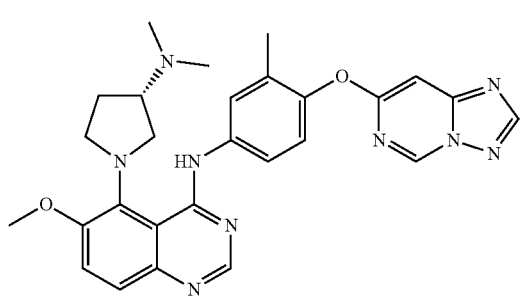
4
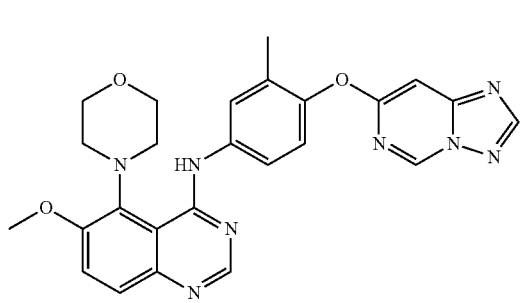
5
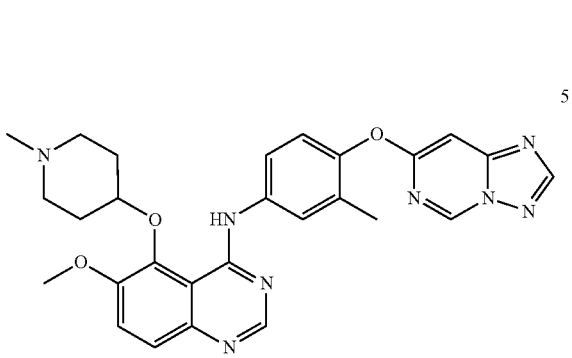
6
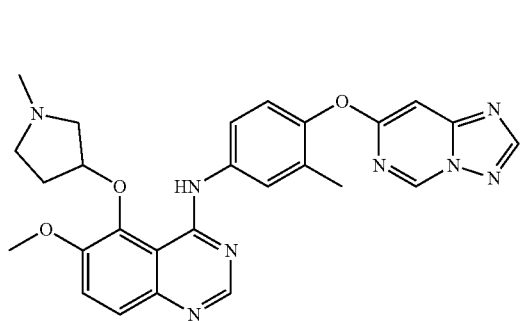
-continued
7
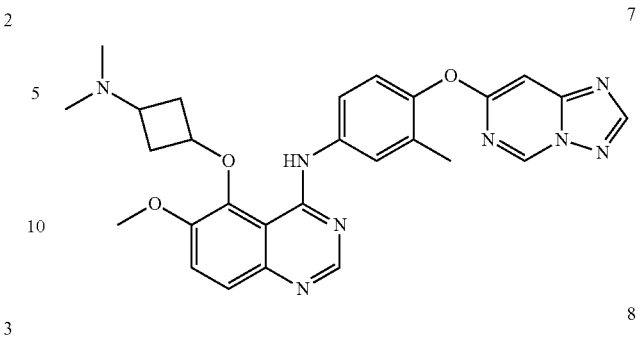
8
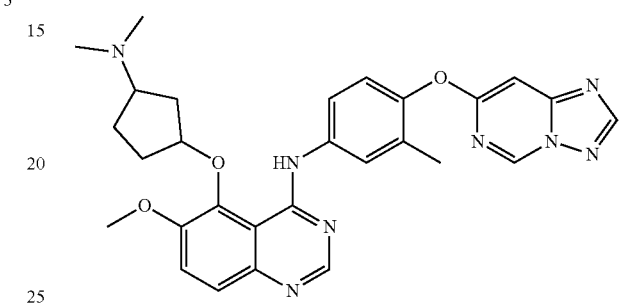
9
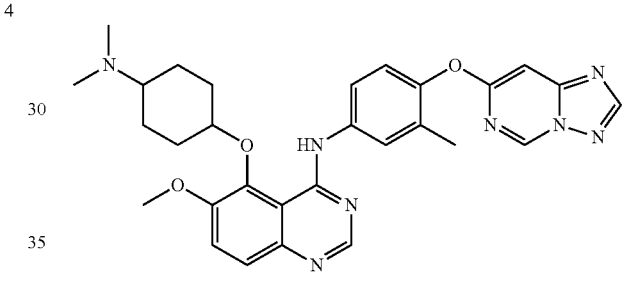
10
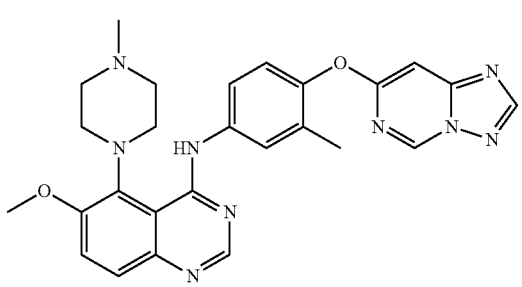
11
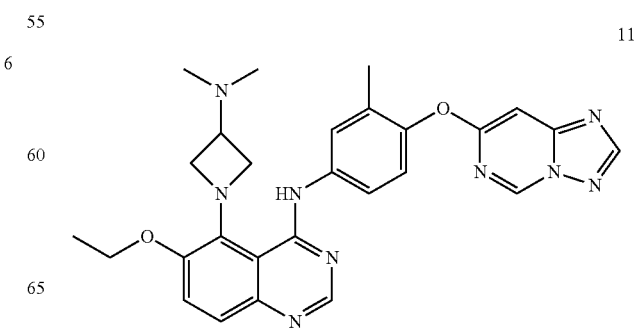

-continued
12
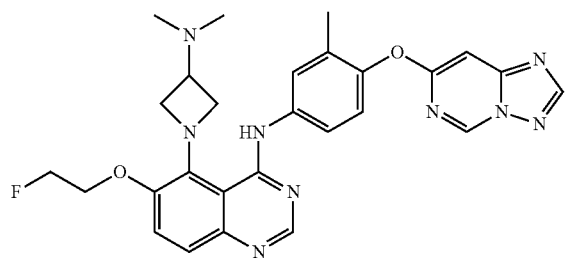
13
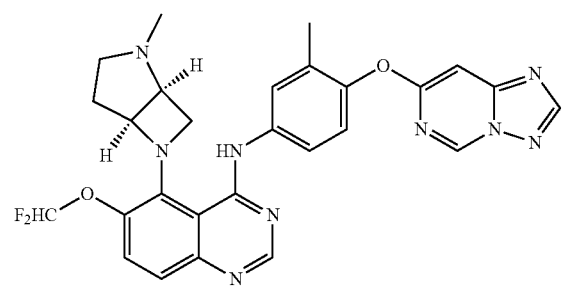
14
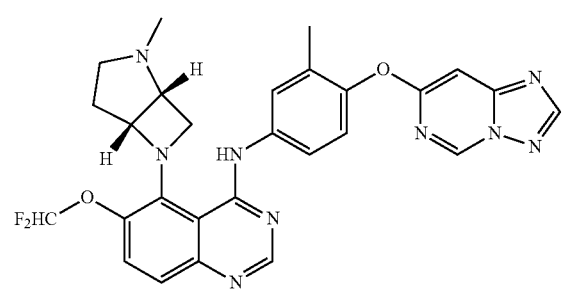
15
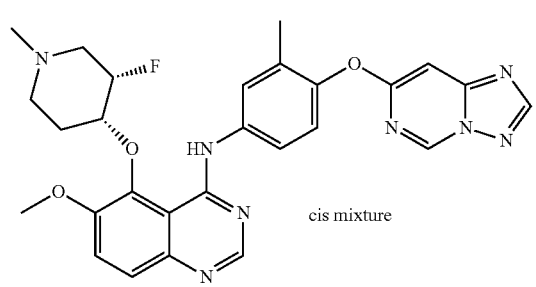
cis mixture
16
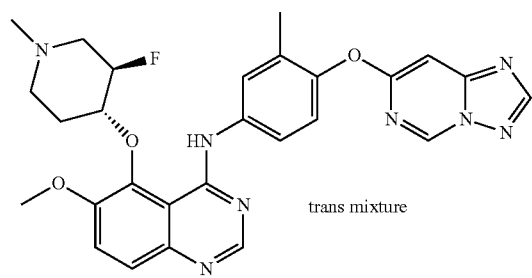
trans mixture
-continued
17
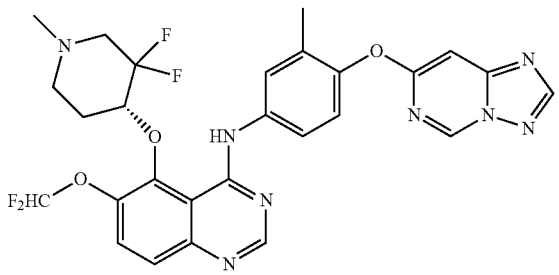
18
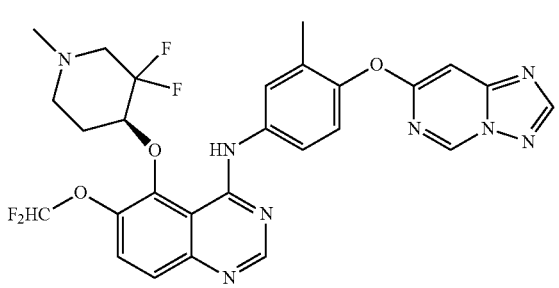
19
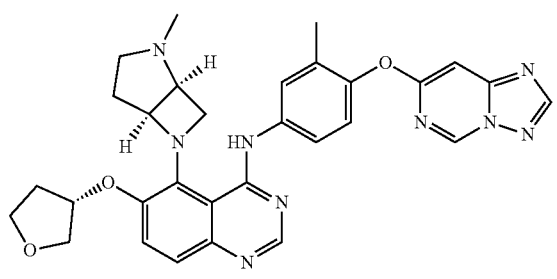
20
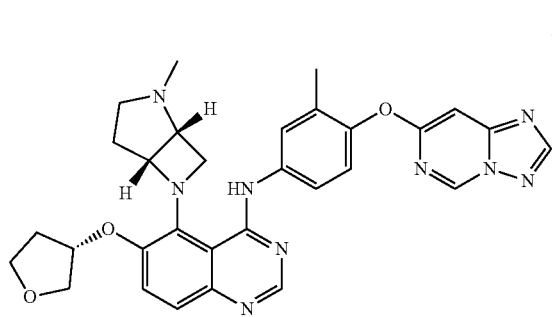
21
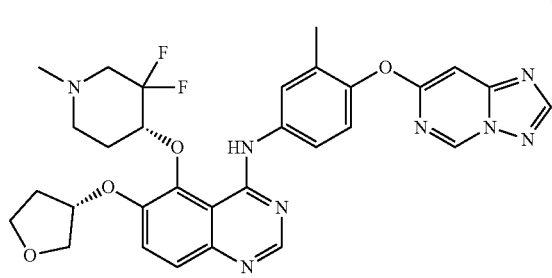

22
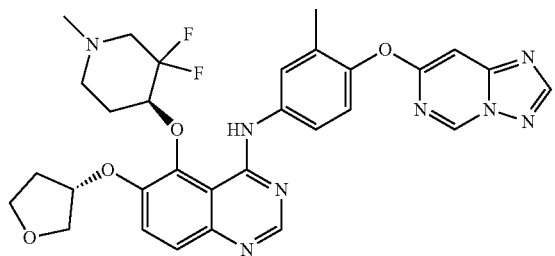
23
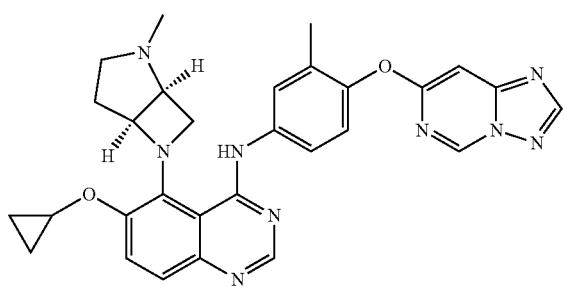
24
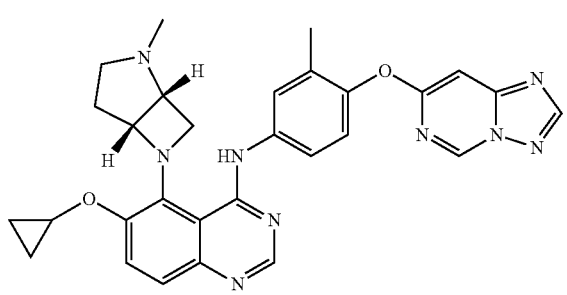
25
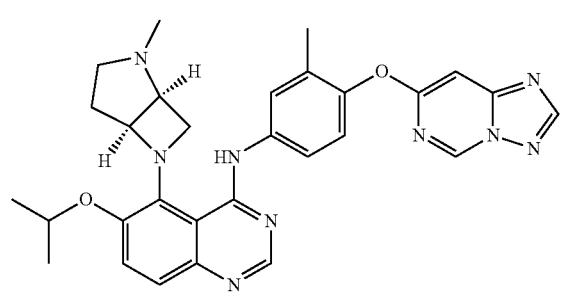
26
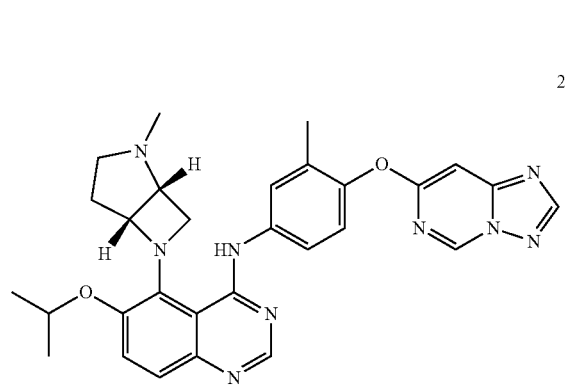
27
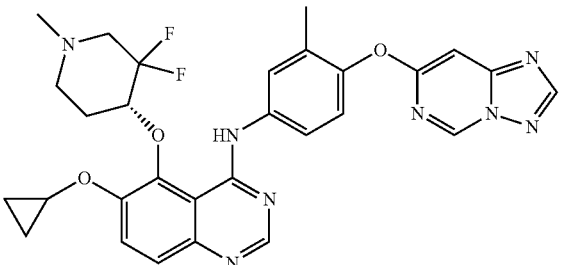
28
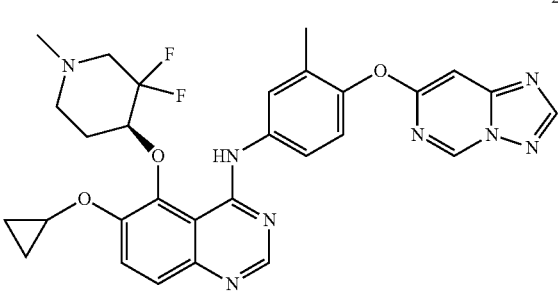
29
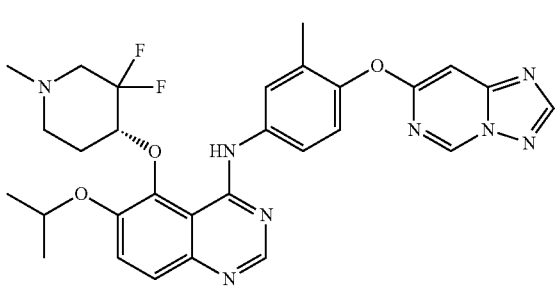
30
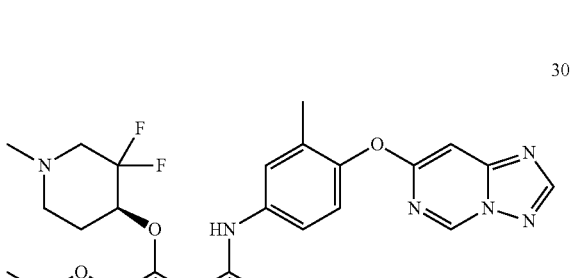
31
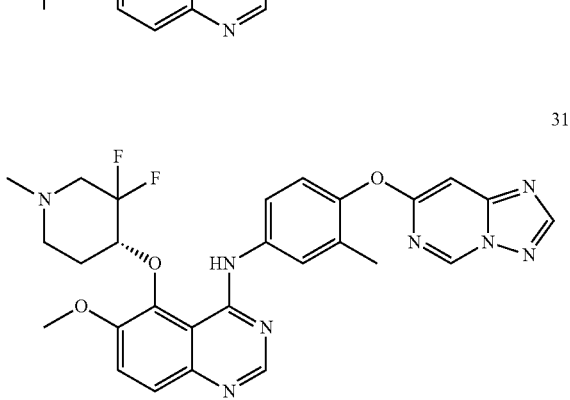

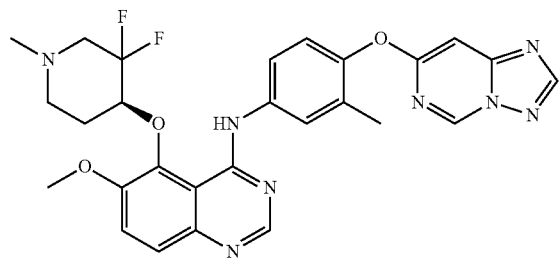
32
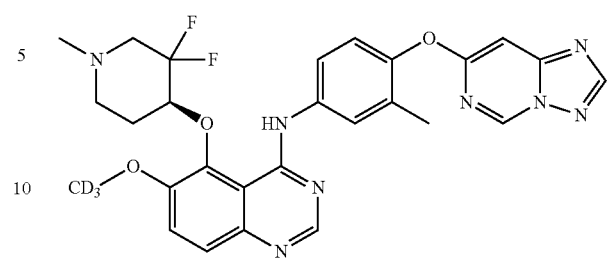
37
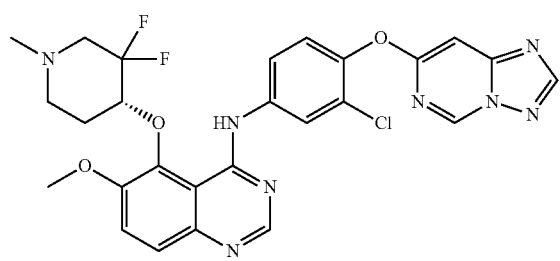
33
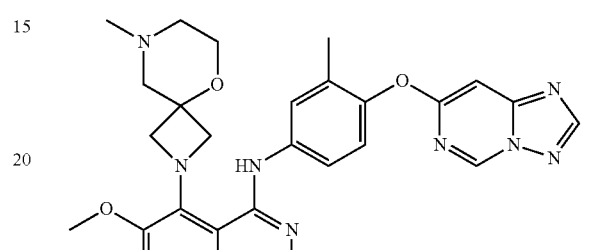
38
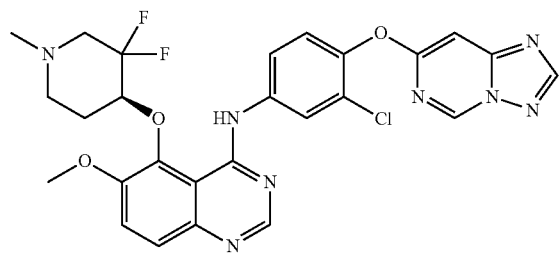
34
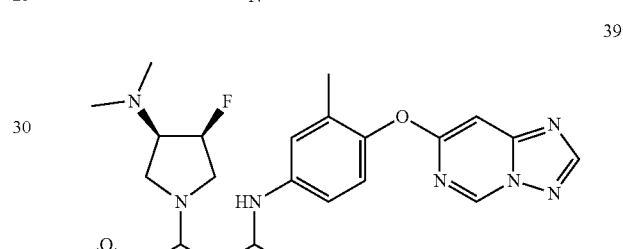
39
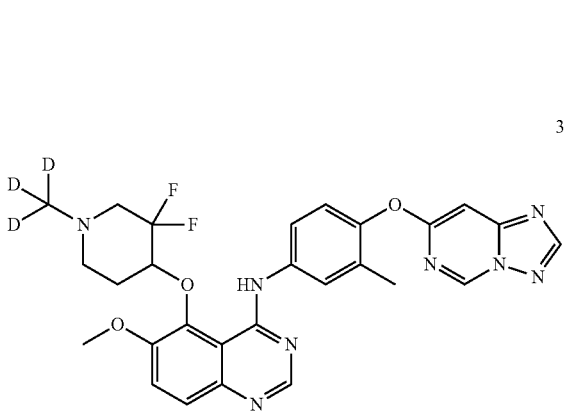
35
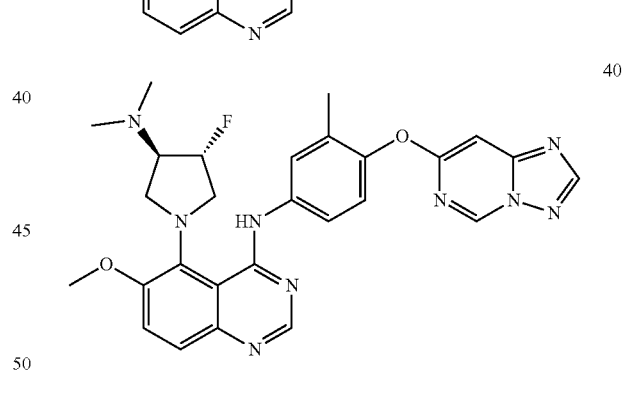
40
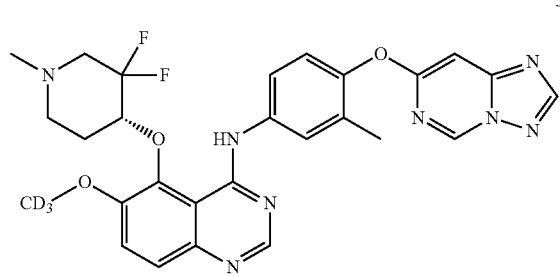
36
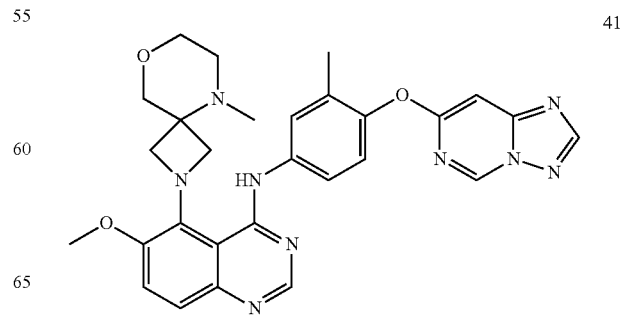
41

42
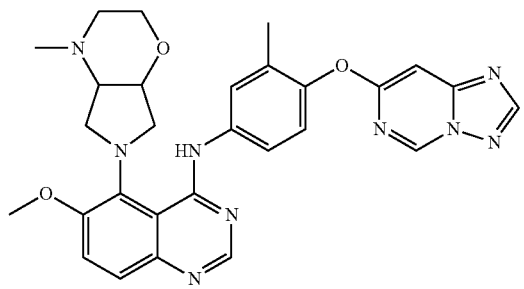
43
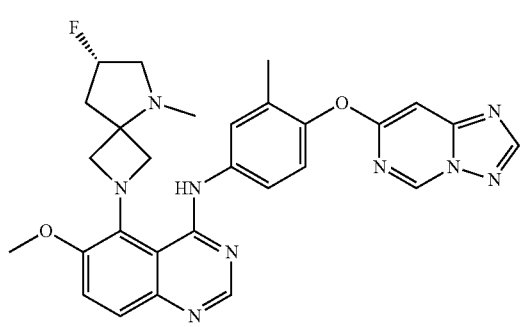
44
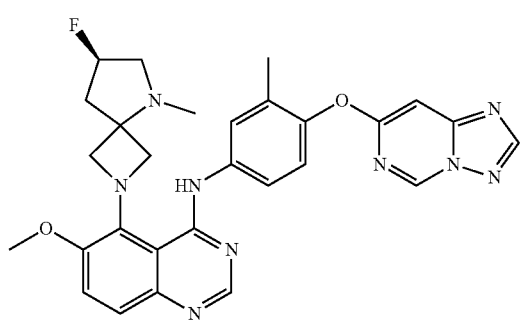
45
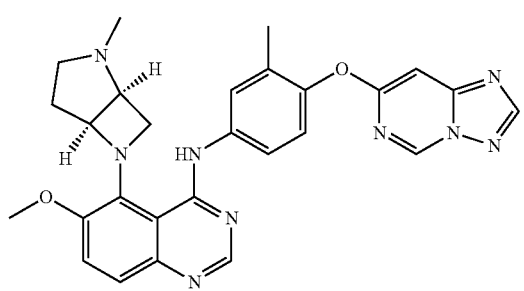
46
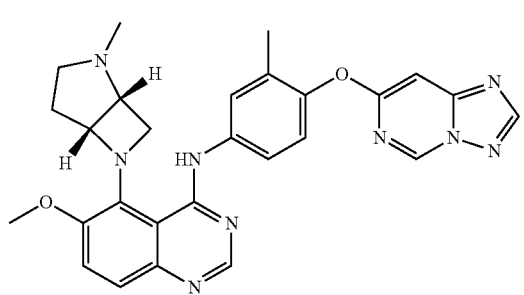
47
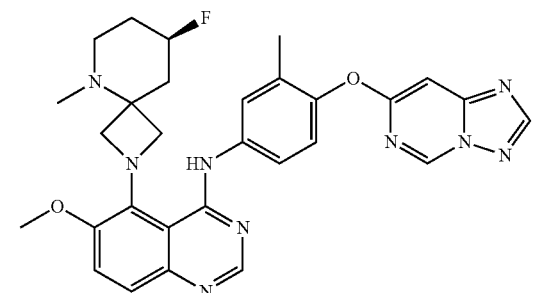
48
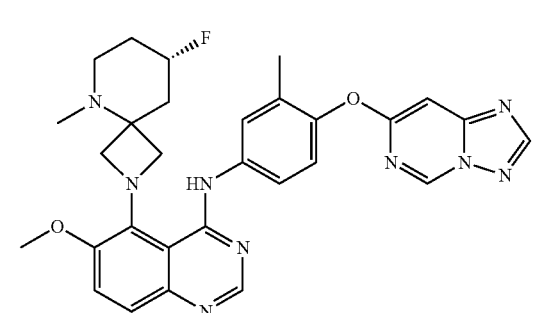
49
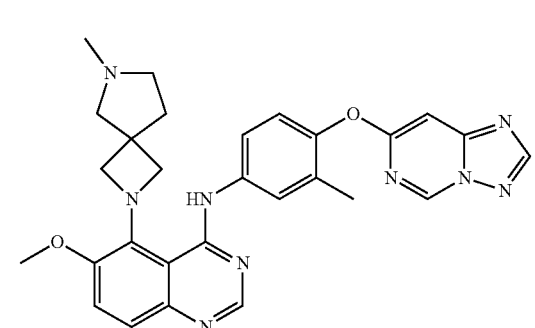
50
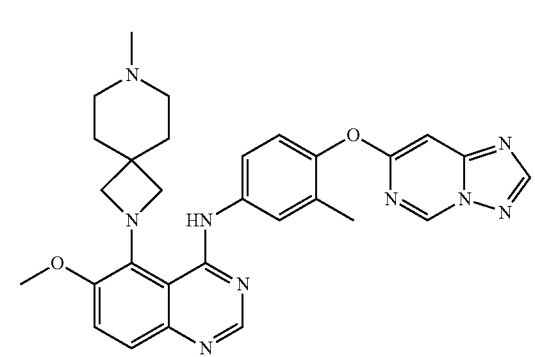
51
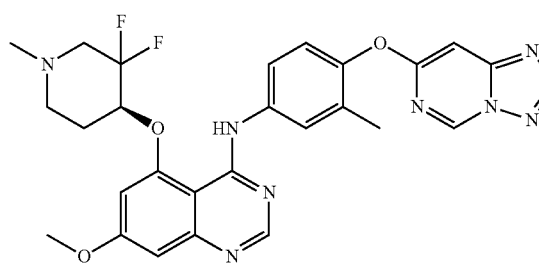

52
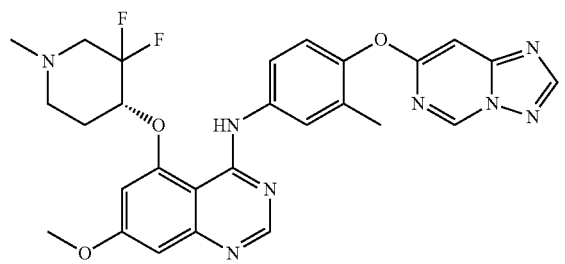
53
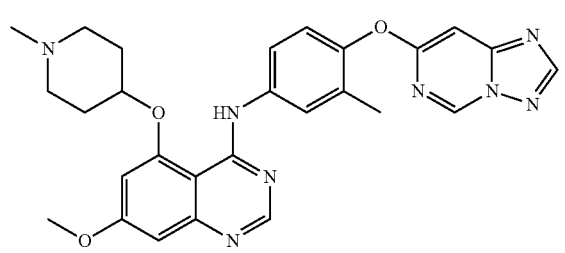
54
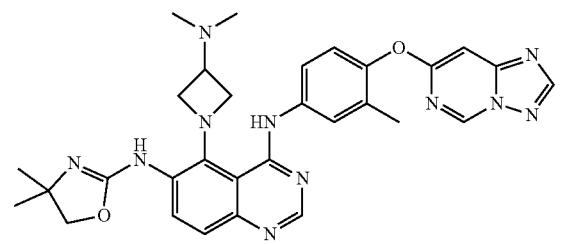
55
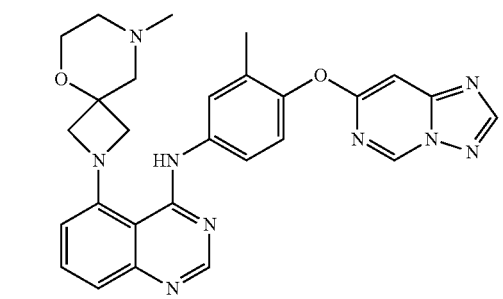
56
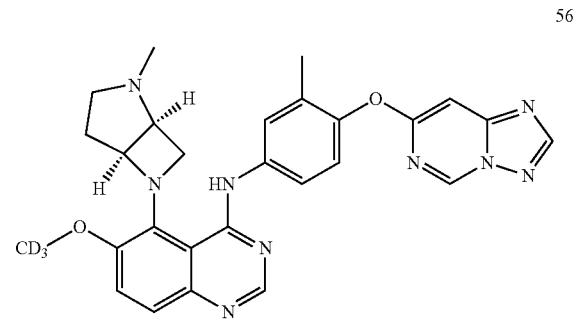
57
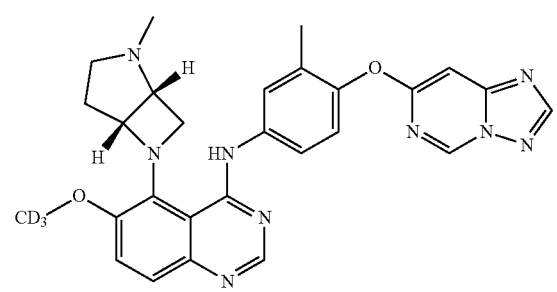
58
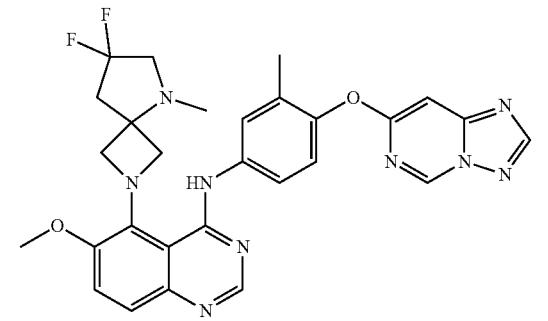
59
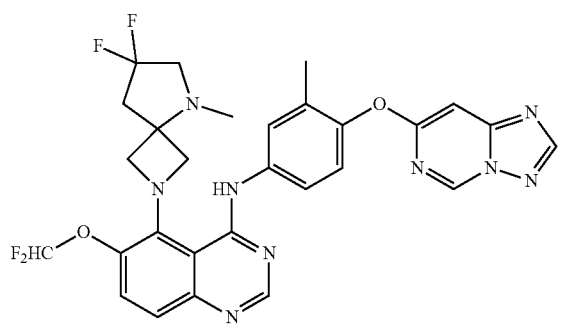
60
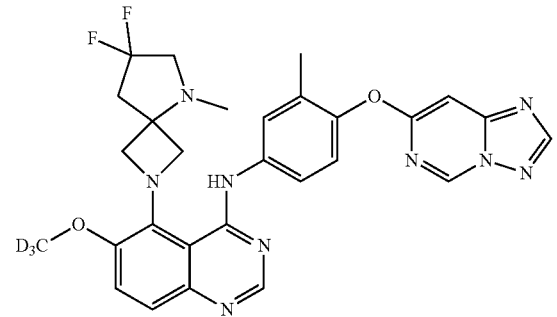

61
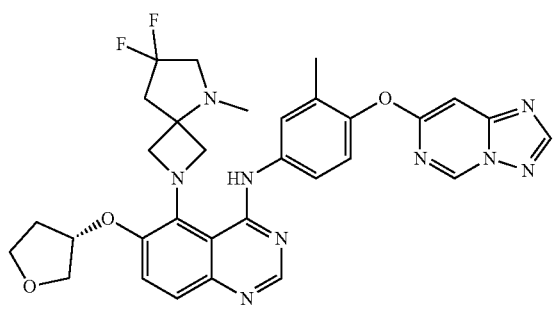
62
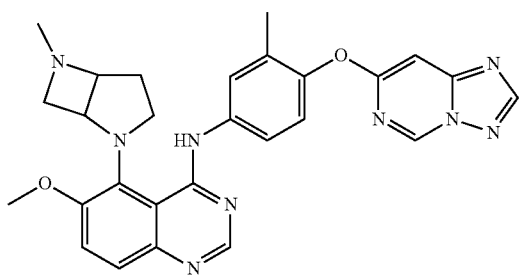
63
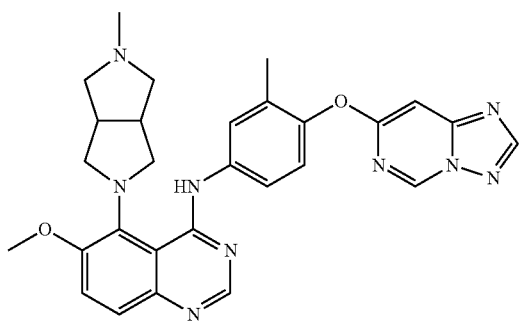
64
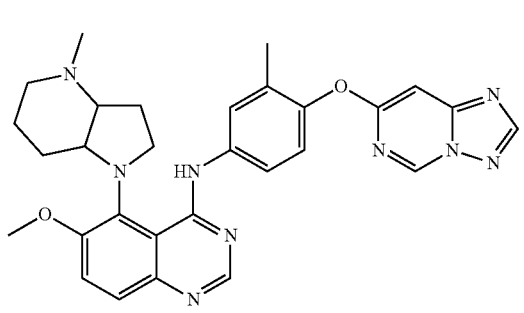
65
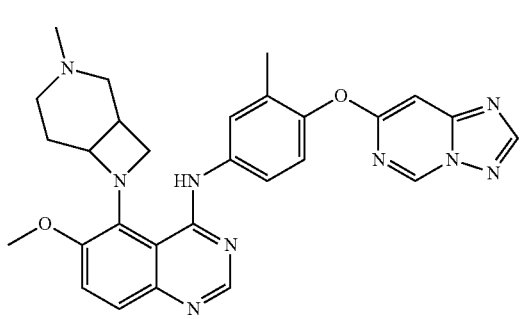
66
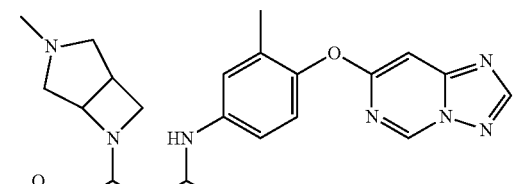
67
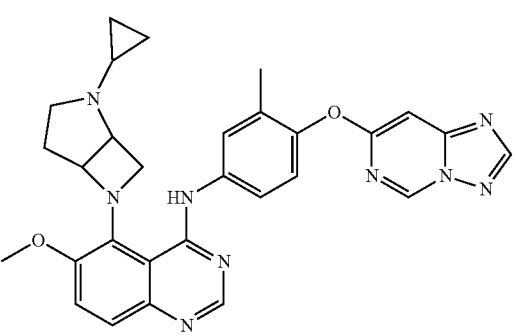
68
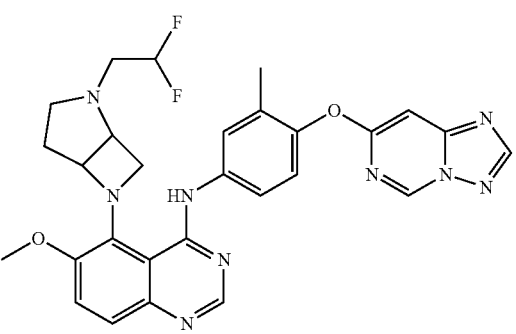
69
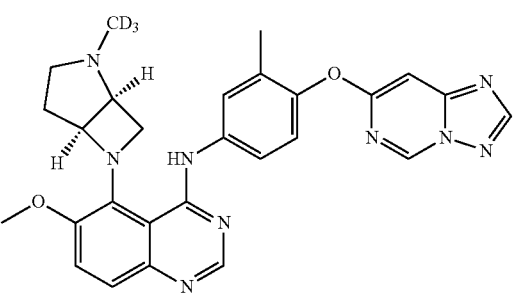
70
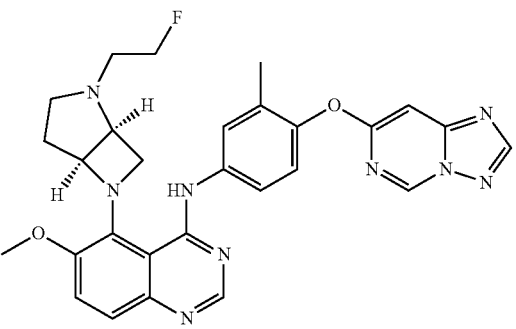

71 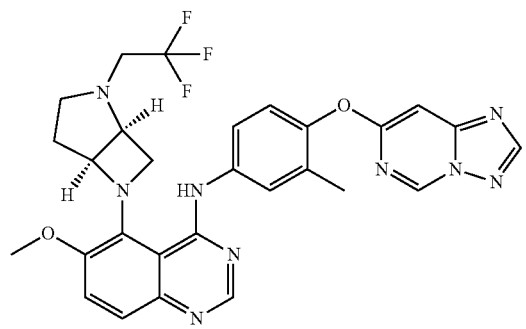
72 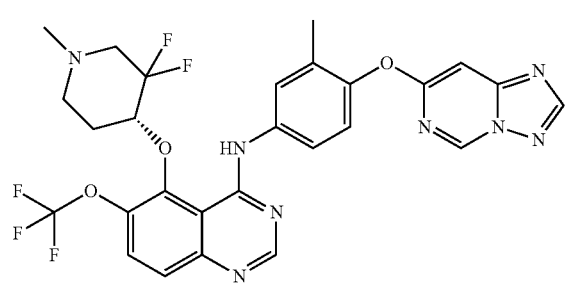
73 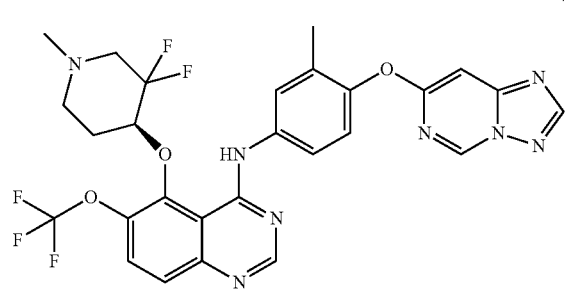
74 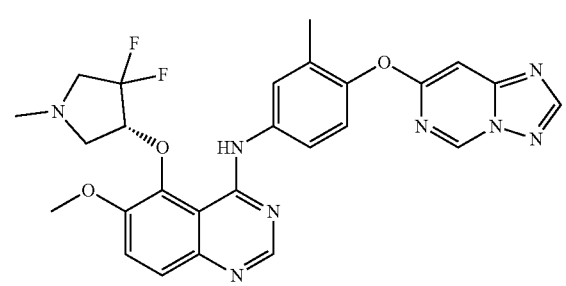
75 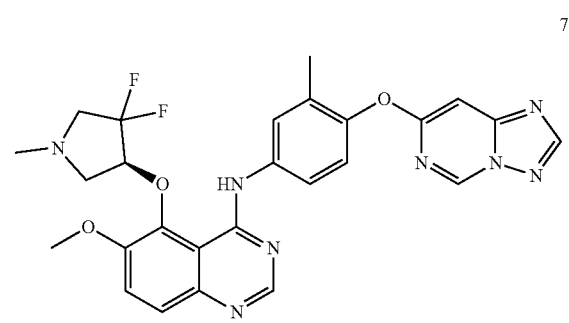
76 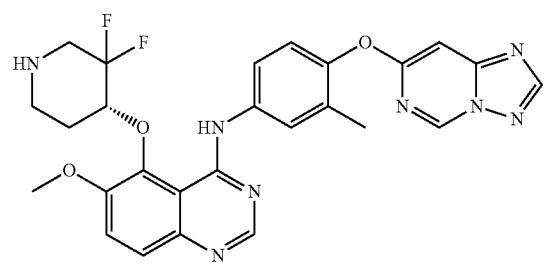
77 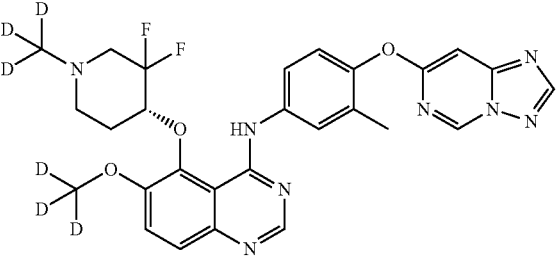
78 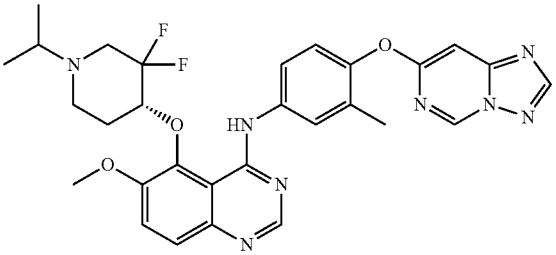
79 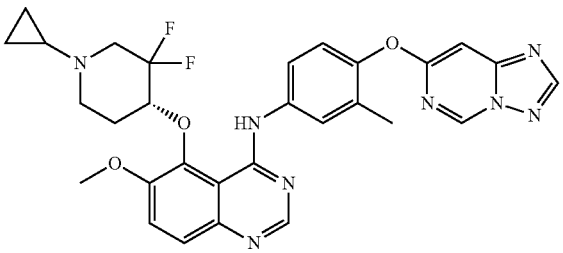
80 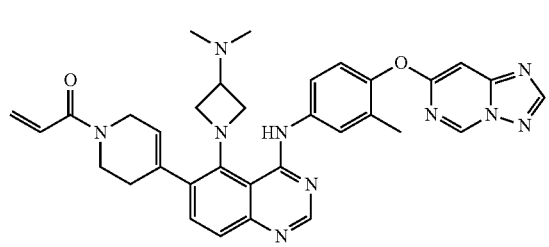
81 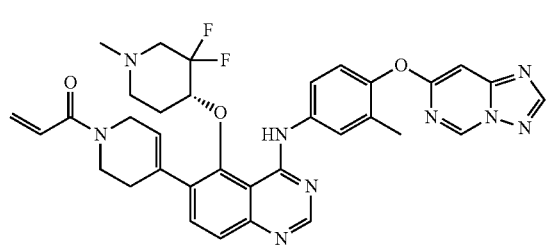

82
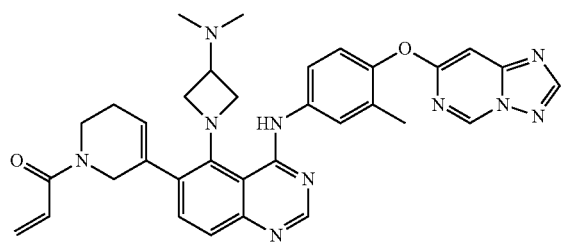
83
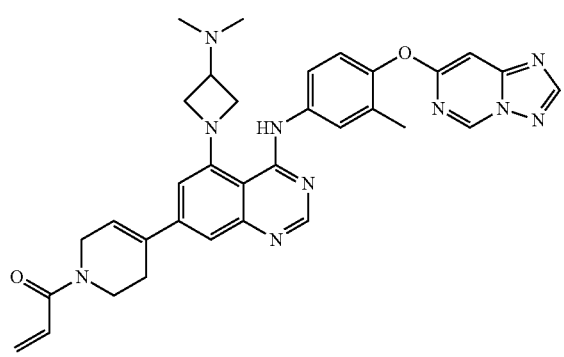
84
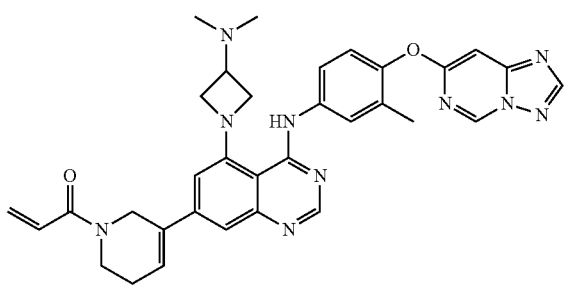
85
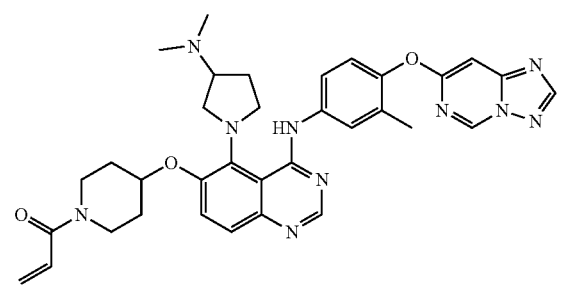
86
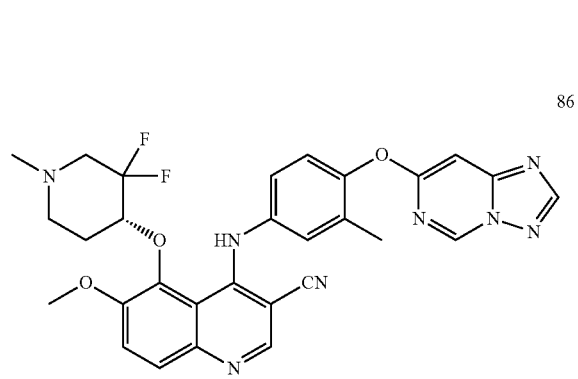
87
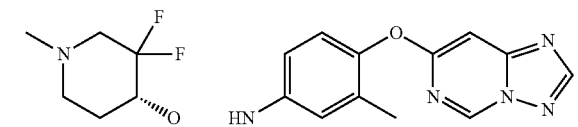
88
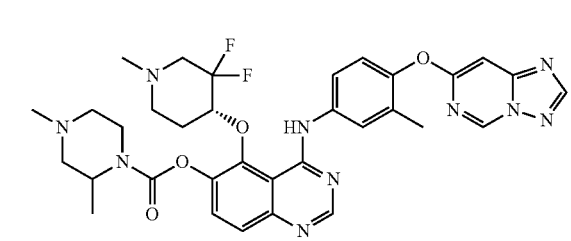
89
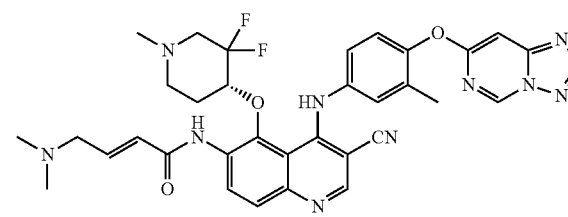
90
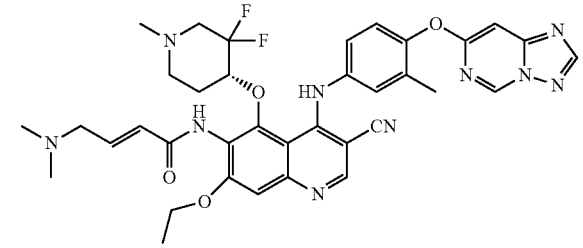
91
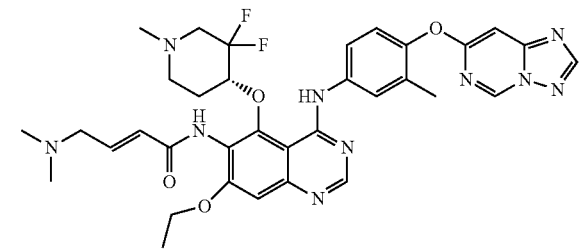
92
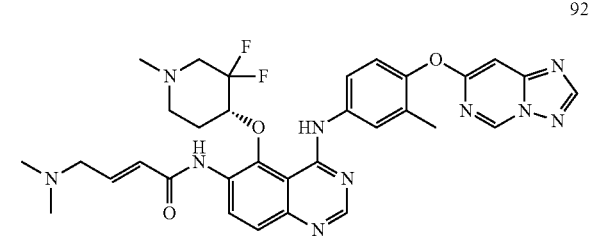

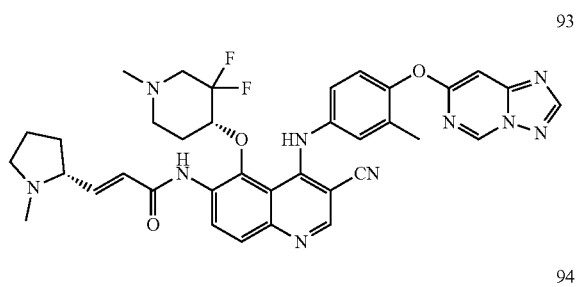

93

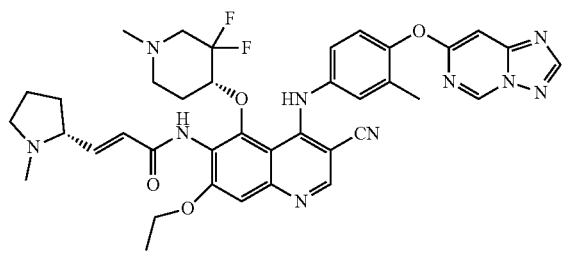

94

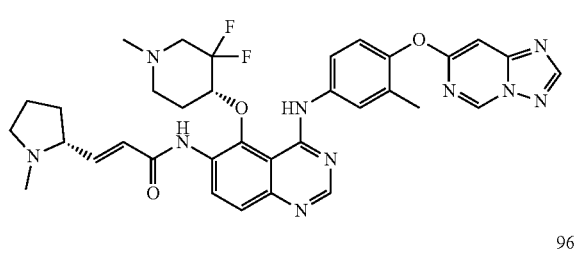

95

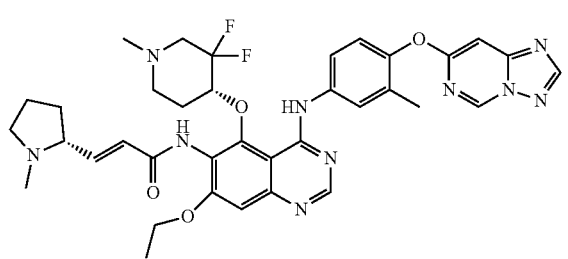

96

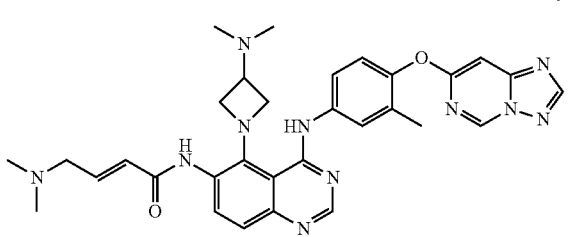

97

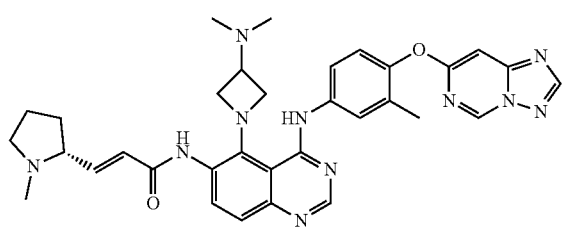

98

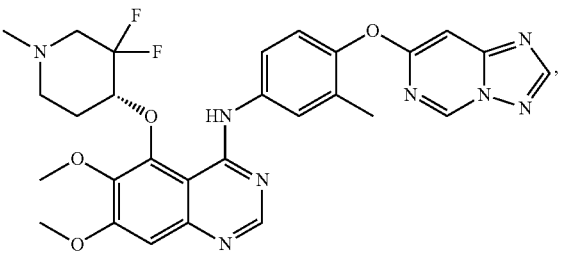

99 or a pharmaceutically acceptable salt thereof.

15. A pharmaceutical composition comprising a compound or a pharmaceutically acceptable salt thereof, as claimed in claim 1, and at least one pharmaceutically acceptable excipient.

16. The pharmaceutical composition of claim 15, which does not comprise an agent for facilitating BBB entry.

17. A method of treating HER2-associated diseases or conditions in a subject in need thereof, comprising administering to the subject a therapeutically effective amount of a compound or a pharmaceutically acceptable salt thereof, as claimed in claim 1.

18. The method of claim 17, wherein the compound or a pharmaceutically acceptable salt thereof is capable of BBB entry in the absence of an agent for facilitating BBB entry.

19. The method of claim 17, wherein the compound is administered simultaneously, separately or sequentially with one or more chemotherapeutic agents, radiotherapy or anti-HER2 antibody.

20. The compound or a pharmaceutically acceptable salt thereof, as claimed in claim 7, wherein $R_2$ and $R_6$ together with the nitrogen atom to which they are attached form a 4 to 9 membered saturated or partially unsaturated heterocyclyl ring optionally containing one or more additional heteroatoms selected from N, O and S, wherein said heterocyclyl ring is optionally substituted with one or more groups independently selected from the group consisting of halogen, alkyl, haloalkyl, saturated and partially unsaturated cycloalkyl, and $N(R_{10})(R_{11})$.

21. The compound or a pharmaceutically acceptable salt thereof, as claimed in claim 9, wherein $R_2$ is selected from $C_{4-6}$ saturated cycloalkyl or 5 to 6 membered saturated heterocyclyl, wherein said cycloalkyl and heterocyclyl are optionally substituted with one or more groups independently selected from the group consisting of halogen, alkyl, and $N(R_{10})(R_{11})$.

22. The compound or a pharmaceutically acceptable salt thereof, as claimed in claim 13, wherein in formula (IVa), (IVb), (IVc), (IVd), (IVe) and (IVf), L is $N(R_6)$;

$R_1$ is selected from the group consisting of halogen, cyano, nitro, hydroxyl, alkyl, alkenyl, alkynyl, heteroalkyl, heteroalkenyl, heteroalkynyl, saturated or partially unsaturated cycloalkyl, saturated or partially unsaturated heterocyclyl, aryl, $N(R_7)(R_8)$, and $O(R_9)$; and $R_2$ and $R_6$ together with the nitrogen atom to which they are attached form a 4 to 9 membered saturated heterocyclyl ring optionally containing one or more additional heteroatoms selected from N, O and S, wherein said 4 to 9 membered saturated heterocyclyl ring is optionally substituted with one or more groups independently selected from the group consisting of halogen, alkyl, haloalkyl, saturated and partially unsaturated cycloalkyl, and $N(R_{10})(R_{11})$.

23. The method of claim 17, wherein the HER2-associated diseases or conditions are cancer.

24. The method of claim 23, wherein the cancer is selected from breast cancer, gastric cancer, mCRC, NSCLC or metastasis thereof.

25. The method of claim 24, wherein the metastasis is in brain.

26. The method of claim 19, wherein the chemotherapeutic agent is capecitabine or T-DM1.

27. The compound as claimed in claim 1, wherein the compound has a structure of:

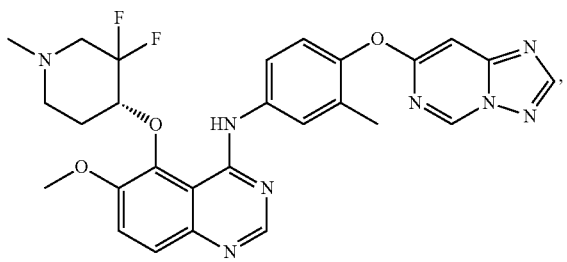 [SMILES: COc1ccc2ncnc(Nc3ccc(Oc4cc5ncnn5cn4)c(C)c3)c2c1O[C@@H]1CCN(C)CC1(F)F]

or a pharmaceutically acceptable salt thereof.

28. The compound as claimed in claim 1, wherein the compound has a structure of:

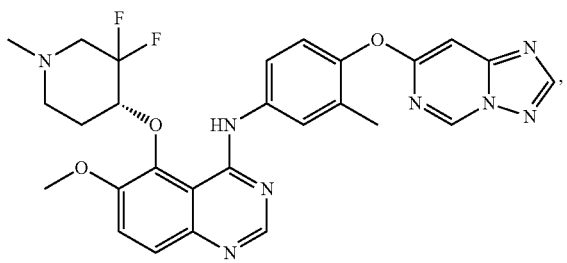 [SMILES: COc1ccc2ncnc(Nc3ccc(Oc4cc5ncnn5cn4)c(C)c3)c2c1O[C@@H]1CCN(C)CC1(F)F]

29. The compound as claimed in claim 1, wherein the compound has a structure of:

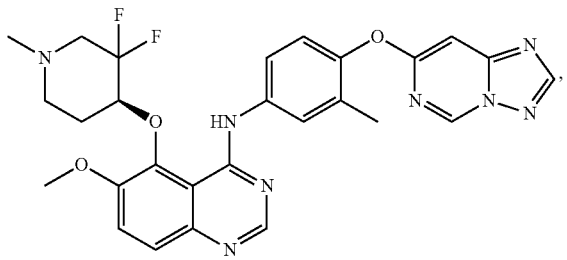 [SMILES: COc1ccc2ncnc(Nc3ccc(Oc4cc5ncnn5cn4)c(C)c3)c2c1O[C@H]1CCN(C)CC1(F)F]

or a pharmaceutically acceptable salt thereof.

30. The compound as claimed in claim 1, wherein the compound has a structure of:

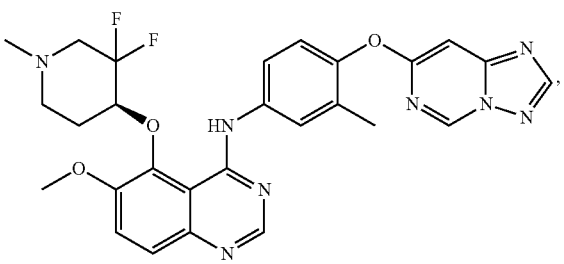 [SMILES: COc1ccc2ncnc(Nc3ccc(Oc4cc5ncnn5cn4)c(C)c3)c2c1O[C@H]1CCN(C)CC1(F)F]

31. The compound as claimed in claim 1, wherein the compound has a structure of:

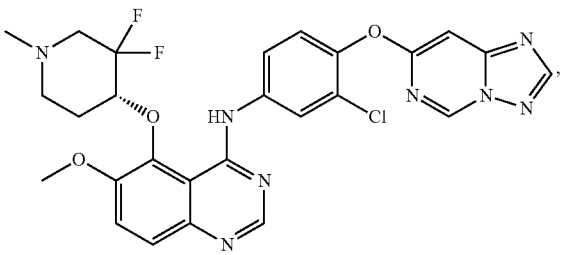 [SMILES: COc1ccc2ncnc(Nc3ccc(Oc4cc5ncnn5cn4)c(Cl)c3)c2c1O[C@@H]1CCN(C)CC1(F)F]

or a pharmaceutically acceptable salt thereof.

32. The compound as claimed in claim 1, wherein the compound has a structure of:

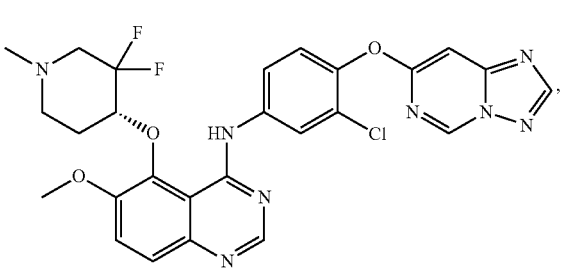 [SMILES: COc1ccc2ncnc(Nc3ccc(Oc4cc5ncnn5cn4)c(Cl)c3)c2c1O[C@@H]1CCN(C)CC1(F)F]

33. The compound as claimed in claim 1, wherein the compound has a structure of:

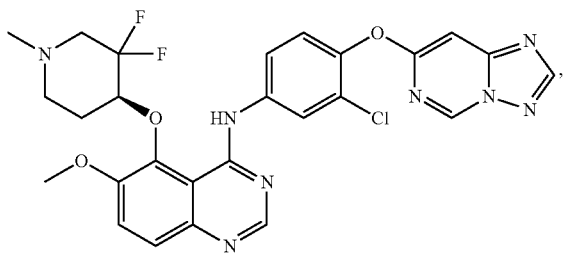

or a pharmaceutically acceptable salt thereof.

34. The compound as claimed in claim 1, wherein the compound has a structure of:

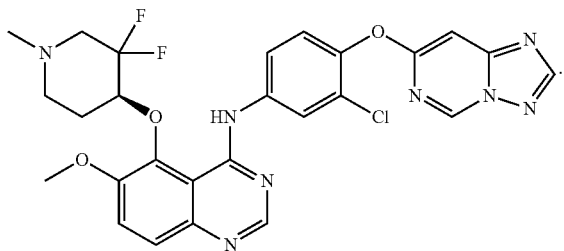 [SMILES: COc1ccc2ncnc(Nc3ccc(Oc4cc5ncnn5cn4)c(Cl)c3)c2c1O[C@H]1CCN(C)CC1(F)F]

35. The compound as claimed in claim 1, wherein the compound has a structure of:

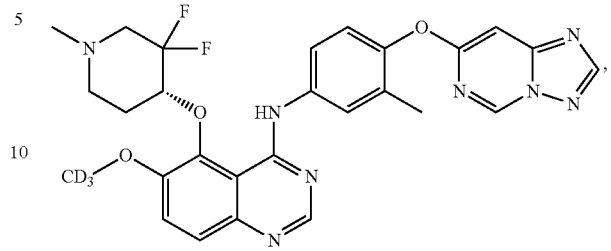

or a pharmaceutically acceptable salt thereof.

36. The compound as claimed in claim 1, wherein the compound has a structure of:

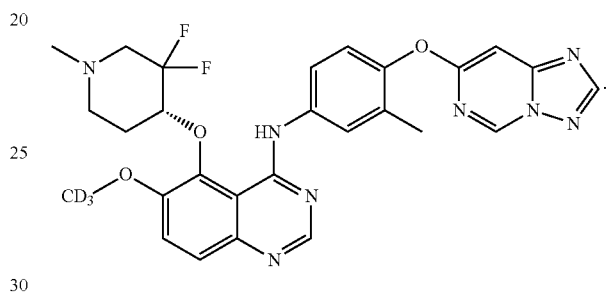

* * * * *